US009025727B2

(12) United States Patent
Gertner et al.

(10) Patent No.: US 9,025,727 B2
(45) **Date of Patent: *May 5, 2015**

(54) METHODS AND DEVICES FOR ORTHOVOLTAGE OCULAR RADIOTHERAPY AND TREATMENT PLANNING

(71) Applicant: Oraya Therapeutics, Inc., Newark, CA (US)

(72) Inventors: Michael Gertner, Menlo Park, CA (US); Mark Arnoldussen, San Carlos, CA (US); Erik Chell, Oakland, CA (US); Steven D. Hansen, Concord, CA (US); Junzhong Liang, Fremont, CA (US)

(73) Assignee: Oraya Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/949,063

(22) Filed: Jul. 23, 2013

(65) Prior Publication Data

US 2014/0037063 A1 Feb. 6, 2014

Related U.S. Application Data

(63) Continuation of application No. 12/887,419, filed on Sep. 21, 2010, now Pat. No. 8,494,116, which is a continuation of application No. 12/262,031, filed on Oct. 30, 2008, now Pat. No. 7,801,271, said (Continued)

(51) Int. Cl.
*A61N 5/10* (2006.01)

(52) U.S. Cl.
CPC ............ *A61N 5/1037* (2013.01); *A61N 5/1017* (2013.01); *A61N 5/103* (2013.01); *A61N 5/1064* (2013.01); *A61N 2005/1091* (2013.01)

(58) Field of Classification Search
USPC ........................................................... 378/65
See application file for complete search history.

(56) References Cited

U.S. PATENT DOCUMENTS

| | | | |
|---|---|---|---|
| 2,849,621 | A | 8/1958 | Clark |
| 3,073,960 | A | 1/1963 | Guentner |

(Continued)

FOREIGN PATENT DOCUMENTS

| | | | |
|---|---|---|---|
| CN | 1612713 | A | 5/2005 |
| EP | 2152145 | | 2/2010 |

(Continued)

OTHER PUBLICATIONS

Bailey, Edgar D., CHP, Chief Radiologic Health Branch, "Syllabus on Radiography Radiation Protection, Filtration Regulatory Requirements," California Department of Health and Human Services, pp. 11-12 (2004).

(Continued)

*Primary Examiner* — Glen Kao

(74) *Attorney, Agent, or Firm* — James W. Hill; Mark Bentley; McDermott Will & Emery LLP

(57) ABSTRACT

A method, code and system for planning the treatment a lesion on or adjacent to the retina of an eye of a patient are disclosed. There is first established at least two beam paths along which x-radiation is to be directed at the retinal lesion. Based on the known spectral and intensity characteristics of the beam, a total treatment time for irradiation along each beam paths is determined. From the coordinates of the optic nerve in the aligned eye position, there is determined the extent and duration of eye movement away from the aligned patient-eye position in a direction that moves the patient's optic nerve toward the irradiation beam that will be allowed during treatment, while still maintaining the radiation dose at the patient optic nerve below a predetermined dose level.

7 Claims, 58 Drawing Sheets

Related U.S. Application Data application No. 12/887,419 is a continuation-in-part of application No. 12/103,534, filed on Apr. 15, 2008, now Pat. No. 8,363,783, and a continuation-in-part of application No. 12/100,398, filed on Apr. 9, 2008, now Pat. No. 7,693,260, and a continuation-in-part of application No. 12/027,083, filed on Feb. 6, 2008, now Pat. No. 8,512,236, and a continuation-in-part of application No. 12/027,094, filed on Feb. 6, 2008, and a continuation-in-part of application No. 12/027,069, filed on Feb. 6, 2008, now Pat. No. 8,506,558.

(60) Provisional application No. 61/101,013, filed on Sep. 29, 2008, provisional application No. 61/093,092, filed on Aug. 29, 2008, provisional application No. 61/076,128, filed on Jun. 26, 2008, provisional application No. 61/016,472, filed on Dec. 23, 2007, provisional application No. 61/020,655, filed on Jan. 11, 2008.

(56) References Cited

U.S. PATENT DOCUMENTS

| | | | |
|---|---|---|---|
| 4,391,275 | A | 7/1983 | Fankhauser et al. |
| 4,521,905 | A | 6/1985 | Hosokawa |
| 4,710,193 | A | 12/1987 | Volk |
| 4,718,418 | A | 1/1988 | L'Esperance, Jr. |
| 4,817,432 | A | 4/1989 | Wallace et al. |
| 5,008,907 | A | 4/1991 | Norman et al. |
| 5,027,818 | A | 7/1991 | Bova et al. |
| 5,065,031 | A | 11/1991 | Moscovitch |
| 5,116,115 | A | 5/1992 | Lange et al. |
| 5,139,494 | A | 8/1992 | Freiberg |
| 5,171,254 | A | 12/1992 | Sher |
| 5,189,687 | A | 2/1993 | Bova et al. |
| 5,207,223 | A | 5/1993 | Adler |
| 5,216,255 | A | 6/1993 | Weidlich |
| 5,304,167 | A | 4/1994 | Freiberg |
| 5,336,215 | A | 8/1994 | Hsueh et al. |
| 5,339,347 | A | 8/1994 | Slatkin et al. |
| 5,354,323 | A | 10/1994 | Whitebook |
| 5,373,844 | A | 12/1994 | Smith et al. |
| 5,411,026 | A | 5/1995 | Carol |
| 5,422,926 | A | 6/1995 | Smith et al. |
| 5,427,097 | A | 6/1995 | Depp |
| 5,430,308 | A | 7/1995 | Feichtner et al. |
| 5,446,548 | A | 8/1995 | Gerig et al. |
| 5,468,238 | A | 11/1995 | Mersch |
| 5,528,652 | A | 6/1996 | Smith et al. |
| 5,556,417 | A | 9/1996 | Sher |
| 5,635,721 | A | 6/1997 | Bardi et al. |
| 5,644,616 | A | 7/1997 | Landi et al. |
| 5,651,043 | A | 7/1997 | Tsuyuki et al. |
| 5,668,847 | A | 9/1997 | Hernandez |
| 5,708,696 | A | 1/1998 | Kantor |
| 5,724,400 | A | 3/1998 | Swerdloff et al. |
| 5,727,042 | A | 3/1998 | Brenneisen |
| 5,737,384 | A | 4/1998 | Fenn |
| 5,744,919 | A | 4/1998 | Mishin et al. |
| 5,745,545 | A | 4/1998 | Hughes |
| 5,771,270 | A | 6/1998 | Archer |
| 5,778,043 | A | 7/1998 | Cosman |
| 5,820,553 | A | 10/1998 | Hughes |
| 5,870,697 | A | 2/1999 | Chandler et al. |
| 5,901,199 | A | 5/1999 | Murphy et al. |
| 6,001,054 | A | 12/1999 | Regulla et al. |
| 6,104,778 | A | 8/2000 | Murad |
| 6,118,848 | A | 9/2000 | Reiffel |
| 6,126,668 | A | 10/2000 | Bair et al. |
| 6,134,294 | A | 10/2000 | Gibbs |
| 6,135,996 | A | 10/2000 | Kolesa et al. |
| 6,144,875 | A | 11/2000 | Schweikard et al. |
| 6,149,643 | A | 11/2000 | Herekar et al. |
| 6,179,422 | B1 | 1/2001 | Lai |
| 6,245,059 | B1 | 6/2001 | Clapham |
| 6,257,722 | B1 | 7/2001 | Toh |
| 6,260,005 | B1 | 7/2001 | Yang et al. |
| 6,278,764 | B1 | 8/2001 | Barbee, Jr. et al. |
| 6,287,299 | B1 | 9/2001 | Sasnett et al. |
| 6,299,054 | B1 | 10/2001 | Gibbs, Jr. |
| 6,299,307 | B1 | 10/2001 | Oltean et al. |
| 6,301,328 | B1 | 10/2001 | Sliski et al. |
| 6,301,329 | B1 | 10/2001 | Surridge |
| 6,307,914 | B1 | 10/2001 | Kunieda et al. |
| 6,312,393 | B1 | 11/2001 | Abreu |
| 6,359,963 | B1 | 3/2002 | Cash |
| 6,373,571 | B1 | 4/2002 | Juhasz et al. |
| 6,385,286 | B1 | 5/2002 | Fitchard et al. |
| 6,405,072 | B1 | 6/2002 | Cosman |
| 6,436,113 | B1 | 8/2002 | Burba et al. |
| 6,459,762 | B1 | 10/2002 | Wong et al. |
| 6,494,878 | B1 | 12/2002 | Pawlowski et al. |
| 6,501,981 | B1 | 12/2002 | Schweikard et al. |
| 6,512,813 | B1 | 1/2003 | Krispel et al. |
| 6,535,574 | B1 | 3/2003 | Collins et al. |
| 6,544,193 | B2 | 4/2003 | Abreu |
| 6,560,312 | B2 | 5/2003 | Cash |
| 6,609,826 | B1 | 8/2003 | Fujii et al. |
| 6,621,889 | B1 | 9/2003 | Mostafavi |
| 6,690,965 | B1 | 2/2004 | Riaziat et al. |
| 6,714,620 | B2 | 3/2004 | Caflisch et al. |
| 6,728,335 | B1 | 4/2004 | Thomson et al. |
| 6,744,846 | B2 | 6/2004 | Popescu et al. |
| 6,778,850 | B1 | 8/2004 | Adler et al. |
| 6,789,900 | B2 | 9/2004 | Van de Velde |
| 6,792,073 | B2 | 9/2004 | Deasy |
| 6,810,107 | B2 | 10/2004 | Steinberg |
| 6,837,862 | B2 | 1/2005 | Driver, Jr. |
| 6,853,704 | B2 | 2/2005 | Collins et al. |
| 6,863,667 | B2 | 3/2005 | Webb et al. |
| 6,865,253 | B2 | 3/2005 | Blumhofer et al. |
| 6,865,254 | B2 | 3/2005 | Nafstadius |
| 6,875,165 | B2 | 4/2005 | Dejuan, Jr. et al. |
| 6,888,919 | B2 | 5/2005 | Graf |
| 6,937,696 | B1 | 8/2005 | Mostafavi |
| 6,942,656 | B2 | 9/2005 | Pawlowski et al. |
| 6,965,847 | B2 | 11/2005 | Wessol et al. |
| 6,977,987 | B2 | 12/2005 | Yamashita et al. |
| 6,990,175 | B2 | 1/2006 | Nakashima et al. |
| 7,018,376 | B2 | 3/2006 | Webb et al. |
| 7,027,557 | B2 | 4/2006 | Llacer |
| 7,044,602 | B2 | 5/2006 | Chernyak |
| 7,046,762 | B2 | 5/2006 | Lee |
| 7,046,765 | B2 | 5/2006 | Wong et al. |
| 7,070,327 | B2 | 7/2006 | Collins |
| 7,070,554 | B2 | 7/2006 | White et al. |
| 7,085,347 | B2 | 8/2006 | Mihara et al. |
| 7,103,144 | B2 | 9/2006 | Wong et al. |
| 7,103,145 | B2 | 9/2006 | Wong et al. |
| 7,115,120 | B2 | 10/2006 | Lin |
| 7,139,601 | B2 | 11/2006 | Bucholz et al. |
| 7,154,991 | B2 | 12/2006 | Earnst et al. |
| 7,158,607 | B2 | 1/2007 | Dilmanian et al. |
| 7,158,610 | B2 | 1/2007 | Mostafavi |
| 7,166,852 | B2 | 1/2007 | Saracen et al. |
| 7,171,257 | B2 | 1/2007 | Thomson |
| 7,178,666 | B2 | 2/2007 | Huang |
| 7,179,254 | B2 | 2/2007 | Pendekanti et al. |
| 7,187,792 | B2 | 3/2007 | Fu et al. |
| 7,194,063 | B2 | 3/2007 | Dilmanian et al. |
| 7,204,640 | B2 | 4/2007 | Fu et al. |
| 7,221,733 | B1 | 5/2007 | Takai et al. |
| 7,225,012 | B1 | 5/2007 | Susil et al. |
| 7,227,925 | B1 | 6/2007 | Mansfield et al. |
| 7,231,076 | B2 | 6/2007 | Fu et al. |
| 7,239,684 | B2 | 7/2007 | Hara et al. |
| 7,239,908 | B1 | 7/2007 | Alexander et al. |
| 7,260,426 | B2 | 8/2007 | Schweikard et al. |
| 7,266,176 | B2 | 9/2007 | Allison et al. |
| 7,278,787 | B2 | 10/2007 | Hack et al. |
| 7,280,865 | B2 | 10/2007 | Adler |
| 7,283,610 | B2 | 10/2007 | Low et al. |
| 7,346,144 | B2 | 3/2008 | Hughes et al. |

(56) References Cited

U.S. PATENT DOCUMENTS 7,418,079 B2 8/2008 Schildkraut et al.
7,453,983 B2 11/2008 Schildkraut et al.
7,453,984 B2 11/2008 Chen et al.
7,496,174 B2 2/2009 Gertner et al.
7,500,785 B2 3/2009 Moritake et al.
7,505,559 B2 3/2009 Kuduvalli
7,535,991 B2 5/2009 Gertner
7,564,946 B2 7/2009 Gertner
7,587,024 B2 9/2009 Grozinger et al.
7,590,219 B2 9/2009 Maurer, Jr. et al.
7,620,144 B2 11/2009 Bodduluri
7,620,147 B2 11/2009 Gertner et al.
7,672,429 B2 3/2010 Urano et al.
7,680,244 B2 3/2010 Gertner et al.
7,680,245 B2 3/2010 Gertner
7,693,258 B2 4/2010 Gertner
7,693,259 B2 4/2010 Gertner
7,693,260 B2 4/2010 Gertner et al.
7,697,663 B2 4/2010 Gertner
7,792,249 B2 9/2010 Gertner et al.
7,801,271 B2 * 9/2010 Gertner et al. .................. 378/65
7,822,175 B2 10/2010 Gertner
7,831,073 B2 11/2010 Fu et al.
7,894,649 B2 2/2011 Fu et al.
7,912,178 B2 3/2011 Gertner
7,912,179 B2 3/2011 Gertner et al.
7,953,203 B2 5/2011 Gertner et al.
7,961,845 B2 6/2011 Gertner et al.
7,978,818 B2 7/2011 Gertner et al.
7,978,819 B2 7/2011 Gertner et al.
8,059,784 B2 11/2011 Gertner
8,073,105 B2 12/2011 Gertner et al.
8,094,779 B2 1/2012 Gertner
8,180,021 B2 5/2012 Gertner
8,184,772 B2 5/2012 Gertner et al.
8,189,739 B2 5/2012 Gertner
8,229,069 B2 7/2012 Gertner et al.
8,229,073 B2 7/2012 Gertner et al.
8,238,517 B2 8/2012 Gertner et al.
8,295,437 B2 10/2012 Gertner et al.
8,306,186 B2 11/2012 Gertner et al.
8,320,524 B2 11/2012 Gertner
8,363,783 B2 1/2013 Gertner et al.
8,442,185 B2 5/2013 Gertner et al.
8,457,277 B2 6/2013 Gertner et al.
8,494,116 B2 * 7/2013 Gertner et al. .................. 378/65
8,503,609 B2 8/2013 Gertner et al.
8,506,558 B2 8/2013 Gertner et al.
8,512,236 B2 8/2013 Gertner et al.
8,611,497 B2 12/2013 Gertner et al.
2001/0033682 A1 * 10/2001 Robar et al. .................... 378/65
2002/0051513 A1 5/2002 Pugachev et al.
2002/0065461 A1 5/2002 Cosman
2002/0099363 A1 7/2002 Woodward et al.
2002/0106054 A1 8/2002 Caflisch et al.
2002/0106055 A1 8/2002 Cash
2002/0115902 A1 8/2002 Dejuan et al.
2002/0131556 A1 9/2002 Steinberg
2002/0161356 A1 10/2002 Bille et al.
2002/0198453 A1 12/2002 Herrick
2002/0198553 A1 12/2002 Schumer et al.
2003/0112922 A1 6/2003 Burdette et al.
2003/0120141 A1 6/2003 Adler
2003/0125622 A1 7/2003 Schweikard et al.
2003/0161826 A1 8/2003 Arnason et al.
2003/0189689 A1 10/2003 Rathjen
2003/0211075 A1 11/2003 Thorpe et al.
2003/0219098 A1 11/2003 McNutt et al.
2004/0019274 A1 1/2004 Galloway et al.
2004/0037390 A1 * 2/2004 Mihara et al. .................. 378/65
2004/0054359 A1 3/2004 Ruiz et al.
2004/0071261 A1 4/2004 Earl et al.
2004/0131150 A1 7/2004 Pankratov et al.
2004/0138515 A1 7/2004 White et al.
2004/0267294 A1 12/2004 Will
2005/0010109 A1 1/2005 Faul
2005/0049478 A1 3/2005 Kuduvalli et al.
2005/0058245 A1 3/2005 Ein-Gal
2005/0111621 A1 5/2005 Riker et al.
2005/0175218 A1 8/2005 Vertegaal et al.
2005/0180544 A1 8/2005 Sauer et al.
2005/0192562 A1 9/2005 Loesel et al.
2005/0203499 A1 9/2005 Pendekanti et al.
2005/0226482 A1 10/2005 Kuduvalli
2005/0228255 A1 10/2005 Saracen et al.
2005/0234327 A1 10/2005 Saracen et al.
2005/0270486 A1 12/2005 Teiwes et al.
2005/0271590 A1 12/2005 Schwartz et al.
2006/0002601 A1 1/2006 Fu et al.
2006/0002615 A1 1/2006 Fu et al.
2006/0002630 A1 1/2006 Fu et al.
2006/0002631 A1 1/2006 Fu et al.
2006/0002632 A1 1/2006 Fu et al.
2006/0004281 A1 1/2006 Saracen
2006/0033044 A1 2/2006 Gentry et al.
2006/0067469 A1 3/2006 Dooley et al.
2006/0072821 A1 4/2006 Wang
2006/0074292 A1 4/2006 Thomson et al.
2006/0074299 A1 4/2006 Sayeh
2006/0074304 A1 4/2006 Sayeh
2006/0078087 A1 4/2006 Forman et al.
2006/0084952 A1 4/2006 Pallikaris et al.
2006/0093089 A1 5/2006 Vertatschitsch et al.
2006/0170679 A1 8/2006 Wang et al.
2006/0170865 A1 8/2006 Hirohara et al.
2006/0176997 A1 8/2006 Dilmanian et al.
2006/0182326 A1 8/2006 Schildkraut et al.
2006/0192921 A1 8/2006 Loesel et al.
2006/0193441 A1 8/2006 Cadman
2006/0199991 A1 9/2006 Lewis et al.
2006/0203964 A1 9/2006 Nyholm et al.
2006/0245543 A1 11/2006 Earnst et al.
2006/0271025 A1 11/2006 Jones et al.
2006/0274061 A1 12/2006 Wang et al.
2006/0274885 A1 12/2006 Wang et al.
2006/0274924 A1 12/2006 West et al.
2006/0274925 A1 12/2006 West et al.
2006/0285641 A1 12/2006 Scherch
2006/0287662 A1 12/2006 Berry et al.
2006/0291621 A1 12/2006 Yan et al.
2006/0291710 A1 12/2006 Wang et al.
2006/0293583 A1 12/2006 Saracen et al.
2007/0003007 A1 1/2007 Carrano et al.
2007/0003123 A1 1/2007 Fu et al.
2007/0015991 A1 1/2007 Fu et al.
2007/0038058 A1 2/2007 West et al.
2007/0053490 A1 3/2007 Wang et al.
2007/0053491 A1 3/2007 Schildkraut et al.
2007/0071168 A1 3/2007 Allison et al.
2007/0071176 A1 3/2007 Main et al.
2007/0078306 A1 4/2007 Allison et al.
2007/0083087 A1 4/2007 Carda
2007/0093795 A1 4/2007 Melcher et al.
2007/0118010 A1 5/2007 Hillstead et al.
2007/0127622 A1 6/2007 Main et al.
2007/0127845 A1 6/2007 Fu et al.
2007/0140413 A1 6/2007 Saracen
2007/0161884 A1 7/2007 Black et al.
2007/0169265 A1 7/2007 Saracen et al.
2007/0195929 A1 8/2007 Ruchala et al.
2007/0225691 A1 9/2007 Silvestrini et al.
2007/0225693 A1 9/2007 Muehlhoff et al.
2007/0249911 A1 10/2007 Simon
2008/0049896 A1 2/2008 Kuduvalli
2008/0056434 A1 3/2008 Grozinger et al.
2008/0159478 A1 7/2008 Keall et al.
2008/0187099 A1 8/2008 Gertner
2008/0187101 A1 8/2008 Gertner
2008/0192892 A1 8/2008 Dilmanian et al.
2008/0212737 A1 9/2008 D'Souza et al.
2008/0212738 A1 9/2008 Gertner et al.
2008/0317312 A1 12/2008 Carl et al.
2009/0003525 A1 1/2009 Gertner et al.
2009/0163898 A1 6/2009 Gertner et al.

(56) References Cited

U.S. PATENT DOCUMENTS

| | | | |
|---|---|---|---|
| 2009/0182310 | A1 | 7/2009 | Gertner et al. |
| 2009/0182311 | A1 | 7/2009 | Gertner et al. |
| 2009/0182312 | A1 | 7/2009 | Gertner et al. |
| 2010/0239067 | A1 | 9/2010 | Gertner et al. |
| 2011/0081000 | A1 | 4/2011 | Gertner et al. |
| 2011/0081001 | A1 | 4/2011 | Gertner et al. |
| 2011/0170664 | A1 | 7/2011 | Gertner et al. |
| 2012/0057675 | A1 | 3/2012 | Gertner |
| 2012/0076272 | A1 | 3/2012 | Gertner et al. |
| 2012/0177179 | A1 | 7/2012 | Gertner |
| 2013/0243158 | A1 | 9/2013 | Gertner et al. |
| 2013/0315374 | A1 | 11/2013 | Gertner et al. |

FOREIGN PATENT DOCUMENTS

| | | | |
|---|---|---|---|
| EP | 2231277 | | 9/2010 |
| JP | 06-181945 | A | 7/1994 |
| JP | 06-277248 | A | 10/1994 |
| JP | 2000-509291 | A | 7/2000 |
| JP | 2001-079102 | A | 3/2001 |
| JP | 2002-502647 | A | 1/2002 |
| JP | 2002-540837 | A | 12/2002 |
| JP | 2004-501730 | A | 1/2004 |
| JP | 2005-237730 | A | 9/2005 |
| JP | 2007-501057 | A | 1/2007 |
| JP | 2007-509668 | A | 4/2007 |
| JP | 4043028 | B2 | 2/2008 |
| JP | 4354737 | B2 | 10/2009 |
| JP | 4436139 | B2 | 3/2010 |
| JP | 4602356 | B2 | 12/2010 |
| JP | 5086523 | B2 | 11/2012 |
| WO | WO-95/27453 | | 10/1995 |
| WO | WO-00/59395 | | 10/2000 |
| WO | WO-01/26591 | | 4/2001 |
| WO | WO-02/35996 | | 5/2002 |
| WO | WO-03/008543 | A2 | 1/2003 |
| WO | WO-03/039370 | | 5/2003 |
| WO | WO-2005/016258 | A2 | 2/2005 |
| WO | WO-2005/049139 | | 6/2005 |
| WO | WO-2005/079294 | A2 | 9/2005 |
| WO | WO-2006/086631 | A2 | 8/2006 |
| WO | WO-2006/090217 | | 8/2006 |
| WO | WO-2007/027164 | | 3/2007 |
| WO | WO-2007/045075 | | 4/2007 |
| WO | WO-2008/124801 | A2 | 10/2008 |
| WO | WO-2008/150330 | | 12/2008 |
| WO | WO-2009/075714 | | 6/2009 |

OTHER PUBLICATIONS

Bangerter et al., "Forty Years' Experience with a Special, Non-Tumor Application of Radiotherapy for the Eye," European Journal of Medical Research, 1:582-588 (1996).

Bogner, Joachim, et al. "A noninvasive eye fixation and computer-aided eye monitoring system for linear accelerator-based stereotactic radiotherapy of uveal melanoma," International Journal of Radiation: Oncology Biology Physics, vol. 56, No. 4, pp. 1128-1136 (2003).

Cornsweet et al., "Accurate Two-Dimensional Eye Tracker Using First and Fourth Purkinje images," Journal of the Optical Society of America, 63(8):921-928, (1973).

Das et al., "Small Fields: Nonequilibrium Radiation Dosimetry," Medical Physics, 35(1):206-215 (2008).

Dieckmann et al., "A Linac-Based Stereotactic Irradiation Technique of Uveal Melanoma," Radiotherapy and Oncology, 61:49-56 (2001).

Esquivel, Jr. et al., "Novel low-kVp beamlet system for choroidal melanoma," Radiation Oncology 1:36 (2006).

Fakiris et al., "Gamma-Knife-Based Stereotactic Radiosurgery for Uveal Melanoma," Stereiotact. Funct. Neurosurg., 85:106-112 (2007).

Francescon et al., "Total Scatter Factors of Small Beams: A Multidetector and Monte Carlo Study," Medical Physics 35(2):504-513 (2008).

Gao et al., "Orthovoltage radiation therapy treatment planning using Monte Carlo Simulation: treatment of neuroendocrine carcinoma of the maxillary sinus," ISSN: 0031-9155; vol. 42, No. 12., pp. 2421-2433 (1997).

Georgopoulos et al.,"Tumour Regression of Uveal Melanoma after Ruthenium—106 Brachytherapy or Stereotactic Radiotherapy with Gamma Knife or Linear Accelerator," Ophthalmologica, 217:315-319 (2003).

Jaywant et al., "Stereotactic Radiotherapy in the Treatment of Ocular Melanoma: A Noninvasive Eye Fixation Aid and Tracking System," Journal of Applied Clinical Medical Physics, 4(2):156-161 (2003).

Kim et al., "Combination hyperthermia and radiation therapy for malignant melanoma," Cancer, 50:478-482 (1982).

Kirwan et al., Effect of ? radiation on success of glaucoma drainage surgery in South Africa: randomized controlled trial,: BMJ doi:10.1136/bmj.38971.395301.7C (Oct. 5, 2006).

Kishi et al., "Lead Contact Lens for Crystalline Lens Shielding in Electron Therapy for Eyelid Tumors," Radiation Medicine, 14(2):107-109 (1996).

Kobayashi et al., Radiotherapy for subfoveal neovascularisation associated with pathological myopia: a pilot study., J. Ophth. 87:761-766 (2000).

Marcus et al., "External Beam Irradiation of Subfoveal Choroidal Neovascularization Complicating Age-Related Macular Degeneration," Arch Ophthalmology, 119:171-180 (2001).

Marcus et al., "The Age-Related Macular Degeneration Radiotherapy Trial (AMDRT): One Year Results from a Pilot Study," American Journal of Ophthalmology, 138:818-828 (2004).

Petersch, Bernhard et al. "Automatic real-time surveillance of eye position and gating for stereotactic radiotherapy of uveal melanoma," Medical Physics, vol. 31, No. 12, Dec. 2004, pp. 3521-3527.

Sagerman et al., "Radiation Techniques for the Treatment of Retinoblastoma and Orbital Tumors," Radiotherapy of Intraocular and Orbital Tumors, 2nd Revised Edition (2003), pp. 233-237.

Schilling et al., "Long Term Results After Low Dose Ocular Irradiation for Choroidal Haemangiomas," British Journal of Ophthalmology, 81:267-273 (1997).

Schipper et al., "Management of Retinoblastoma by Precision Megavoltage Irradiation," Dept. of Radiation Therapy of the Univ. Hospital and the Royal Dutch Eye Hospital, Utrecht, The Netherlands (1983), pp. 534-540.

Senan et al., Design of Clinical Trials of Radiation Combined with Antiangiogenic Therapy,: The Oncologist, 12(4):465-477 (2007) (www://theoncologist.alphamedpress.org).

Toma et al., "External Beam Radiotherapy for Retinoblastoma: II Lens Sparing Technique," British Journal of Ophthalmology, 79:112-117 (1995).

* cited by examiner (Inventive embodiment example compared with prior art)

Test X-ray beam azimuth
(directed via pars plana to macula)

Optic nerve test angles
(extending medially-posteriorly from retina)

FIG. 22A-D
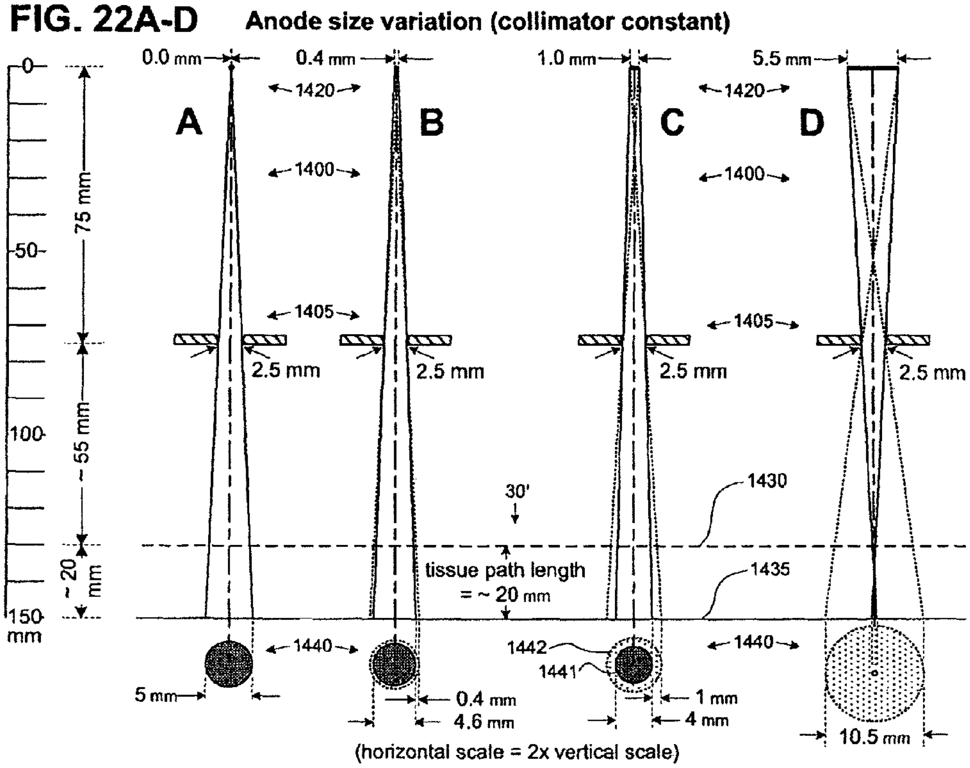
FIG. 23
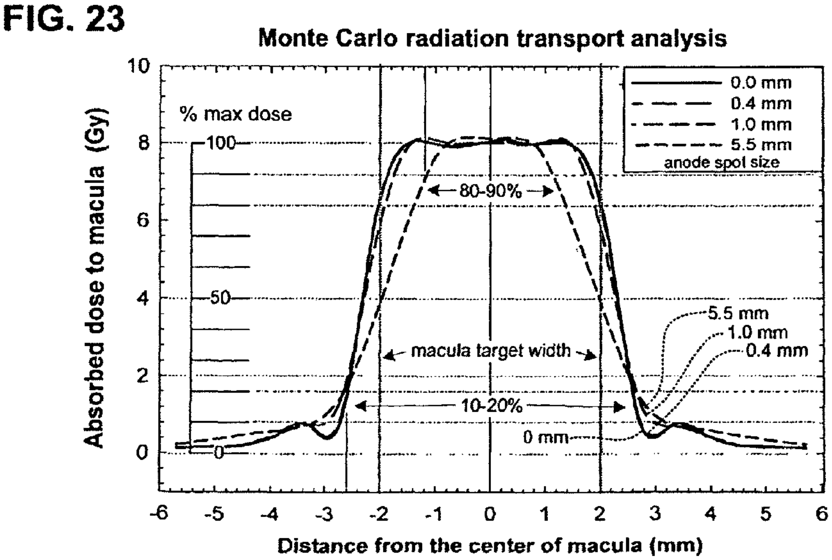

FIG. 24A-B
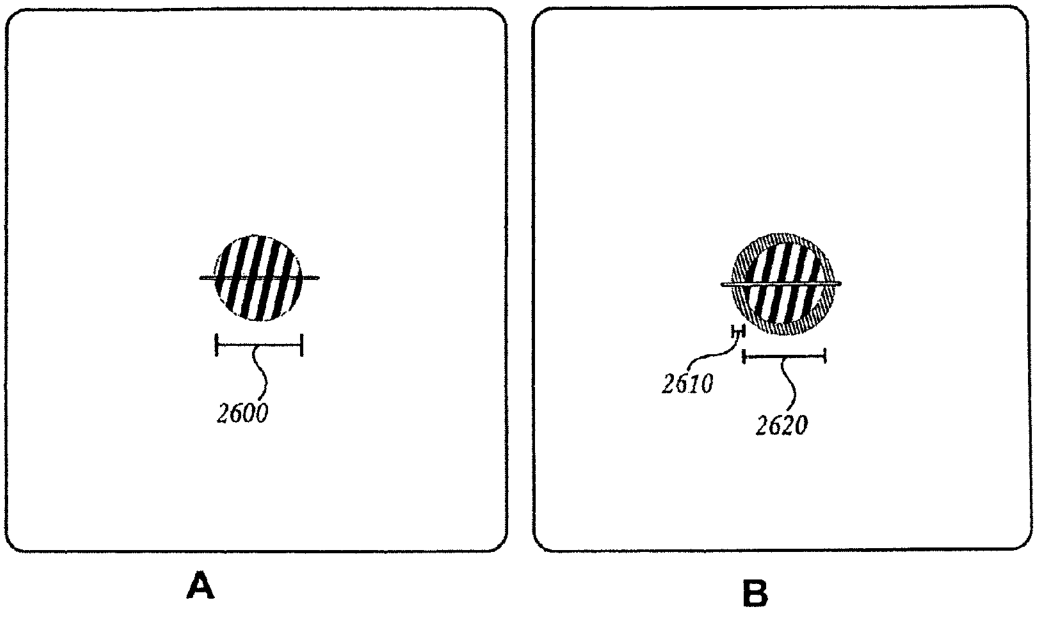
FIG. 24C
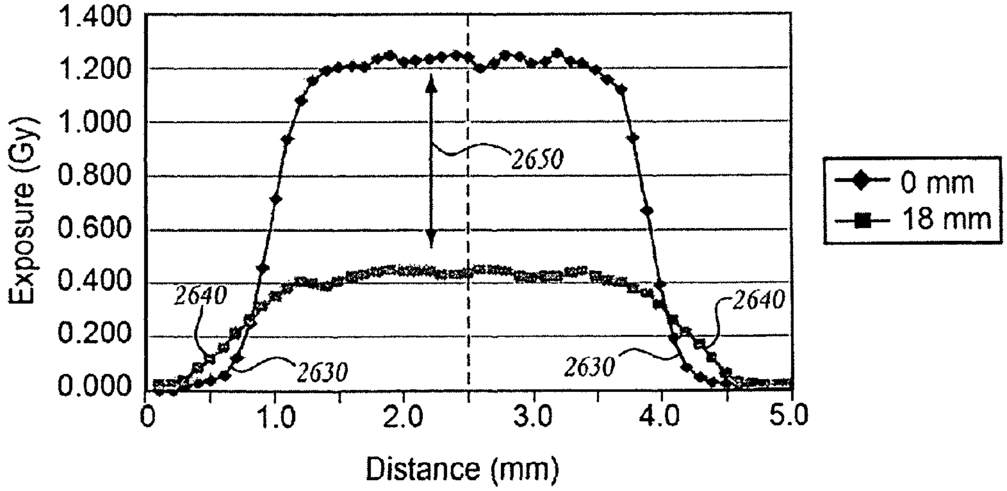

FIG. 25A-D
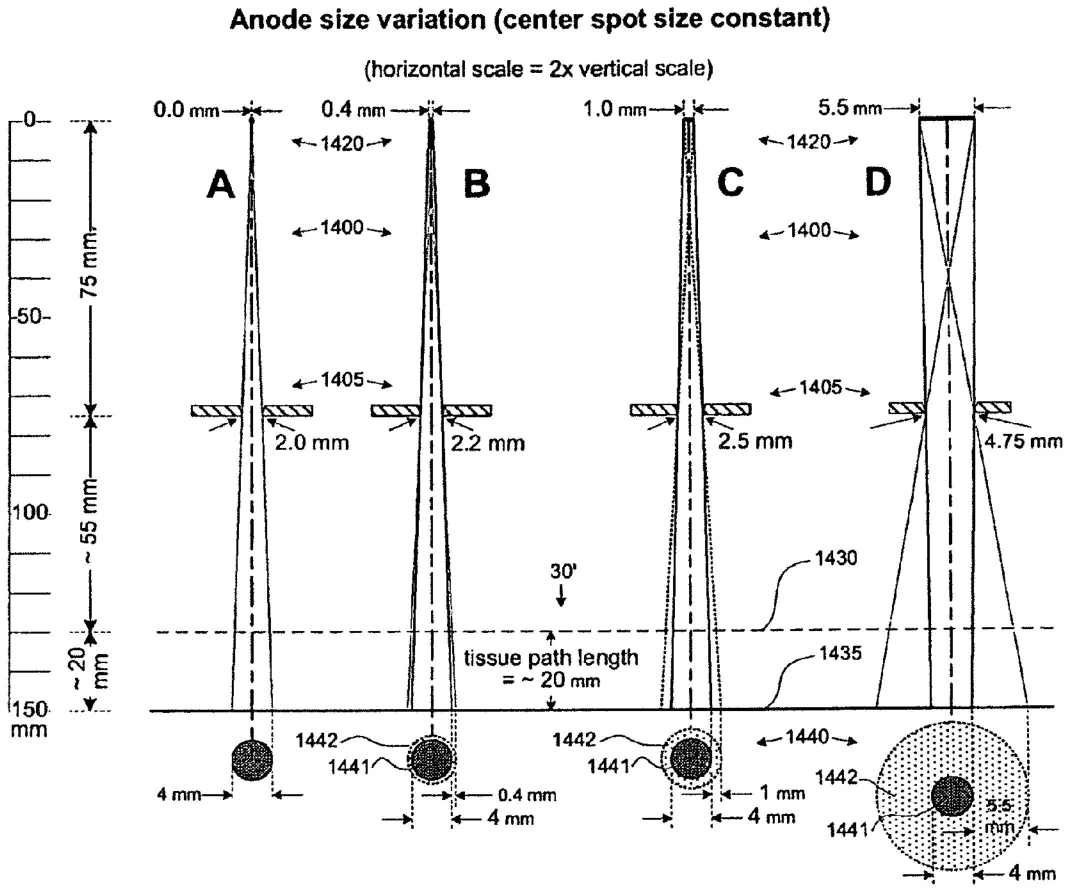

FIG. 26A-C
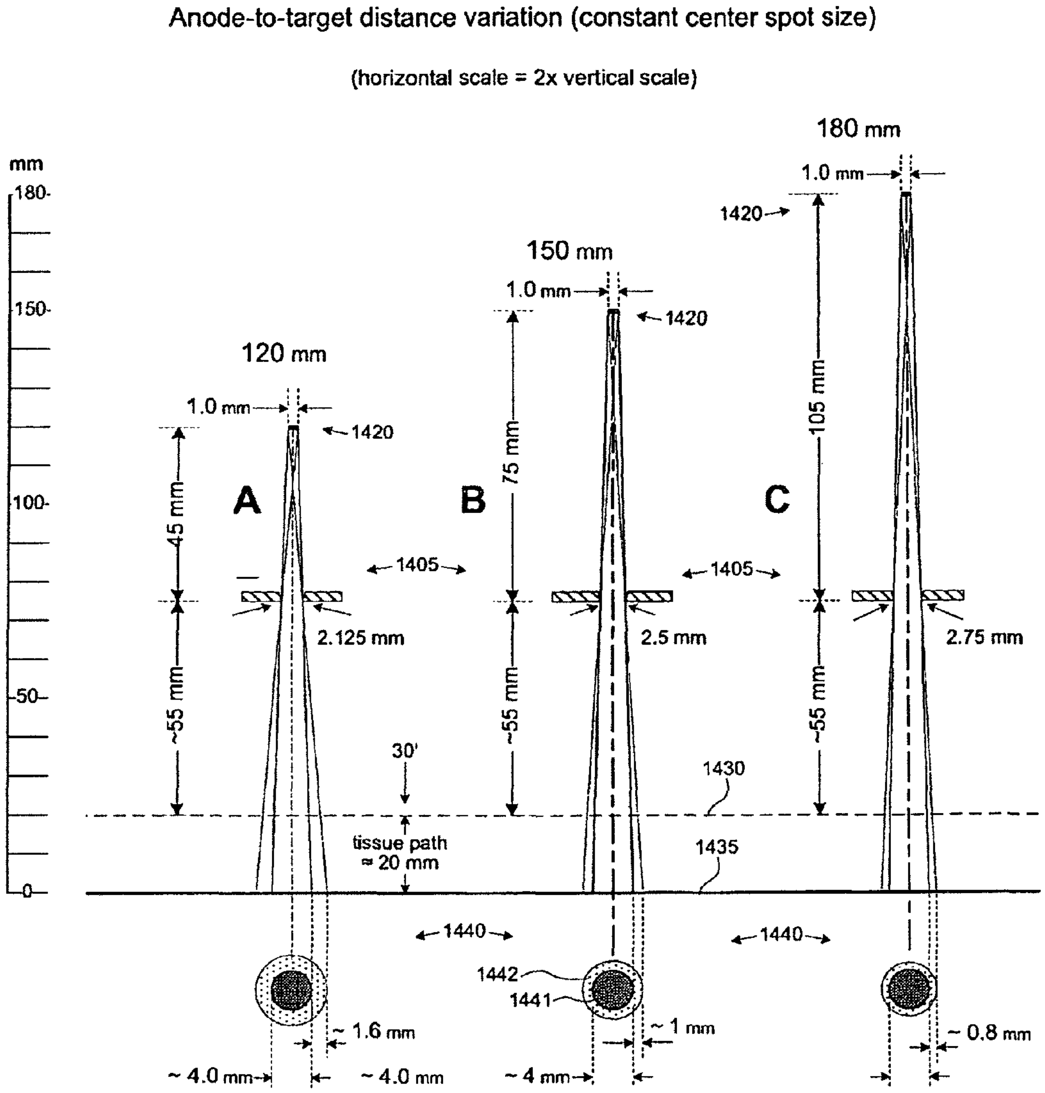

FIG. 27A-C
Collimator length variation (constant center spot size)
(horizontal scale = 2x vertical scale)
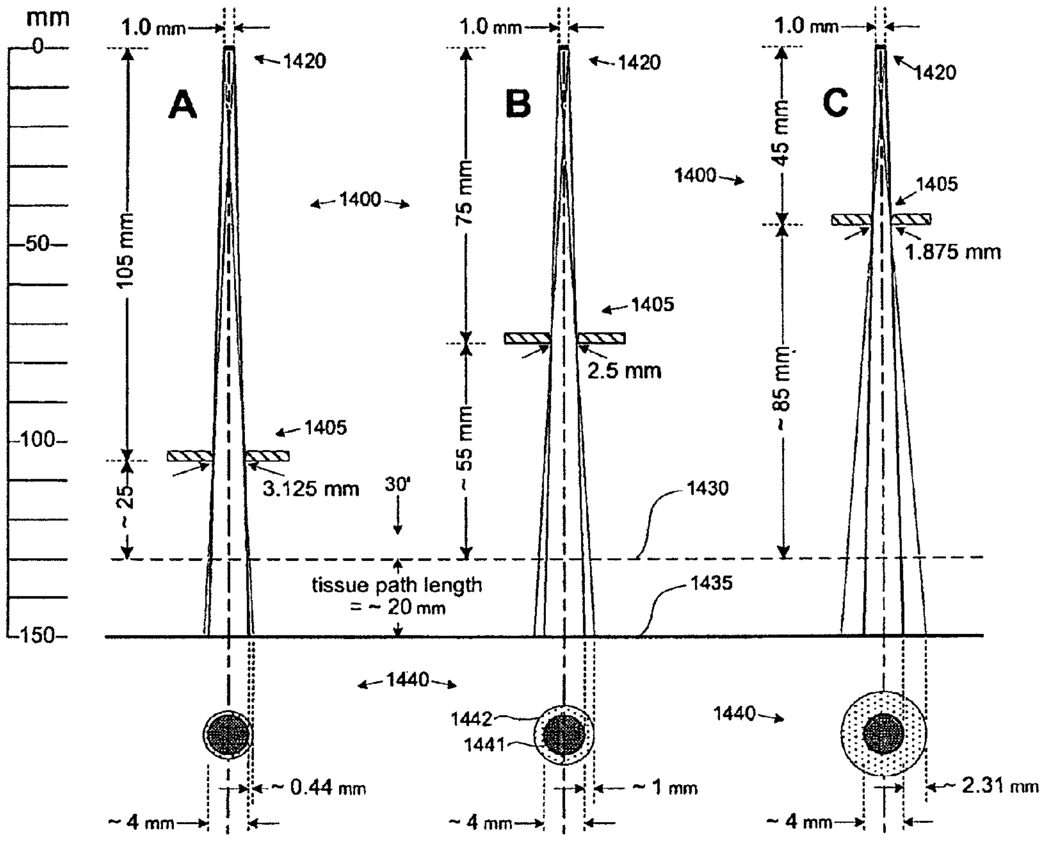
FIG. 28
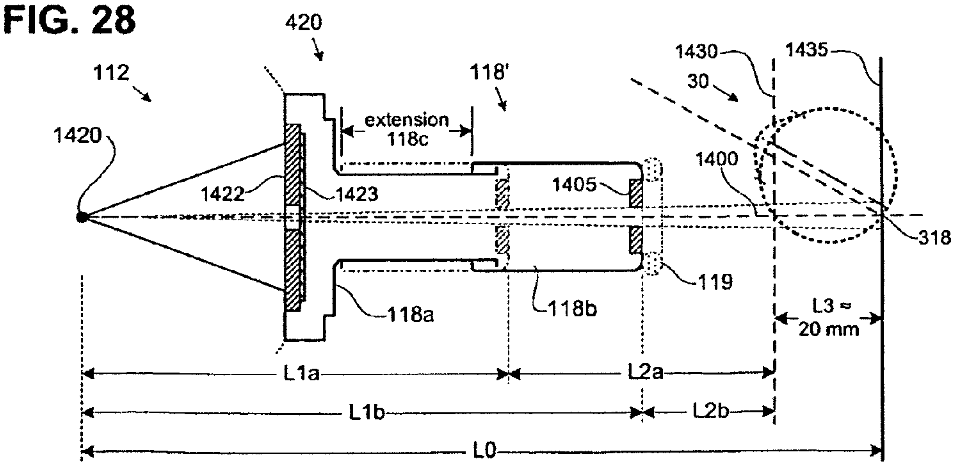

FIG. 29A Monte Carlo radiation transport analysis
(single collimated beam at retinal depth)

FIG. 29B Measured dose at retinal depth in solid water equivalent
(radiographic film optical density analysis)

FIGS. 30C-D
Phantom-eye measured retinal dose map (3-beam stereotactic)
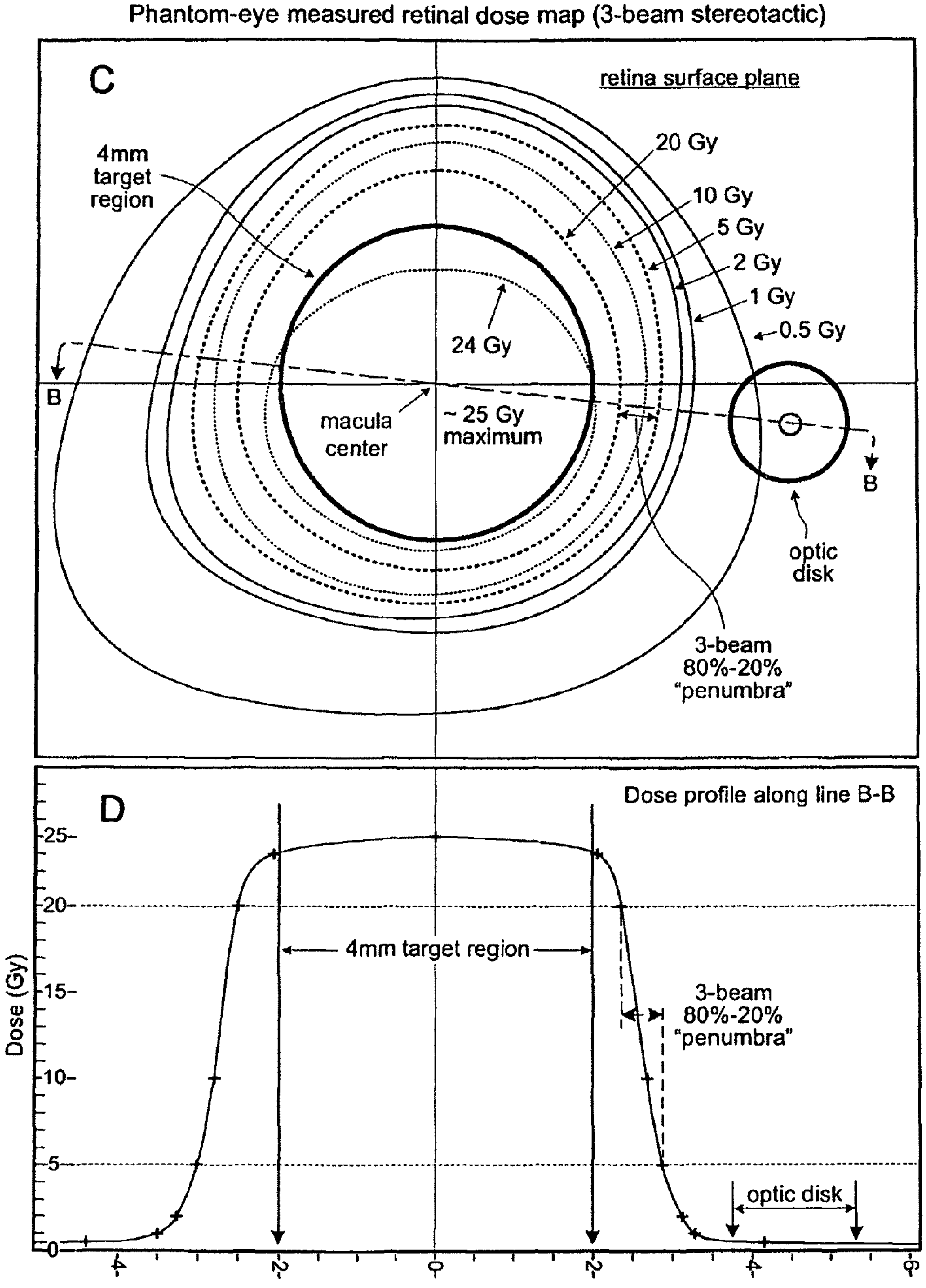

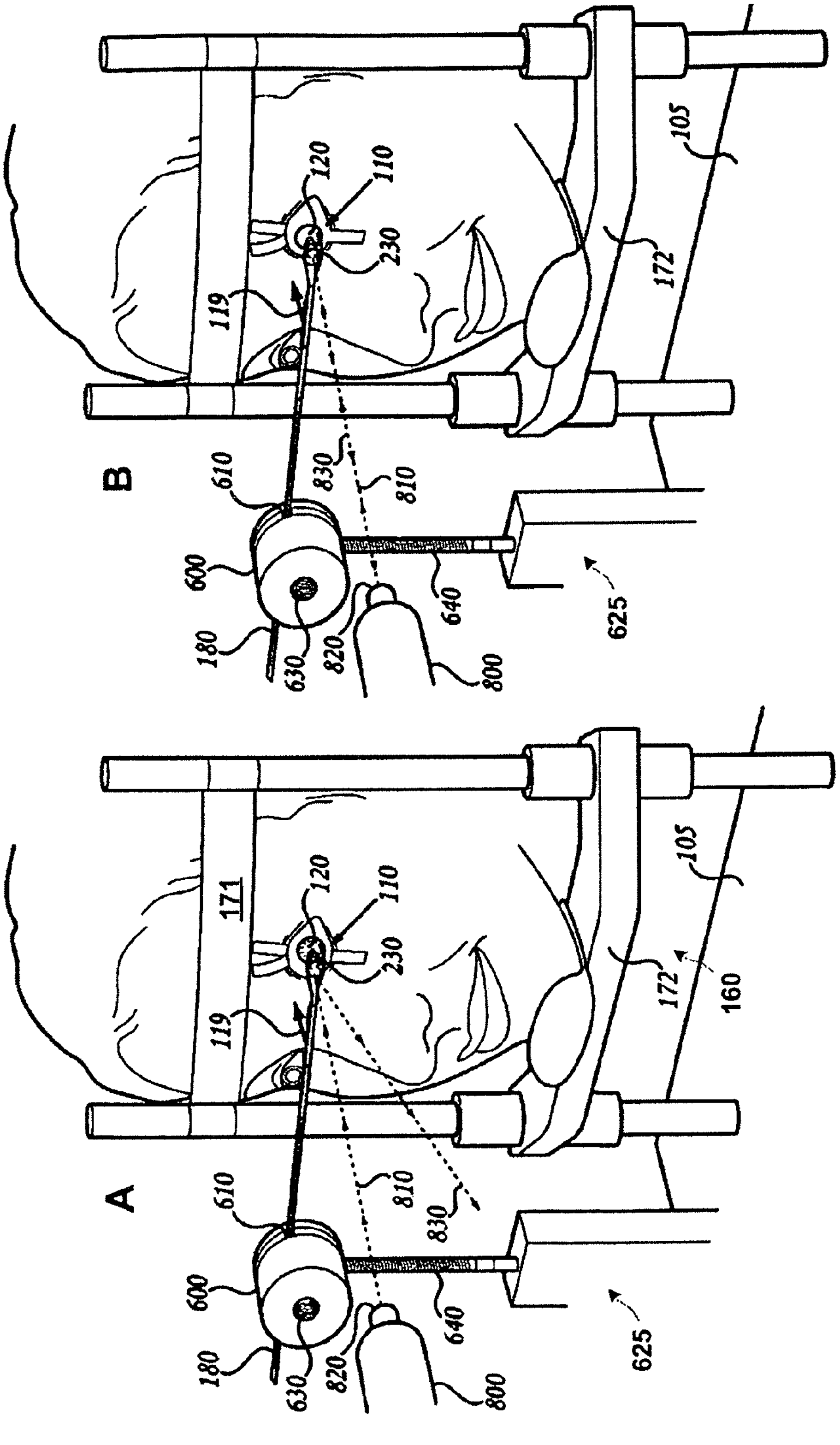
FIGS. 40A-B

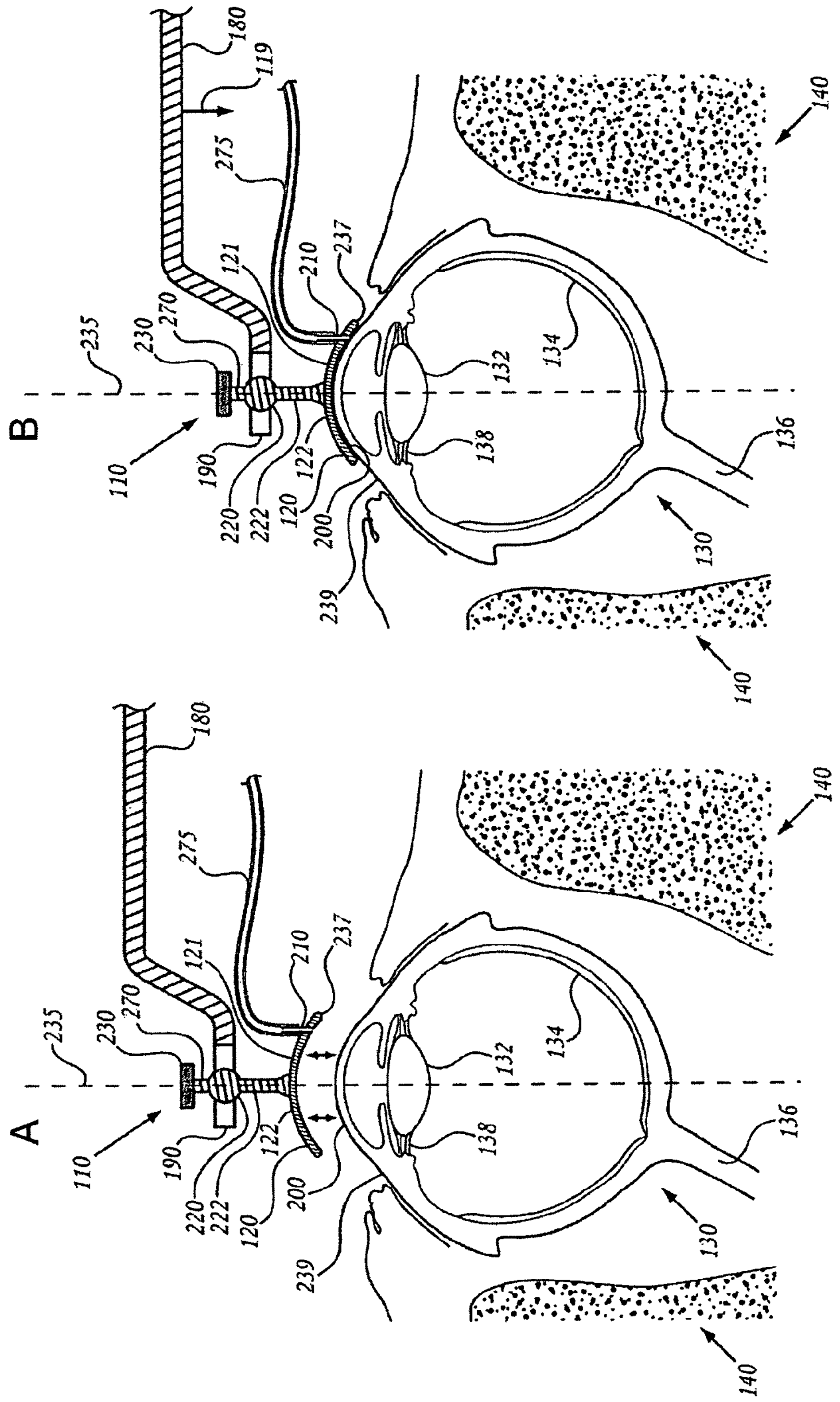
FIGS. 41A-B

FIGS. 42A-D
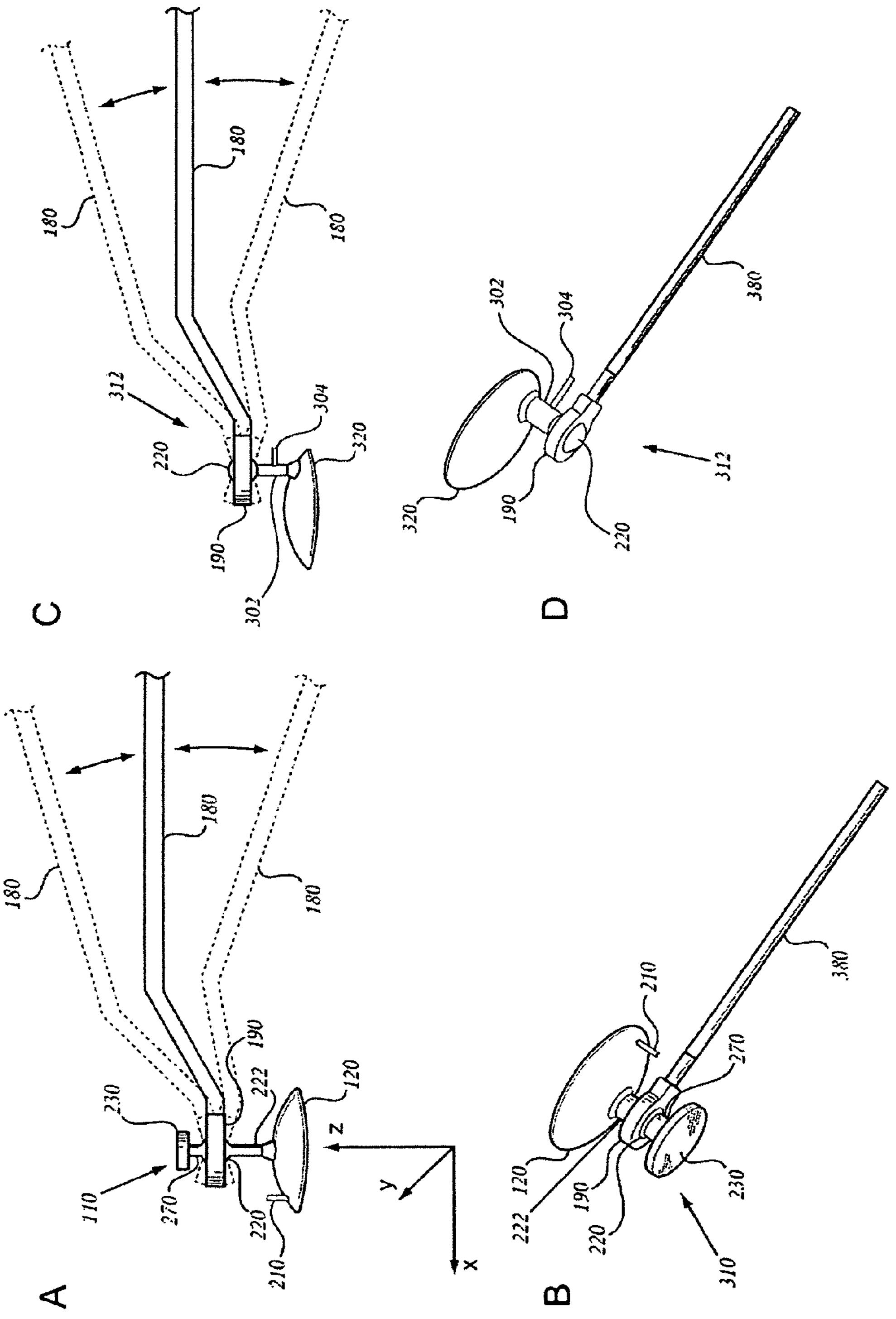

FIG. 43B
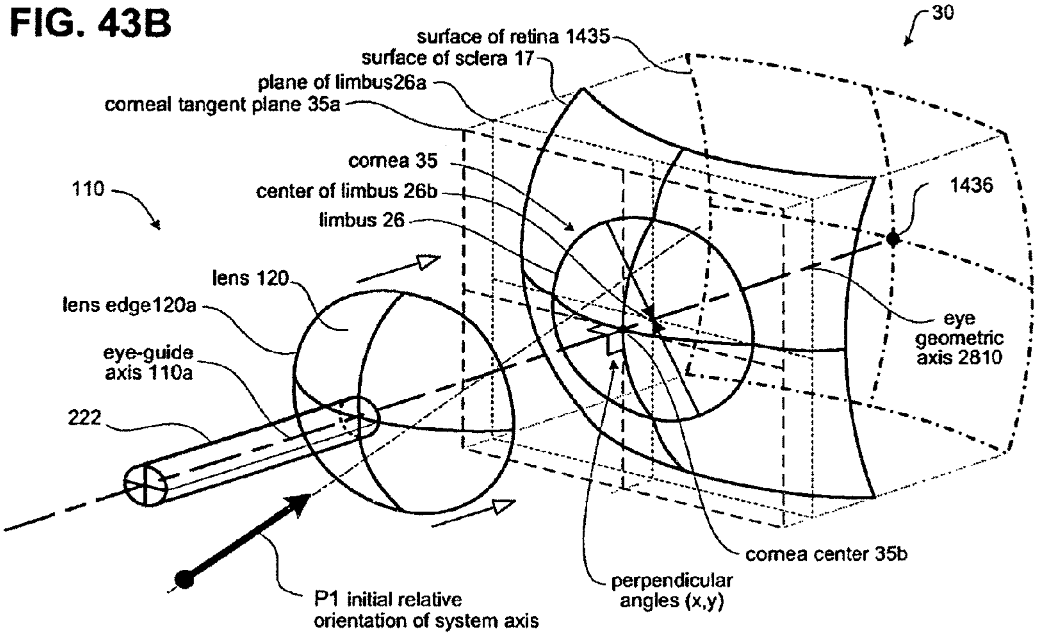
FIG. 43C(1)
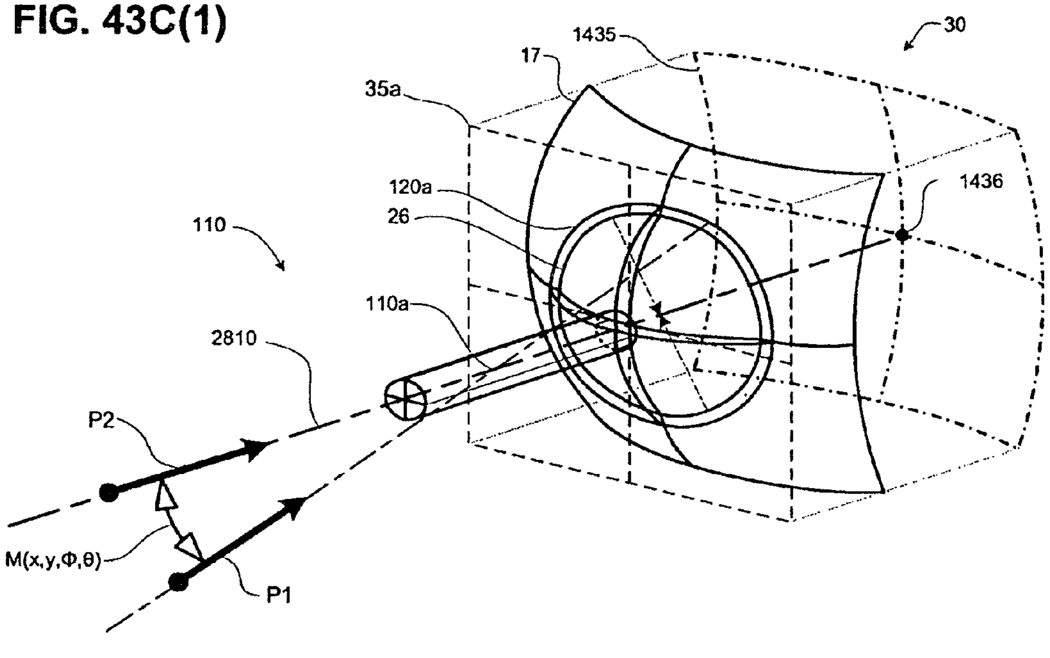

FIG. 43C(2)
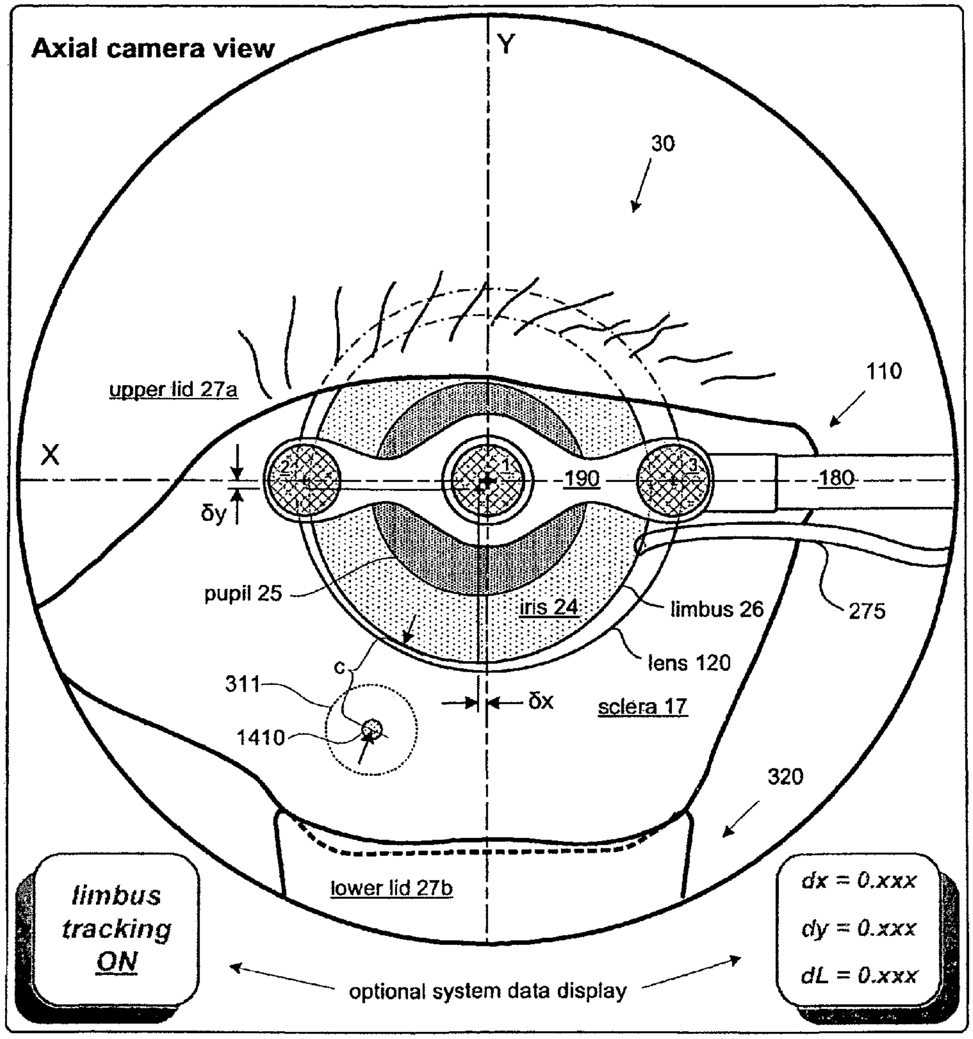

FIG. 47A
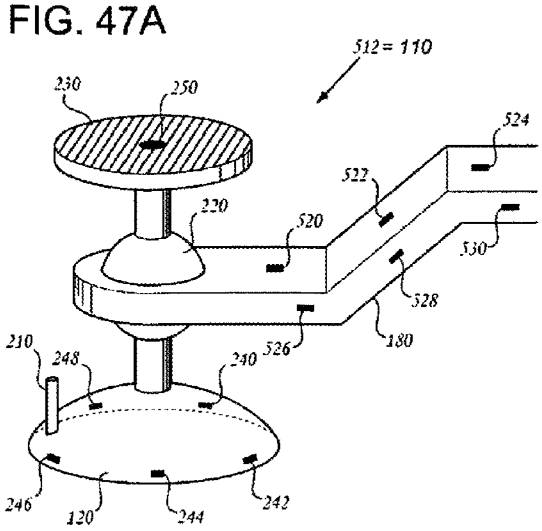
FIG. 47B1 FIG. 47B2
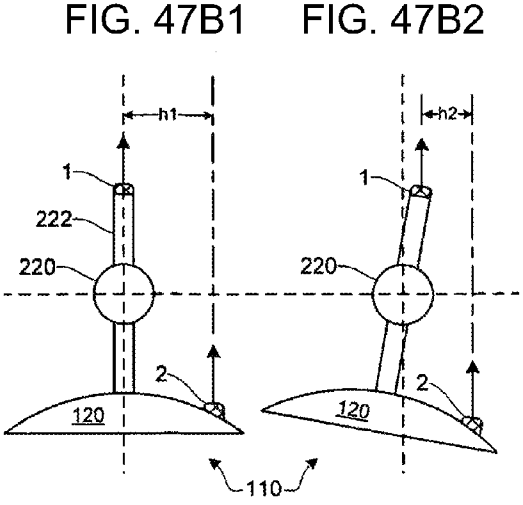
FIGS. 47C-I
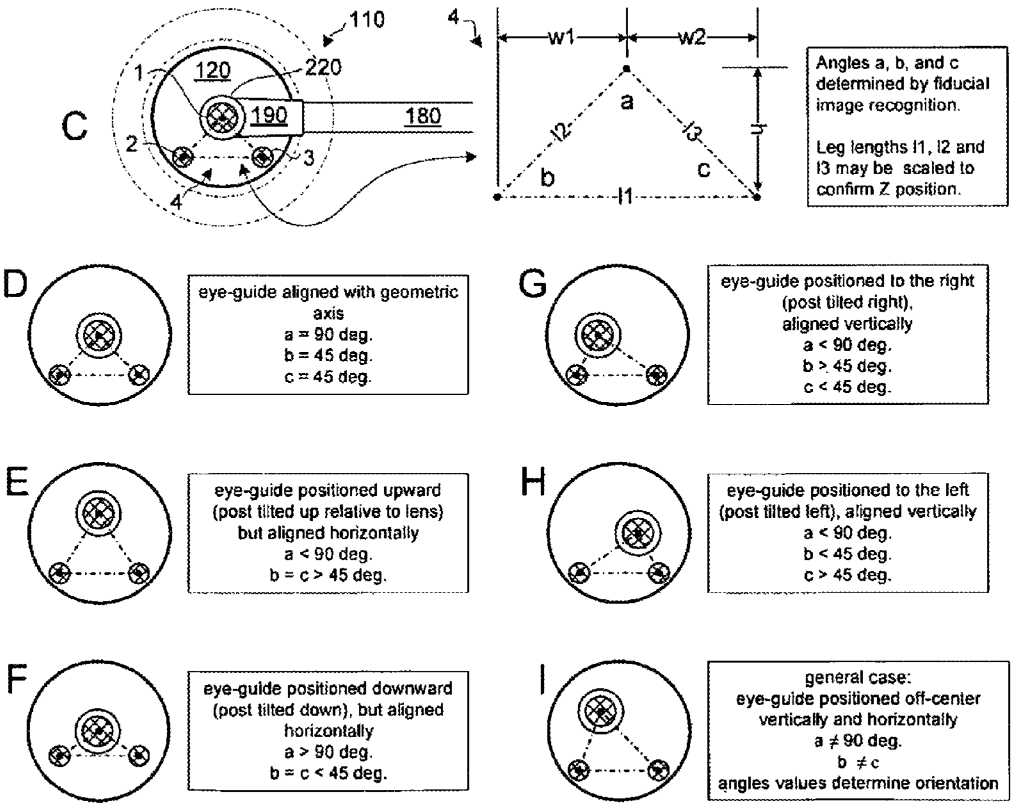

FIGS. 48A-F
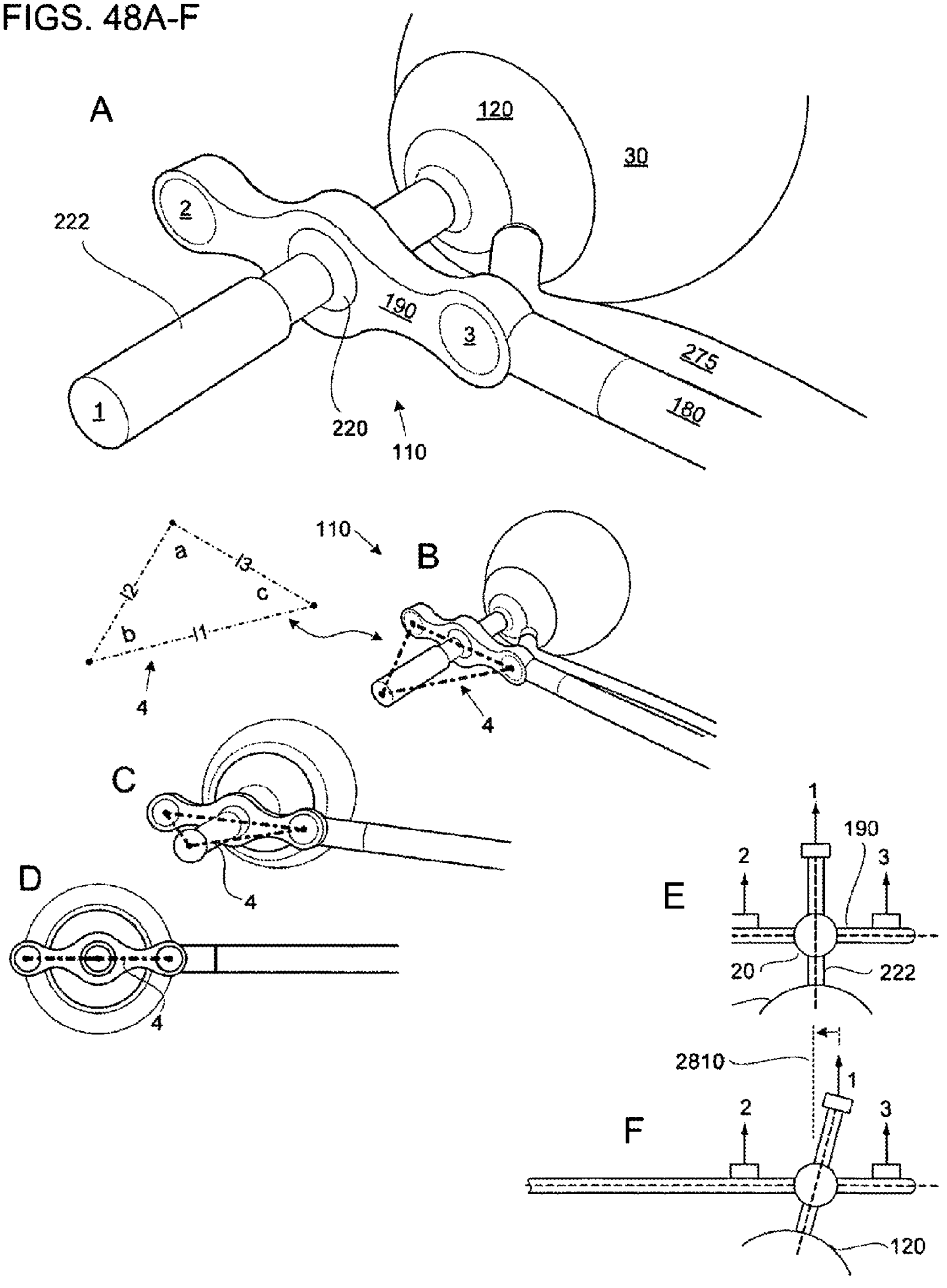

FIGS. 49A-E
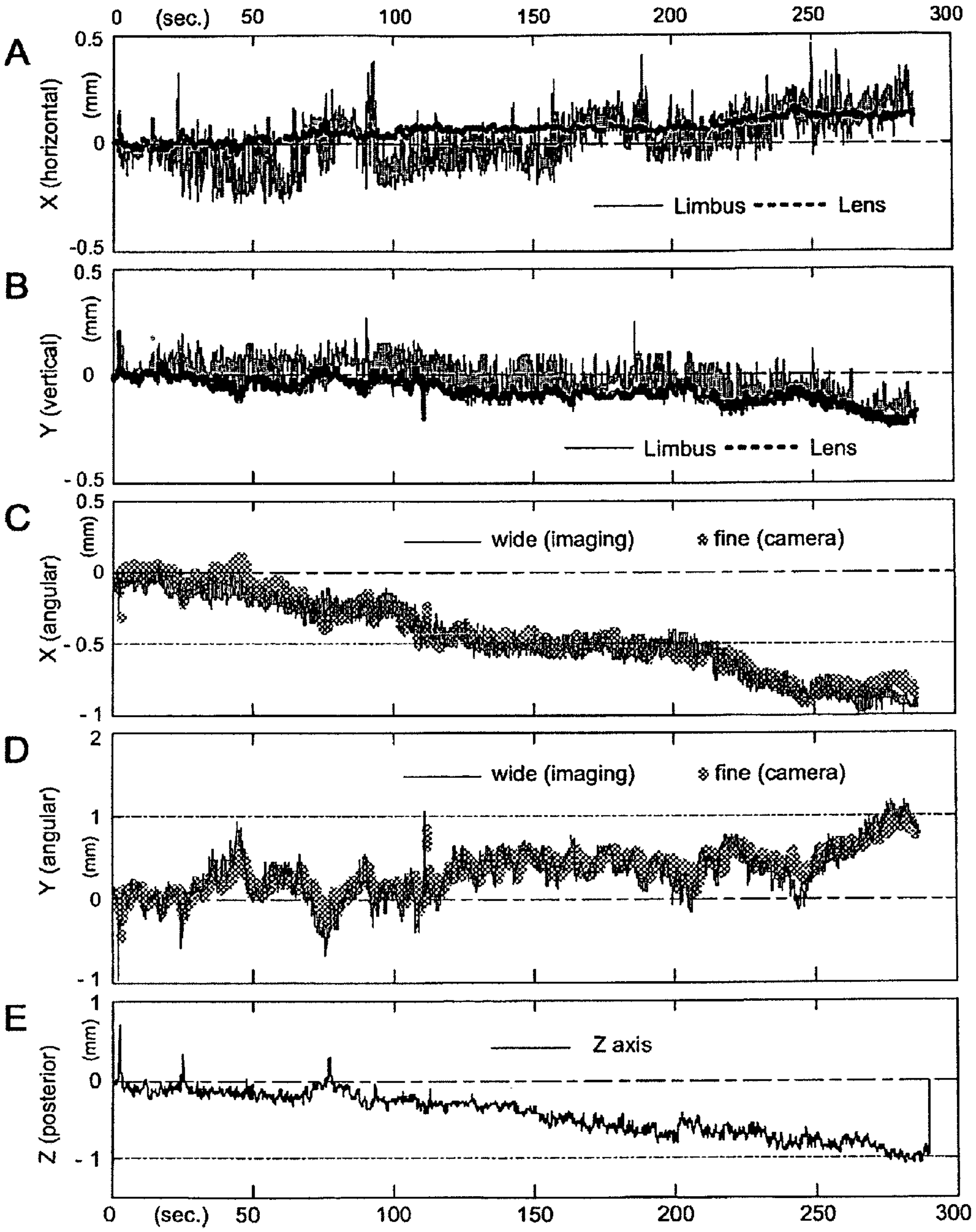

Flowchart (continued next sheet)

Flowchart

FIGS. 51A-B

FIG. 54C
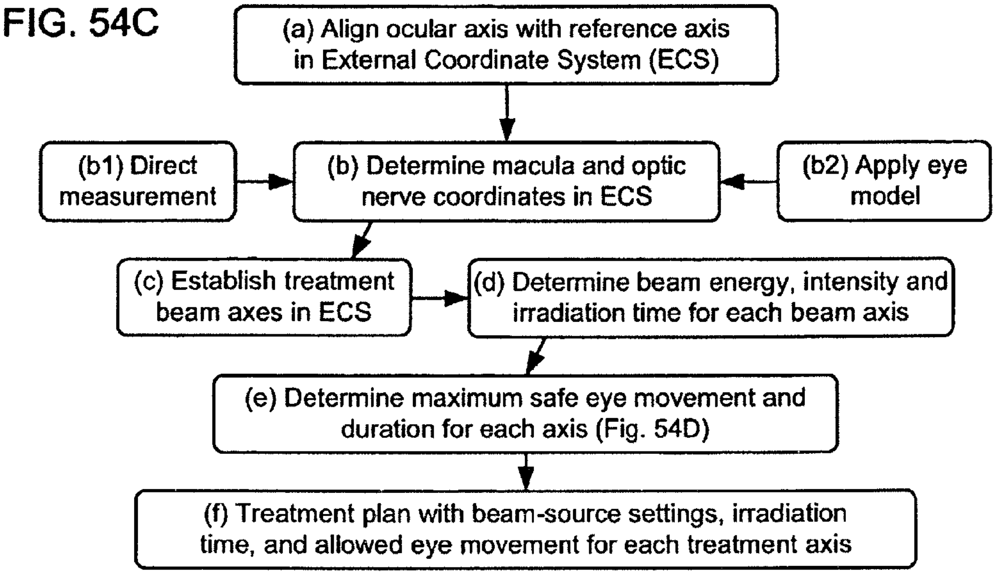
FIG. 54D (1), (2) & (3)
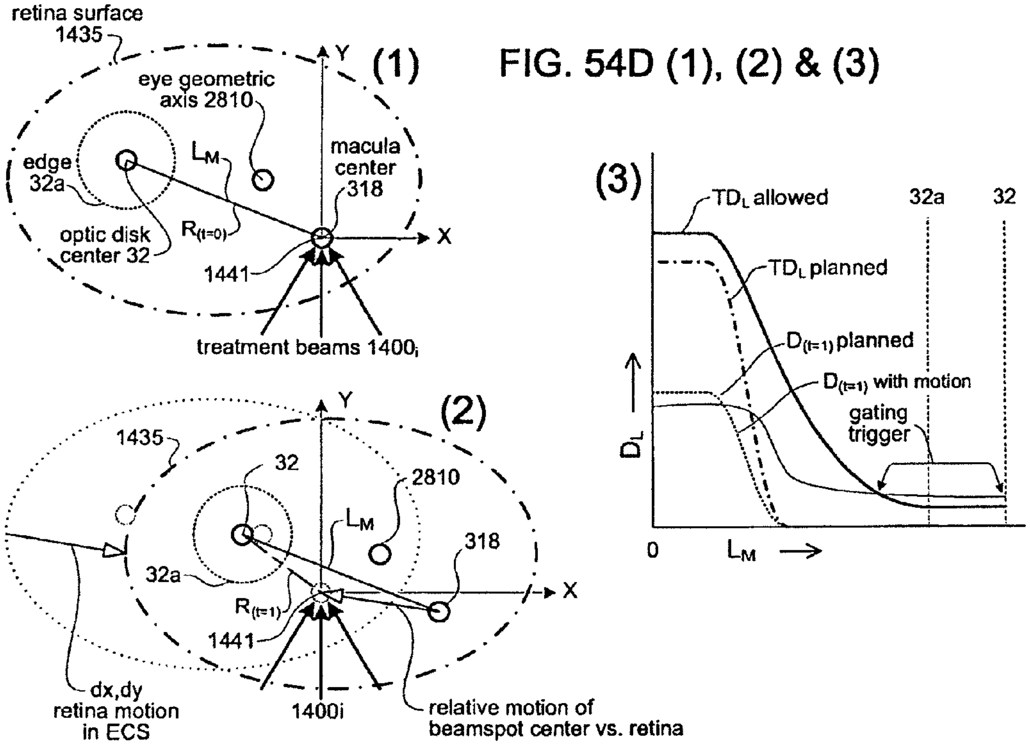

FIGS. 55A-D
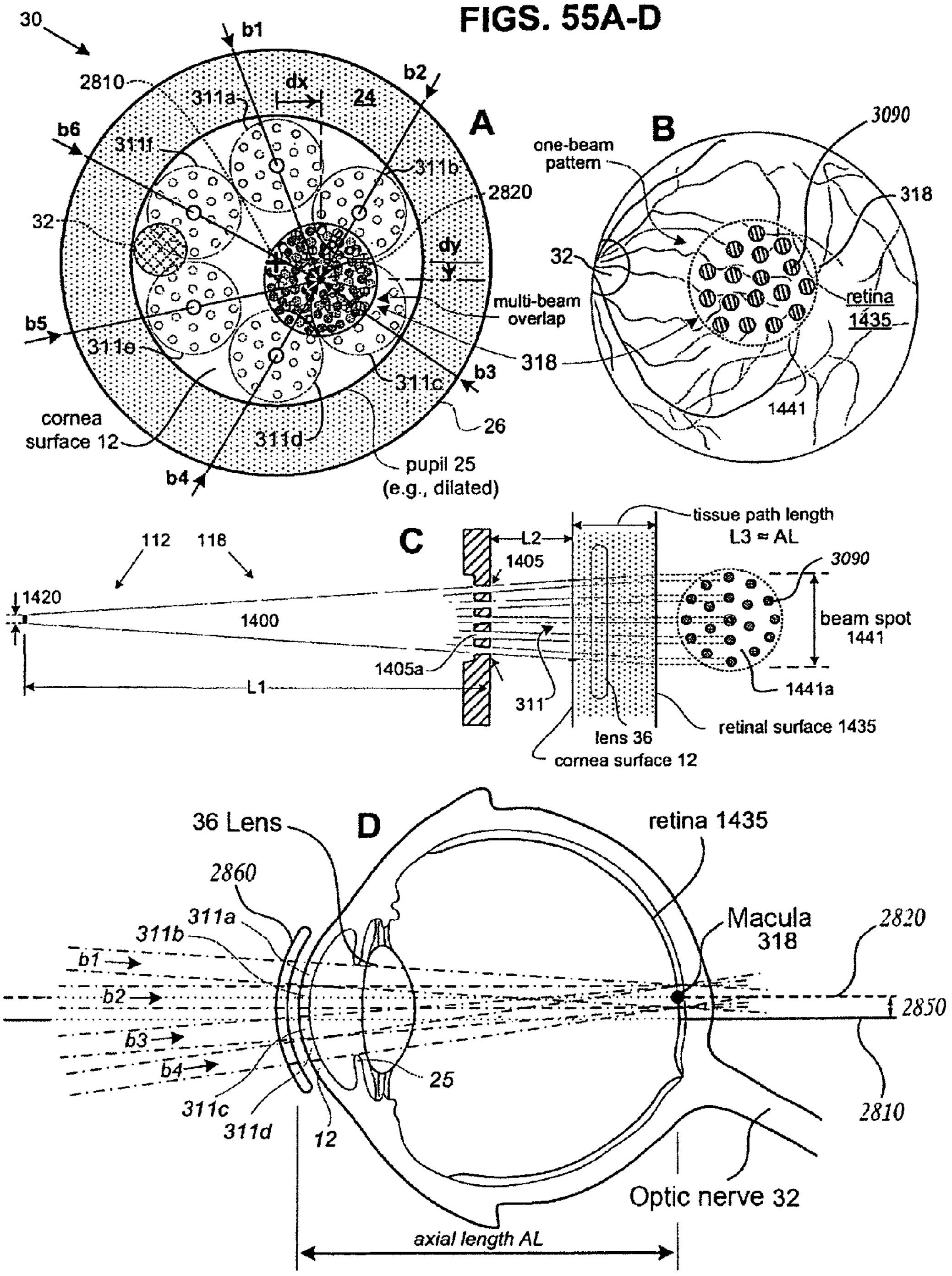

FIGS. 57A-E
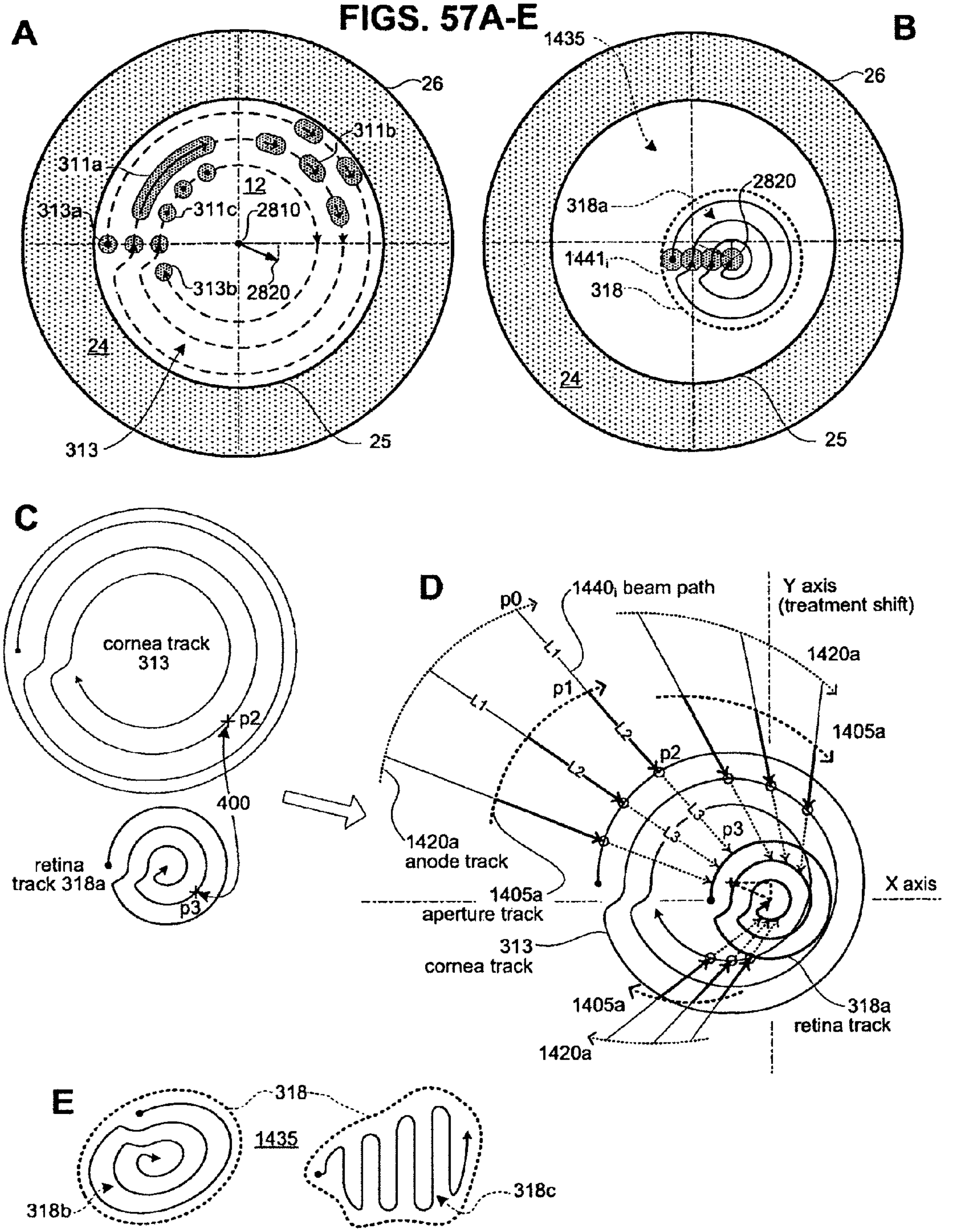

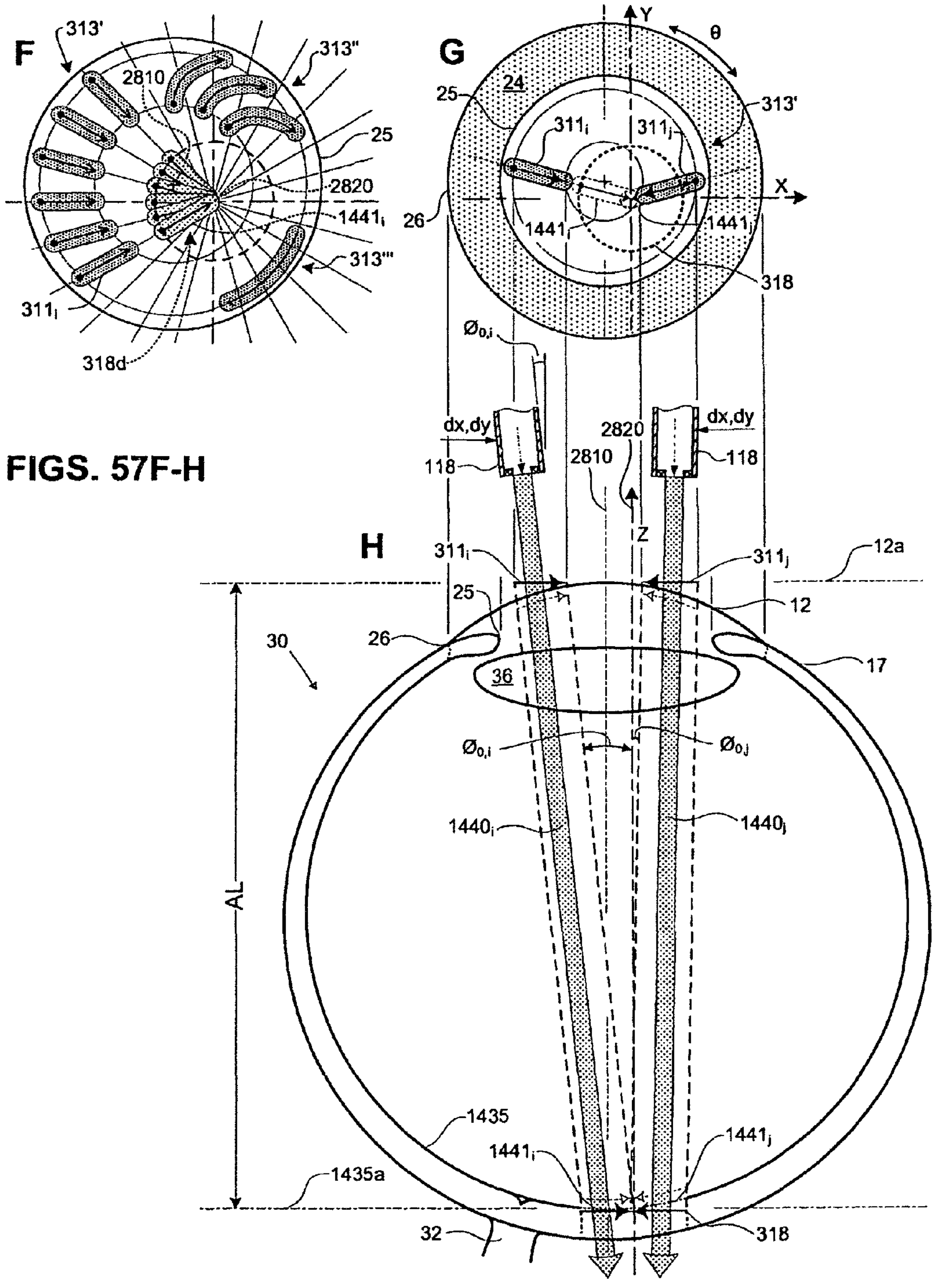
FIGS. 57F-H

FIG. 58A
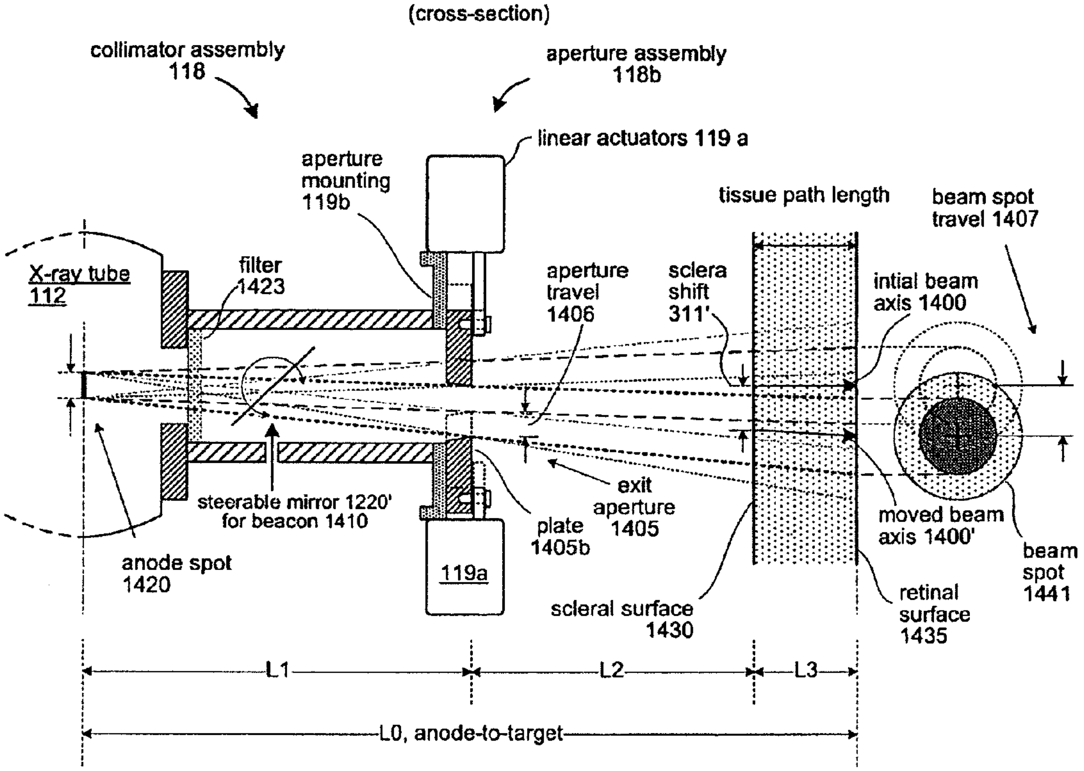
FIGS. 58B-C
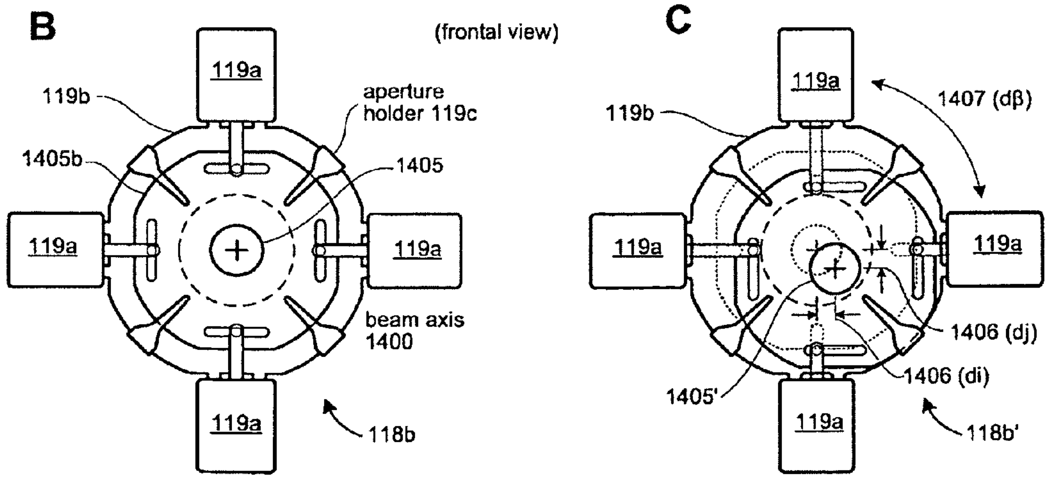

FIGS. 59A-D
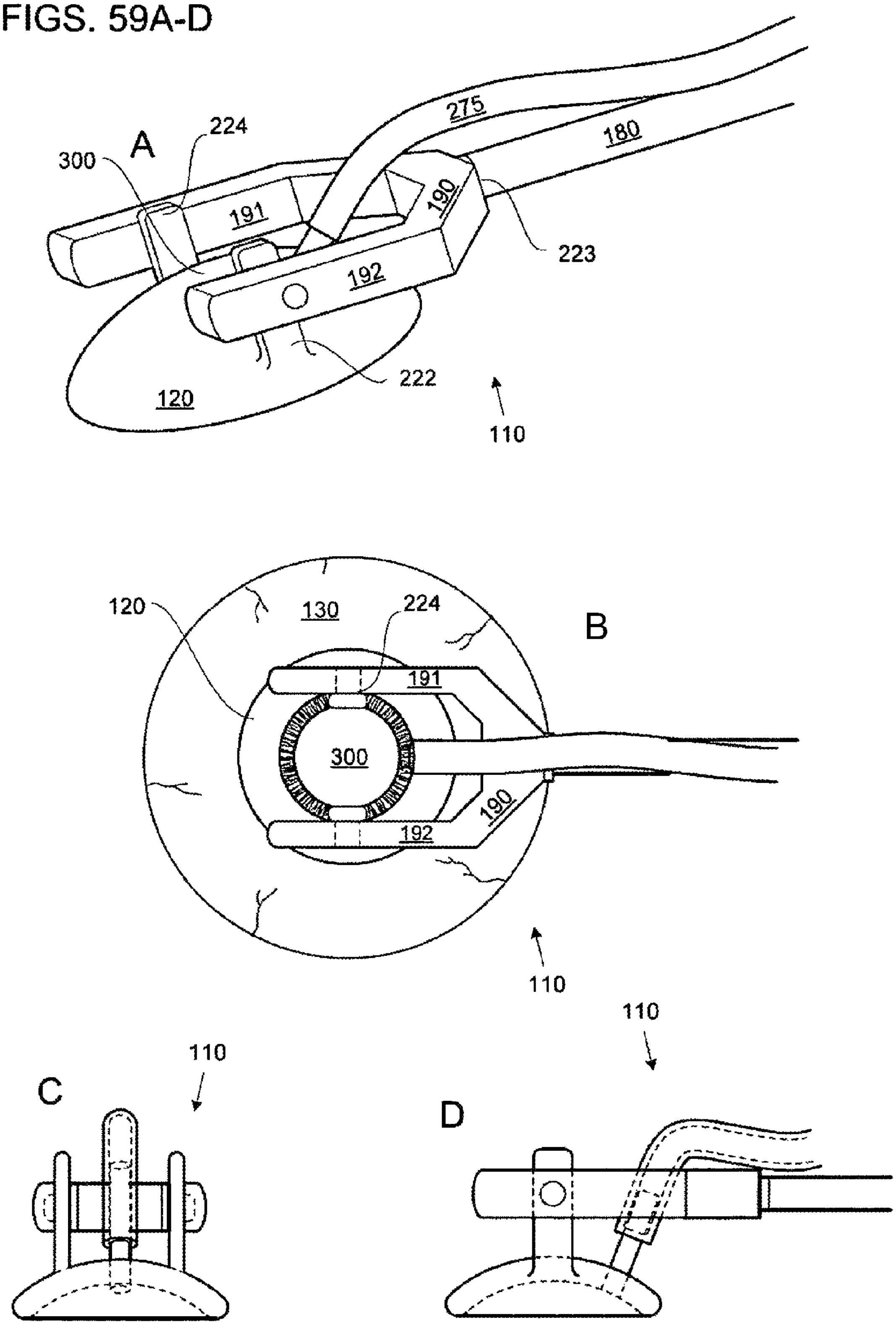

METHODS AND DEVICES FOR ORTHOVOLTAGE OCULAR RADIOTHERAPY AND TREATMENT PLANNING

RELATED APPLICATIONS

This application is a continuation of U.S. patent application Ser. No. 12/887,419 filed Sep. 11, 2010, which is a continuation of U.S. patent application Ser. No. 12/262,031 filed Oct. 30, 2008, now U.S. Pat. No. 7,801,271, which claims the benefit of priority of U.S. Application Nos. 61/101,013 filed Sep. 29, 2008; 61/093,092 filed Aug. 29, 2008; and 61/076,128 filed Jun. 26, 2008. U.S. patent application Ser. No. 12/887,419 is also a continuation-in-part of U.S. application Ser. No. 12/103,534 filed Apr. 15, 2008, now U.S. Pat. No. 8,363,783, which claims benefit of priority to U.S. Application Nos. 61/016,472 filed Dec. 23, 2007; and 61/020,655 filed Jan. 11, 2008; U.S. application Ser. No. 12/103,534 is also a continuation-in-part of U.S. application Ser. No. 12/100,398 filed Apr. 9, 2008, now U.S. Pat. No. 7,693,260, U.S. application Ser. No. 12/103,534 is also a continuation-in-part of U.S. application Ser. No. 12/027,083 filed Feb. 6, 2008, now pending. U.S. application Ser. No. 12/103,534 is also a continuation-in-part of U.S. application Ser. No. 12/027,094 filed Feb. 6, 2008, now pending. U.S. application Ser. No. 12/103,534 is also a continuation-in-part of U.S. application Ser. No. 12/027,069 filed Feb. 6, 2008, now pending; the entirety of each of which is incorporated herein by reference.

The following U.S. patent applications are incorporated herein by reference: Ser. No. 11/873,386 filed Oct. 16, 2007; Ser. No. 11/833,939 filed Aug. 3, 2007; Ser. No. 11/879,901 filed Jul. 18, 2007; Ser. No. 11/879,843 filed Jul. 18, 2007; No. 60/933,220 filed Jun. 4, 2007; No. 60/922,741 filed Apr. 9, 2007; No. 60/869,872 filed Dec. 13, 2006; No. 60/862,210 filed Oct. 19, 2006; No. 60/862,044 filed Oct. 18, 2006; and No. 60/829,676 filed Oct. 16, 2006.

BACKGROUND

1. Field of the Inventions

This disclosure relates to the using targeted photon energy for the treatment of disorders of the human and animal body. In particular, the present disclosure pertain to systems and methods for performing an image-guided low-energy X-ray therapy procedure on a patient's eye, to systems for planning and controlling such treatments, and to eye alignment-stabilization systems useful in ophthalmologic procedures.

2. Description of the Related Art

Macular degeneration is a condition where the light-sensing cells of the macula, a near-center portion of the retina of the human eye, malfunction and slowly cease to work. Macular degeneration is the leading cause of central vision loss in people over the age of fifty years. Clinical and histologic evidence indicates that macular degeneration is in part caused by or results in an inflammatory process that ultimately causes destruction of the retina. The inflammatory process can result in direct destruction of the retina or destruction via formation of neovascular membranes which leak fluid and blood into the retina, quickly leading to scarring.

Many treatments for macular degeneration are aimed at stopping the neovascular (or "wet") form of macular degeneration rather than geographic atrophy, or the "dry" form of Age-related Macular Degeneration (AMD). All wet AMD begins as dry AMD. Indeed, the current trend in advanced ophthalmic imaging is that wet AMD is being identified prior to loss of visual acuity. Treatments for macular degeneration include the use of medication injected directly into the eye (Anti-VEGF therapy) and laser therapy in combination with a targeting drug (photodynamic therapy); other treatments include brachytherapy (i.e., the local application of a material which generates beta-radiation).

Accurate alignment of a subject's eye is important in a number of situations. For example, when taking certain types of eye measurements, it is critical to know that the eye is in a particular reference position. When measuring the cornea of a patient's eye before therapeutic treatment, it can be important to repeat those measurements after the treatment to determine how much, if any, the treatment has affected the measurements. In order to accomplish this, one must ensure that the eye alignment is in the same position each time the particular measurements are made. Otherwise, the difference in data from before and after the treatment might be due to a change in eye alignment rather than the treatment.

A number of treatment and surgery procedures, typically involving irradiating one or more selected targets in the eye, require a patient's eye to be stabilized or positioned prior to and/or during treatment. For example, refractive laser surgery involves ablating corneal tissue of the eye with an ultra-fast, ultra-short pulse duration laser beam, to correct refractive errors in a patient's eye. As such, the patient's eye must be stabilized, and either the laser system must be properly and precisely aligned with the patient's eye, or the patient's eye must be properly and precisely aligned with the laser system. The eye is predisposed to saccades, which are fast, involuntary movements of small magnitude. A patient may voluntarily shift their gaze during surgery, and furthermore, eye position stability is affected by the patient's heartbeat and other physiological factors.

In order to achieve the goal of maximizing results while minimizing risks to the patient during such eye treatment, it is important to eliminate, or at least significantly reduce, as many system errors as possible. This includes the improper alignment of the patient's eye relative to the treatment system. Alignment errors may result from either a misconfiguration of the system, or from the patient's interaction with the system. Insofar as patient/system interaction is concerned, any voluntary or involuntary movement of the patient's eye during treatment can significantly alter the alignment of the eye relative to the treatment system. It is necessary, therefore, to hold the eye of the patient stationary during these procedures.

In addition, there is a need to control the distribution of radiation absorption by ocular structures during treatment, such as to assure an adequate dosage to a lesion being treated, and to avoid damaging collateral structures by stray radiation.

SUMMARY

Further description may be found in the priority applications, in particular Ser. No. 12/103,534 filed Apr. 15, 2008; Ser. No. 12/027,069 filed Feb. 1, 2008; and Ser. No. 12/100,398 filed Apr. 9, 2008; each of which is incorporated by reference. An embodiment having aspects of the invention comprises an eye-contact device (eye-guide) for securing a patient eye at a selected position, such as may be used cooperatively with an ocular stabilization and alignment device, such as is described in the co-invented priority applications, particularly Ser. No. 12/103,534 filed Apr. 15, 2008 and Ser. No. 12/027,083 filed Feb. 1, 2008; each of which is incorporated herein by reference.

A treatment method embodiment having aspects of the invention includes treating a lesion on or adjacent to the retina of an eye of a patient (which by be referred to regardless of histology as a "retinal lesion") by directing collimated X-radiation at the lesion in a patient's eye. The method comprises the steps of: (a) based on an aligned patient-eye position, establishing at least two treatment beam paths directed from a source of a collimated x-radiation beam through the patient's sclera beyond the limbus and directed at the retinal lesion; (b) determining, based on the known spectral and intensity characteristics of the source beam along the established beam paths and from the coordinates of the lesion in the aligned patient-eye position, a total treatment time for irradiation along the beam paths that is effective to produce a desired radiation dose at the lesion of the patient's eye; and (c) determining, based on the known spectral and intensity characteristics of the source beam along the established beam paths, and from the coordinates of the optic nerve in the aligned eye position, the extent and duration of eye movement away from the aligned patient-eye position in a direction that moves the patient's optic nerve toward the irradiation beam that will be allowed during treatment, while still maintaining the radiation dose at the patient optic nerve below a predetermined dose level.

The treatment method may further provide that the retinal lesion to be treated includes one of macular degeneration; a drusen, a tumor or a vascular abnormality, and step (c) includes determining the coordinates of the lesion and the optic nerve in an external coordinate system. In particular embodiments, the retinal lesion to be treated includes macular degeneration, and step (c) includes determining the coordinates of the macula and the optic nerve in an external coordinate system.

The treatment method may further provide that the aligned patient-eye position places the optical axis of the eye in alignment with an axis normal to the cornea of the eye with the patient looking straight ahead. Step (a) may include the steps of determining, for the source of collimated x-radiation beam; (i) a beam-source collimator configuration that is based on an X-ray emission source-to-target distance, a collimator exit aperture-to-body surface distance, an emission or anode source size, and a collimator exit aperture size, and that is calculated to provide an X-ray beam-spot at the retina having a diameter or characteristic dimension to the 80% isodose of less than about 8 mm, and a penumbra width between the 80% isodose and the 20% isodose of less than about 40% of the beam-spot diameter or beam spot characteristic dimension; and (ii) a maximum photon energy and a beam filtration configuration to provide a maximum photon energy between 25-150 keV.

The treatment method may further provide that the maximum photon energy and a beam filtration are such as to provide a sclera surface-to-retina target dose ratio for the beam of less than N:1, where N is the number of established beams. Step (a) may include establishing at least three beam paths having a total beam angular divergence of between 20-60 degrees. Step (a) may include establishing a series of beam paths produced a continuously moving the beam source along an arcuate path.

The treatment method may further provide that step (b) includes (i) measuring an ocular dimension of the patient's eye; (ii) scaling a model of the eye that includes the coordinates of retinal features, including the macula and optic nerve, and a virtual ocular medium to the ocular dimension measured in step, and (iii) determining from the known distance of travel of the beam within the model along each path, and from the virtual ocular medium through which the beam travels, the dose of radiation from the source that needs to be delivered along each path, to produce the desired radiation dose at the macula of the patient's eye.

The treatment method may further provide that step (c) includes determining, from the known distance of travel of the beam within the model along each beam path, and from the virtual ocular medium through which the beam travels, the dose of radiation that is received by the optic nerve as a function of eye movement in a direction that moves the patient's optic nerve toward the irradiation beam.

A machine-readable code embodiment having aspects of the invention can operate on a computer to execute machine-readable instructions for performing the steps in a treatment planning method for treating a lesion on or adjacent to the retina of an eye of a patient ("retinal lesion"), by directing collimated X-radiation beams at the lesion in a patient's eye, the code providing instructions for steps comprising: (a) based on an aligned patient-eye position, establishing at least two treatment beam paths directed from a source of a collimated x-radiation beam through the patient's sclera beyond the limbus and directed at the lesion; (b) determining, based on the known spectral and intensity characteristics of the source beam along the established beam paths and from the coordinates of the ocular lesion in the aligned patient-eye position, a total treatment time for irradiation along the beam paths that is effective to produce a desired radiation dose at the ocular lesion of the patient's eye; and (c) determining, based on the known spectral and intensity characteristics of the source beam along the established beam paths, and from the coordinates of the optic nerve in the aligned eye position, the extent and duration of eye movement away from the aligned patient-eye position in a direction that moves the patient's optic nerve toward the irradiation beam that will be allowed during treatment, while still maintaining the radiation dose at the patient optic nerve below a predetermined dose level.

The code embodiment may provide that the retinal lesion to be treated includes one of macular degeneration; a drusen, a tumor or a vascular abnormality; and that step (c) includes determining the coordinates of the lesion and the optic nerve in an external coordinate system. In particular embodiments the retinal lesion to be treated includes macular degeneration, and step (c) includes determining the coordinates of the macula and the optic nerve in an external coordinate system.

The code may be operable, in performing step (a), to determine, for the source of collimated x-radiation beam, (i) a beam-source collimator configuration that is based on an X-ray emission source-to-target distance, a collimator exit aperture-to-body surface distance, an emission or anode source size, and a collimator exit aperture size, and that is calculated to provide an X-ray beam-spot at the retina having a diameter or characteristic dimension to the 80% isodose of less than about 8 mm, and a penumbra width between the 80% isodose and the 20% isodose of less than about 40% of the beam-spot diameter or beam spot characteristic dimension; and (ii) a maximum photon energy and a beam filtration configuration to provide a maximum photon energy between 25-150 keV.

The code may further be operable, in performing step (b) and based on a measured ocular dimension of the patient's eye, to (i) scale a model of the eye that includes the coordinates of retinal features, including the macula and optic nerve, and a virtual ocular medium to the ocular dimension measured in step, and (ii) determining from the known distance of travel of the beam within the model along each path, and from the virtual ocular medium through which the beam travels, the dose of radiation from the source that needs to be delivered along each path, to produce the desired radiation dose at the macula of the patient's eye.

A treatment planning system embodiment having aspects of the invention includes planning a treatment for a lesion on or adjacent to the retina of an eye of a patient ("retinal lesion"), the treatment carried out by directing a collimated X-radiation beam at the lesion in a patient's eye. The system comprises: (a) a device for aligning the patient eye; (b) a processor operable to receive coordinates of the aligned eye in an external coordinate system, and which stores information effective for determining, from the received coordinates, coordinates of the lesion and optic nerve in the patient eye; and (c) machine-readable code which operates on the processor to execute machine-readable instructions. The code provides machine-readable instructions which may be executed to perform the steps of: (i) based on the an aligned patient-eye coordinates, establishing at least two treatment beam paths directed from a source of a collimated x-radiation beam through the patient's sclera beyond the limbus and directed at the lesion; (ii) determining, based on the known spectral and intensity characteristics of the source beam along the established beam paths and from the coordinates of the lesion in the aligned patient-eye position, a total treatment time for irradiation along the beam paths that is effective to produce a desired radiation dose at the lesion of the patient's eye; and (iii) determining, based on the known spectral and intensity characteristics of the source beam along the established beam paths, and from the coordinates of the optic nerve in the aligned eye position, the extent and duration of eye movement away from the aligned patient-eye position in a direction that moves the patient's optic nerve toward the irradiation beam that will be allowed during treatment, while still maintaining the radiation dose at the patient optic nerve below a predetermined dose level.

The treatment planning system embodiments may further provide that the retinal lesion to be treated includes one of macular degeneration; a drusen, a retinal tumor or a retinal vascular abnormality; and step (c)(iii) includes determining the coordinates of the lesion and the optic nerve in an external coordinate system. In particular embodiments. the retinal lesion to be treated includes macular degeneration, and step (c)(iii) includes determining the coordinates of the macula and the optic nerve in an external coordinate system.

The treatment planning system embodiments may further provide that the code may be operable, in performing step (c), to determine, for the source of collimated x-radiation beam, (i) a beam-source collimator configuration that is based on an X-ray emission source-to-target distance, a collimator exit aperture-to-body surface distance, an emission or anode source size, and a collimator exit aperture size, and that is calculated to provide an X-ray beam-spot at the retina having a diameter or characteristic dimension to the 80% isodose of less than about 8 mm, and a penumbra width between the 80% isodose and the 20% isodose of less than about 40% of the beam-spot diameter or beam spot characteristic dimension; and (ii) a maximum photon energy and a beam filtration configuration to provide a maximum photon energy between 25-150 keV. The code may also be operable, in performing step (b) and based on a measured ocular dimension of the patient's eye, to (i) scale a model of the eye that includes the coordinates of retinal features, including the macula and optic nerve, and a virtual ocular medium to the ocular dimension measured in step, and (ii) determining from the known distance of travel of the beam within the model along each path, and from the virtual ocular medium through which the beam travels, the dose of radiation from the source that needs to be delivered along each path, to produce the desired radiation dose at the macula of the patient's eye.

A treatment planning method embodiment having aspects of the invention includes treating macular degeneration in a patient according to a treatment plan by directing collimated X-radiation at the macula in a patient's eye. The method comprises: (a) measuring an ocular dimension of the patient's eye, (b) scaling a model of the eye that includes the coordinates of retinal features, including the macula, and a virtual ocular medium to the ocular dimension measured in step (a), (c) establishing at least two treatment axes along which a collimated beam of X-radiation will be directed from an external radiation source at the macula in the eye model, and (d) determining from the known distance of travel of the beam within the model along each treatment axis, and from the virtual ocular medium through which the beam travels, the dose of radiation from the source that needs to be delivered along each treatment axis, to produce a predetermined total radiation dose at the macula of the patient's eye.

The method may further provide that step (a) includes measuring along an ocular axis, the ocular length of the patient's eye between the cornea and retina of the eye, and step (b) includes scaling the ocular length of the model to the patient's measured ocular length. Step (c) may include establishing treatment axes directed through the sclera and converging at the macula in the eye model, and having a total beam-to-beam angular divergence of between 20-60 degrees. The eye model may include coordinates of the optic nerve at the retina. The dose of radiation determined in step (d) may be determined as specified beam intensity over a given irradiation period, and step (d) may further include determining a permitted extent of eye movement over the irradiation period that maintains the radiation dose received at the patient optic nerve below a predetermined level.

A machine-readable code embodiment having aspects of the invention can operate on a computer to execute machine-readable instructions for performing the steps in a treatment planning method for treating macular degeneration in a patient by directing collimated X-radiation beams at the macula in a patient's eye, the code providing instructions for steps comprising: (a) scaling a model of the eye that represents retinal features, including the macula, and a virtual ocular medium to a patient-eye ocular dimension supplied as input; (b) establishing at least two treatment axes along which a collimated beam of X-radiation will be directed from an external radiation source at the macula in the eye model; and (c) determining from the known distance of travel of the beam within the model along each treatment axis, and from the virtual ocular medium through which the beam travels, the dose of radiation from the source that needs to be delivered along each treatment axis, to produce a predetermined total radiation dose at the macula of the patient's eye.

An method embodiment having aspects of the invention for treating a patient with a radiation beam from a orthovoltage X-ray emission source to a treatment target region on or adjacent to the retina, comprises the steps of:

(a) determining a radiation treatment plan, the plan including one or more of: (i) determining one or more distinct X-ray beam paths intersecting both the sclera surface and the target region, each beam path configured to substantially avoid both of the lens and the optic nerve of the treated eye; (ii) providing one or more X-ray beam collimators having a configuration including an X-ray emission source-to-target distance, a collimator exit aperture-to-body surface distance, an emission or anode source size, and a collimator exit aperture size, the collimator providing an X-ray beam having a X-ray beam-spot at the retina having a diameter or characteristic dimension to the 80% isodose of less than about 8 mm, and a penumbra width between the 80% isodose and the 20% isodose of less than about 40% of the beam-spot diameter or beam spot characteristic dimension; (iii) determining one or both of an X-ray source maximum photon energy and a beam filtration configuration configured to provide a collimated beam spectrum such that, as administered on the X-ray beam path, the maximum photon energy is less than about 300 keV;

(b) determining one or more of an X-ray beam duration and/or X-ray flux intensity level so as to provide a selected absorbed radiation dose to the retina target;

(c) aiming the collimator of step (a)(ii) to align with at least one beam path determined treating the patient according to the radiation treatment plan; and (d) emitting the calculated X-ray beam duration and/or flux level along each distinct X-ray beam path, so as to administer the selected beam radiation absorbed dose to the retina target.

In one alternative, step (b) may be based at least in part on one or more of: (i) at least one measurement of patient-specific eye anatomy; (ii) a selected sclera surface-to-retina target dose ratio for each X-ray beam; and (iii) the number of distinct X-ray beam paths. The method embodiment may further include the steps of: (e) engaging the treated eye during irradiation with an eye contact member; and (f) supporting and/or controlling the eye contact member so as to substantially reduce eye motion during radiation treatment. Optionally, the method may include (g) tracking at least one motion of the treated eye during irradiation; (h) determining at least one alignment of an X-ray beam path with the retinal target during irradiation based on tracked eye motion so as to determine an alignment error relative to the planned beam path; and (i) in the event that a selected threshold of error is determined, either or both of interrupting or discontinuing irradiation of the treated eye; or re-aligning the X-ray beam path with the retinal target.

A treatment method embodiment having aspects of the invention includes treating a patient with external radiation beam from a radiation source, the radiation beam emitted so as to propagate along an tissue path to reach a target tissue region within the patient's body, the treatment carried out according to a radiotherapy treatment plan anatomically specifying the tissue path. The method comprises the steps of: (a) selecting one or more input parameters ($P_1$, $P_2 \ldots P_i$,), the input parameters selected from human anatomical measurements, other human measurements, and other person-specific characteristics; (b) characterizing variation with respect to the selected parameters in a human population which includes the patient, the variation correlated with the tissue path length (PL) for the radiotherapy treatment plan; (d) determining a mathematical function and/or calculation algorithm effectively expressing a relationship between the selected parameters and the tissue path length ($PL=f(P_1, P_2 \ldots P_i)$; (e) determining values of the selected parameters ($P_1$, $P_2 \ldots P_i$,) for the patient; (f) using the mathematical function and/or calculation algorithm, determining PL for the patient ($PL_0$); (g) modifying or adjusting one or more aspects of the radiotherapy treatment plan based on the determined value $PL_0$; and (h) treating the patient according to the modified or adjusted treatment plan.

The method may further provide that the modified or adjusted aspects of the treatment plan include one or more of beam duration, total radiation dose, beam spectral energy, beam filtration, beam collimation geometry, and beam orientation. The radiation beam may include an orthovoltage X-ray beam having a maximum photon energy of less than 500 keV. The target tissue region within the patient's body may include tissue within an eye of the patient, such as a portion of the retina, and the anatomical tissue path may include a path from an entry point on the sclera surface propagating through the eye to the target region. The selected parameters may include an eye axial length, e.g., as determined by an ultrasonic A-scan measurement.

A treatment method embodiment having aspects of the invention includes treating an ocular lesion in a patient by directing collimated X-radiation at the lesion in a patient's eye. The method comprises the steps of: (a) based on an aligned patient-eye position, establishing at least two treatment beam paths directed from a source of a collimated X-radiation beam through the surface of the patient's e and directed at ocular lesion; (b) determining, based on the known spectral and intensity characteristics of the source beam along the established beam paths and from the coordinates of the lesion in the aligned patient-eye position, a total treatment time for irradiation along the beam paths that is effective to produce a desired radiation dose at the lesion of the patient's eye; and (c) determining, based on the known spectral and intensity characteristics of the source beam along the established beam paths, and from the coordinates of a selected radiation sensitive structure in the eye, in the aligned eye position, the extent and duration of eye movement away from the aligned patient-eye position in a direction that moves the patient's radiation-sensitive structure toward the irradiation beam that will be allowed during treatment, while still maintaining the radiation dose at the patient radiation-sensitive structure below a predetermined dose level.

The method may further provide that (i) the ocular lesion to be treated includes one of a pterygium, a vascular malformation; an ocular tumor; an ocular premalignant lesion; a choroidal hemangioma; an ocular metastasis; a nervus; a conjunctival tumor; an eyelid tumor; an orbital tumor, and tissue associated with glaucoma; and (ii) the radiation-sensitive structure includes one of the lens of the eye, the cornea and the optic nerve.

These and other objects and features of the invention will be more fully appreciated when the following detailed description of the invention is read in conjunction with the accompanying figures.

BRIEF DESCRIPTION OF THE FIGURES

The FIGURES and the associated descriptions are provided to illustrate embodiments of the disclosure and not to limit the scope of the disclosure. Throughout the figures, reference numbers are reused to indicate correspondence between referenced elements. The FIGURES are in simplified form and are not necessarily precise in scale. In reference to the disclosure herein, for purposes of convenience and clarity only, directional terms, such as top, bottom, left, right, up, down, over, above, below, beneath, rear, and front are used with respect to the accompanying figures. Such directional terms are not to be construed as limiting the scope of the invention in any manner. Likewise, reference numerals in the figures are for purposes of convenience and are discussed in the description in the context of the figures in which they appear. Generally, the same reference numeral is used to denote a homologous or similar element in more than one figure. However, in some cases, a particular structure or element may be referred to in one figure by one reference numeral, and the same or substantially similar structure or element may be referred to in another figure by a different reference numeral.

The FIGURES include the following:

A. Radiotherapy Treatment Parameters and Planning

Figure 1:
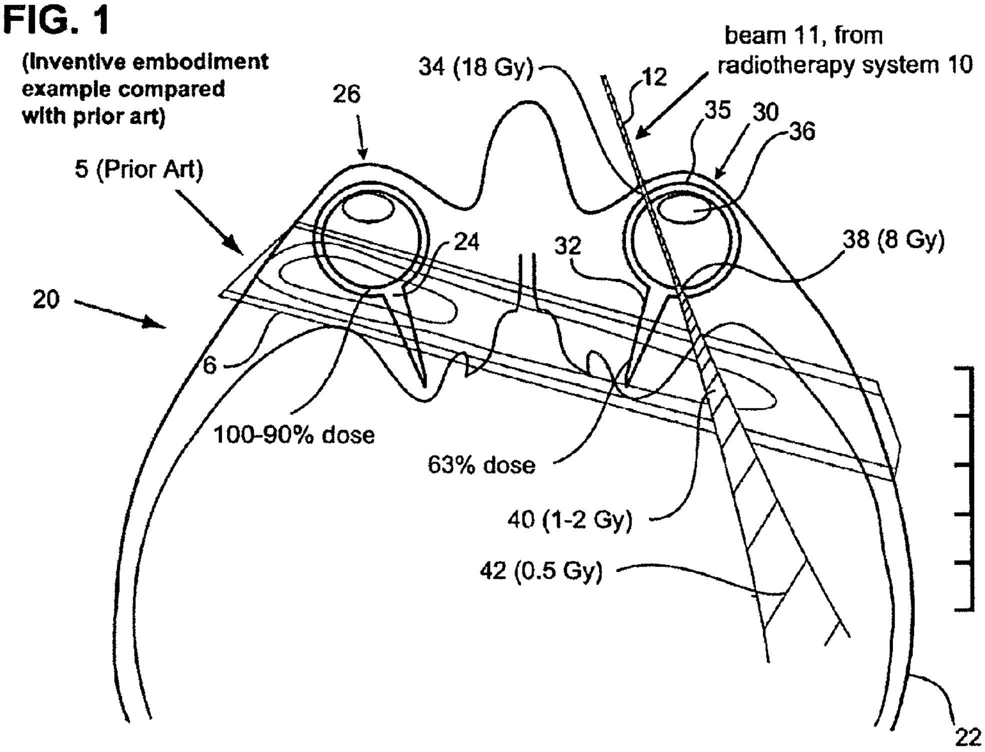

FIG. 1 is a cross-sectional view representing a CT scan of a portion of a patient's head, depicting a prior art ocular radiotherapy procedure, and in comparison depicts a orthovoltage ocular radiotherapy procedure according to methods and devices having aspects of the invention herein.

Figure 2:
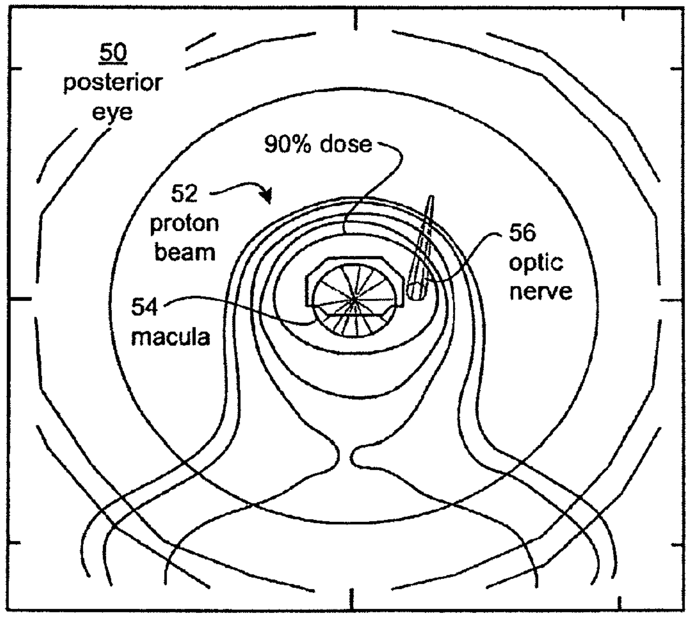

FIG. 2 is a cross-sectional view of a region of a posterior eye, depicting a prior art proton beam treatment.

Figure 3:
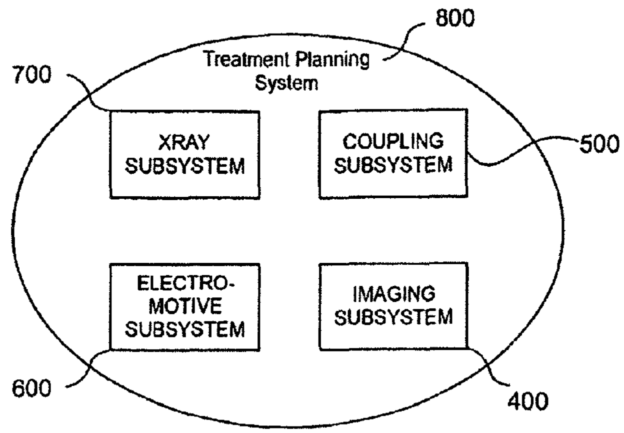

FIG. 3 shows a schematic overview of an embodiment of a treatment planning system and method having aspects of the invention.

FIGS. 4A-C illustrate the relation between the treatment planning system and eye model with various components of radiotherapy system having aspects of the invention in the treatment of eye.

Figure 5:
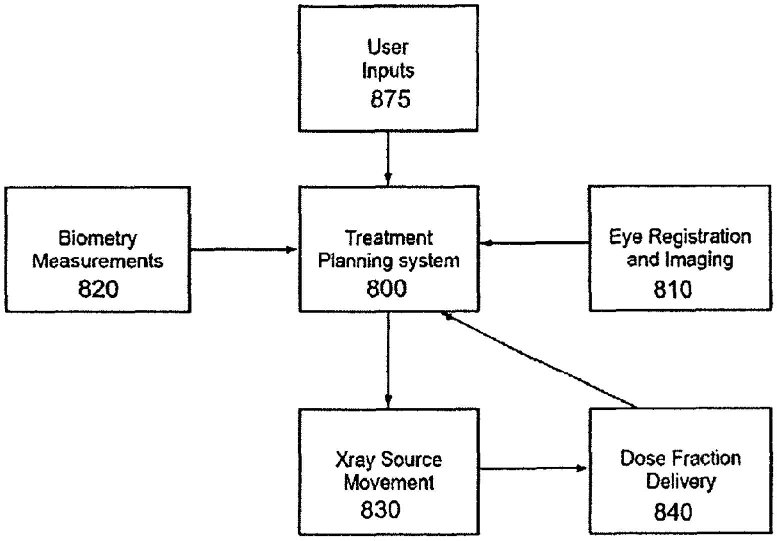

FIG. 5 is a schematic chart illustrating a method of clinical application of a radiotherapy system having aspects of the invention.

Figure 6:
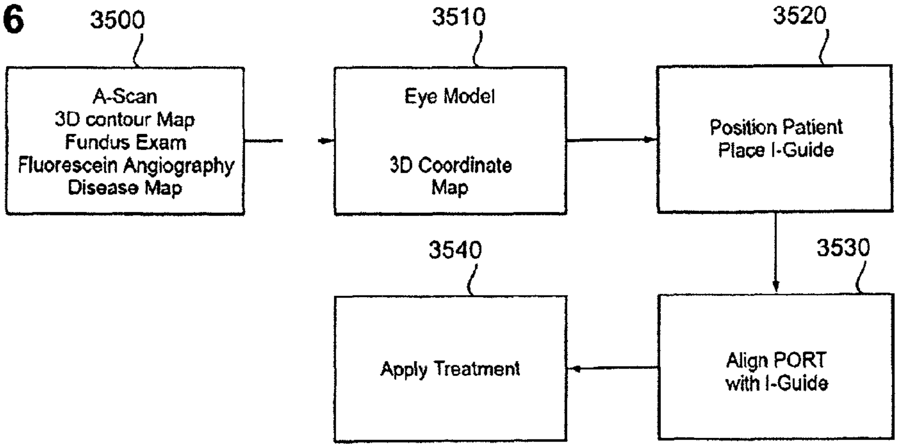

FIG. 6 depicts an exemplary clinical flow method involving the radiotherapy device in accordance with treatment planning embodiments described herein.

Figure 7:
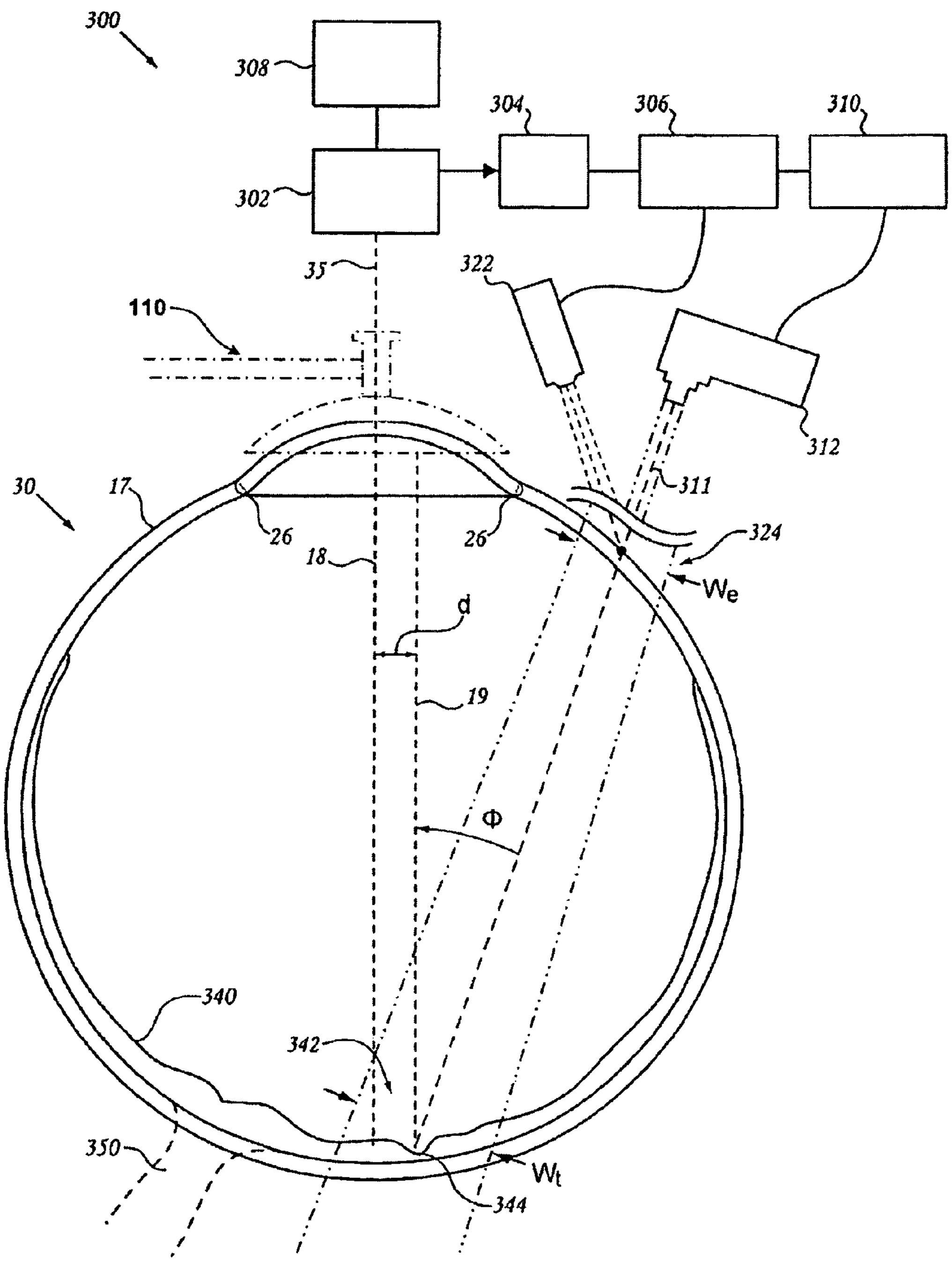

FIG. 7 a cross-sectional view of an eye, shown in association with an embodiment of a radiotherapy system having aspects of the invention.

Figure 8:
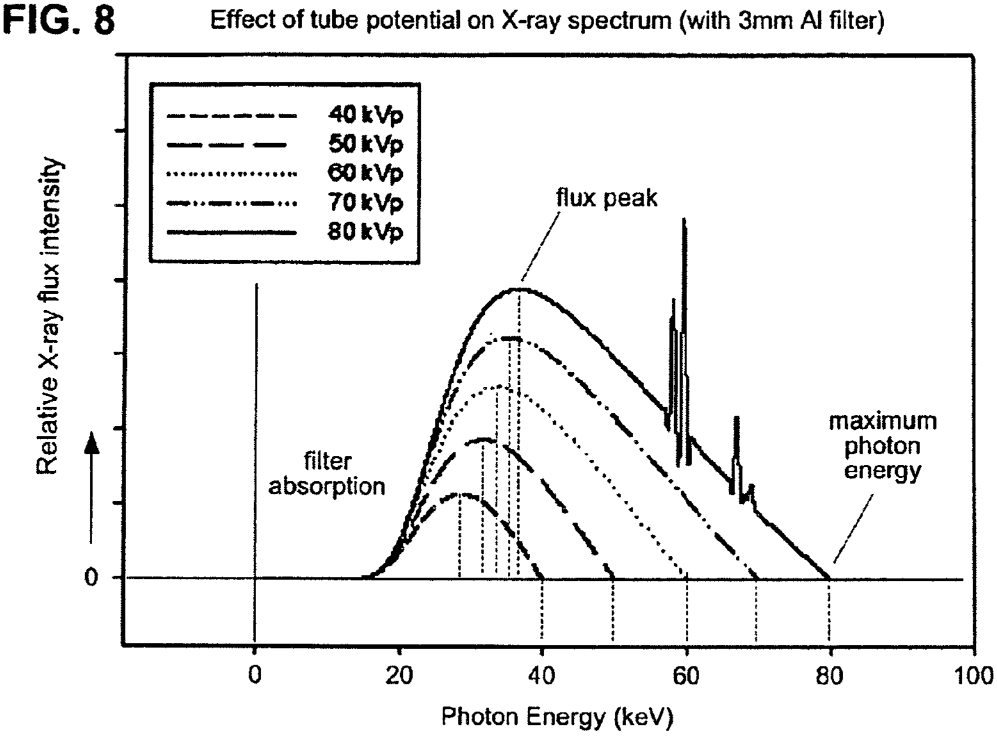

FIG. 8 depicts an exemplary set of orthovoltage X-ray spectra showing a trend of characteristic photon energy distribution with increasing source tube voltage.

Figure 9:
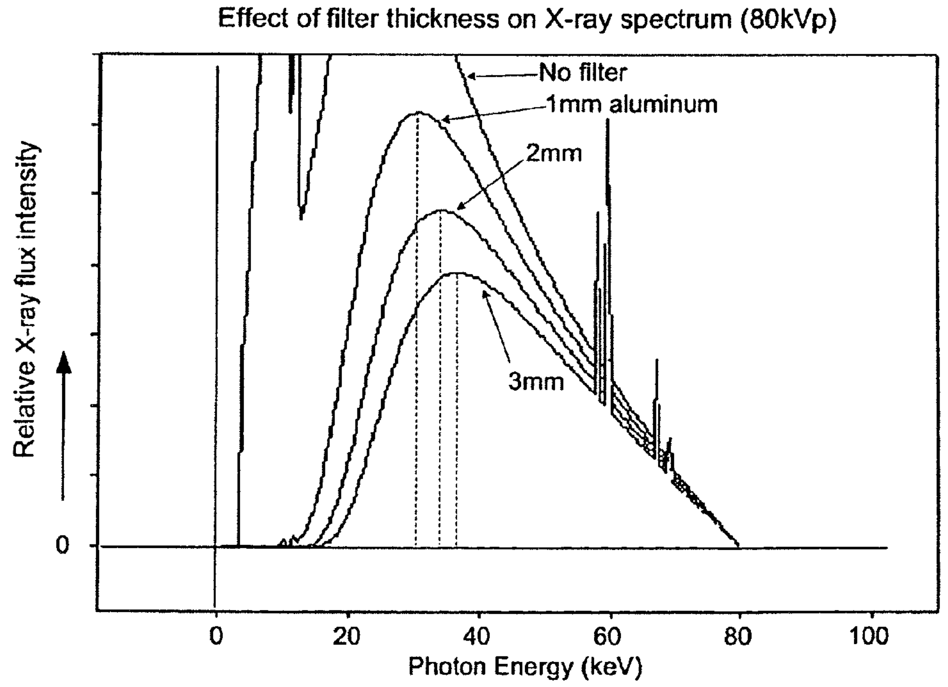

FIG. 9 depicts an set of 80 kVp X-ray spectra showing a trend of photon energy distribution with increasing thickness of Al filter material.

Figure 10:
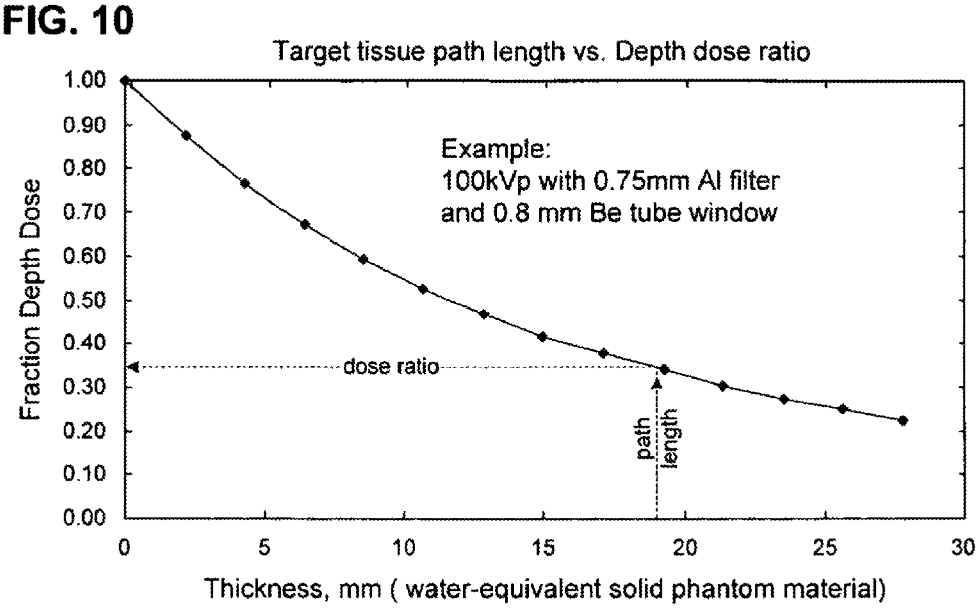
Figure 11:
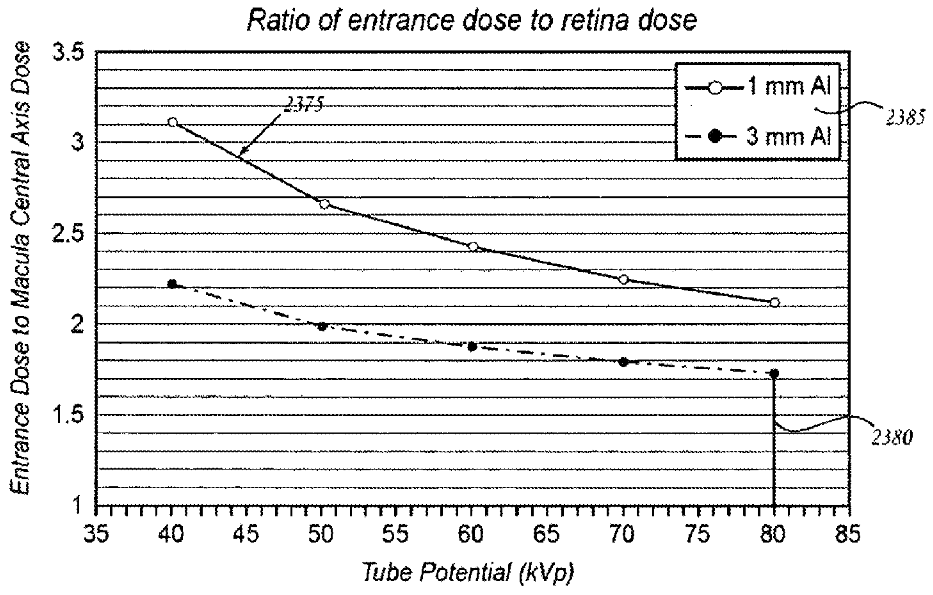

FIG. 10 is a plot showing the depth propagation/absorbs ion curve for an exemplary treatment beam penetrating simulated tissue FIG. 11 is a plot showing the effect of a range of X-ray tube potentials and two different filter thickness on depth-dose ratio measured at a typical retinal depth.

Figure 12:
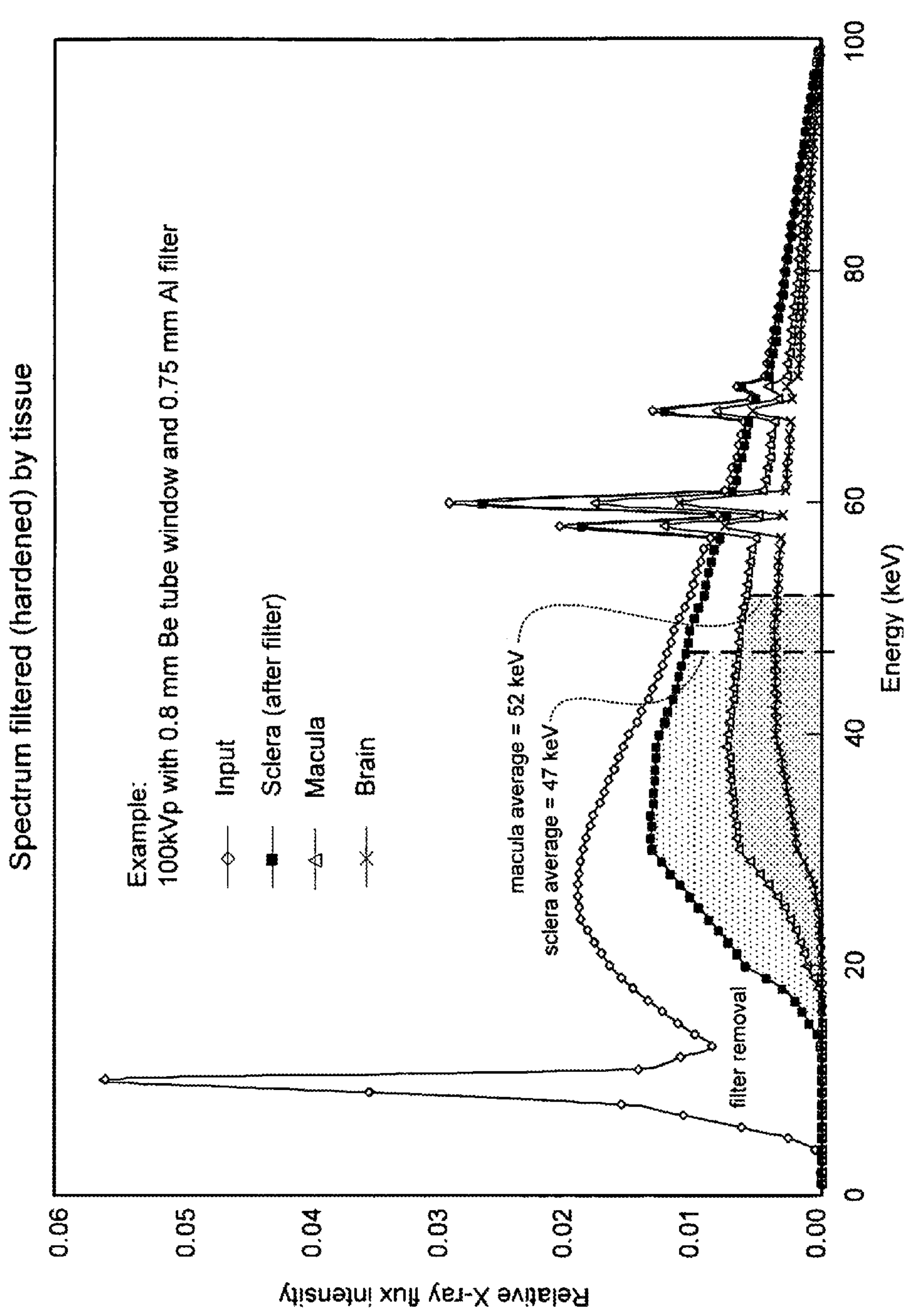

FIG. 12 depicts an exemplary sequence of spectra corresponding to the propagation of a radiotherapy beam through system filters and simulated patient tissue anatomy.

Figure 13:
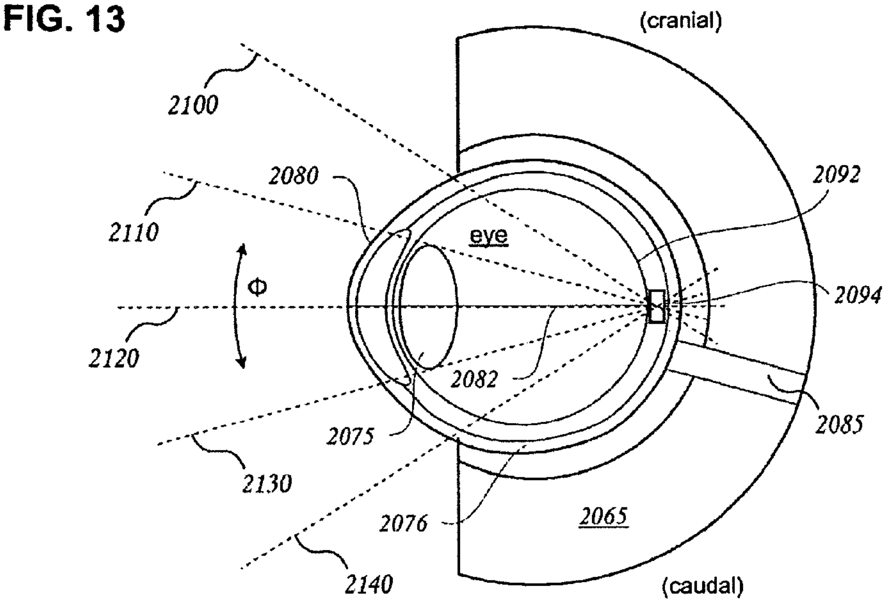

FIG. 13 illustrates a representative geometric model of the eye used for modeling purposes, showing representative radiation beam angles with respect to an anterior surface and geometric axis of the eye.

Figure 14:
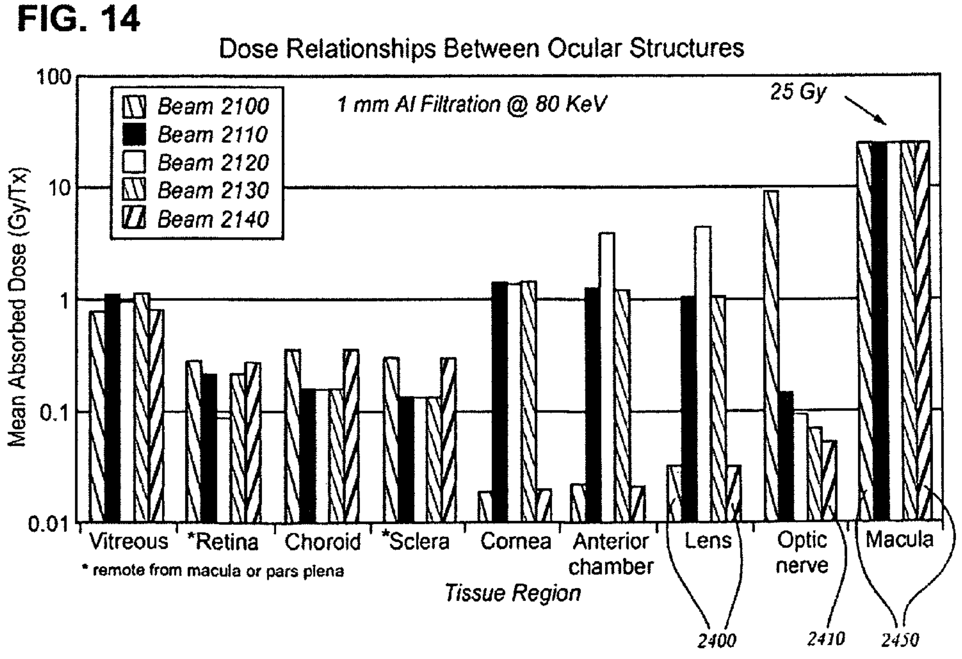

FIG. 14 depicts results of Monte Carlo simulations performed to analyze the effect of various treatment regimes on the various structures of the eye.

FIGS. 15-17D depict the results of a radiation modeling study of varying optic nerve angles with respect to the posterior sclera, the geometry of the beam cases of the study, and the anatomic geometry of different optic nerve cases studied.

Figure 18:
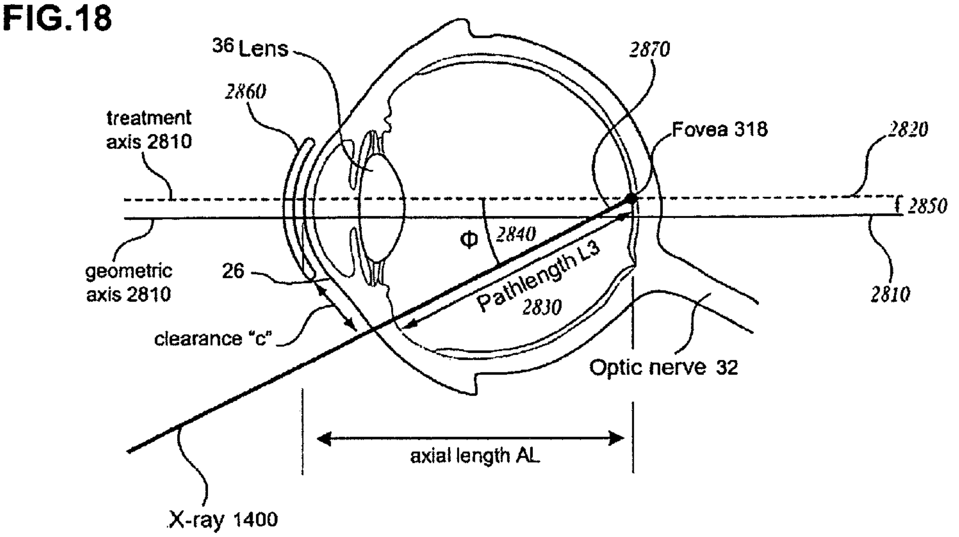

FIG. 18 depicts an eye in cross section, further showing aspects of an anatomical targeting method for radiotherapy.

Figure 19A:
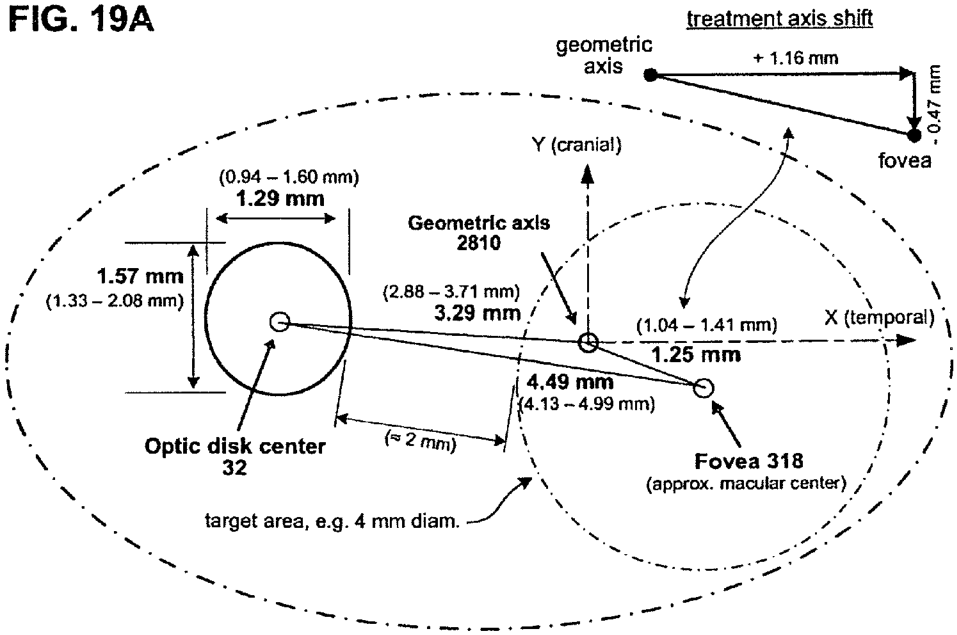

FIG. 19A is a schematic view of a fundus image on a patient's retina showing one example of a treatment plan for AMD.

Figure 19B:
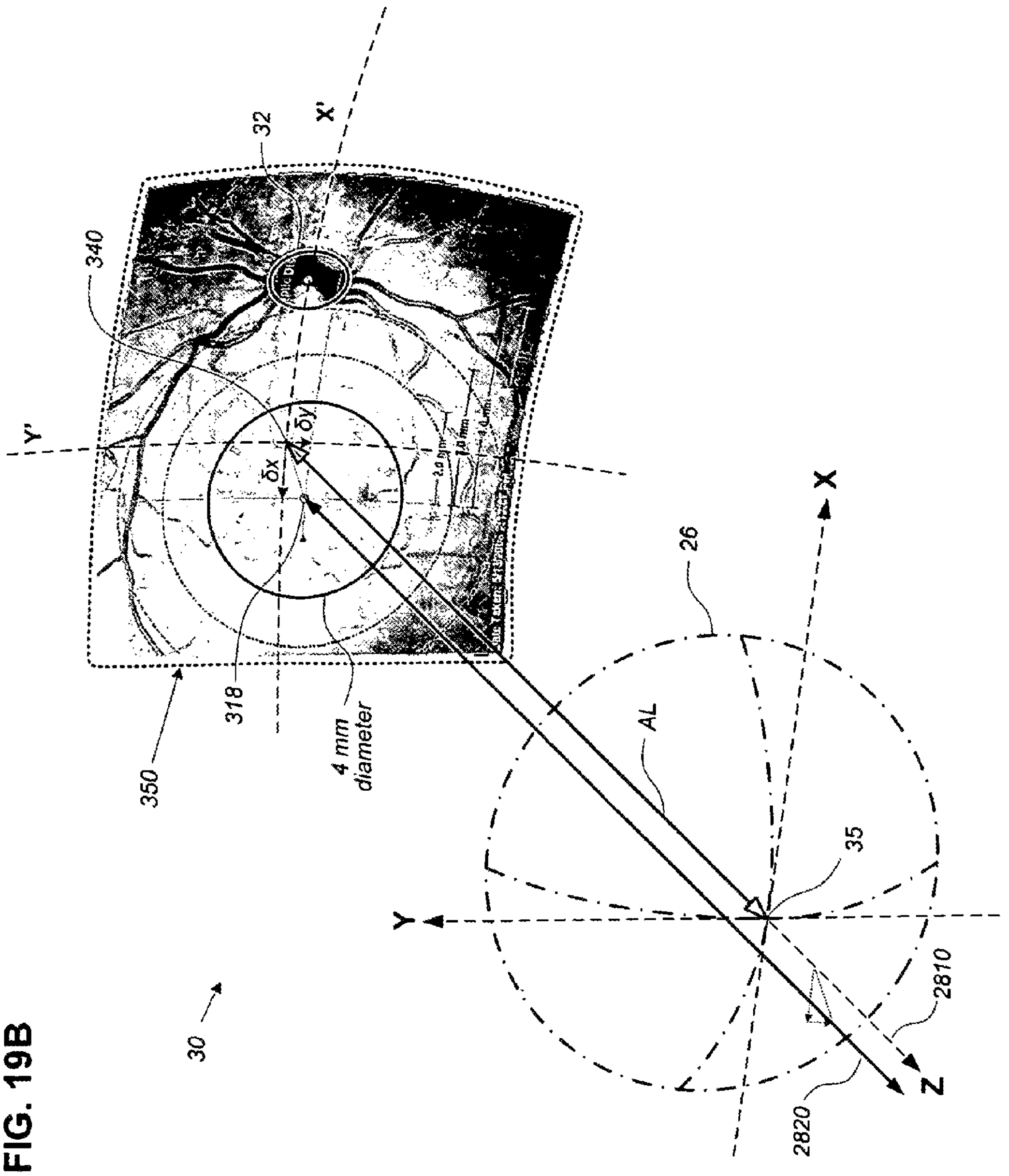

FIG. 19B is a schematic view of an virtual eye model including a medical image registered with eye anatomy.

Figure 20:
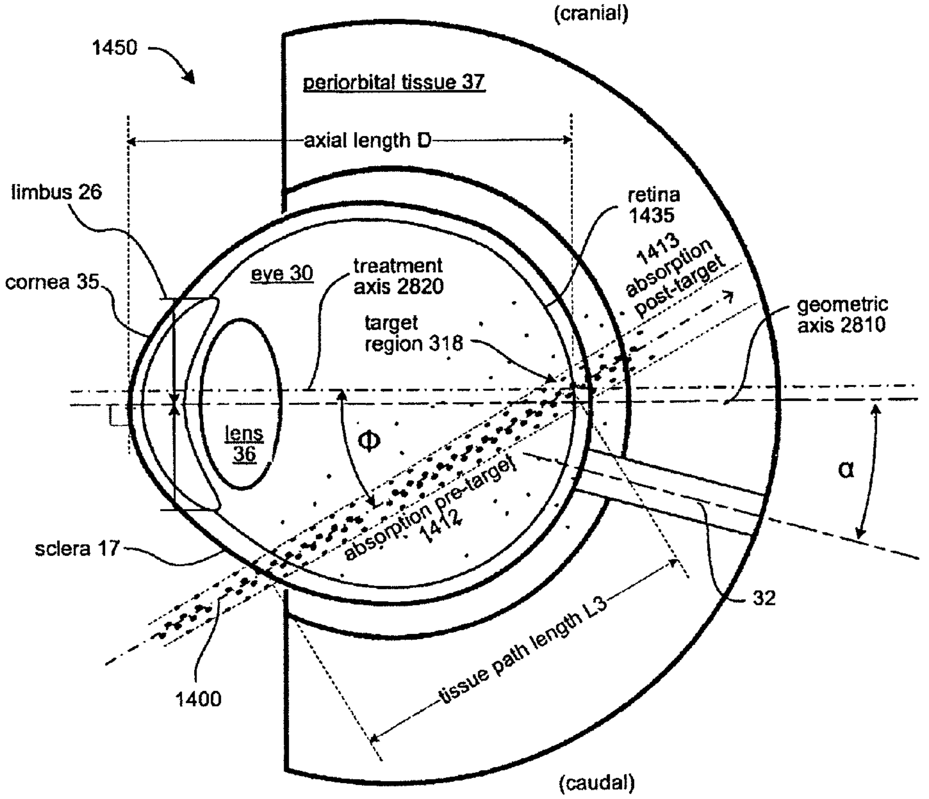

FIG. 20 schematically depicts an example of a virtual or phantom model of a human eye which is included in treatment planning and control embodiments having aspects of the invention.

Figure 21:
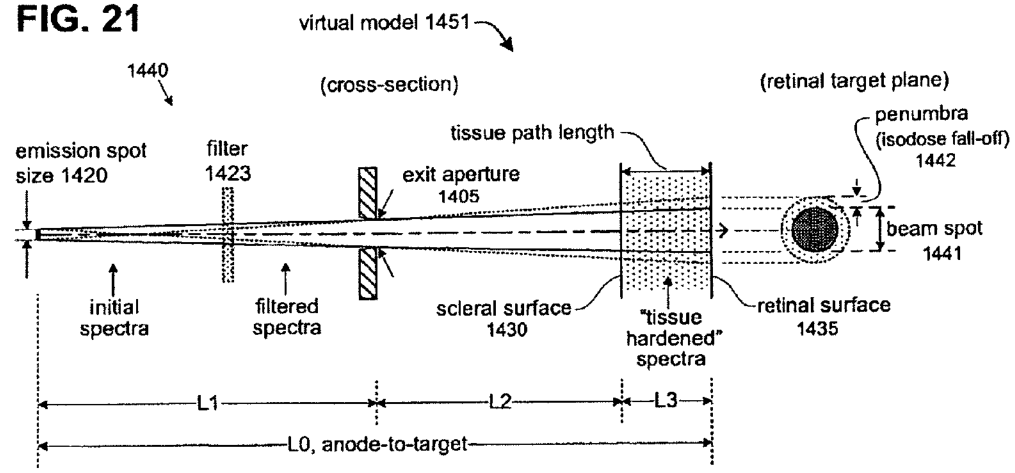

FIG. 21 schematically depicts a virtual or phantom model of an X-ray source and collimator system associated with a simplified anatomical representation of an eye being treated.

FIGS. 22A-22D schematically depicts a model similar to that of FIG. 21, comparing graphically the effect of four different examples of X-ray source anode sizes on target beam spot and penumbra for a constant collimator configuration.

FIG. 23 is a plot showing the results of a Monte Carlo computational simulation of example configurations generally similar to those shown in FIG. 22.

FIGS. 24A and 24B depict the results of a single collimated x-ray beam 2600, both at the collimator aperture and after it has penetrated through about 20 mm of solid water phantom material.

FIG. 24C shows a plot of penumbra from measurements within an x-ray detection films at a macular and retinal locations of a solid water eye model.

FIGS. 25A-25D schematically depicts a model similar to that of FIGS. 22A-D, comparing the same four different examples of source anode sizes, but for collimator configurations having apertures sized to produce a constant central beam-spot size at the target plane.

FIGS. 26A-26C schematically depicts a model similar to that of FIG. 21, comparing graphically the effect of three different examples of anode-to-target distance on penumbra, for collimator configurations having apertures sized to produce a constant central beam-spot size at the target plane.

FIGS. 27A-27C schematically depicts a model similar to that of FIG. 21, comparing graphically the effect of three different examples of collimator exit plane-to-target distance on penumbra, for source configurations having constant anode-to-target distances, and apertures sized to produce a constant central beam-spot size at the target plane.

FIG. 28 is cross-sectional diagram of a variable length collimator having an extensible support for the exit plane aperture, shown in this example in the form of a "zoom-lens"-like mounting of an aperture disk.

Figure 29A:
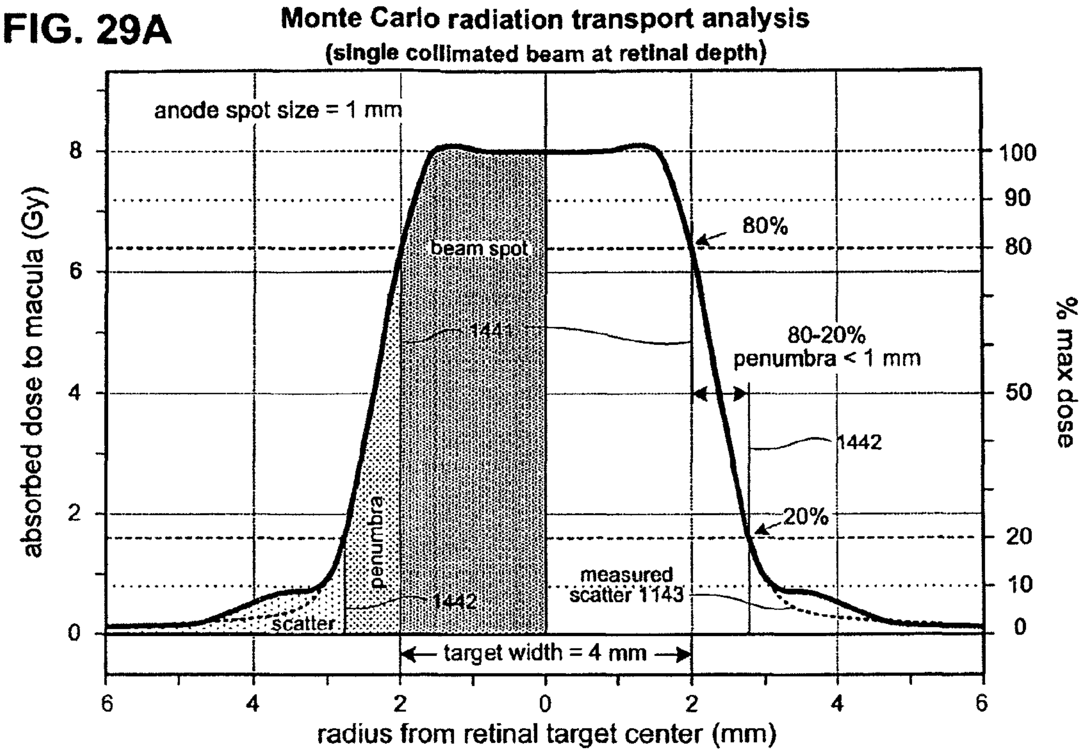

FIG. 29A is a plot showing the results of a Monte Carlo computational simulation for absorption of X-ray energy in a configuration generally similar to that shown in FIG. 12.

Figure 29B:
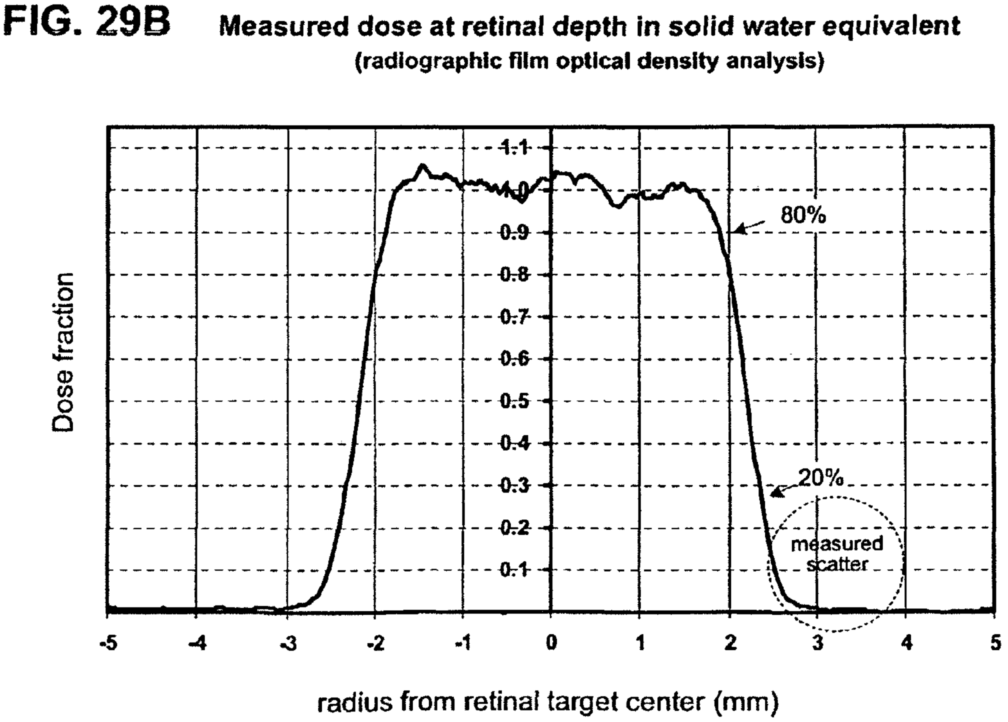
Figure 30A:
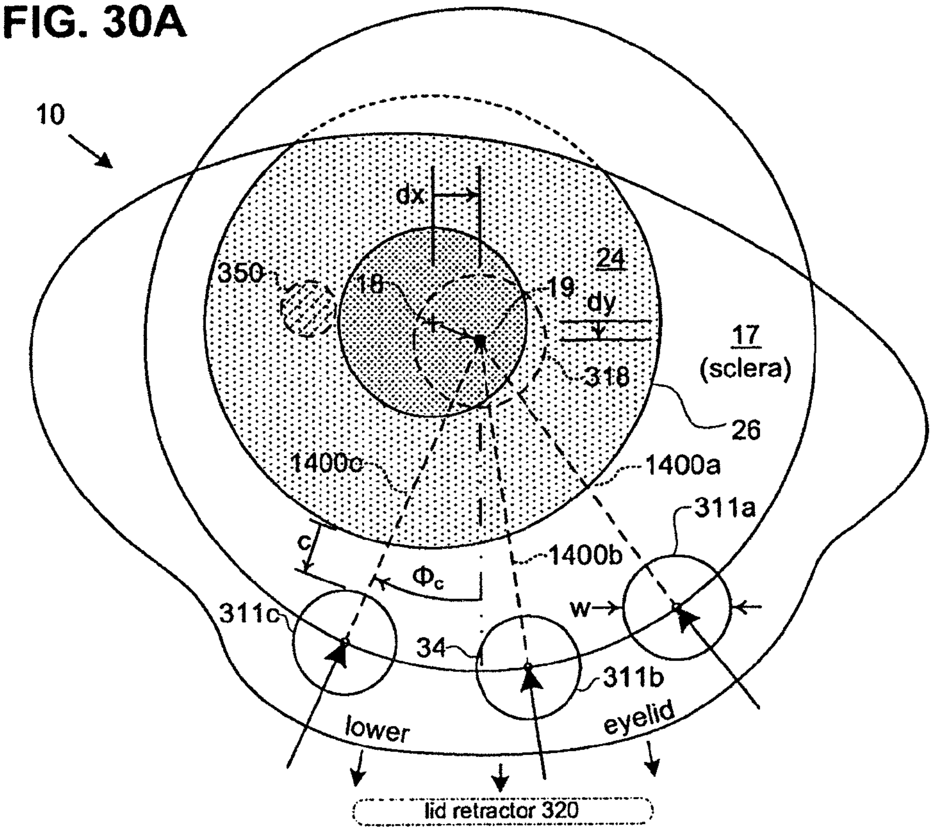
Figure 30B:
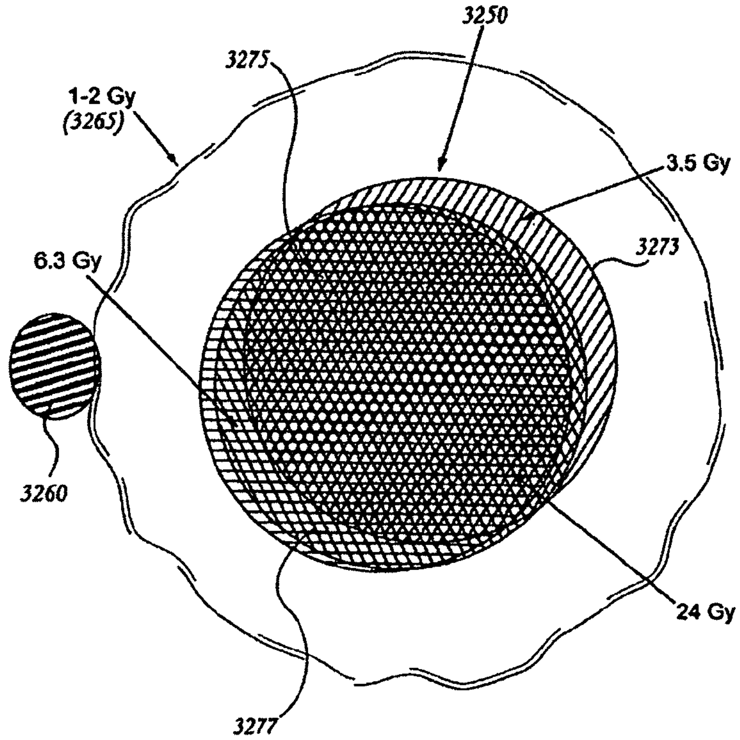

FIG. 29B shows a plot of measured dose intensity at retinal depth for an X-ray/collimator configuration comparable to that of FIG. 30B.

FIG. 30A is a frontal view of an eye as seen aligned with a system reference axis, and depicting stereotactic X-ray treatment beam geometry, FIG. 30B depicts results of a procedure in which three beams were focused on the back of an phantom eye model using a robotic system, and represents overlapping x-rays at a target site.

FIG. 30C-D are plots illustrating a stereotactic 3-beam dose map of retinal dose measured by radiometry on a phantom eye or mannequin.

Figure 31A:
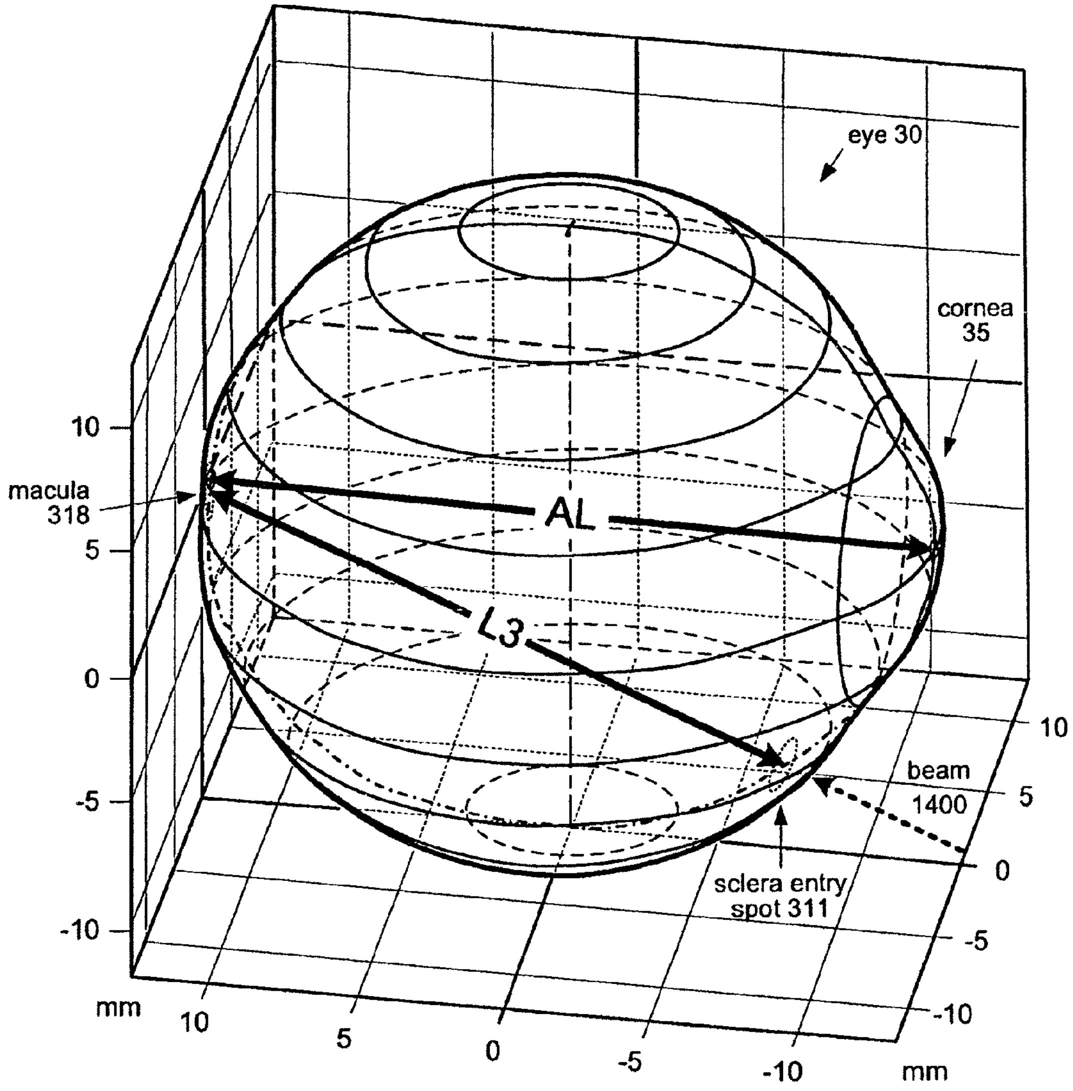

FIG. 31A shows a typical example of the mapping eye geometry using laser-scanner measurements on cadaver eyes.

Figure 31B:
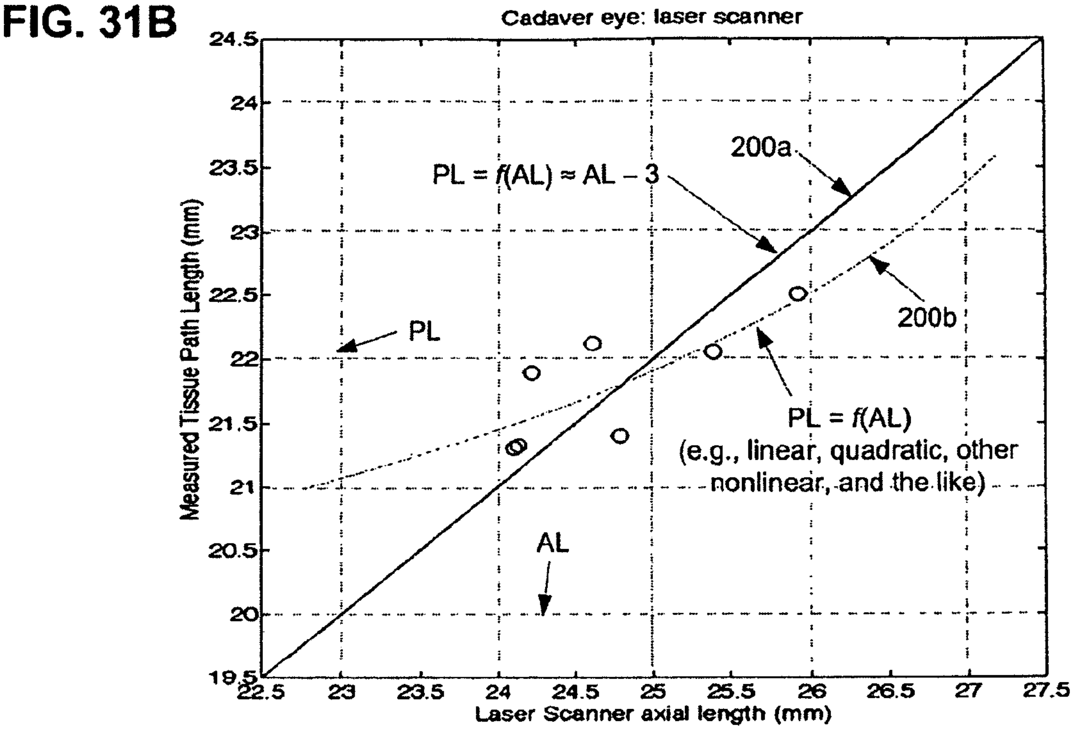

FIG. 31B is a plot showing the relationship between tissue path length and axial length from measurements such as are shown in FIG. 31A.

Figure 31C:
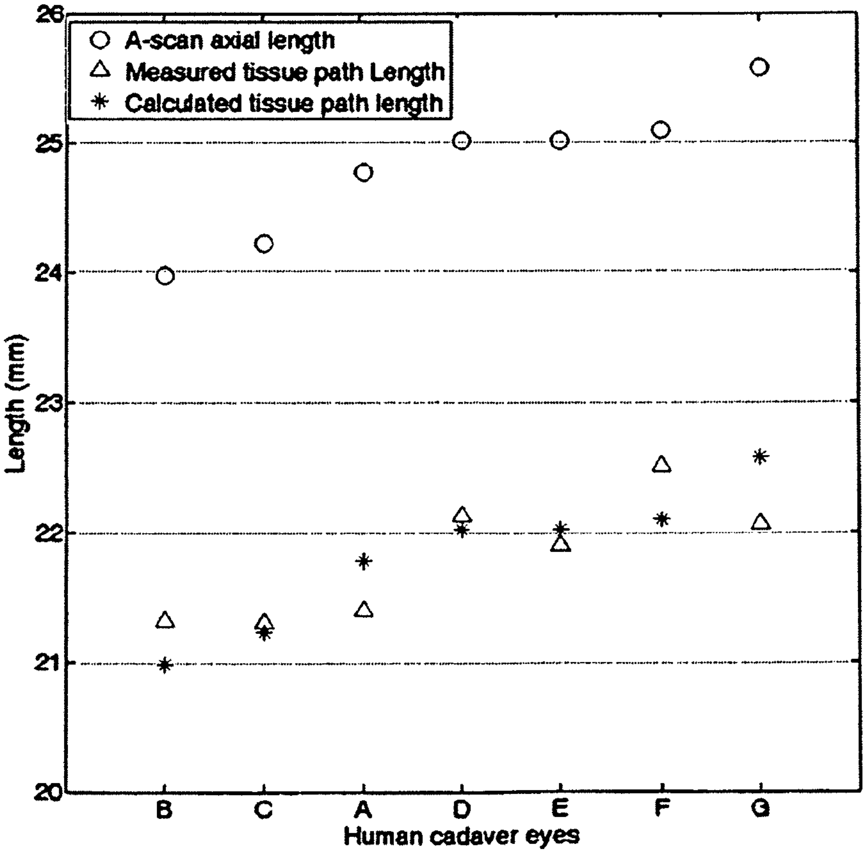

FIG. 31C is a plot showing for each of seven example cadaver eyes, the A-scan derived axial length, together with the laser-scanner value of tissue path length, and a calculated tissue path length according to an example linear formula.

Figure 31D:
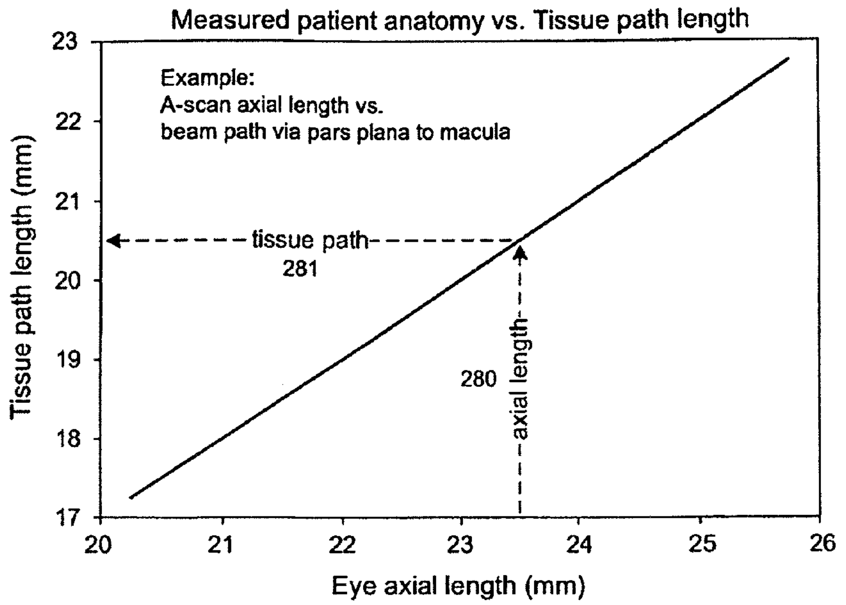

FIG. 31D is a plot depicting the relation between measured patient anatomy and tissue path length for an exemplary radiotherapy treatment plan.

Figure 32:
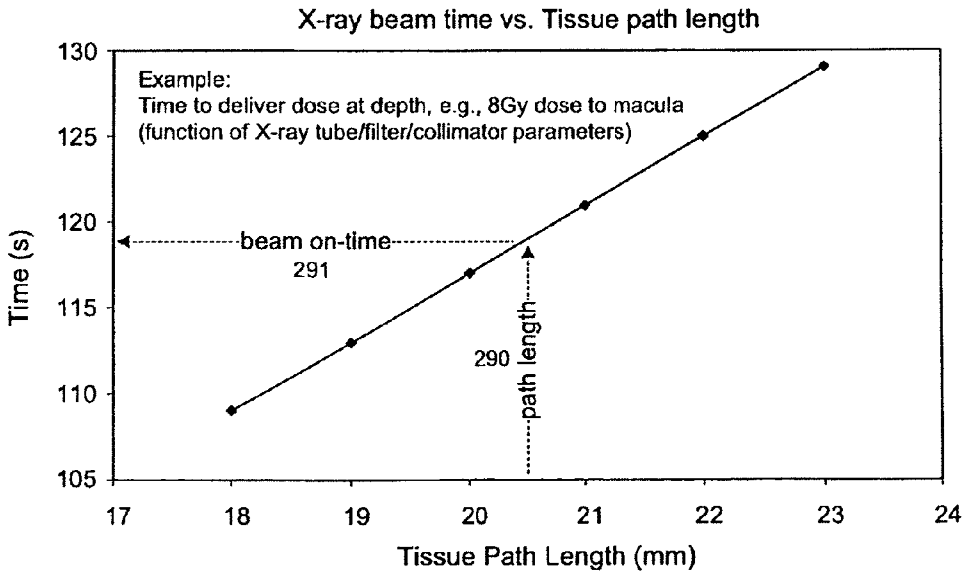

FIG. 32 is a plot depicting the relation between the beam tissue path length and the duration of beam emission required to deliver a planned target dose for an exemplary embodiment of a X-ray treatment system.

B. Radiotherapy Treatment Delivery

Figure 33A:
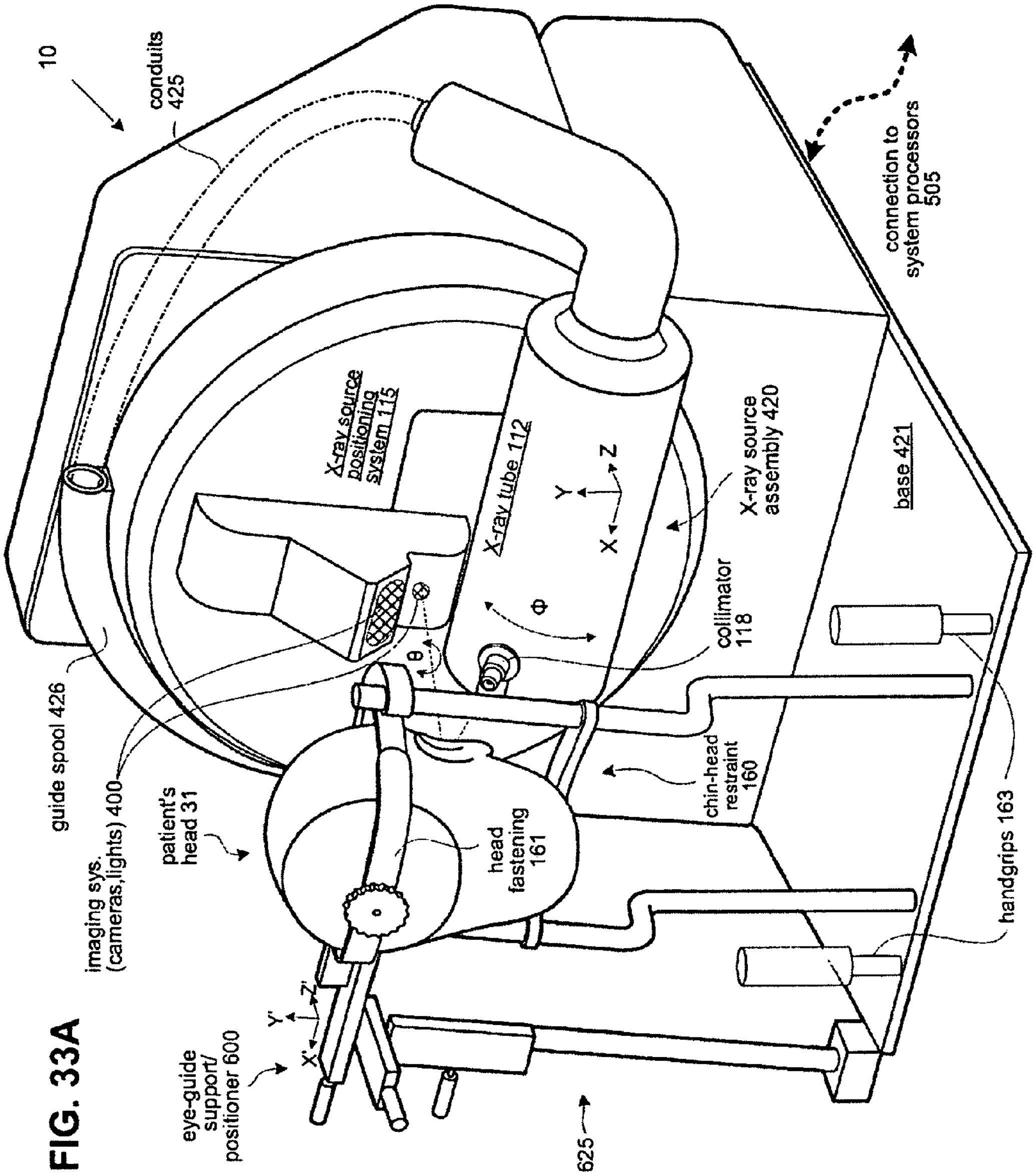
Figure 33B:
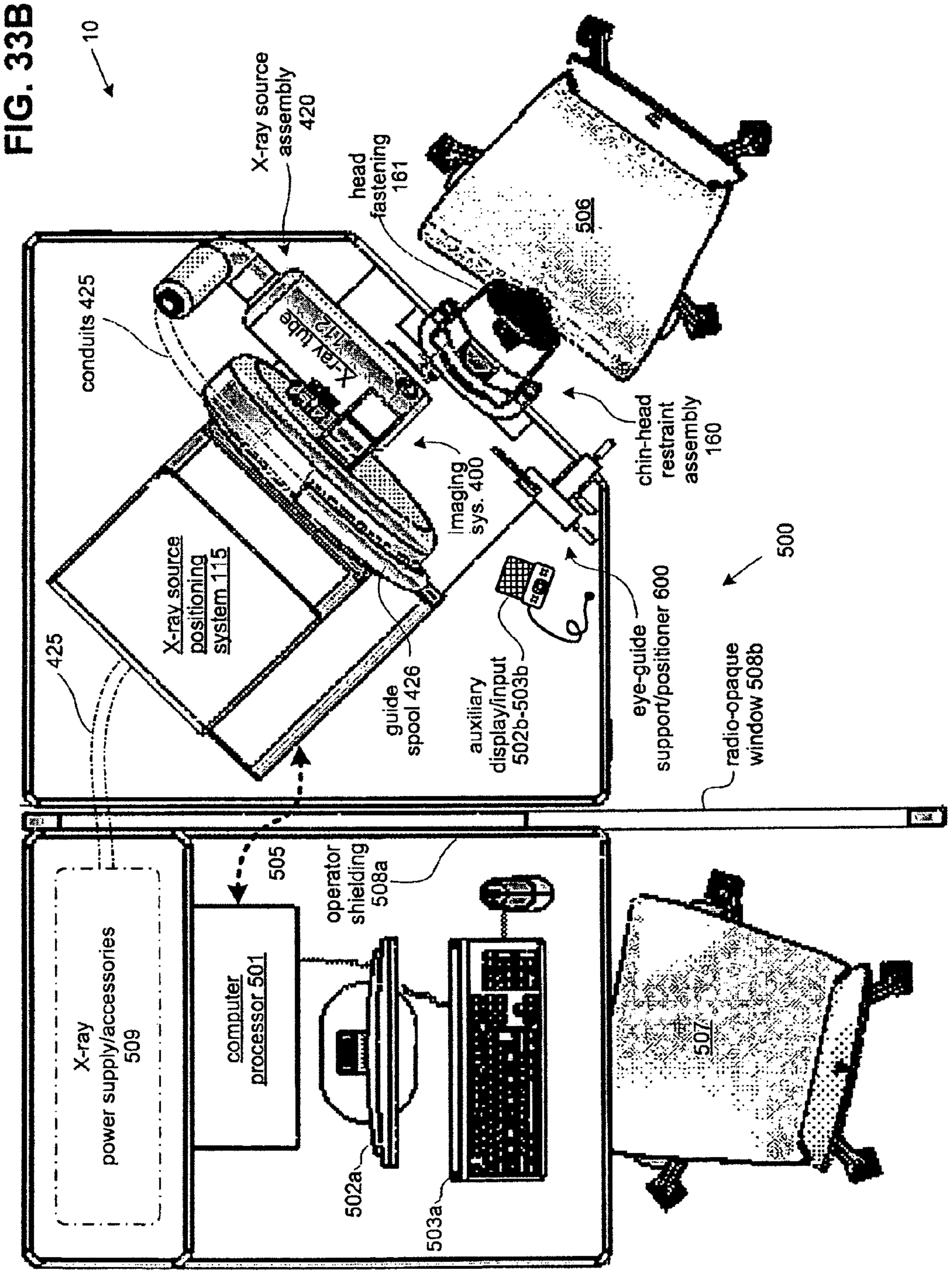

FIGS. 33A and 33B is a perspective view and plan layout of an exemplary embodiment of an X-ray treatment system having aspects of the invention, for treating ocular diseases.

Figure 34:
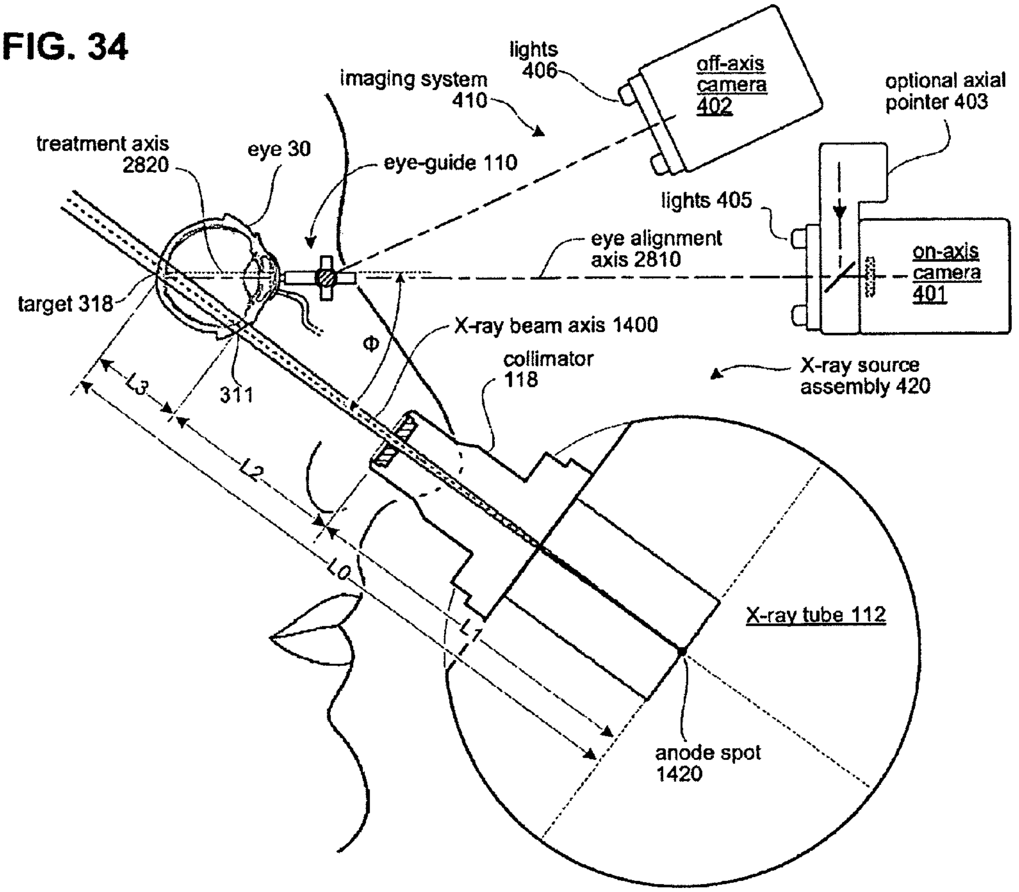

FIG. 34 shows a patient's head including cross-section of an eye in the vertical plane of symmetry of the eye, shown in association with embodiments of an imaging system and an X-ray source assembly having aspects of the invention.

Figure 35:
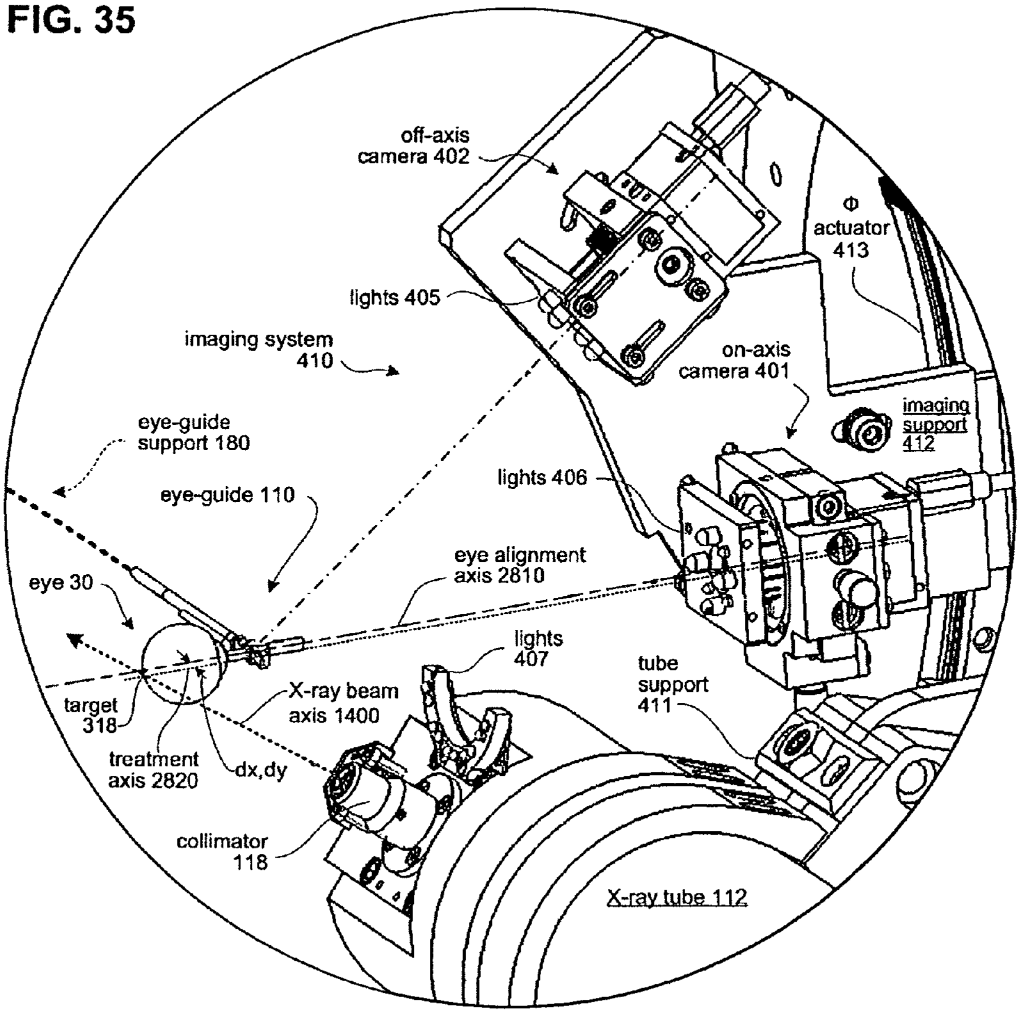

FIG. 35 is a perspective detail view of the system components shown in FIG. 31 together with portions of an automated positioning system having aspects of the invention.

Figure 36:
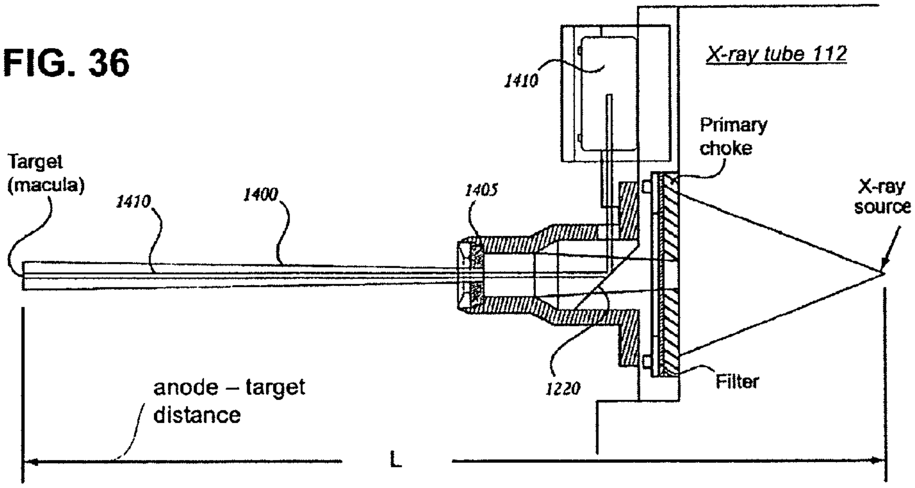

FIG. 36 is a longitudinal cross-sectional view of the collimator and a portion of X-ray tube.

Figure 37:
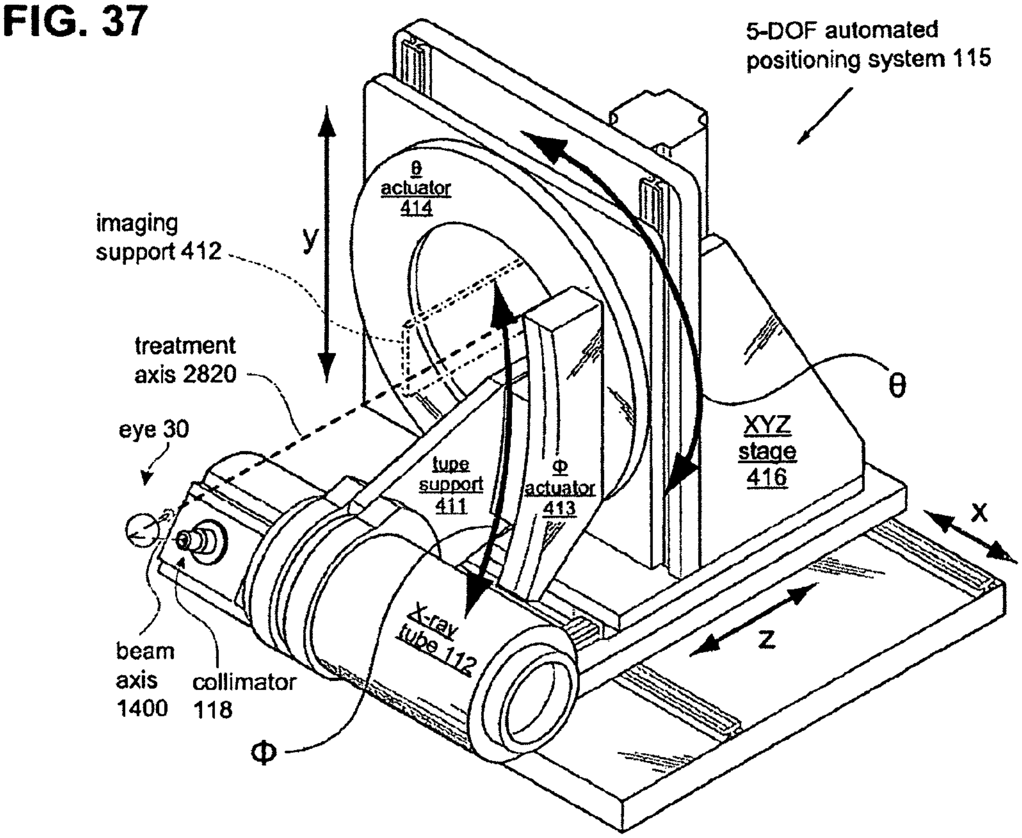

FIG. 37 is a perspective illustration of an embodiment of a positioning system having aspects of the invention.

Figure 38:
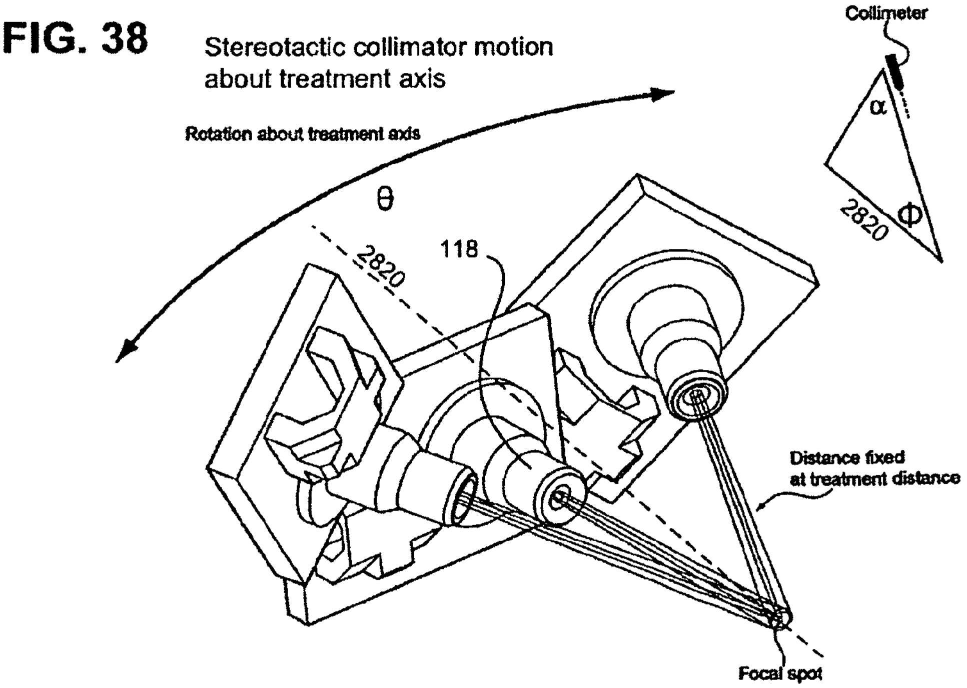

FIG. 38 is a perspective detail showing collimator rotational motion as moving in one operational alternative of the positioning system of FIG. 37.

Figure 39:
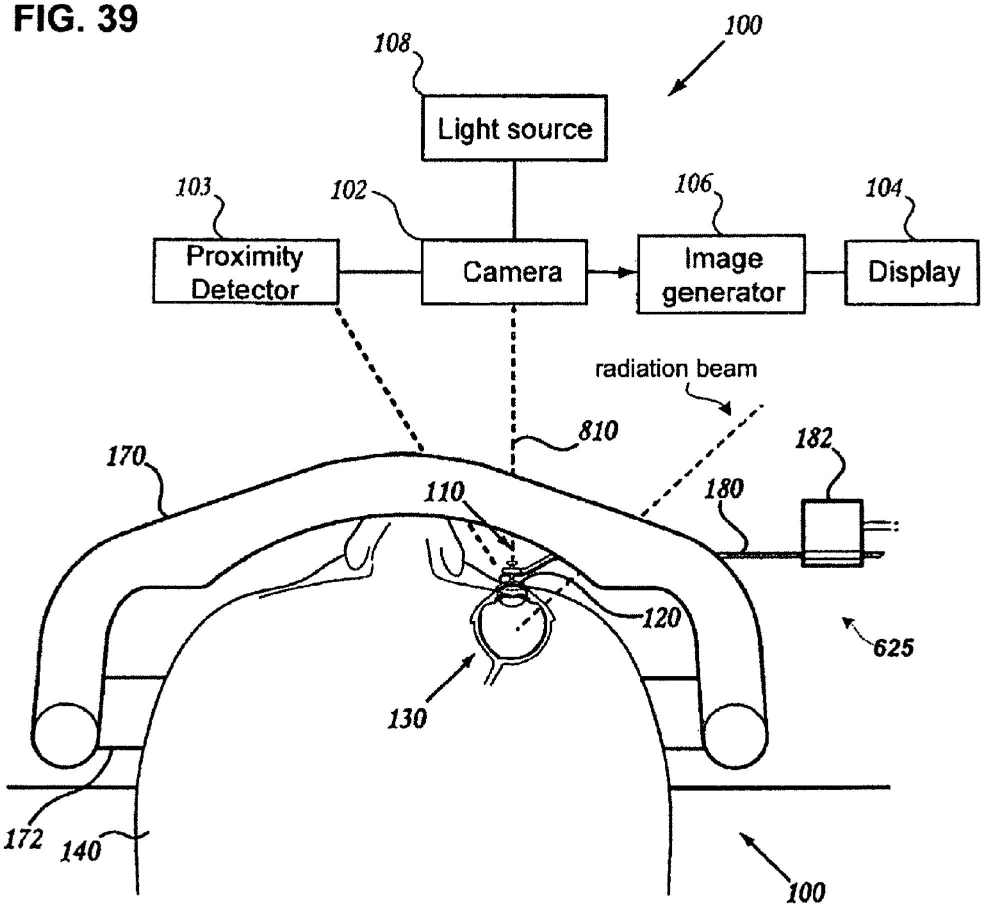

FIG. 39 illustrates a top view of one embodiment of a system for controllably positioning and/or stabilizing the eye of a subject for therapeutic treatment.

FIGS. 40A-B illustrate perspective views of the contact device or eye guide having aspects of the invention in various cases of alignment with a system axis.

FIGS. 41A-B illustrate top views of an embodiment of a system for engaging the eye of a subject.

FIG. 42A-D depicts perspective views of the contact device with the control arm attached having aspects of the invention.

FIGS. 43A-E are a flow chart and related schematic drawings which illustrate an exemplary method of eye alignment and treatment employing an eye-guide device having aspects of the invention.

Figure 44A:
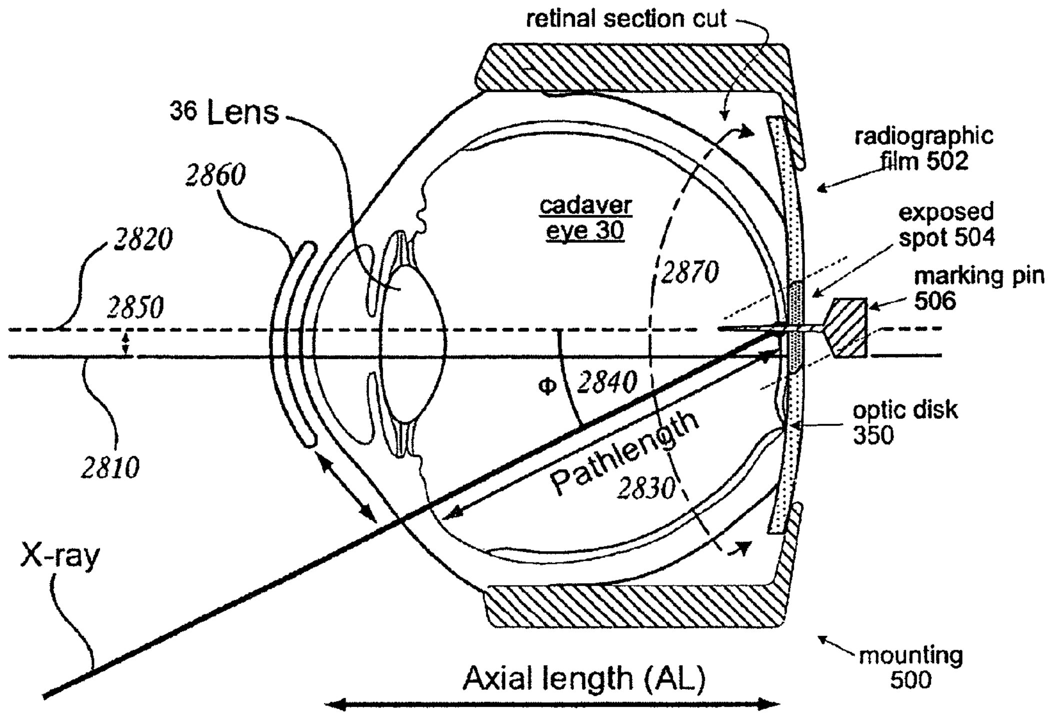
Figure 44B:
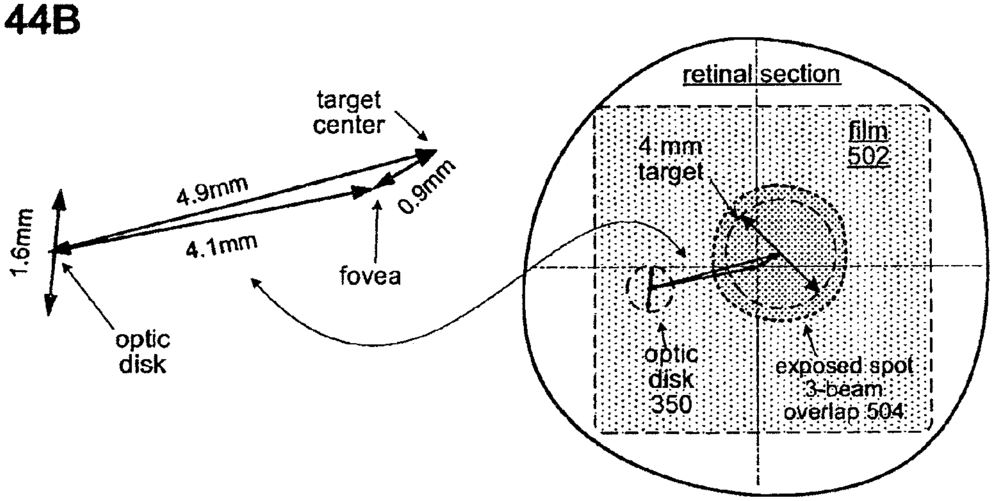
Figure 45A:
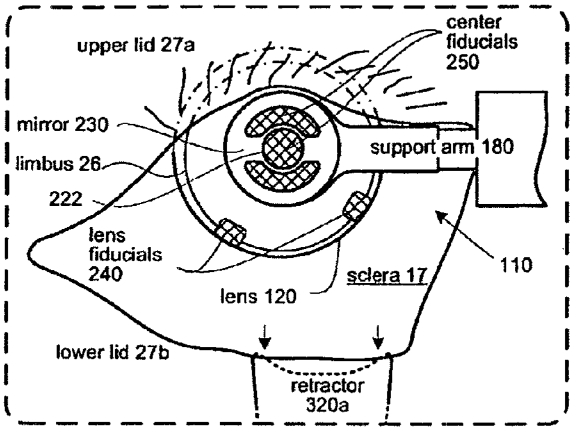
Figure 45B:
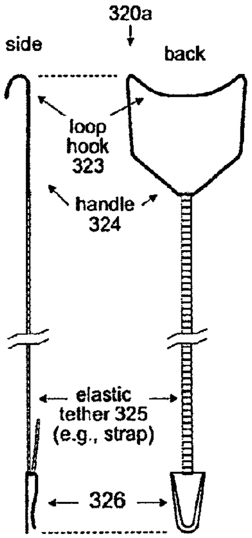

FIGS. 44A-B depicts a method of confirming an embodiment of a radiotherapy treatment plan having aspects of the invention using radiographic measurements on a cadaver eye FIGS. 45A-B depicts one embodiment of an eye-guide having aspects of the invention engaged with an eye having one embodiment of an eyelid retractor.

Figure 46A:
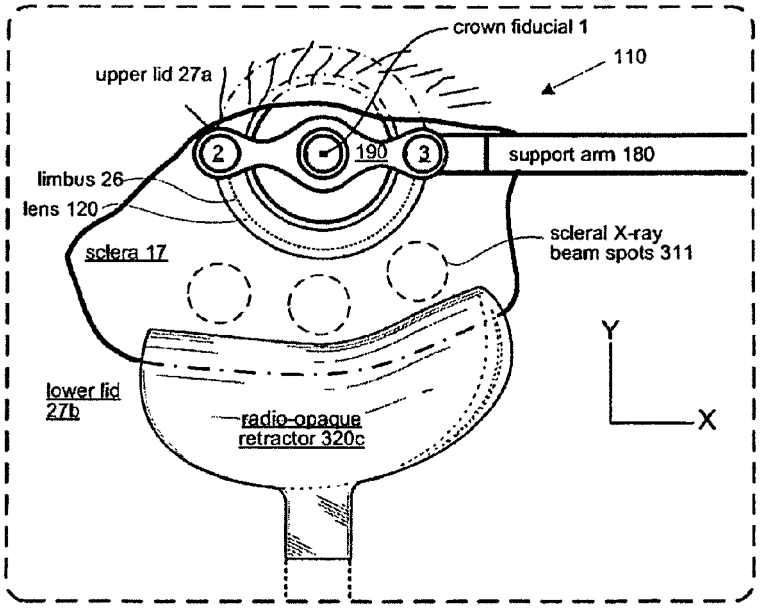
Figure 46B:
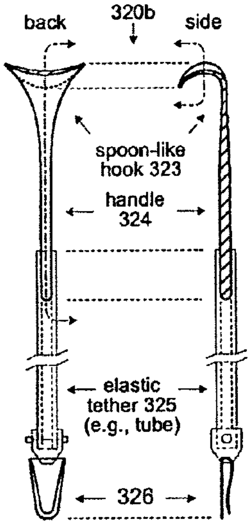

FIGS. 46A-B depicts an alternative embodiment of an eye-guide having aspects of the invention engaged with an eye having an alternative embodiment of an eyelid retractor.

FIG. 47A schematically illustrate a eye-guide device for use in a eye stabilizing system having aspects of the invention having a number of alternative fiducial configurations.

FIGS. 47B1-I schematically illustrate a eye-guide device for use in a eye stabilizing system having aspects of the invention, and having patterned fiducials, and a method of determining orientation by image recognition.

FIGS. 48A-F illustrate an eye-guide device having a pattern of fiducials, the guide for use in a eye stabilizing system having aspects of the invention, shown in contact with an eye and depicting the method of determining alignment.

FIGS. 49A-E are plots showing eye movements experimentally measured with an embodiment of a system for controllably positioning and/or stabilizing the eye of a subject.

Figure 50:
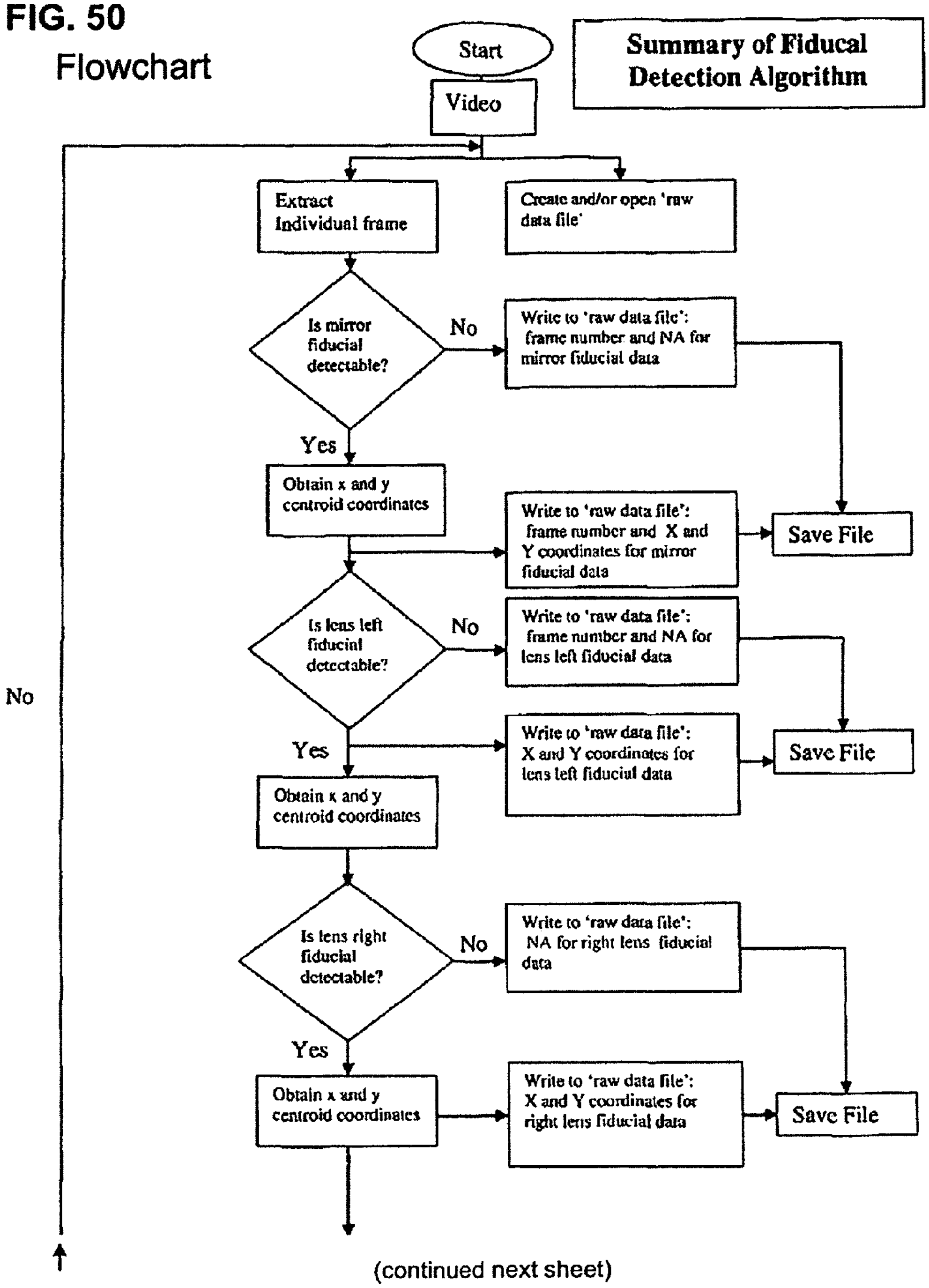
Figure 50:
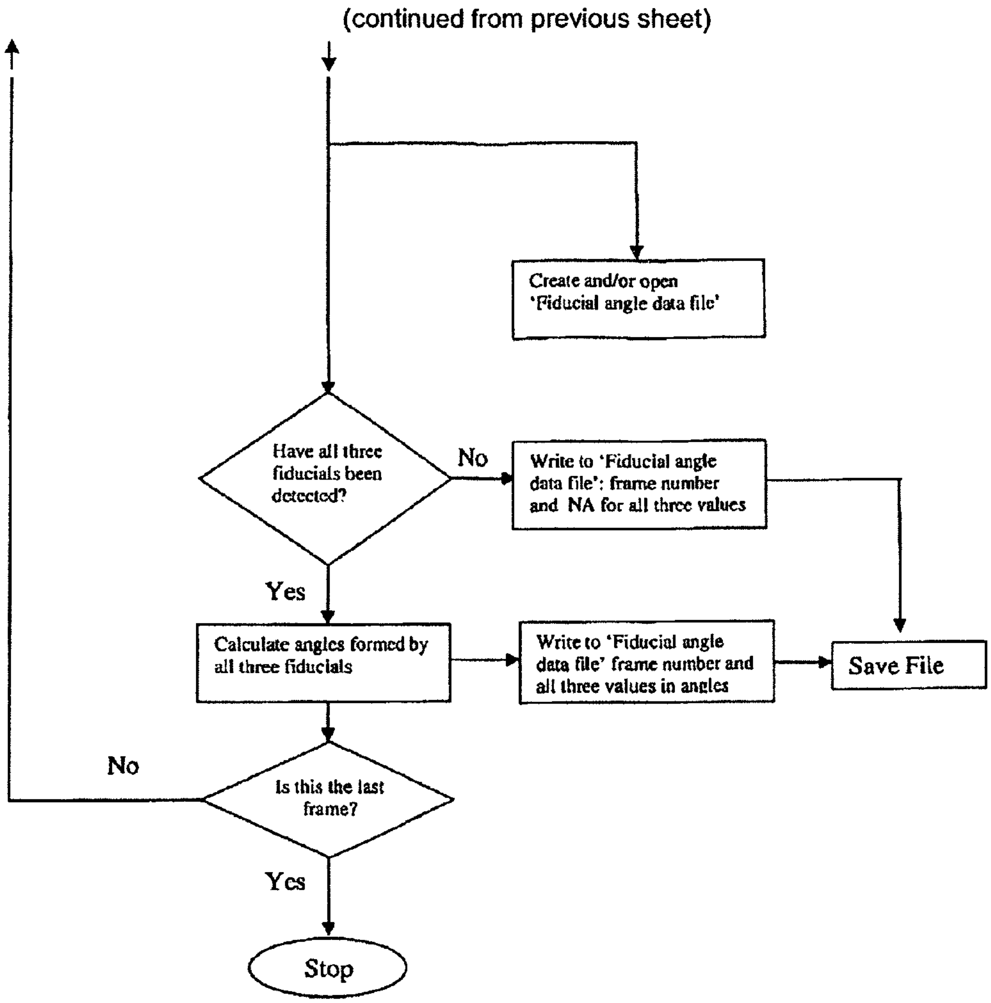
Figure 51:
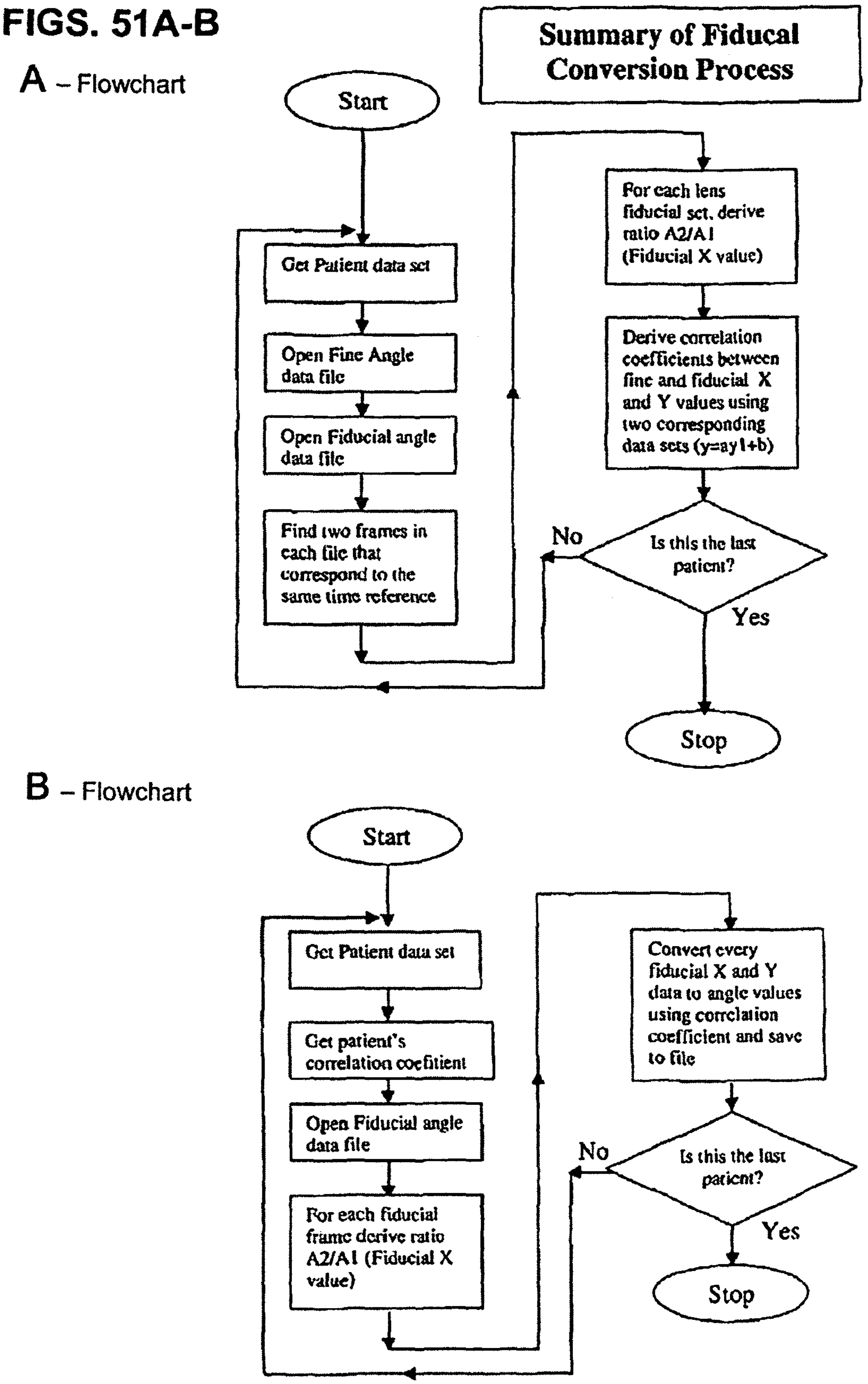

FIGS. 50 and 51A,B are flowcharts illustrating eye-guide fiducial image data acquisition and processing methods.

FIGS. 52A-B are two views plan view of an eye-guide included in a eye stabilizing system having aspects of the invention, shown in contact with an eye during X-ray treatment, illustrating the effect on retinal position of motion of the eye in the system Z direction.

FIGS. 53A-B are two views plan view of an eye-guide having aspects of the invention in contact with an eye during X-ray treatment, illustrating the effect on retinal position of rotational motion of the eye.

FIGS. 54A-B are views illustrating from a frontal perspective the motion shown in FIGS. 53A-B.

FIG. 54C is a flow chart illustrating an exemplary planning method including determining a safe or allowable eye movement threshold to be permitted during treatment.

FIG. 54D, view (1)-(3) illustrate the relation of retinal motion to radiation dose distribution.

C. Alternative Radiation Beam Treatment.

FIGS. 55A-D are views illustrating an alternative methods and devices having aspects of the invention including micro-fractionated beams directed through the cornea to a retinal target.

FIGS. 56A-E are views illustrating an alternative methods and devices having aspects of the invention including a plurality of narrowly collimated beams directed through the cornea to a retinal target.

FIGS. 57A-H are views illustrating an alternative methods and devices having aspects of the invention including a narrowly collimated beams directed via continuous or semi-continuous motion along corneal track patterns, so as to penetrate through the cornea to a retinal target.

FIGS. 58A-C illustrate an embodiment for tracking retinal motion by altering beam path using a moveable collimator exit plate.

FIGS. 59A-D illustrate an eye-guide device for use in a eye stabilizing system having aspects of the invention, the guide having a widow or transparent portion permitting retinal imaging during treatment.

FIGS. 60A-E illustrate an alternative eye-guide device having a widow or transparent portion; and having a support arm structure comprising a plurality of joints.

DETAILED DESCRIPTION

The following disclosure is related to the subject matter with is found in the priority applications, in particular U.S. application No. 61/093,092 filed Aug. 29, 2008; No. 61/076,128 filed Jun. 26, 2008; Ser. No. 12/103,534 filed Apr. 15, 2008; Ser. No. 12/100,398 filed Apr. 9, 2008; Ser. No. 12/027,069 filed Feb. 1, 2008; each of which is incorporated by reference, to which the reader is directed for further description and examples which are relevant to the disclosure herein. In particular, these applications describe devices and methods of ocular radiotherapy, methods of planning treatments, and eye alignment and stabilization devices and methods having aspects of the invention.

Embodiments for Highly-Collimated External Beam Therapy

As described in detail below, embodiments of methods and devices of the invention include a number of aspects which may be usefully employed in combination or separately, and which may be advantageously used to treat a range of disease conditions, both of the eye and other regions of the body. The examples described in particular detail focus on treatment of conditions of the eye, and in particular, the retina of the eye, such as the treatment of wet age-related macular degeneration (AMD).

It should be noted, however, that the methods and devices of the invention are not limited to such use, and the priority applications incorporated by reference describe a broad range of applications (see for example Ser. No. 11/956,295 filed Dec. 13, 2007). Examples include radiotherapy on tissue in the anterior chamber following glaucoma surgery, such as trabeculoplasty, trabeculotomy, canaloplasty, and laser iridotomy, to reduce the likelihood of postoperative complications; and in the treatment of drusen, and the like. In some embodiments, x-ray therapy is combined with invasive surgery such as a vitrectomy, cataract removal, trabeculoplasty, trabeculectomy, laser photocoagulation, and other surgeries.

In addition, while the embodiments described in particular detail below employ treatment beams of orthovoltage X-rays, many aspects of the invention may be usefully applied with other forms of externally delivered electromagnetic radiation. Planned and directed radiotherapy may include gamma radiation, higher energy x-rays, ultraviolet, visible, infrared, microwave, and radiowave energies.

A principal embodiment having aspects of the invention includes an integrated system optimized for treatment of ocular diseases such as AMD, providing stereotactic, low energy X-rays delivered externally as tightly collimated beams, together with synchronous application of real-time ocular tracking and/or ocular stabilization and control. In the preferred embodiments, the treatment is delivered a multiple X-ray beams through selected sites of the pars plana to precisely overlap on the macula over small, well-defined treatment regions, so as to minimize or avoid dosage to critical non-target structures such as the ocular lens, optic disk and optic nerve. Additional aspects of the invention include integration of patient-specific data in phantom models representing the treated eye, and use of these models to plan treatment and treatment beam parameters, to assess the effects of eye motion on actual absorbed radiation dosage, and to provide real-time confirmation and control of treatment dose distribution. Additional embodiments include sub-systems and sub-methods which may be employed with various treatment and diagnostic modalities.

Comparison of Prior Art with Inventive Treatment Embodiments

A body of published literature describes the use of radiation treatment of diseases of the eye, including malignancies as well as benign diseases such as pterygia, AMD, glaucoma, and vascular malformation. These studies indicated that radiation has promise in the treatment of such diseases, and in particular Age Related Macular Degeneration. It should be noted that in prior art radiation treatment of the eye for AMD (and for other diseases treated), the devices used in the trials were not customized or developed to treat the eye and specifically the macula for macular degeneration. In addition, during treatment, there was limited, if any, verification of the orientation of the eye relative to the pre-operative CT scan or verification of maintenance of eye orientation during treatment.

An example of prior art radiation treatment for AMD is shown in FIG. 1 (see also FIG. 11H and discussion in priority application Ser. No. 12/100,398 filed Apr. 9, 2008, which is incorporated by reference). FIG. 1 compares a prior art radiation beam 5 (see Marcus et. al., *Radiotherapy for recurrent choroidal neovascularization complicating age-related macular degeneration*; Br. J. Ophthalmology, 2004; 88 pps., 114-119, which is incorporated by reference), with a finely collimated orthovoltage radiosurgery treatment beam 11 emitted by a radiotherapy system 10 having aspects of the inventions herein, each treatment beam shown superimposed on a CT scan 20 of the anterior portion of a patients head 22.

The prior art treatment beam 5 is representative of previous treatments using external beam radiation to treat AMD, and is produced by a large linear accelerators were used without localization or customization specifically for the eye, having an energy of about 6 MeV. The prior treatment beam path 6 has a very large field size (about 3 cm diameter) which covers the entire posterior pole of the retina and the optic nerve 24 of the treated eye 26. Furthermore, although the prior art beam path 6 has been angled to reduce radiation to the non-target eye 30, the contralateral optic nerve 32 extends well within the beam path 6.

Due the penetrating nature of the MeV radiation and the beam width, among other things, prior art treatment beam 6 results in substantial irradiation of the non-targeted structures. Note that the 90-100% isodose volumes encompass the entire ipsiliateral retina, optic nerve and optic disk, while the contralateral optic nerve of the non-target eye receives about 63% of the maximum dose. The dosage of the trials described in Marcus were: at 100% isodose about 2 Gy per fraction, and at 63% isodose, about 1.26 Gy per fraction (Marcus, D. M. et al., *External beam irradiation of subfoveal choroidal neovascularization complicating age-related macular degeneration: one-year results of a prospective, double-masked, randomized clinical trial*, Arch Ophthalmol, 2001 119(2): p. 171-80, which is incorporated by reference).

Due to substantial irradiation of the non-targeted structures, the prior art treatment, the treatments performed in Marcus et. al. required fractionation of the dose over many days and with small fractions in order to prevent damage to normal tissues. In addition, these prior art attempt at applying radiation to the macula did not consider eye movements or eye position. This requires administering the doses under a fractionation protocol with up to 7 treatments of the lesion. Such fractionation and minimalist dosing and planning schemes likely lead to the lack of efficacy in those studies. The study generally showed that at 1-year follow-up, the particular low-dose external beam irradiation used, at 14 Gy in 7 fractions of 2 Gy each, is neither beneficial nor harmful for subfoveal CNV complicating ARMD.

In contrast, the beam path 12 of a finely collimated orthovoltage X-ray beam 10 is also depicted. In the particular treatment embodiment shown, a micro-collimated beam 10 of about 100 keV is emitted to enter the sclera of eye 30 in a very small beam spot at the pars plana region 34, the beam path 12 having an orientation configured to effectively avoid cornea 35, lens 36 and optic nerve 32 of target eye 30. Beam 10 has been experimentally and theoretically verified to deliver a dose of about 18 Gy to the sclera, penetrating there-from to the retina to deliver a therapeutic dose of about 8 Gy to the macular region 38. Thereafter, the radiation is scattered by the bone behind the eye to about 1-2 Gy at point 40 in the brain and quickly attenuates to about 0.5 Gy at point 42 in the brain tissue and the bone of the skull 22.

As is discussed in detail elsewhere in this application, embodiments of radiosurgery treatment beams having aspects of the inventions employ orthovoltage X-ray beams of a carefully selected maximum energy and spectral characteristics, a favorable ratio of scleral surface dose to delivered macular dosage may be provided (in this example, about 2.25:1). In addition, modest maximum photon energy provides rapid attenuation of the treatment beam beyond the target region, minimizing dosage to non-targeted structures. When multiple beams having stereotactically aligned target regions, these advantages be increased. In the example shown in FIG. 1, three such beams emitted along paths at different angles on the eye (different surface entry points) can provide a dosage summation on the macula of 24 Gy, with only 18 Gy to each entry points on the sclera.

Another significant limitation of the treatments in prior art external beam trials, there was no accounting for eye movement and position during the treatment. The CT scan 20 in FIG. 1 represents an ideal case and it was assumed that the eye position during the treatment time (30-60 s) was similar to the CT scan and constant. However, the eye movement and the center of rotation vary from patient to patient, and it is difficult to know the exact dose applied to the macula.

FIG. 2 similarly depicts the target region of the posterior eye 50 receiving a prior art proton treatment beam 52 (Adams, J. et. al; Medical Dosimetry 24(4) 233-238, which is incorporated by reference). In this study, the proton beam is centered on macula 54, although the 90% isodose line encompasses both the macular and the entire optic nerve 56. In addition, eye location and movement were not controlled in this study. The authors of this study reported significant complications, likely due to the very broad coverage of the retina with 20-24 Gy of proton beam radiation in 12 Gy fractions. Such complications likely negated any benefit of the therapy. The x-ray delivery methods having aspects of the invention described herein allow for delivery only to the macula where the disease exists while limiting or avoiding delivery of x-rays to other regions that are not diseased.

As is discussed in detail elsewhere in this application, embodiments employ a number of methods for incorporating both control and verification of eye position and movement during radiation treatment. Other embodiments incorporate patient-specific data such as fundus images, OCT and A-scans, in phantom models used to plan and control treatment and used to assess actual administered dosage distribution on a real-time basis.

It should be noted with emphasis that device and methods having aspects of the invention have utility and advantages over the prior art in treatments other than those described in particular detail below. For example, higher energy radiation (greater than 500 keV) may also be advantageously employed using methods of the invention for treatment of lesions of the eye and other parts of the body. Methods of controlling and tracking eye motion described herein may be advantageously employed with other treatment and diagnostic modalities. Methods of producing and using phantom models incorporating patient-specific data may be used for treatments for diseases other than AMD, and for treatments other than to the eye.

Radiotherapy Overview

FIG. 3 shows a schematic overview of an embodiment of a treatment planning system and method 800 having aspects of the invention, which is depicted as a global interconnect encompassing four subsystems. The treatment planning system (TPS) 800 also provides the interface between the physical world of the eye, the physical components of the system, and a virtual computer environment which interacts with the physician and treatment team and contains the specific patient and disease information. The treatment planning system 800 directs the four subsystems in treatment of the region and/or disease as directed by the physician. The four subsystems in general terms include an X-ray subsystem 700 (producing treatment radiation), a coupling subsystem 500 (aligning to and/or stabilizing the tissue being treated), an electromotive subsystem 600 (positioning the x-ray subsystem), and an imaging subsystem 400 (capturing information from the coupling system, the x-ray subsystem and the patient). In some embodiments, maximum beam energy X-ray subsystem 700 is set by the treatment planning system 800 in order to create doses and plans for specific diseases. The coupling system 500 and the imaging system 400 function to link the physical world (patient and treatment device) and the virtual world (e.g., computer model of treatment plan incorporating patient-specific data. These subsystems or modules interact to provide an integrated treatment to the eye of a patient.

The treatment plan is developed based on a combination of biometric modalities including an imaging subsystem 400 that can include, for example, fundus photography, or optical coherence tomography, CT scans, MRI scans, and/or ultrasound modalities. The information from these modalities are integrated into a computer-generated virtual model of the eye which includes the patient's individual anatomic parameters (biometry) as well as the individual's specific disease burden. Any or all of these modalities can be utilized by the system in real time or integrated into the system prior to treatment. The treatment plan is output, for example, on the interface display 130 module of the radiotherapy system 10. The physician can then use the virtual model in the treatment plan to direct the radiation therapy to the disease using the radiotherapy system 10.

As used herein, "eye model" or "model of the eye" refers to any representation of an eye based on data, such as, without limitation, an anteroposterior dimension, a lateral dimension, a translimbal distance, the limbal-limbal distance, the distance from the cornea to the lens, the distance from the cornea to the retina, a viscosity of certain eye structures, a thickness of a sclera, a thickness of a cornea, a thickness of a lens, the position of the optic nerve relative to the treatment axis, the visual axis, the macula, the fovea, a neovascular membrane, a curvature of a cornea or a retina, a curvature of a scleral region, and/or an optic nerve dimension. Such data can be acquired through, for example, imaging techniques, such as ultrasound, scanning laser ophthalmoscopy, optical coherence tomography, other optical imaging, imaging with a phosphor, imaging in combination with a laser pointer for scale, CT scan with or without contrast, and/or T2, T1, or functional magnetic resonance imaging with or without contrast. Such data can also be acquired through keratometry, refractive measurements, retinal nerve-fiber layer measurements, corneal topography, direct caliper measurement, etc. The data used to produce an eye model may be processed and/or displayed using a computer. As used herein, the term "modeling" includes, without limitation, creating a model.

The eye model is a virtual model which couples the anatomy of the eye with the coordinate system of the radiotherapy device. The eye model can be based on the geometry of the ocular structures and can be derived with parametric data and mathematical formulas to generate the model. Alternatively, the ocular geometries are derived from cross-sectional imaging, such as from CT scans or MRIs. With the treatment axis defined and the ocular anatomy defined, the coupling device can contact the ocular surface and link to the radiotherapy device via the eye model. The radiotherapy device may then be positioned based upon the eye model.

Figure 4:
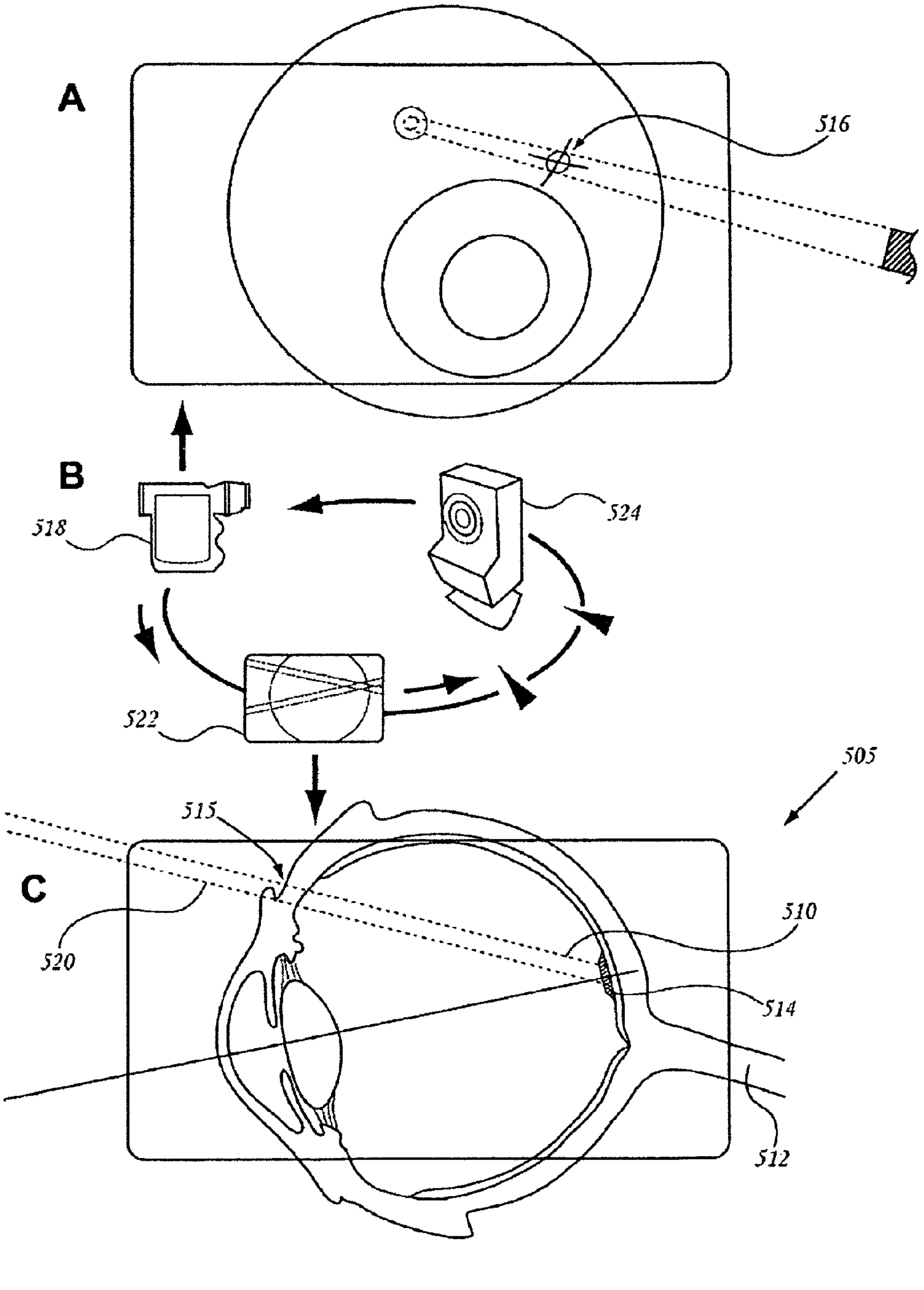

FIG. 4, views A-C, show a schematic overview of the relation between the treatment planning system and its eye model with various components of radiotherapy system 10 in the treatment of eye 30. Within the virtual world, the treatment planning system creates a computer-generated virtual model of the patient's eye 505 based on physical and biometric measurements taken by a health practitioner or the imaging system 400 itself. The computer model 505 in the virtual world further has the ability to simulate the projection 510 of an x-ray beam 520 from a radiation system 524 through an anterior region of the eye, which can include a traversal or intersecting zone 515, to the structure 514 to be treated based on different angles of entry into the eye. The model can also identify and include important eye structures, such as the optic nerve 512, to consider during the treatment planning process. The virtual world also contains the physician interface to control the device 524 and interface the device with respect to the physical world, or that of the actual physically targeted structure. After integrating the inputs from the physician and modeling the beam angles and desired direction to direct the therapy, the virtual world outputs the information to the electromotive subsystem to move the x-ray device to the appropriate position in three-dimensional space. The coupling subsystem 500 (in the physical world) can include a mechanism to determine the angle of incidence of the x-ray beam with respect to the surface of the eye using one or more laser or angle detectors, as discussed above.

In some embodiments, the coupling system 500 contains a camera 518 which can image a spot (real, reflected, fiducial, or projected fiducial) 516 on or in an eye; the camera can also visualize structures such as the pupil, cornea, sclera, limbus, iris, fundus, optic nerve, macula, or a lesion to be treated. Information from the camera is then preferably transferred to the virtual eye model 522 and again to the motion and radiotherapy system 524. In certain embodiments, the coupling system 500 is a physical connection with the eye. In some embodiments, the coupling system 500 is not a physical link but is a communication link between a lens on the eye and a detection system. For example, a lens can be a communication beacon to relay eye position to the system 500. In some embodiments, the lens can contain markers that are imaged by the imaging camera 518, through which the next stage in the therapy can be determined. In some embodiments, a combination of these techniques is used.

FIG. 5 depicts the relation of the treatment planning system 800 to other system components. Treatment planning system 800 forms the focus of an exemplary method of treatment using radiosurgery system 10. In certain embodiments, the imaging module 400 of the system 10 includes an eye registration and imaging system 810. In certain embodiments, the eye-tracking system is configured to track patient movement, such as eye movement, for use by the treatment planning system 800. The eye-tracking system 810 can calculate a three-dimensional image of the patient's eye via physician inputs, and can include real-time tracking of movement of the patient's eye. The eye-tracking system obtains data for determining radiotherapy treatment planning for a number of medical conditions relating to the eye, as described herein. For example, the eye-tracking system may create an image of the posterior region of the patient's eye using the data it obtains.

The treatment planning system 800 may utilize, or be coupled to, imaging systems such as, for example, optical coherence tomography systems (OCT), ultrasound imaging systems, CT scans, MRI, PET, slit lamps microscopy systems, direct visualization, analogue or digital photographs (collectively referred to as Biometry Measurements 820). In some embodiments, these systems are integrated into real-time feedback systems with the radiotherapy device such that second be second system updates of eye position and status can take place. Although relatively sophisticated, the system 800 may be limited to the ophthalmic region and therefore takes advantage of specific imaging equipment only available for the eye. In some embodiments, the treatment planning system incorporates the soft tissue and bony structures of the head of a patient in addition to treated eye 30.

In some embodiments, the treatment planning system incorporates physical modeling techniques such as Monte Carlo (MC) simulation into the treatment plan so that the real time x-ray doses can be delivered to the ocular structures. In these embodiments, the inputs to the treatment planning system 800 are integrated with Monte Carlo simulation of the planned treatment plan and the effects of the plan, both therapeutic and potentially toxic, can be simulated in real time. In some embodiments, geometric ray tracing models are used with estimates based on prior Monte Carlo simulation. Ray tracing models with prior Monte Carlo support rapid and real time simulation of dosimetry.

As depicted in FIG. 5, biometry measurements 820 and user controls 875 such as anatomic structure and radiation dose may entered into the treatment planning system 800. Other inputs include information from an eye registration and imaging system 810. The output from the treatment planning system 800 consists of commands sent to the x-ray source and electromotive subsystem to move and position the source as well as to direct the on and off times (dose control) of the x-ray source 830. In some embodiments, maximum beam energy is set by the treatment planning system in order to create doses and plans for specific diseases. After a dose 840 is delivered, the treatment planning system 800 then signals x-ray source movement to deliver an additional dose 840. This cycle can iterate several times until the treatment is completed.

FIG. 6 depicts an exemplary clinical flow method involving the radiotherapy device 10. An imaging modality and physical exam 3500 are used to create an eye model 3510, through which a 3D coordinate map is generated. The dose for a specific disease is chosen as is the maximum beam energy based on the region to be treated as well as the region to be avoided. These variables can be determined by treatment software as well as physician input related to the disease as well the depth of the diseased tissue. The patient is then positioned, and the optional contacting device is placed against or close to the eye of the patient 3520. The patient and radiotherapy device are aligned with the guide 3530, and the treatment of a dose of radiation is applied 3540. Optionally, an imaging system is included in the unit and optionally an eye tracking system is included in the unit. Furthermore, a gating system may also be incorporated into the system in which the device is turned off with a pre-determined amount of eye movement.

FIG. 7 depicts a cross-sectional view of an eye 30, shown in association with an embodiment of a radiotherapy system 300 having aspects of the invention. In the example shown in FIG. 7, target 318 is centered approximately the fovea 344, and collimated orthovoltage X-ray beam 311 at entry to the sclera may have a effective beam with of $W_e$ (e.g., as defined by a boundary at the 90% isodose). The beam 311 spreads at it propagates through the eye, to have an effective beam width of $W_t$, which covers an area surrounding the target constituting the treatment region, in this case corresponding to the macula.

In the example shown, for beam axis 311, a rotational angle Φ may be selected to define a propagation path for the beam which avoids vulnerable structures such as the optic nerve 350. Note that the treatment axis 19 may be different from geometric axis 18, selected having a known position and orientation with respect to axis 18. For example, axis 19 may have a lateral offset from geometric reference axis 18, and the rotational angle Φ may be selected to assure a desired minimum corneal clearance for beam entry.

The positioning device 310 may conveniently have actuators providing for several degrees of freedom of motion for treatment device 312, such a 5 DOF device providing x-y-z adjustment relative to the patient's eye, and rotation for the angles Φ (angle with respect to treatment axis 18) and θ (angle of rotation around treatment axis 18) as is further described below. See, for example the constrained positioning system for an X-ray source and collimator, as described and shown with respect to FIGS. 12E-F of co-invented/owned U.S. patent application Ser. No. 12/100,398, entitled "Orthovoltage Radiosurgery" filed Apr. 9, 2008 by Gertner et al., which is incorporated by reference. Further exemplary embodiments of radiation source positioning systems are described with respect to FIGS. 33-38 herein.

Radiotherapy system 300 may include an eye positioning and/or stabilizing device 110, such as is described further in FIGS. 39-49 herein. See also in particular the eye positioning, aligning and/or stabilizing devices and methods described in co-invented/owned U.S. patent application No. 61/076,128 filed Jun. 26, 2008; Ser. No. 12/103,534 filed Apr. 15, 2008; and Ser. Nos. 12/027,083, 12/027,094 and 12/027,069, each filed Feb. 1, 2008; each of which is incorporated by reference.

Without departing from the spirit of the invention, one of ordinary skill in the art will appreciate that for a specialized device optimized for a particular range of treatments, fewer degrees of freedom may be provided, as, for example, when certain of the parameters described may reasonably be fixed. Note in this regard that an eye positioning and/or stabilizing device 110, such as shown if FIGS. 39-40 herein, may include actuators (or employ manual patient movement) sufficient to change the position and orientation of the treated eye 30, so as to substitute for degrees of freedom of the positioning device 310 with respect to the treatment device 312. Thus, the patient and/or eye may be moved in one or more parameter with respect to device 312, until it is determined that the treatment path 311 is correctly aimed at target 318 (which may be confirmed by the alignment system).

In some embodiments, one or more additional imaging camera systems may be included. In the example shown in FIG. 7, camera 322 is configured to be positioned by positioning device 310, and aimed so as to obtain an image of the area of intersection of therapeutic beam 311 with an exposed body surface, such as an exposed area of the scleral surface of the eye. Additionally, a reference light beam may be provided to illuminate and/or mark the of intersection area. For example, device 312 may incorporate a laser pointer beacon along a path coincident with therapeutic beam 311 (e.g., directed by a co-aligned mirror), so as to indicate the intersection of beam 311 on a surface of the eye (e.g., for visual or automated confirmation of the alignment of beam 311, or the like). Alternatively, a reference light beam may be provided which is not aimed along a path coincident with therapeutic beam 311, for example, configured to be aimed by positioning device 310 on a path intersecting the surface at area (see FIG. 2C and related description of co-owned U.S. application Ser. No. 11/873,386 filed Oct. 16, 2007, which is incorporated by reference).

Further description of particular aspects of system 10 may be found below and in the priority applications, in particular Ser. No. 12/103,534 filed Apr. 15, 2008; Ser. No. 12/027,069 filed Feb. 1, 2008; and Ser. No. 12/100,398 filed Apr. 9, 2008; each of which is incorporated by reference.

Orthovoltage Radiation Characteristics

Medical X-rays are typically produced by accelerating electrons in order to collide with a metal target, the X-rays being emitted as the electrons interact with the target material. Higher energy X-rays (typically greater than about 1 MV) may be produced by electrons accelerated by linear particle accelerators (LINAC). Lower energy X-rays (typically less than about 600 kV) are generally produced by electrons accelerated from cathode to anode in an X-ray tube.

In the X-ray tube, the electrons suddenly decelerate upon colliding with an metal anode target. The X-ray spectrum produced is characterized by a broad "bremsstrahlung" or braking radiation spectral curve resulting from the interaction of the accelerated electrons with the target anode material. This process induces X-ray emission over a smoothly varying range of photon energy levels (wavelengths), corresponding to the statistical variation in the electron energy loss during deflection by atomic nuclei, the spectrum reaching a maximum photon energy corresponding to the magnitude of anode-to-cathode tube potential field. There are also superimposed distinct narrow spectral peaks (characteristic lines) corresponding to discrete energy level transitions within the atoms of the anode material (e.g., tungsten, copper or the like) as atomic electrons interact with the field-accelerated electrons.

Within the x-ray regime of electromagnetic radiation, low energy x-rays can be referred to as orthovoltage. In some usages, the X-ray regime is more finely subdivided with respect to maximum spectrum photon energy so as to correspond to types of medical and industrial applications (such as diagnostic X-rays 20-50 kV; superficial X-rays 50-200 kV; orthovoltage X-rays 200-500 kV; super-voltage X-rays 500-1000 kV; and megavoltage X-rays 1 to 25 MV).

However, for the disclosure herein, the term "orthovoltage X-rays" includes X-ray radiation having a spectrum with maximum photon energies from about 20 kV to about 500 kV. This includes radiation which in certain medical usage may be referred to as "superficial" or "diagnostic" in reference to a relatively reduced tissue penetration. Methods of selection of an X-ray spectrum, including maximum photon energy and filtration, for employment in a particular radiotherapy treatment plan are described and shown with respect to various alternative embodiments having aspects of the invention.

FIG. 8 depicts an exemplary set of orthovoltage X-ray spectra showing a trend of characteristic photon energy distribution with increasing source tube voltage, for a number of examples of tube potential. The term "kVp" refers to the maximum (peak) voltage of the x-ray power supply to the X-ray tube. When x-rays are generated by electrons accelerated in the high voltage electrical potential field of typical X-ray tube, a spectrum of x-ray of various photon energies is obtained. This spectrum is characterized by a broad bremsstrahlung spectral curve for each x-ray source kVp level. For the higher tube kVp levels (e.g., about 80 kVp and above), there is superimposed on the bremsstrahlung spectrum a series of characteristic lines corresponding to atoms of the anode material (e.g., tungsten).

The maximum voltage (tube kVp) is typically identical to maximum X-ray photon energy of the emitted spectrum, showing linear variation over the plotted range of tube potentials. For example, the 80 kVp spectra in FIG. 8 has a maximum of 80 keV with a leftward tail of lower energy radiation. Similarly, the 60 kVp spectrum has a maximum of 60 keV with a similar leftward tail. It may be also seen that the photon energy corresponding to the peak of the photon flux curve (peak flux energy) increases with increasing tube potential, although non-linearly. In this filtered example, the peak flux energy changes from about 28 keV to about 35 keV over the potential range of 40 to 80 kVp.

All spectra in FIG. 8 have been filtered through 3 mm of aluminum (extrinsic filtration) in addition to penetrating the X-ray tube structure at the exit window (intrinsic filtration, e.g., 0.8 mm beryllium). Filtering re-shapes the spectral curve. Each energy of photon attenuates through matter at a different rate, whether the matter is patient tissue or an extrinsic filter material such as aluminum. For instance, a mono-energetic flux of 10 kV x-rays incident on a block of aluminum will be attenuated by a factor of 2 (to half intensity) after about 0.1 mm, while a mono-energetic flux of 100 kV photons will be able to penetrate almost 22 mm before losing half their intensity. Thus lower energy photons (longer wavelengths) are filtered or absorbed to a greater degree than higher energy photons (shorter wavelengths). Absorption by the filter material tends to eliminate variation in the spectra of the different tube kVp levels over the low photon energy range, with each spectrum in this example substantially absorbed at photon energies below about 20 keV.

Filtering of the raw spectra is useful to customize the x-ray energy for the application at hand where the lower energy photons, if not filtered, would be absorbed by superficial structures near the body surface (e.g., the sclera of the eye), while higher energy photons can propagate to deeper tissue. In an example of radiotherapy applied to a retinal lesion, to the extent that it is desired that x-ray energy reach the structures of the retina with minimal energy absorption by the anterior structures of the eye, filtering of the raw spectra is advantageous; with filtering, the resulting spectrum contains a greater amount of high energy photons than low energy photons. As described, for some disease processes, it is desirable to have a predominance of low energy x-ray reach the anterior structures of the eye in which case the lower voltages will be used with correspondingly lower keV peaks. Adjustment of the power on the power supply will result in a decrease in the peak voltage of x-rays, limiting the amount of higher energy photons. In some embodiments, it may be desirable that a non-uniform filter be used. For example, the filter may have varying thicknesses across it to accommodate varying differences in the X-ray spectra in one treatment region.

FIG. 9 depicts an set of 80 kVp X-ray spectra showing a trend of photon energy distribution with increasing thickness of filter material (aluminum plate). It may be seen that without external filters, the spectrum emitted by a typical X-ray tube includes a large flux at low photon energies. The effect of increasing filter thickness (curves for 1 mm, 2 mm and 3 mm of Al plate) may be seen to substantially reduce the total area under each curve, reducing the total X-ray flux.

However, it is also readily apparent that the reduction in X-ray flux (moving towards increased filter thickness) is more dramatic at the low energy portion of the spectrum at the right of the plot (least penetrating photons), and has little effect on the flux of the higher energy photons at the left of the plot (most penetrating photons). This effect can be seen indicated by the shift of peak flux energy to the left with increasing filter thickness, from about 30 keV to about 37 keV over that thickness range of 1 to 3 mm aluminum. As a consequence, where the filtered X-ray beam is to be directed into tissue, the selection of the filter thickness alters the proportion of photons which are absorbed near the tissue surface relative to the portion absorbed at any selected target depth, as further describe herein. Embodiments having aspect of the invention employ this effect to obtain highly advantageous treatment beam properties.

FIGS. 10 and 11 demonstrate the effect of filter selection on the ratio of radiation dosage absorbed at tissue surface to that absorbed at a selected tissue depth, as a function of filter thickness and X-ray tube potential (maximum photon energy). The data shown has been demonstrated by inventors herein both through simulations ("Monte Carlo" simulation using MCNP Radiation Transport Code developed by Los Alamos National Laboratory), and by radiometric experiments using water-equivalent phantom material, which may be referred to herein as "solid water". Several generally similar water-equivalent phantom formulations are commercially available from different sources; the one used in the data presented was Solid Water® by Gammex Inc. of Middleton, Wis.

FIG. 10 is a plot showing the depth propagation/absorbs ion curve for an exemplary treatment beam penetrating simulated tissue (solid water). The beam is emitted at 100 kVp, filtered by a 0.8 mm Be tube window and 0.75 mm Al external filter. The plot is the dose fraction (vertical axis) reaching a given depth or thickness of solid water (horizontal axis), which may be referred to as "path length". In an example relevant to certain ocular radiotherapy embodiments, a tissue path length of about 19 mm is within the typical anatomical range for the retinal depth for a beam entering near the pars plana of the eye.

It may be seen that for this path length, the fractional depth dose is about 0.35, and thus for these beam parameters, about ⅓ of the X-ray flux reaches this tissue depth, the balance of about ⅔ of the flux having been absorbed within the volume extending from 0 to 19 mm. This may be referred to herein as dose surface-to-depth ratio, which is the inverse of fractional depth dose, although both expressions may be seen to be indicative of the same physical effect.

FIG. 11 is a plot showing the effect of a range of X-ray tube potentials (maximum photon energy) and the effect of two different filter thicknesses (1 mm and 3 mm Al) on the depth-dose ratio in simulated tissue, measured at a typical retinal depth or path length of about 20 mm. While differing soft tissue composition and anatomical dimensions will alter data in detail, the trends shown are characteristic and instructive of the principles employed in method and device embodiments herein.

It will be seen in FIG. 11 that for both filter thicknesses, there is a trend towards a lower ratio of surface or entrance dose to depth dose as the tube potential increases, which is implied also by the data of FIG. 8, in that for a given filter thickness, increased tube kVp results a flux dominated by more penetrating photons. It will also be seen in FIG. 11 that the effect of increasing filter thickness is to reduce the surface-to-depth ratio over the entire range of tube potentials. The trend for both filter thicknesses is that the slope of each curve decreases as the tube potential is increased, further increments of tube potential resulting in smaller decreases in surface-to-depth ratio.

FIG. 12 depicts an exemplary sequence of spectra corresponding to the propagation of a radiotherapy beam through system filters and simulated patient tissue anatomy. This example is configured as an ocular treatment via a narrowly collimated beam entering through the sclera near the limbus and penetrating through the macula and orbital tissue and bone. The beam parameters include a tube potential of 100 kVp with a 0.8 mm Be tube window and 0.75 mm Al filter. An energy spectra analysis was performed based on an "Monte Carlo" simulation (MCNP Radiation Transport Code developed by Los Alamos National Laboratory) of the effects of matter on the propagation and absorption of a typical X-ray beam emitted at a potential of 100 kVp (e.g., Comet MXR160HP/11 tube). Monte Carlo modeling begins with a defined input spectrum, and determines to dose at any arbitrary point of propagation by statistical modeling, and thus may be used to determine the dose received by various levels within tissue.

The modeled beam begins with a 100 kVp bremsstrahlung spectrum at the surface of the tube anode. The "scleral spectrum" is the spectrum after filtration through the beryllium window and aluminum filtration, propagating through air to the tissue surface. The resulting average beam energy is determined to be about 47 keV at the scleral surface (half the photon flux higher, half lower). The "macular spectrum" is further "hardened" by the passage through 19 mm of tissue and the average energy is determined to be about 52 keV at the macula. These spectra were verified with bench-top measurements using a spectrometer; however, the Monte Carlo simulations are more precise. A further filtered or hardened "brain" spectrum is shown representing the flux passing from the macula through orbital tissue and bone. Note from the surface areas under the curves that the flux passing beyond the macular treatment target is a small fraction of the input to the sclera.

Note that an X-ray tube potential voltage employed in orthovoltage radiotherapy systems having aspects of the invention may be greater or less than the ranges of kVp shown in FIG. 8 through FIG. 12, without departing from the spirit of the invention. A source voltage and/or filter properties may be selected according to embodiments described herein to obtain particular therapy beam properties (e.g., depending on depth of target, propagation tissue path, desired dose distribution and the like).

Monte Carlo Simulation and Validation of Ocular Treatment

Figure 15:
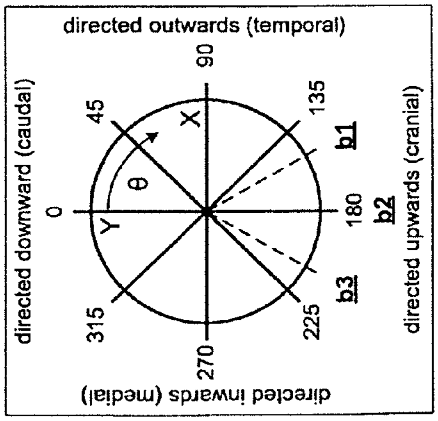
Figure 16:
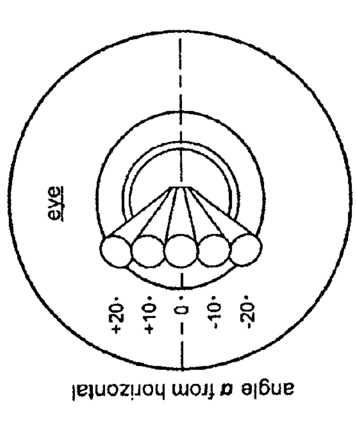

As may be seen from FIG. 12, radiation modeling may be employed to predict the effect of a particular radiation beam on structures within the body. FIGS. 13 to 17 illustrate the application of these techniques, combined with anatomical models of treatment regions to determine the most advantageous treatment plan for a particular therapeutic application. In the examples shown, the treatment plan is directed to radiation applied to a lesion on or adjacent the retina, near the central axis of the eye. In general, FIGS. 13 and 14 illustrate a sub-method embodiment of treatment planning including selecting beam paths in the Φ angular direction (with respect to an Y-Z plane); and FIGS. 15-17 illustrate a sub-method embodiment of treatment planning including selecting beam paths in the azimuth θ angular direction (with respect to an X-Y plane). Both sub-methods may be advantageously carried out using computational simulations of radiation effects, by physical measurements, or by a combination of these.

As described with respect to FIGS. 8-12, Monte Carlo (MC) simulations are used to model x-ray absorption, scatter, and dosing to structures impinged on by x-rays. An example of a tool useful for this type of analysis is the MCNP Radiation Transport Code developed by Los Alamos National Laboratory (see D B Pelowitz; *MCNPX User's Manual Version* 2.5.0, LA-CP-05-0369; Los Alamos National Laboratory, Los Alamos, N. Mex., 2005, which is incorporated by reference herein). Monte Carlo methods are widely used computational algorithms for simulating the behavior of various physical and mathematical systems, and for other computations. They are distinguished from other simulation methods (such as finite element modeling) by being stochastic, that is, non-deterministic in some manner. Computational radiation simulations, such as Monte Carlo analysis and the like, are included in embodiments of treatment planning systems having aspects of the invention, and may be used to assist in treatment planning where radiation is involved.

Monte Carlo simulation can also be used to predict and dictate the feasibility and other elements of the radiotherapy system 10 (e.g., optimization of the collimator and treatment planning schemes); for example, the collimation designs, the energy levels, and the filtering regimes, can be predicted using Monte Carlo simulation. The results of Monte Carlo simulation have been experimentally verified and further improved, based on initial MC simulation. In some embodiments of radiotherapy where the anatomy, beam energies, and treatment volume are similar, the Monte Carlo simulations can be run once and then the path variables altered (e.g., through ray tracing or other geometric methodology) without need to repeat Monte Carlo simulation.

In some embodiments, MC simulation is integrated into the treatment planning systems and in other embodiments, MC simulation provides certain algorithms used by the treatment planning system 800 (see FIGS. 3-6). MC simulation may be in a treatment planning system to create boundaries of treatment. For example, MC simulation can predict the penumbra of an x-ray beam. The penumbra of the x-ray beam is used in virtual world models (see FIGS. 20-24) of to direct the x-ray beam and set boundary limits for the x-ray beam with respect to the lens, optic nerve, etc.

Some embodiments of X-ray treatment system having aspects of the invention are optimized for treatment of age-related macular degeneration (AMD). In alternative embodiments, the x-ray system 10 is used to treat post-surgical scarring in procedures such as laser photocoagulation and laser trabeculotomy or laser trabeculectomy. In some embodiments, the x-ray system is used to treat pterygia, ocular tumors or premalignant lesions such as hemangiomas and nevi. Importantly, the x-ray treatment system allows for selective irradiation of some regions and not others. In some embodiments, radiation is fractionated over a period of days, months, or weeks to allow for repair of tissues other than those which are pathologic or to be otherwise treated. The description of embodiments herein demonstrate that orthovoltage radiation can be delivered to the retina to treat AMD in a clinically relevant time period from a clinically relevant distance; and describe the parameters of such a treatment system.

FIG. 13 illustrates a representative geometric model of the eye used for modeling purposes, showing representative radiation beam angles with respect to an anterior surface and geometric axis of the eye. FIG. 14 depicts results of Monte Carlo simulations performed to analyze the effect of various treatment regimes on the various structures of the eye.

The model of FIG. 13 illustrates a virtual or phantom model of a human eye and adjacent structures, such as may be digitally defined using conventional software tools, displays and input/output devices, and the like. A virtual model may include multiple components, which include different representations of the same anatomical structures. Soft tissue and hard tissue (e.g., bone 2065) was incorporated into the model. Axis 2082 is the geometric axis of the eye, which is further described herein with respect to alignment systems for a radiotherapy device 10.

Within the model are defined representative radiation beam paths, in this example indicated as beam angles 2100, 2110, 2120, 2130, 2140 respectively, the beam paths being defined with respect to the axis 2082 to simulate therapy to the macular region to treat AMD. In this simulation, each beam enters the eye at a different polar angle Φ from the geometric central axis 2082. In this example, the geometric axis is assumed to be the treatment axis of the eye, although as described herein, the treatment axis may have a different position and orientation, relative to the geometric axis. Each of beams 2011-2140 follows a different path through the eye and affects structures, such as, for example, the macula 2094, optic nerve 2085, lens 2075, sclera 2076 (adjacent but removed from the pars plana), cornea 2080, and fovea 2092 differently depending on the path through the eye. This modeling may be used to determine the angle of radiation delivery of the radiotherapy device and may be incorporated into a treatment planning algorithm. For example, in FIG. 13, beam 2120 enters the eye directly through the eye's geometric axis; whereas beam 2100 enters through the pars plana.

In the study, a series of x-ray energies were modeled using an exemplary range of X-ray tube potentials from about 40 kVp to about 80 kVp. A collimation structure was included in the model, configured to produce a narrow, near-parallel beam, as was a series of different filters (about 1 mm to about 3 mm thickness aluminum). The combination of angle of entry of the beam, photon energy of the beam, and filtration of the beam all factor into the relative amounts of energy deposition to the various structures.

FIG. 14 is a bar graph showing representative results from the Monte Carlo study using the model of FIG. 13, for an exemplary study case of beams emitted at an 80 kVp tube potential with the spectrum modified by a filter of 1 mm aluminum. The graph shows scatter doses to ophthalmic regions other than the retina and pars plana, and comparing them to the macula dose. In this plot, the dose is the radiation absorbed by the tissues indicated, measured in Gray (Gy), for a treatment which is scaled to deliver a 25 Gy dose absorbed by the macula target.

As can be seen in the logarithmic figure, the dose to the lens 2400 (beams 2100 and 2140) and optic nerve 2410 (beam 2140 alone), the two most sensitive structures in the eye, are at least an order of magnitude lower than the dose delivered to the macular region 2450 of the retina. Other beam angles result in distinctly higher doses to these structures. Therefore, a 25 Gy dose of radiation can be delivered to a region of the retina through the pars plana region of the eye with at least an order of magnitude less radiation reaching other structures of the eye such as the lens, the sclera, the choroids, retinal regions remote from the macula, and so forth. Beam 2140 is generally representative of the beam orientations (as exemplified in the Y-Z plane of the eye) which are employed in preferred embodiments of methods and devices described in detail herein (see FIGS. 15-17).

These simulations may be advantageously employed in the design of X-ray treatment systems and subsystems having aspects of the inventions. These simulations can also be integrated into the treatment planning system 800 as a component of the plan so that doses to therapeutic targets may relative to doses to critical structures may be predicted. In addition, as further described herein, the data from such radiation simulations may be adjusted to specific patient anatomical imagery and measurements, and may be used to determine actual treatment results, including the effects of unintended patient movement and the like (see discussion with respect to FIG. 19, among other places). For example, the planning system, which incorporates the unique anatomy of each patient, can simulate the amount of radiation delivered to each structure dependent on the angle and position of delivery through the sclera. Depending on the angle, beam size, and beam energy, the radiation delivered to the ocular structures will vary and alternative direction can be chosen if the x-ray dose is too high to the structures such as the lens and the optic nerve.

As shown in FIGS. 13 and 14, the lowest and highest angled beams 2100 and 2140 avoid significant absorbed dosage to the lens by adopting a polar angle Φ sufficient to provide clearance from the limbus of the eye, thus avoiding irradiation of the cornea or lens. For example, for a beam spot diameter of a few millimeters with entry point in the pars plana region, a polar angle Φ of about 30 degrees from the geometric axis may be selected, and this is the constant polar angle for each of the beams defined in FIG. 15. Note that further increases in polar angle may present inconvenience or discomfort with respect to the range of eyelid retraction, or by interference with the beam by tissues adjacent the eye. For such a fixed polar angle of about 30°, the collimated beam might still result in some radiation scatter from eye tissue producing a certain dose gradient across the lens margin. However, it may be seen from FIG. 14 that this scatter (2400) is at least 2 orders of magnitude less than the macular dose. Furthermore, in a multiple beam stereotactic treatment plan, by entering the eye from more than one azimuth angle to deliver the selected total macula dose, any such scatter gradient will further "smeared out" around the lens margin by the orientations of different beams. Thus the scatter dose region will shift to different portions of the edge of the lens, thus minimizing the dose to any part of the lens.

The treatment planning embodiments having aspects of the invention include sub-methods for selecting beam paths which substantially avoid irradiating the optic nerve. Unlike the lens and macula, is not symmetric with respect to the beam azimuthal entry angle. In the example shown in FIG. 13 and in further detail in FIG. 16, the optic nerve was modeled as a cylindrical cuboidal structure tilted to the center of the patient's face (extending nasally or medially from retina) by about 20°. See NCRP, "Biological effects and exposure limits for hot particles", Report No. 130, National Council on Radiation Protection and Measurements, Bethesda, Md., 1999, which is incorporated by reference. In particular, the method may be employed to determine advantageous or undesirable azimuth angles with respect to optic nerve exposure.

FIGS. 15-17A,B depict the test cases and results of an exemplary radiation modeling study of varying optic nerve angles with respect to the posterior sclera, the geometry of the beam cases of the study, and the anatomic geometry of different optic nerve cases studied. FIG. 15 shows the beam angles in the X-Y plane of the eye (azimuth angles θ rotating around geometric axis 2082), indicating the relative position of the entry point of the beam on the pars plana, oriented to propagate to the macula target.

As shown in the example of FIG. 15, a range of 8 space azimuth angles θ as beam entry directions were selected as test cases for Monte Carlo analysis (0-315° by 45° increments), thus defining a cone of possible irradiation directions (an angle of 0° corresponds to the 12 o'clock position when viewing the patient's treated eye). These angles can be described using a spherical 3D polar coordinate system with the macula at the origin and the z-axis defining the geometric axis. In all 8 beam azimuthal angles, the X-ray source-to-target distance was assumed to be 130 mm, and the polar angle Φ was fixed at 30° from the geometric axis.

FIG. 16 illustrates a range of modeled geometries of the optic nerve as it extends in the medially-posterior direction from retina toward the brain. A range of 5 possible angles are included, ranging from an upward extension at +20°, from the horizontal plane to a downward extension at −20° (cranial +; caudal −), as test cases for Monte Carlo simulation.

Figure 17A:
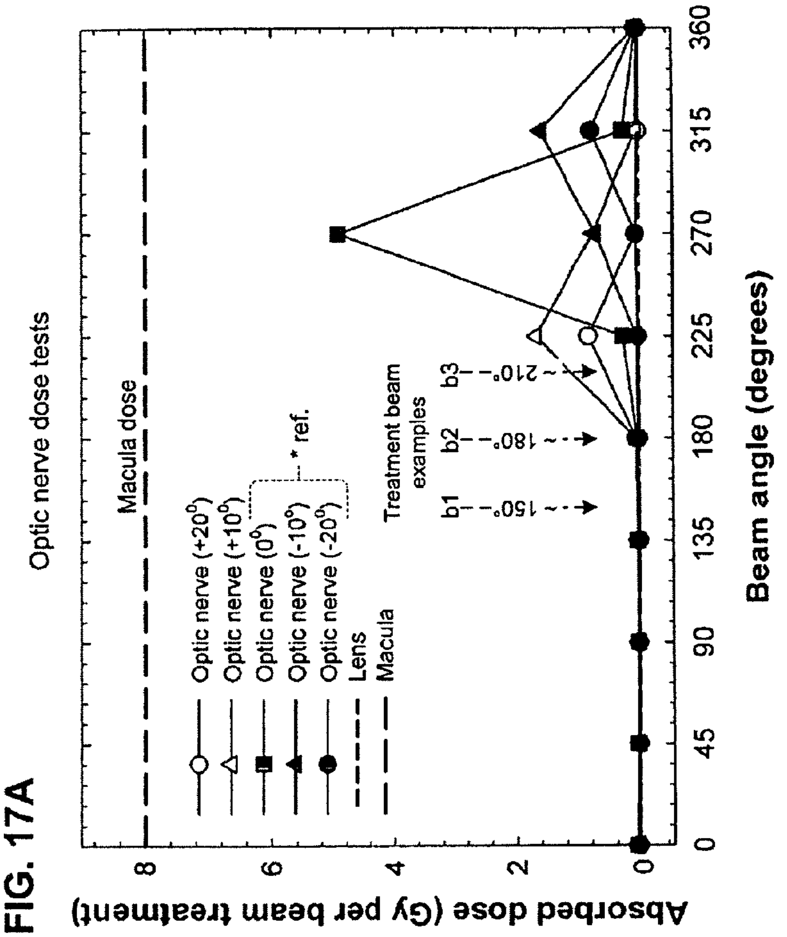

FIG. 17A shows a plot showing the results of a Monte Carlo tests for the cases shown in FIGS. 15-16, including the mean absorbed dose for the lens, and to the optic nerve as a function of vertical tilt angle. In this test, each beam is targeted to deliver fixed dose to the macular target of 8 Gy, for a 100 kVp X-ray source having 2-mm Al total filtration. The mean dose to the lens was found be insignificant (51 to 53 μGy) for all beam directions and optic nerve tilt angles. With respect to the optic nerve, from the plot it may be seen that:

(a) For treatment beam azimuthal angles θ between 0° and 180°, the mean optic nerve doses were also found to be insignificant (47 to 92 μGy) for all vertical optic nerve tilt angles.

(b) For a treatment beam angle of 225°, the doses were very small for an optic nerve angle of −20° or −10°, rising only slightly to about 0.30 Gy at the optic nerve angle of 0°, but becoming more significant at the optic nerve angles +10° and +20° (about 0.85 Gy and 1.7 Gy respectively).

(c) For a treatment beam angle of 270°, the optic nerve doses were at significant levels for optic nerve angles of −10°, 0° and +10°.

(d) For a treatment beams angle of 315°, the optic nerve doses were at significant levels for optic nerve angles of 0°, +10° and +20°.

It is believed that the patient population will be characterized by angles within the −20° to 0° range (see R Unsold, J DeGroot, and T H Newton; "*Images of the optic nerve: anatomic-CT correlation*"; AJR Am J Roentgenol 135, 767-773 (1980), which is incorporated by reference herein).

Figure 17B:
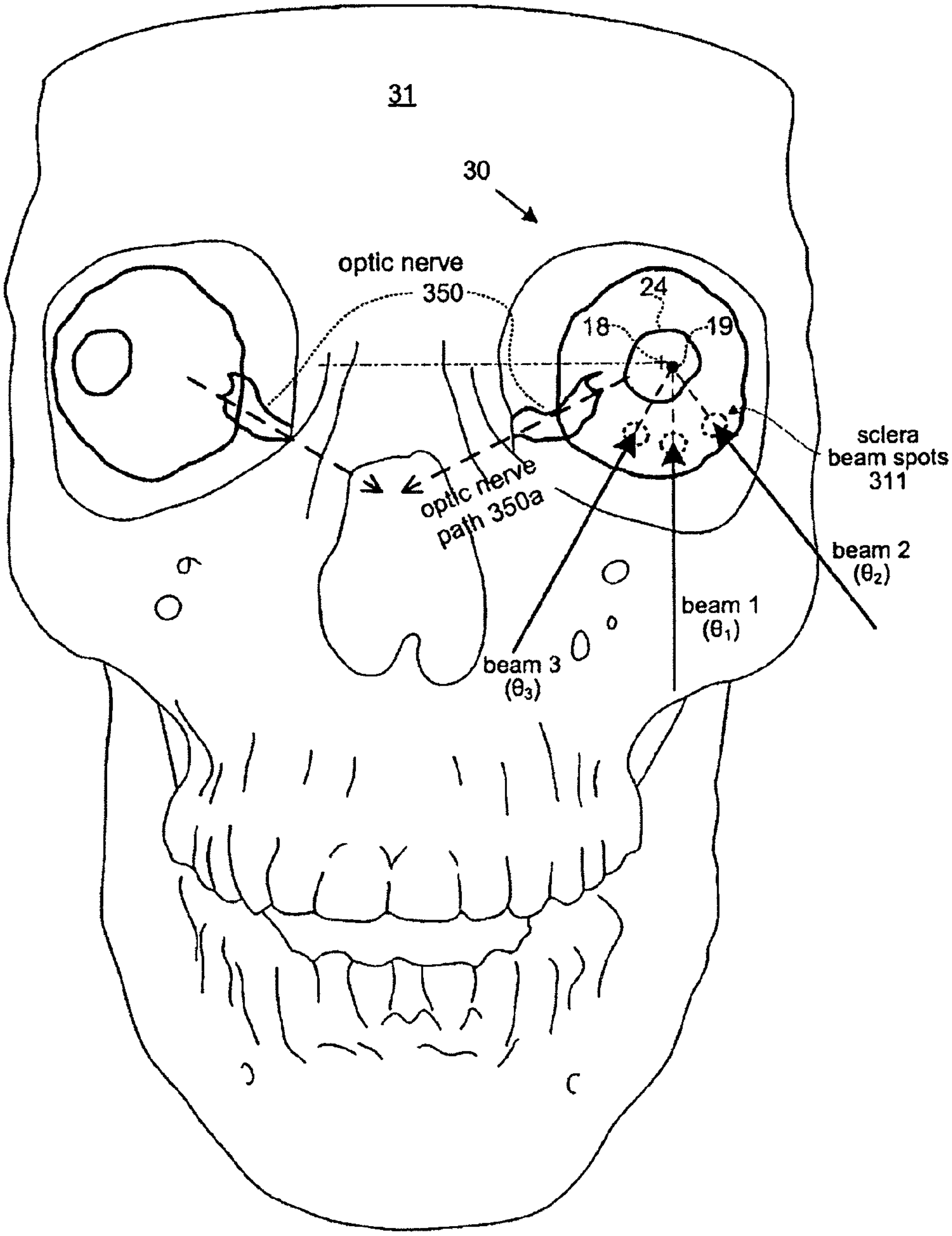
Figure 17C:
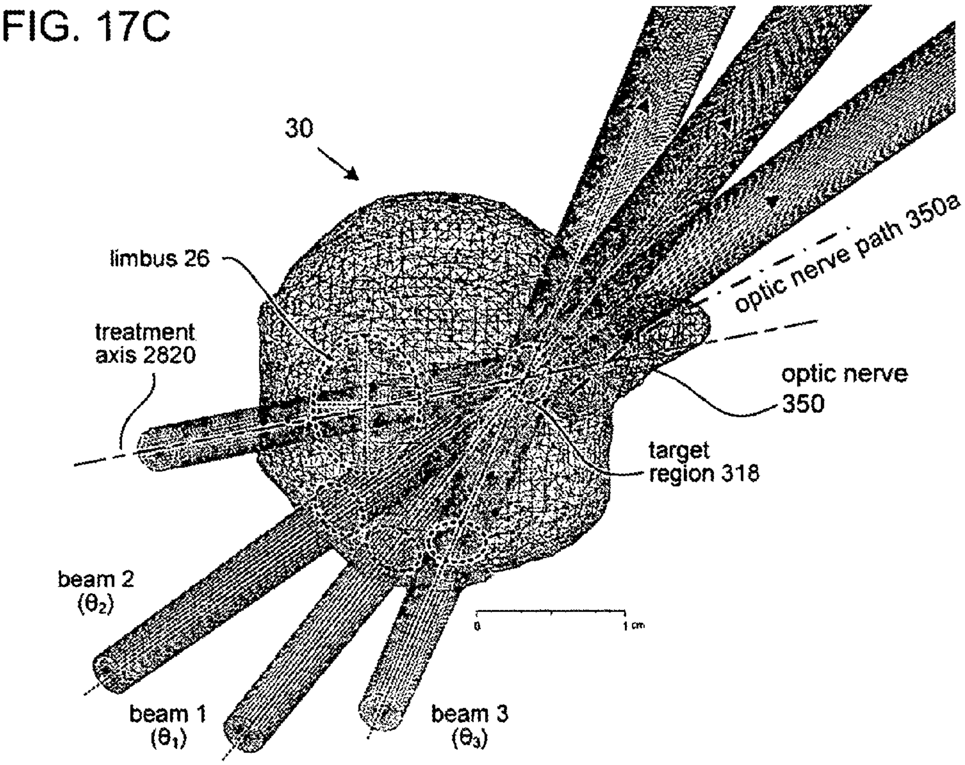
Figure 17D:
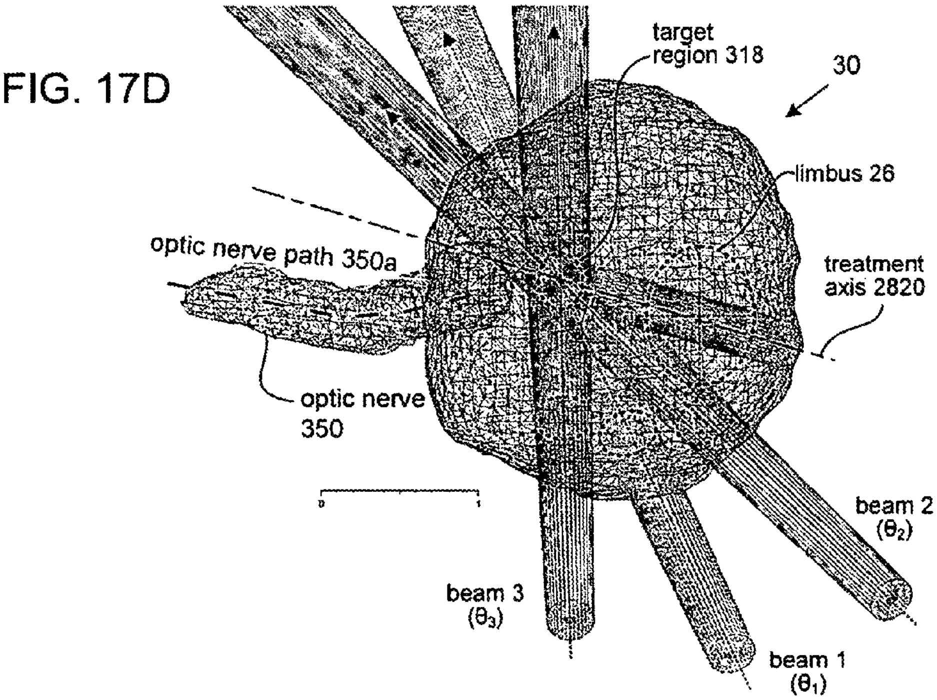

In addition, FIG. 17B-D are drawings taken from superimposed images compiled from CT scans of a human being, the images have been processed electronically to enhance and define certain tissue contrasts and graphically represent tissue geometry. FIG. 17B shows a human head, processed to enhance contrast of eye structures relative to bone tissue. FIGS. 17C and D are perspective views of a right and left eyes respectively, with bone and other orbital tissues removed electronically, also showing superimposed modeled images of three stereotactic radiation beams focused on a retinal target.

FIG. 17B shows the extent of the optic nerves 350 in frontal aspect. It may be seen that both the right and left optic nerves 350 have a path 350*a* that trends downward (caudally) as well as medially as it extends backward to the brain. This data supports one embodiment of a radiotherapy treatment plan as described in detail herein which employ exemplary beam azimuth angles θ of about 150°, 180° and 225°, shown as b1, b2, and b3 respectively in FIGS. 15 and 17A (see also FIG. 30A). These are consistent with very low to negligible optic nerve radiation doses for realistic optic nerve anatomy. These are also consistent with extremely low doses to the lens and cornea, as shown in FIGS. 13 and 14. However, other or additional treatment beam orientations may be selected without departing from the spirit of the invention.

FIGS. 17C-D likewise show the optic nerve path 350*a* descending below the treatment axis 2820. The three radiation or X-ray beams (beams 1-3) are generally oriented as shown in FIGS. 30A and 43E, entering the sclera adjacent the limbus 26 and propagating upward to target region 318 centered approximately on the macula. As can be seen, the beam paths 1-3 avoid the optic nerve 350.

Figures 56A, 56B, 56C, 56D, 56E:
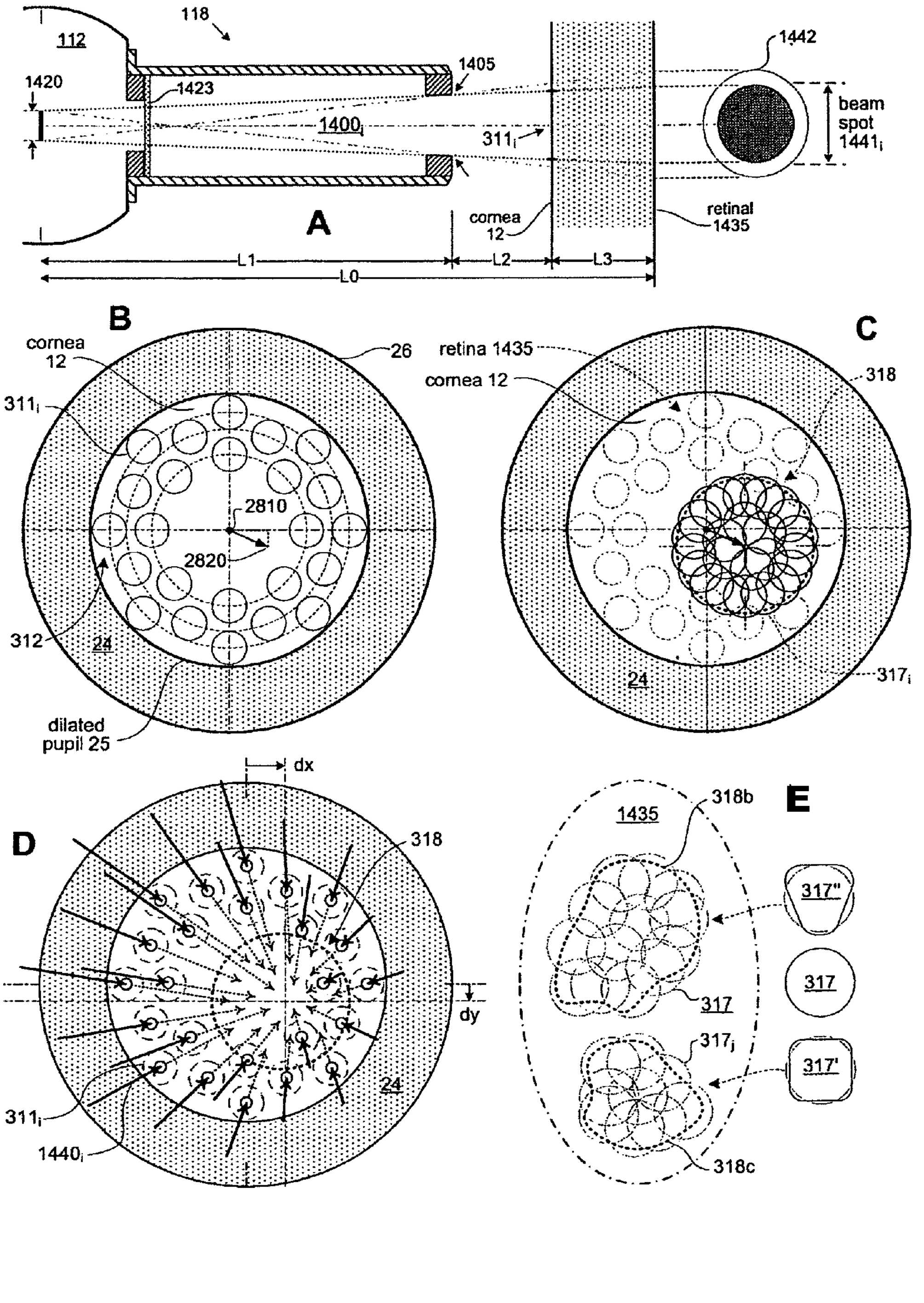

FIG. 56E depicts retinal beam patterns on the surface of a retina, depicting an example where a target lesion is irregular or discontinuous.

Eye Anatomy and Targeting

FIG. 18 depicts an anatomical targeting method for radiotherapy. The central or geometric axis 2810 of the eye may be defined approximately by the eye-guide 2860 (or alternative eye-alignment methods), which in some cases is a lens which fits the curvature of the front of the eye. The geometric axis 2810 of the eye 30 may be defined as perpendicularly intersecting the cornea surface 35 at the center of limbus 26. In some embodiments, geometric axis 2810 can be the treatment axis, or a distinct treatment axis 2820 may be defined. In the example shown, the treatment axis 2820 is offset vertically and/or laterally and lies generally parallel to the geometric axis 2810, intersecting the fovea 318 of the eye (approximately the macular center). In one embodiment, angle Φ is set so that the x-ray beam 1400 travels into the eye at a spot adjacent to the edge of the limbus 26 on the front of the eye, e.g., near the pars plana, so as to have a clearance "c" from limbus to center of beam entry point of about 2 to 6 mm). The central axis, in some embodiments, can be assumed to be the axis which is perpendicular to the center of the cornea or limbus and extends directly posterior and anterior to the cornea and to the center of the retina, as discussed previously. In some embodiments, the central axis is the treatment axis, about which a radiotherapy device can rotate; this axis can also be referred to as the system axis. In some embodiments, the treatment axis 2820 can be a parallel line to the central axis 2820 and offset from the geometric axis 2810 by a distance 2850. The treatment axis can intersect the retina at the macula or the center of a lesion to be treated. The axis 2820 can be any axis in any orientation relative to the central axis 2810, axis 2810 being continually identified by the guide 2860. Path length 2830 (indicated also as "L3") is a distance of the path followed by the X-ray beam during propagation from tissue surface to the treatment target, and is helpful for predicting the dose at the intersection of the retina, as there will be attenuation of energy by the time the x-rays reach the retina and, to some extent, this attenuation will be dependent on the beam tissue propagation path length 2830. The tissue path length for a selected planned treatment procedure may be correlated with a measurement of the patient's eye, most conveniently to the eye axial length, as further described herein in detail with respect to FIGS. 31A-C.

Optic nerve points in the medial (toward the midline) direction as it travels behind the eye. In addition, it has been demonstrated by inventors herein, that the typical path of the optic nerve is also inferior (downward or caudally) from the eye as it travels behind the eye. The example of a multiple-beam stereotactic treatment plan for macular irradiation having aspects of the invention, as depicted in FIG. 30A, accounts for the path of the optic nerve in minimizing absorbed radiation dose to this structure. Reference is made to application Ser. No. 12/100,398 filed Apr. 9, 2008 for further description; which application is incorporated by reference.

FIG. 19A is a schematic view of a fundus image on a patient's retina showing one example of a treatment plan for AMD. The effect of the axis shift on the treatment region of the retina can be seen, the geometric axis 2810 is offset from is the treatment axis 2820 (centered on the fovea). Also shown are the dimensions defining relationship with the optic disk, as the treatment plan preferably assures low dosage to this structure. FIG. 19A below illustrates data from a study of several normal volunteers in which the intersection of the geometric axis with the retina was determined and related by distance to the fovea and the optic nerve. In some embodiments, only one shift geometry is used for all patients. Alternatively, a scaled shift geometry may be used based on one or more patient-specific parameters, such as axial eye length, e.g. determined by an A-scan or OCT. Shown are averages and maxima and minima for the depicted measurements. Also shown is a triangular diagram summarizing the average shift data to offset the treatment axis from the geometric axis: x=+1.16 mm temporally, and y=−0.47 mm caudally, and as further shown and described with respect to FIG. 43D. Inventors herein have demonstrated from clinical data that an exemplary radiotherapy treatment plan having aspects of the invention and incorporated treatment axis offsets at or near these values accurately predicts the center of a macular target. Reference is made to application Ser. No. 12/100,398 filed Apr. 9, 2008 for further description; which application is incorporated by reference.

It has been found that the average shift values shown lead to surprisingly small errors in the population studied, a maximum error of 0.20 mm in the horizontal direction and 0.08 mm in the vertical direction. Thus, when the geometric axis 2810 intersection with the retina is identified using guide 2860, the fovea or a lesion nearby can be targeted. A treatment plan can therefore be developed. For example, a known spot on the lens placed on the front of the eye can be determined and then the axial length can be used to locate the inner limit of the retina. After locating the point (either virtually by a model or visually through an imaging device) on the retina where the axis of the lens on the eye intersects the retina, any point along the retina such as a lesion center can be targeted with by the radiation positioning system.

FIG. 19B is a perspective view of a virtual model of an eye 30, including a registered retinal image 350, such as an optical coherence tomography (OCT) image, a fundus camera image, or other medical image of a patient. In this example, the eye model 30 is shown as aligned with a radiotherapy system Z axis, which is collinear with the geometric axis 2810 of the eye. Axis 2810 perpendicularly intersects the cornea 35 at a central point defined by the center of limbus 26, the axis extending through the eye to the retinal pole 340. An X-Y coordinate plane for the eye model 30 is shown centered on the Z axis tangent to the cornea at the corneal center 35 (see the alignment method example described with respect to FIGS. 43 A-E).

A subsidiary retinal reference plane X'-Y' is defined centered on pole 340 (in typical patients, the retinal surface plane X'-Y' may be substantially parallel to the corneal X-Y plane). A ophthalmologic retinal image may be incorporated into eye model 30, such as OCT image 350, for example by capturing an electronic image of a patient to be treated, and geometrically registering the image data with the model (aligning the image data to retinal plane X'-Y'). A convenient scale factor for sizing image data to the eye model is the eye axial length A1, the distance from the anterior corneal center 35 to the surface of the retina at pole 340, which may be measured non-invasively by an ultrasonic A-scan.

As described further with respect to FIGS. 19A and 43E, a treatment axis 2820 may be defined by offsets from pole 340 (δx, δy in the X' and Y' coordinate plane), the treatment axis intersecting the retina at a treatment target center 318. By incorporating a patient-specific retinal image 350 into an eye model 30 and registering the image congruently to the geometry of a radiotherapy treatment plan (e.g., as shown in FIGS. 19A and 30A), the relationship between treatment axis 2820 and the patient's retinal lesion may be visualized by a physician. Radiation target parameters of the treatment plan may either be confirmed or modified, in preparation for treatment.

Eye Models and Treatment Planning

As described herein with respect to FIGS. 3-6, virtual or phantom models of anatomy may be employed in treatment planning embodiments having aspects of the invention. Information such as described with respect to FIGS. 13-19B may be used to construct a virtual or phantom model of the eye having aspects of the invention (e.g., using software and interfaces with a computer processor). The eye model may represent the eye to be treated and related anatomy.

The model may be based on generalized human ocular anatomy, and may be based on patient-specific ocular anatomy. Although human ocular geometry is distinctly variable within patient populations, appropriate adjustments and modifications to a generalized eye model may be made taking into account one or more patient-specific measurements, so as to accurately represent a particular patient's eye anatomy. For example, a virtual eye model may conveniently and economically include an overall structure based on generalized human ocular anatomy, which may then be adjusted or scaled by measurements taken from a patient to be treated, such as an A-scan measurement of eye axial length, routine type of diagnostic test used in ophthalmology (A-scan ultrasound biometry can provide, for example, the central or axial eye length from anterior corneal surface to retinal surface).

FIGS. 20 and 21 schematically depicts exemplary embodiments of virtual or phantom models of a human eye and adjacent structures, such as may be digitally defined using conventional software tools, displays and input/output devices (or by using alternative graphic or representational modalities). A virtual model may include multiple components, which include different representations of the same anatomical structures. For example, in embodiment shown in FIG. 20, the eye model includes a virtual representation of much of the ocular anatomy shown in FIG. 18, including the relationship between different anatomical features and eye geometry.

FIG. 21 shows a model 1451 of an X-ray collimator system 1440 including the physical parameters that effect the radiation beam characteristics, as applied to a simplified anatomical representation of the anatomy of FIG. 20. However, in contrast to FIG. 20, the model 1440 of FIG. 21 is simplified, so that the surface of sclera 17 is depicted as a perpendicular planar surface 1430, and retina surface 1435 is likewise depicted as a plane perpendicular to the beam axis 1400.

Note also that "emission spot" 1420 is depicted in FIG. 21 as a planar surface of a defined cross-sectional dimension perpendicular to beam path 1400, and represents an idealized X-ray emitting surface emitting photons through collimator 118. Actual X-ray devices may have an X-ray emitting source having an number of alternative shapes, orientations and configurations. For example, the X-ray-emitting electron-beam target of an linear accelerator source may be high atomic number material aligned in the path to the electron beam and presenting an exit plane which may be substantially perpendicular the collimated X-ray beam 1400. Alternatively, the target anode material of an commercial orthovoltage X-ray tube may comprise a surface at a substantial angle to the collimated X-ray beam 1400, the output X-rays being emitted through a window (e.g., thin Be sheet) oriented in a generally transverse direction to the cathode beam impinging on the anode surface. The anode material may be formed to have a planar surface, or a truncated conical surface in the case of a rotating anode. To simplify the model 1440, the effective X-ray emission spot 1420 from the perspective of aperture 1405 may be represented as a disk of defined diameter oriented perpendicularly to beam 1400 and uniformly emitting X-rays of a certain initial spectrum. For convenience, such an emission source 1420 is referred to herein as an "anode" or "anode spot" without loss of generality.

Likewise, the aperture 1405 is represented in FIGS. 21-30 as single circular opening, but need not be circular and need not comprise a single opening. See for example, collimator embodiments described in Ser. No. 11/873,386 filed Oct. 16, 2007, which is incorporated by reference and in the microfractionated patterns shown in FIGS. 55A-D herein. Where an collimator exit opening and/or projected radiation beam-spot on a tissue surface or target plane is non-circular (elliptical, rectangular, elongate, irregular or the like), the diameter may be conveniently considered to be a selected geometrically characteristic dimension, such as maximum width, a major or minor axis, a mean width or the like.

A model such as FIG. 21 permits convenient modeling of photon energy spectral change as the beam propagates from anode to treatment target. The initial spectra emitted by anode spot 1420 may pass through a filter 1423 which shifts the spectrum to a higher mean photon energy by absorbing predominately lower energy photons (see FIG. 8). The effective filter 1423 may comprise any device structure material in the beam path (inherent filtration, e.g., an X-ray tube window, a laser beacon deflection mirror, aperture covering, or the like) and any additional filter material positioned for this purpose (e.g., one or more aluminum plates of selected thickness mounted at a selected position in along the axis of collimator 118).

A filter for penetrating radiation is often characterized by its absorption properties scaled relative to a half-value-layers or half-value thickness (HVL), related to mean free path of a photon or particle. An HVL may be defined as the thickness of specified material which reduces the intensity of a particular input radiation spectrum entering the material by half. However, a filter element need not be an integral HVL and may be of any selected thickness. Likewise, a filter element need not be of a single or uniform material. For example, filters may have a series of layers, such as layers in decreasing order of atomic number such as tin, copper, and aluminum layers in the direction of propagation. Although the examples described may have filters of uniform cross-sectional thickness or composition, in alternative embodiments, a filter may be non-uniform with respect to the beam cross-section, so as to produce a spectral variation from one side the beam to another (wedge shaped), radially variation about a center, or other variable distribution.

The filtered spectrum is further "hardened" by upward shift in mean photon energy as it propagates along tissue path L3 of eye 30 towards retina plane 1435 ("tissue hardened spectrum", see FIG. 12). As is further described with respect to FIGS. 22-29, the intersection of beam 1400 with retina 1435 ("retinal target plane") may be represented in this simplified model as a circular central 1441 and a concentric penumbra or "isodose fall off" margin 1442. However, in alternative embodiments, the beam-spot geometry (1441, 1442) may be configured to be non-circular.

It is apparent that the relevant anatomical structure can be defined mathematically and geometrically, optionally including convenient simplifications and generalizations, without loss of utility in planning and predicting radiotherapy treatment.

Empirically and/or theoretically determined radiation beam characteristics and human tissue characteristics may be correlated with the eye model to allow modeling of radiation transmission and absorption along a beam propagation path. For example radiation propagation and absorption through tissue may be simulated employing software such as the Monte Carlo Radiation Transport Code developed by Los Alamos National Laboratory. As shown in FIG. 20, a virtual model may include a geometric representation of position of the optic nerve extending posteriorly from the optic disk of the retina (in this example characterized by angle $\pi$), which is useful in determining beam propagation paths which minimize dosage to the optic nerve, such as from the portion of applied radiation passing through and beyond a treatment target adjacent the macula.

In the examples shown in FIGS. 20 and 21, the virtual or phantom eye model 1440, 1450 is configured to represent a narrowly collimated external radiation beam directed to enter an exposed scleral surface 17, such as the pars plana 1430, and propagate to the surface of the retina 1435 at or near the macula 318. See co-invented application Ser. No. 12/100,398 filed Apr. 9, 2008 (which is incorporated herein by reference) for further description of methods having aspects of the invention for determining suitable beam paths for ocular treatments, and in particular, beam paths which may be used to treat a macular region, while minimizing absorbed dosage to such structures as the lens and optic nerve.

In an embodiment of a treatment planning method having aspects of the invention, beam tissue path length L3 is determined (i.e., radiation beam distance through tissue from air entry point to treatment target), and the path length is in turn employed with a radiation transport model to account for reduction in beam strength and spectral profile as it passes through tissue. This permits determination the dosage at the target relative to the air kerma beam dosage. In actual treatment, the magnitude of radiation can then be adjusted to provide an accurately predictable absorbed dosage at the target (e.g., by adjusting the radiation duration).

As one example, it has been shown in studies conducted by inventors herein that, for a treatment plan to irradiate the macular region via a beam entry point near the pars plana, that the tissue path length of a wide range of patients can be accurately predicted using a virtual model and a single A-scan measurement of a patient's ocular axial length. Indeed, an linear approximation can give good results for a particular treatment plan, such as a formula PL(mm)=AL(mm)−k, where k is a constant such as about 3. See further description with respect to FIGS. 31A-C. In addition, patient-specific imagery may be incorporated into the eye model, such as is schematically depicted in FIG. 19. In one embodiment, a fundus image is obtained from a patient prior to radiotherapy treatment, the image may then be scaled in proportion to a patient measurement such as ocular axial length, the image being aligned and superimposed on the virtual model.

An eye model may be used in planning treatment, as is depicted in FIG. 30A, such as by determining a treatment axis 19 with reference to a radiotherapy system reference 18, and defining one or more radiation target regions 318 suited to the disease being treated. One or more radiation beam paths 1400 may also be defined with reference to the model. In the example shown, three stereotactic beam paths 1400*a*-1400*c* are planned so as to be coincident adjacent target region 318 centered on treatment axis 19. Planned positions/orientation of X-ray beam 1400 may likewise be superimposed on the model by correlation of the model coordinate system with the planned system coordinates. A image displayed to an operator/physician may thus include model data; scaled and registered fundus image data (and/or other medical image data); together with planned radiotherapy beam geometry data. Among other things, this permits a physician to confirm that the planned treatment is appropriate for the lesion of the patient, as seen in the fundus image.

The model may be used to determine patient-specific parameters relevant to radiation propagation, such as a tissue path length along a beam path 1400 to a target region 318 to apply radiation dosage to a target beam spot 1441 (see FIG. 21). In this manner, an eye model having aspects of the invention may be used to compile a patient-specific treatment plan which accurately predicts radiation dosage levels and distribution in a target region 318 as shown in FIG. 20, and which accurately predicts radiation dosage distribution relative to anatomical structures such as the lens 36 and optic nerve 32 see optic disk 3260 in FIG. 30B). See for example the retinal dose map of FIGS. 30C-D. Data from such radiographically-measured and/or computationally simulated dose distribution may be incorporated and registering with a phantom or virtual model. Planned radiation beam geometry (See FIGS. 20 and 30A) may then be included in the model as virtually-projected radiation beams 1400 from a virtual radiation source, and used to simulate dose deposition at a target region 318 in the phantom model.

A combination of anode size, anode-to-target distance and collimator length may be selected by methods having aspects of the invention for an X-ray source providing a tightly collimated beam spot of appropriate maximal intensity, sized to a selected target region dimension, and having sharply defining penumbra or area of dosage fall-off surrounding the beam spot. A combination of X-ray tube field potential and filter dimensions may be selected by methods having aspects of the invention which provides a favorable ratio of radiation dosage at a scleral entry point to target region (pre-target absorption or "tissue hardening"), while permitting rapid attenuation of beam dosage beyond the target region, such as be absorption in orbital skull bone (post-target absorption). See co-invented application Ser. No. 12/100,398 filed Apr. 9, 2008 (which is incorporated herein by reference) for further description of the characteristics of radiotherapy beams and configuration of X-ray treatment devices having aspects of the invention. The embodiments have selected parameters which provide radiation treatment beam characteristics which are particularly well suited to the treatment of ocular lesions, including lesion of the retina such as occur in AMD.

Dependence of Penumbra and Dose Distribution on Anode Spot Size

FIGS. 22 and 23 illustrate a study in which theoretical anodes (via Monte Carlo simulation) of different sizes were utilized to determine, in connection with the beam penumbra, effects of different sized anodes for usage in the radiotherapy system. X-ray tubes are commercially available providing a wide range of anode spot sizes (focal spot size) 1420. The term "anode size" as used herein is the characteristic effective X-ray emitting anode spot dimension as seen from the vantage of the emitted beam axis. The physical anode, such as a fixed plate or rotating plate of target material (e.g., tungsten or tungsten alloy) is typically set at an angle to the impinging accelerated electron stream from cathode (e.g., about 10 to 20 degrees), and the useful X-ray beam is allowed to escape through a tube window (e.g., thin Be plate) at approximately right angle to the impinging cathode electrons.

The anode is considered the radiation emitting source of a typical X-ray tube, and its size, structure, and cathode focusing devices have roles in penumbra determinations. For example, an idealized point source may be approximated by a anode with a largest diameter of equal to or less than about 1 mm; point sources can deliver the highest quality beam with the tightest penumbra 1442. Less optimal are sources with anodes greater than about 1 mm; for example, 2-mm, 3-mm, 4-mm, or 5-mm sources can also be used in connection with the embodiments described herein.

FIGS. 22A-22D depicts a virtual model showing an exemplary range of four anode sizes, and depicting an exemplary collimator configuration arranged to direct an X-ray beam 1400 at a simulated eye 30'. This virtual model assumes for convenience that both the scleral surface 1430 and the retinal target surface 1435 are planes perpendicular to the X-ray beam axis. The X-ray tube potential, filter characteristics, anode-to-target distance, collimator length, collimator exit diameter/shape, and tissue path length may all be selected to model a desired treatment beam and radiotherapy plan.

In the example shown in FIGS. 22A-22D, the collimator configuration is a constant typical example, the only variation being anode size, so as to demonstrate the effect of the anode size independent of other factors. The X-ray tube is positioned to have the anode 1420 about 150 mm from the retinal target 1435, penetrating through about 20 mm anterior eye tissue to the retinal target, a tissue path length consistent with the more anatomically complex model shown in FIG. 20, and with the typical range of patient anatomy. The collimator has a 2.5 mm diameter circular exit aperture 1425 positioned about 75 mm from the anode 1420.

The examples of anode sizes are: (A) 0.0 mm (point source); (B) 0.4 mm; (C) 1.0 mm; and (D) 5.5 mm. The characteristics are illustrated by ray tracing, idealized to assume unscattered and undeflected propagation through the collimator exit aperture from each point on a circular anode surface to the retinal target plane. For each anode diameter, (a) a cross section along the axis of beam 1400 is shown projected to (b) a cross section perpendicular to the beam path taken at the retinal plane 1435 and illustrating the beam spot 1440 in the target region. It may be seen in each case, the target region is illustrated showing by a darkly-shaded central spot 1441 (fully illuminated by the anode) and a lightly-shaded annular penumbra region 1442 (partially shadowed by the collimator aperture).

It may be seen that the relative width of the annular penumbra region increases progressively as the anode size increases. In the case of the idealized point source (anode diameter=0.0), the annular width is zero. For the largest anode shown (anode diameter=5.5 mm), the annular penumbra region covers the entire illuminated area. Clearly, there are advantages to a small anode, when a tightly-defined dose region is desired. Although the models of FIG. 22 might be interpreted to suggest that the smallest possible anode would give the optimum therapeutic beam spot, the model can be interpreted in light of the physical characteristics of a typical X-ray source.

The anode is also a major determinant of the x-ray flux. The heat generated by the anode is the major limiting factor in the ultimate flux which can be achieved by the x-ray source. To the extent the anode can be cooled, the x-ray flux can be increased accordingly. This is part of the trade-off in penumbra; larger anodes can tolerate larger currents due to their larger thermal mass. X-ray output is related to current so higher current for a lower temperature allows a greater x-ray flux. In some embodiments, rotating anode sources are used so that the anode is "cooled" by virtue of the anode being moved to different points with time. While technical features such as liquid cooling, rotating anodes, and the like can alleviate anode heat concentration and increase available X-ray source intensity for a given anode size, there remain technical trade-offs to be considered in anode parameter selection. These include the desired dose rate at the target (Gy/min), filter thickness (reduce flux), anode-to-target distance (inverse-square beam divergence), collimator configuration parameters effecting beam application (e.g., exit aperture size, shape and distance from anode), and particular clinical goals and requirements.

FIG. 23 is a plot showing the results of a Monte Carlo computational simulation (see description re FIGS. 10-17) for four anode size test configurations generally similar to those shown in FIG. 20. The computational simulation accounts for radiation propagation effects, such as scattering in tissue, and provides additional description of the effect of X-ray source focal spot or anode size on the resulting dose profile across the macula target. Cross sectional profile to the absorbed dose to the macula target for a 100 kVp x-ray beam as a function of focal spot size. A collimator was selected to create approximately a 4.0 mm beamspot, and too simply the MCNP geometrical setup, a non-clinical normally incident beam angle is assumed. Absorbed dose profiles at the center of macula are shown for focal spot sizes of 0.0, 0.4, 1.0, and 5.5 mm, respectively, for a targeted central dose of 8 Gy. Vertical lines are placed at +2 mm and −2 mm radius, to represent the anatomic size of a macular lesion target region of 4 mm diameter.

In FIG. 23, no significant differences in the dose profile are seen for focal spot sizes from 0.0 to 1.0 mm, and the penumbra of each extends outward 1 of 2 mm radially. For the larger 5.5 mm spot size, dose uniformity is significantly reduced within the target region, such that the dose at the edges of the target are only one-half that at center, and the penumbra extends outward at slightly higher dose values than seen for the smaller spot sizes. Dose coefficients in the central region were estimated to be 7.8, 7.7, and 7.7 Gy/Gy for spot sizes of 0, 0.4, and 1.0 mm, respectively, where the reference air kerma value is again set at 100 cm from the x-ray source. The dose coefficient for the 5.5 mm spot size beam is 18 Gy/Gy, thus requiring only ~42% of the integrated tube current (mAs)

needed to deliver 8 Gy central dose using the smaller focal spot sizes. However, its dose uniformity is significantly reduced within the macula target. As can be seen in the graph in FIG. 23, the 0.0 mm anode is the ideal case of a point source, and there is a corresponding sharp drop-off of dose; as the collimator increases in size to 1.0 mm, there is a very limited effect or change from the ideal case. However, when the anode reaches 5.5 mm, as can be seen in the figure, there is a much broader spread of dose, or penumbra. The same collimator that creates essentially a 4 mm beamspot in the O-mm case creates over a 5-mm beamspot when it is 5.5 mm in size. In essence, a larger penumbra is realized as the anode size increases.

The sharpness of the falloff of the target spot from full dose to zero dose is measured by the penumbra. Penumbra represents the portion of the target that does not "see" the entire anode focal spot and hence does not receive the full dose. The sharper the penumbra, the tighter and more conformal the dose can be delivered. One metric that may be used to characterize the dose profile and size of an the X-ray beam spot and effective penumbra dimension makes use of isodose contours, conveniently expressed as a percentage of a maximum central region dose. Penumbra may be given an empirically convenient definition as the distance between the 80% the 20% isodose lines (the 80-20 penumbra) and the distance between the 90% and 10% isodose lines (the 90-10 penumbra).

The plots of FIG. 23 illustrate such usage. The left hand of the plot includes a secondary vertical axis depicting percent of central dose (e.g., an exemplary clinical plan dose of 8 Gy per beam). Several generalized features may be seen in a comparison of the four curves in this example according to isodose levels:

(a) Below about the 10% dose level, all the anode plot curves show a certain amount of spreading or scatter, as indicated by the generally shallow gradient of the curves, although the larger anodes produce a greater spreading of dose.

(b) At about the 20% dose level, all four anode plot curves are nearly superimposed (nearly the same radial dimension) regardless of anode size and all have a fairly steep downward gradient.

(c) Between about 80% and about 90%, the curves for 0.0, 0.4 and 1.0 mm anodes have vary similar radial dimensions, whereas the 5.5 mm anode has a substantially smaller radial dimension.

Thus a delimiting value may be conveniently selected of about 10-20% as a useful measure of the maximum penumbra radius in the example shown, for purposes of comparison of different beam parameters. Similarly a delimiting value may be conveniently selected of about 80-90% as a useful measure of the inner boundary of the penumbra or central beamspot radius. In the example of the 1.0 mm anode curve in FIG. 23, the 80% isodose contour is shown to have a radius of about 2.0 mm and the 20% isodose contour has a 2.6 mm radius, then the 80-20 penumbra is 2.6−2.0=0.6 mm, or expressed as a percentage 0.6/2.0=30%.

An alternative meaning of the term penumbra that may be used in the context of collimated external beam applications so as to include the effects of beam inverse-square divergence in combination with the effects of anode size, scattering and the like. In this usage, outer margin of the penumbra (e.g., the 20% isodose contour) is compared with the collimator exit aperture. For example, if it is assumed that the 1.0 mm anode curve in FIG. 23 was emitted through a collimator aperture of 2.5 mm diameter (1.25 mm radius), and the 20% isodose contour has a 5.2 mm diameter (2.6 mm radius), then the penumbra based on collimator aperture is 2.60−1.25=1.35 mm, or expressed as a percentage 1.35/1.25=108%.

It can be seen in the example of FIG. 23, that while each of the smaller anode sizes (0.0, 0.4 and 1.0 mm) deposit about 80% or more of the maximum dose within the indicated 4 mm diameter target region, the 5.5 mm anode deposits a profile with a substantial "undertreated" area with the 4 mm diameter target region, dropping to about 50% dose lever at the 2 mm radius. Stated another way, only the smaller anode sizes in this example configuration provide a fairly uniform dose profile (at least 80% maximum) within the central target region, changing to a steep isodose drop-off (penumbra gradient) to a 10%-20% dose level within a small penumbra radius.

A clinical objective certain embodiments of methods and devices described in detail herein is to achieve a therapeutic dose level within particular dimensions of a target lesion (e.g., AMD lesion), while minimizing dosage to sensitive or vulnerable structures adjacent to the target lesion (e.g., optic disk and nerve). For example, the treatment plan may provide a therapeutic dose to the 4 mm diameter macular target while avoiding undue dose to the optic disk, the margin of which may be only about 1.5-2.5 mm from the edge of the target region. FIGS. 22 and 23 demonstrate that selection of a small anode is useful in achieving this objective, in conjunction with suitable selection of other X-ray source and collimation parameters. In addition, a sharp dose drop-off advantageously limits the dose to other structures remote from the target volume but adjacent the beam axis, such as portions of the lens and cornea adjacent a scleral beam entry point.

FIG. 24A depicts the results of a single collimated x-ray beam 2600 as depicted at the collimator aperture. FIG. 24B depicts the beam 2620 after it has penetrated through approximately 20 mm of solid water phantom material (modeling an eye); the shaping collimator is approximately 50 mm from the surface model. The beamspot was captured on radiochromic film at the 20 mm target depth. As can be seen in FIG. 24B, there is a small penumbra width 2610 about an original beam width 2620 after penetration through the eye which is less than about 10% of the diameter of the shaping beam shown in FIG. 24A. These data incorporate both divergence as well as isodose drop off from scatter and reveal that for a collimator within about 100 mm of the target, the penumbra can be very small. The beam energy in this example is approximately 80 keV.

FIG. 24C depicts a graphical representation of the penumbra from measurements within an x-ray detection films at two different locations of a solid water eye model. Delta 2650 represents the absorption in the energy between the surface and the depth as recorded by x-ray sensitive film. This models the sclera-to-macula tissue path.

FIG. 24C shows quantitatively the rapid falloff on the sides of the beam. The tails seen in 2640 versus 2630 indicate a small degree of penumbra effect as the beam loses energy through the eye. Note that the width of the sides (the penumbral region) is small compared to the central, full-dose region. These measured results closely match Monte Carlo simulations shown in FIG. 23. Also evident from the plots is that the macular dose from the single example beam is roughly one-third the dose at the sclera. This dose ratio provides that for a three port stereotactic treatment of a macular target, the scleral and macular doses would be similar in magnitude.

FIGS. 25A-25D schematically depicts a model similar to that of FIGS. 22A-D, comparing the same four different examples of source anode sizes 1420, but for collimator configurations having apertures sized to produce a constant central beam-spot size 1441 at the target plane. Note that in certain embodiments of radiotherapy methods and systems having aspects of the invention, a treatment plan is tailored to apply radiation to a lesion of known size, and a beam spot may projected on a target plane having a pre-determined target region diameter 1441, within which there may be applied a generally uniform dosage, surrounded by a annular region of rapidly-falling dose intensity (penumbra 1442). Thus it is useful to also compare the effect of variation in anode size in a model in which the collimator configuration is adjusted so that each example has a constant central beam-spot size (e.g., corresponding a target region). Similarly, comparisons may be useful in which other parameters are held constant, such as collimator aspect ratio, total X-ray flux, and the like.

In the examples of FIGS. 25A-25D, the central beam spot 1441 is held at 4 mm diameter by adjustment of the diameter of aperture 1405 for each anode size example. The results shown are generally similar to those of FIGS. 22A-D, with the exception of the penumbra for the largest anode size (5.5 mm) for which the penumbra radius is dramatically larger, due to the relatively large aperture needed to project a 4 mm center spot (region illuminated by the entire anode surface). The width of the surrounding annular region which is only partially illuminated by the anode surface is thus proportional to anode size (for clarity in the examples, it is made equal to anode size due to the arbitrary collimator geometry, in which L1=L2+L3, see FIG. 21).

Effect of Other Collimator Parameters on Penumbra.

FIGS. 26A-26C schematically depicts a model similar to that of FIG. 21, comparing graphically the effect of three different examples of anode-to-target distance (L0) on penumbra, for collimator configurations having apertures sized to produce a constant central beam-spot size at the target plane. In order to show the effect of anode distance independent of collimator to target distance, in the examples shown the collimator exit plane to target distance (L2+L3 in FIG. 21) is held constant (in this example, about 75 mm). As in the examples of FIGS. 25A-D, the aperture diameter 1405 is adjusted in each example to maintain the central beam spot size constant (in this example, 4 mm).

It may be readily seen that the penumbra region 1442 decreases as the anode-to-target distance increases, for a given central spot size. However, the anode-to-target distance places is an important parameter in determining central spot does intensity. For a given X-ray source condition providing a particular X-ray input intensity, the anode-to-target distance places a physical limit on the beam spot central radiation intensity, the intensity at the center of a beam spot. This is as a consequence of the inverse-square law governing the decrease in radiation intensity with distance and divergence of a collimated beam.

In determining a treatment plan by methods having aspects of the invention, X-ray source parameters may be selected determining a particular beam input intensity and spectra. An anode-to-target distance may then be selected, so as to provide desired central beam-spot dose intensity, permitting a desired target radiation dose within a selected treatment time interval. In certain exemplary embodiments having aspects of the invention, a treatment plan and corresponding device operation are determined so as to deliver sequential stereotactic beam treatments in which the anode-to-target distance is held constant for each beam position.

For such a selected anode-to-target distance, the size of the penumbra is directly related to geometrical issues with the collimation and the size of the anode focal spot. The smaller the anode focal spot is, the smaller the penumbra will be. Similarly, the closer the beam-defining final aperture is to the patient, the sharper (smaller) the penumbra. Embodiments of radiotherapy systems having aspects of the invention include selected anode sizes and collimator lengths to provide a beamspot with a desired central radiation intensity while having a small penumbra.

FIGS. 27A-27C schematically depicts a model similar to that of FIG. 21, comparing graphically the effect of three different examples of collimator exit plane-to-target distance (L2+L3 in FIG. 21) on penumbra 1442, for source configurations having constant anode-to-target distances (L0), and apertures 1405 sized to produce a constant central beam-spot size 1441 at the target plane 1435. Consequently each example has a different distance of collimator exit from the eye surface (L2 in FIG. 21), as it is assumed that the tissue path length is the same in each example. Note that these examples, like those of FIG. 22, are illustrated by ray tracing, the characteristics idealized to assume unscattered and undeflected propagation through the collimator exit aperture from each point on a circular anode surface to the retinal target plane.

Thus the differences in the penumbra and beam spot profiles between the examples FIGS. 27A-C are due to the effect of collimator length, other factors being fixed. It may be readily seen that the penumbra size decreases as the collimator length increases (L1 increases for a fixed L0, per FIG. 21). It may be seen from the geometry, that the penumbra is decreased as the collimator length increases and the beam is successively delimited closer to the target plane.

For example, it in certain embodiments of radiotherapy systems having aspects of the invention, the collimator aperture may be positioned close to the tissue surface (e.g., with a small clearance from the sclera, or alternatively, in contact with the sclera or nearly so) to minimize the annular penumbra at the target region. See examples of FIGS. 24A-D described herein.

Alternatively and advantageously, in the exemplary embodiments of radiotherapy systems that are described in detail herein, a relatively small anode and suitable exit aperture may be included to reduce penumbra, while patient comfort and operating convenience may be provided by providing a selected clearance distance between collimator structure and the patient's body (this distance is indicated as L2 in FIG. 21, and is shown as about 55 mm in the example of FIG. 22). A clearance distance L2 may be selected for operating convenience and patient comfort, and this is particularly advantageous when treatment is administered using a automated stereotactic positioning system (see FIGS. 37-38), which adjusts the collimator orientation through successive beam positions, while moving structure near a patient's face (See, for example, FIG. 37).

Note that embodiments of positioning systems having aspects of the invention as shown in FIGS. 37 and 38 may be used so as to solely rotate the collimator 118 about a single axis (e.g., θ axis 2820) without further movement of other degrees of freedom between successive stereotactic beam positions. This 1-DOF stereotactic procedure is advantageous in operational simplicity, in intuitive appeal to both operator and patient, and in increased precision of movement. Outer portion 118*b* may be moved manually or by an automated mechanism, such as by action of a actuator providing linearly-aligned extension movement (not shown), e.g., a linear or helical electro-mechanical actuator mechanism such as used in camera zoom lenses.

The example of FIG. 28 is shown in the form of a "zoom-lens"-like mounting of an exit-aperture disk on a collimator body. The telescoping, tube-mounted structure shown is exemplary only, and it should be noted that in alternative embodiments may be made with substantially different structure without departing from the spirit of the invention. For example, outer potion **118*b* need not be directly mounted to base portion 118*a*, but may be independently supported, the independent support configured to permit movement of aperture 1405 distally and axially away from anode 1420, so as to increase distance L1. In this fashion, certain embodiments may be made which omit base portion 118*a***, such as where any desired beam conditioning components (e.g., choke plate, filter, stray radiation shielding) are independently provided.

Note that an extensible collimator may be included as, in effect, an additional degree of freedom for a X-ray source positioned, such as shown in FIGS. 33-38. For example, it in certain embodiments of radiotherapy systems having aspects of the invention, the X-ray source 112 and retracted collimator 118' may be first positioned in one or more degrees of freedom, for example in the X-Y-Z volume and with a selected polar angle Φ. The azimuth angle θ may be selected in sequence for each beam position (e.g., b1-b2-b3 in FIG. 17A-B). For each beam position, prior to emission of radiation but after positioning the X-ray source and collimator, extensible outer portion **118*b* of collimator 118' in may be extended axially (extension 118*c*) or "zoomed" so as to place collimator exit 1405 a selected distance from the surface of the eye 30. Following emission of radiation, the extensible outer portion 118*b*** may be retracted prior to repositioning of the X-ray source and collimator.

Note that collimator 118', and/or the system in which it is used, may contain detectors and safety mechanisms permitting a close approach to sensitive tissue. For example, aperture 1405 may have a covering of compliant biocompatible material 119 so as to cushion and protect the sclera or other ocular structures, permitting operation close to the face or permitting safe eye contact. Likewise proximity detectors and/or servo-controls may be used to automatically maintain a selected non-contact clearance from tissue, or in the alternative, to limit any force applied on tissue contact.

In addition, in certain embodiments, aperture 1405 does not have a simple circular opening arranged symmetrically about the axis of beam 1400. See for example, the various "shaped beam" collimator embodiments described in priority application U.S. Ser. No. 12/100,398 filed Apr. 9, 2008, which is incorporated by reference. These embodiments provide X-ray treatment beam cross-sections having asymmetrical or non-uniform beam patterns, e.g., donut-shaped, elongate, crescent-shaped and/or speckled or micro-fractionated patterns. The outer portion collimator portion **118*b* may be configured to be controllably rotated about axis 1400, in addition or alternatively to being extended along axis 1400**, so as to align an asymmetrical beam cross section with the desired target region.

For example, a collimator embodiment 118 comprises aperture 1405 which provides crescent-shaped beam exit pattern configured to minimize dosage to the optic nerve adjacent a nearby retinal treatment target. The beam pattern created by aperture 1405 includes a maximal dose-intensity region which is shaped to match a retinal target lesion, and a corresponding minimal dose-intensity region of the pattern is shaped to align with the optic disk, thereby sparing that structure. The aperture 1405 may be rotated as mounted in the outer portion **118*b*, so as to align a minimal-intensity region of the pattern with the optic disk. Rotation of portion 118*b*** may thus compensate for overall rotation of the collimator during repositioning of the X-ray source for successive stereotactic treatments.

FIG. 29A is a plot showing the results of a Monte Carlo computational simulation for absorption of X-ray energy in a configuration generally similar to that shown in FIG. 21. See description above of computational simulations such as Monte Carlo simulations with respect to FIGS. 12-17 and 23. The computational simulation accounts for radiation propagation effects, such as scattering in tissue, on the resulting dose profile across a retinal target. Cross sectional profile to the absorbed dose to the macula target for a 100 kVp X-ray beam. A collimator was selected to create approximately a 4.0 mm beamspot, and too simplify the MCNP geometrical setup, a non-clinical normally incident beam angle is assumed. The absorbed dose profile at the center of macula is shown for X-ray tube anode focal spot size of 1.0 mm, positioned 100 mm from the target, for a targeted central dose of 8 Gy. Vertical lines 1441 are placed at +2 mm and −2 mm radius, delineating also the 80% isodose in this model. The ±2 mm region approximates the anatomic size of a macular lesion target region of 4 mm diameter. The penumbra 1442 is indicated as bounded by the 20% isodose, with low dose or "scatter" region 1443 adjacent the penumbra margin.

In FIG. 29A, the dose coefficient in the central region was estimated to be 7.7 Gy/Gy, where the reference air kerma value is again set at 100 cm from the x-ray source. The sharpness of the falloff of the target spot from full dose to zero or very low dose is measured by the penumbra. Penumbra represents the portion of the target that does not "see" the entire anode focal spot and hence does not receive the full dose. The sharper the penumbra, the tighter and more conformal the dose can be delivered. One metric that may be used to characterize the dose profile and size of an the X-ray beam spot and effective penumbra dimension makes use of isodose contours, conveniently expressed as a percentage of a maximum central region dose.

Penumbra may be given an empirically convenient definition as the distance between the 80% the 20% isodose lines (the 80-20 penumbra) and the distance between the 90% and 10% isodose lines (the 90-10 penumbra). The 80-20 penumbra in FIG. 13A is indicated to be less than 1 mm in extent for the 4 mm beamspot diameter. Note that the model also shows a degree of scattered dosage at 10% of less of the maximum dose intensity, extending outward beyond the 20% isodose line, trailing off thereafter to a low level of dosage (>1% of maximum) as the radius from target increases.

For purposes of comparison, FIG. 29B shows a plot of measured dose intensity at retinal depth for an X-ray/collimator configuration comparable to that of FIG. 29A. In this example, a radiographic film was place behind an approximately 20 mm thickness of "solid water" type water-equivalent radiographic phantom material, to simulate the tissue thickness depth of the retina. The optical density of the film, exposed to about 10 Gy of absorbed X-ray dose, was converted mathematically to an equivalent absorbed dosage. It may be observed that the general shape of the beamspot and penumbra is very similar to that shown in the Monte Carlo simulation of FIG. 29A. However, no bolus of scatter immediately beyond the penumbra (believed to be an artifact) is observed in the measurements, the dosage level instead dropping consistently and rapidly to a low level beyond the 20% isodose ("measured scatter"). This distinction between the modeled scatter and the measured scatter is indicated also in FIG. 13A by a dashed line. Note that although the measured penumbra and scatter region is smoothly and consistently characterized in the radiographic measurements of FIG. 29B, the central beamspot is depicted somewhat irregularly, apparently due to saturation exposure of the film at maximum dosage.

Stereotactic Beam Targeting

FIG. 30A is a frontal view of an eye as seen aligned with a system reference axis 18 (temporal to right, nasal to left), and depicting stereotactic X-ray treatment beam geometry, such as described in FIG. 18. Once reference axis 18 is identified (e.g., geometric axis 2810), treatment may be carried out by a device oriented with respect axis 18. Alternatively, a distinct axis 19 may be defined with respect to axis 18, for example by a shift of distance dy and dx, so that axis 19 intersects treatment target 318 positioned off-axis with respect to axis 18. Axis 19 may be called the "treatment" axis. Based on straightforward geometry, the device 312 can now be positioned so that its beam axis 311 intersects treatment axis 19 at tissue target 318. Axis 18 may be used to define one or more correlated geometric axes in the external coordinate system, and to define one or more additional intersection points with respect to beam 311. Note for treatment targets lying on reference axis 18, offset "d" may be about zero, and for treatment delivered through or to the cornea, angle "Φ" may approach zero. The illustrated example is of an embodiment in which the alignment system is coupled to a treatment system adapted for orthovoltage X-ray treatment of a region of the retina generally including the macula.

FIG. 30A can be correlated with FIGS. 15-18 and 20 which show related eye anatomy and the geometry of associated eye alignment-radiation treatment system 300. As shown in FIG. 30A, although a single beam axis 1400 may be employed, a plurality of beam axes may be defined in which two or more treatment beams are aimed to impinge on target 318 stereotactically. Treatment axis 19 may be chosen to intersect a selected target 318 within the eye, and employed as a reference to orient two or more treatment beams aimed to impinge on target 318 stereotactically.

In the example of FIG. 30A, treatment axis 19 is chosen to intersect a selected target 318 within the eye, and employed as a reference to orient three treatment beams projected along three different beam axes 1400*a*, 1400*b* and 1400*c*, the beam axes defined so as to each impinges on target 318 from a different direction. Multiple beams may be projected simultaneously, or sequentially, with intervening periods of no treatment if desired. Likewise, multiple beams may be provided by multiple separately-positioned treatment devices. However, a preferred embodiment employs a single treatment device 312 (e.g. a collimated orthovoltage X-ray source), which is sequentially repositioned by positioning device 310 to administer treatment in sequential doses along each of a plurality of beam axes, such as axes 1400*a*, 1400*b* and 1400*c*. The beam axes each have a different respective point of entry into the body surface (311*a*, 311*b* and 311*c* respectively) and each follows a different tissue path leading to target 318. Likewise each beam follows a different tissue path for any propagation beyond target 318. In this way, treatment beam dosage penetrating tissue remote from target 318 may be minimized relative to the dosage received at target 318.

Note that the number of stereotactic beam paths selected (for emission either sequentially or simultaneously) may be selected from a considerable range to achieve treatment goals. FIGS. 30A-B illustrate a 3-beam pattern example (1400*a-c*), and device embodiments described in detail herein (e.g., FIGS. 37-38) can conveniently administer such a pattern in sequence. However, alternative devices having aspects of the invention may have multiple X-ray source and/or collimators configured to administer such a pattern simultaneously. In other alternatives, treatment goals may be achieved with a single beam path 1400. In still further alternatives, treatment goals may be achieved with a number of beams exceeding three (e.g., 1 to n beams).

In yet further embodiments, a beam path 1400*i* may be continuously moved stereotactically during X-ray emission over a beam track on the sclera (or other body surface) having a selected scope or range, so that while the entry region for radiation is spread out along the surface track so as to reduce local tissue dose (see track 311*a* in the examples of FIGS. 57A-E), at the same time the target region receives a concentrated dose as in target 318, the moving beam path reaching an effective focus on the target region.

In general, where a stereotactic beam pattern is described herein as "one or more beams", "a plurality of beams", or "at least one beam", these expressions include treatment configurations in which a collimated beam is moved continuously or incrementally over a selected stereotactic position range during radiation emission so as to achieve an equivalent treatment goal having a focused or concentrated target radiation dose.

Beam axis 1400 (or for multiple beams, each of axes 1400*a-c*) may be selected to follow a tissue path which avoid vulnerable structures or tissues which are remote from target 318, so as to minimize dosage received by such tissues. For example, in treatment of the macula for macular degeneration, axes 1400*a-c* may be selected to deliver a selected dose of beam treatment (e.g., a selected dosage of absorbed X-ray energy) to a target 318 on or near the retina 340, centered on the macula 342 while minimizing absorbed radiation by the optic nerve 350, the lens, and the like. In the example shown, three beam axis 1400*a*, 1400*b* and 1400*c* are defined, so that the beams directed towards the posterior eye enter the body on the surface of the anterior sclera 17 at points 311*a*, 311*b* and 311*c*, each entry point a selected distance beyond the limbus 26. Such beam orientation can avoid or minimize absorption by the lens and other structures within the eye, by appropriate selection of the beam paths.

As illustrated in FIG. 30A one or more of beam axes (1400*a*, 1400*b* and 1400*c*) are defined such that each axis lies within a conical conceptual surface and whereby each beam intersects the apex of the cone. The cone may be defined having as its conical axis the treatment axis 19 with the apex disposed at target 318. In this example, treatment axis 19 is defined parallel to reference axis 18, having x-y offsets define in an perpendicular plane by "dx" and "dy" respectively (for a treatment target intersected by the reference axis the offsets are zero). Once the treatment axis 19 is defined, the base 34, the apex angle ("Φ" in FIG. 7), and rotational positions of axes 1400*a-c* with respect to axis 19, may be adjusted to provide both beam intersection at about target 318 as well as to provide entry points 311*a-c* located at a desired position of the body surface.

In one example of an orthovoltage X-ray treatment for macular degeneration, offsets dx and dy are selected to define a treatment axis 19 centered on the macula, angle Φ is selected to provide intersection of beams 1400*a-c* on the macular surface, and base 34 is selected to provide surface entry points 311*a-c* in a region of the lower anterior sclera beyond the boundary of limbus 26. In this example, an X-ray beam source may positioned by positioning device (see 115 in FIGS. 33 and 37 so as to project a collimated beam from a selected X-ray source distance so as to form a beam having a characteristic width at tissue entry "w". Note that although a treatment beam may be projected through an eye-lid or other tissue proximal to the eye, the eyelids (in this case the lower eyelid) may be conveniently retracted so as to expose an additional area of the anterior sclera 17.

Note that in the most general case, treatment axis 19 need not be parallel to reference axis 18, and target 318 may be located relative to axis 18 by other analytical methods not including a separately-defined treatment axis. On the other hand, a real or at least conceptual hazard of high degree-of-freedom robotic systems employing energy beam treatment, is the large possible range of beam paths (e.g., upon a control system failure), and associated risk issues, regulatory complexity, and high end-user installation and site modification costs.

FIG. 30B depicts results of a procedure in which three beams were focused on the back of an phantom eye model using a robotic system, and represents a radio chromic film after bench top delivery of 100 keV overlapping x-rays at a target site 3250. A radio surgical phantom model was used in which a model eye was placed in the eye socket. Film was placed on the back of the model eye and x-rays were delivered to a target representing the macula. The region of overlapping x-ray beams 3275 are shown at their overlap region where the dose is 24 Gy. The optic nerve 3260 is depicted lateral to the overlapping set of beams at a scaled distance from the center of the overlap. A rapid isodose fall off 3273, 3277 occurs lateral to the overlapping region 3275 and well away from the optic nerve 3260. Notably, the isodose depicted at region 3265 is indeed between about 1% and about 10% of the dose (0.24 Gy-2.4 Gy) at the treatment spot 3275. These data are a consequence of the overlapping beam geometry as well as the fine beam collimation; they are physical proof of the ability of finely collimated overlapping orthovoltage x-ray beams to create well-defined treatment regions. Due to the 10-100 fold difference in treatment dose to optic nerve dose, fractionation is not required, and the entire dose can be given to the treatment region in one session with minimal concern for injury to important structures, such as the optic nerve. These overlap regions can be optimized and/or placed anywhere within the eye which is determined by the treatment planning system and depends on the beam energies, collimation, and filtering. The degree of overlap is also to an extent determined by system parameters. For example, treatment of the entire region of the retina for macular degeneration may be different than that for tumors or for hemangioma.

FIG. 30C-D are plots illustrating a stereotactic 3-beam dose map of retinal dose measured by radiometry on a phantom eye or mannequin (by optical density analysis of the exposed film), without eye motion, as described herein. In this example, the beam trajectories are substantially as shown in FIG. 30A.

The contour dose map of FIG. 30C shows that the 4 mm target region lies entirely within the 80% isodose (20 Gy based on a maximum level of ~25 Gy). Indeed the area of the 24 Gy isodose (about 96%) is roughly co-extensive with the 4 mm target region. The optic disk lies entirely beyond the 1 Gy isodose, and thus receives substantially less that 4% of the maximum dose. Note that while the term "penumbra" is used herein specifically to refer to dose distribution from a single collimated beam, it is instructive to note the concept as applied to a stereotactic multiple beam dose map, and an 80%-to-20% isodose cumulative "penumbra" is indicated in FIG. 30C and FIG. 30D as the span between the 20 Gy isodose and the 5 Gy isodose, based on a maximum combined dose level of approximately 25 Gy (note, dose levels may vary substantially depending on treatment plan particulars).

FIG. 30D is a plot of the dose profile corresponding to the line B-B in FIG. 30C, which is a transect through the target center and the optic disk center. This profile provides a clear illustration of the isodose fall-off in the "penumbra" region, decreasing rapidly to a low value at the margin of the optic disk.

Measurement of Human Eyes for Radiation Delivery to Target

In embodiments of radiotherapy methods and devices having aspects of the invention, the overall eye axial length (distance from cornea surface to retinal surface) and the beam tissue path length (the path length of tissue to be penetrated by the treatment beam in propagating from surface to target) are relevant to important of treatment parameters. For example, the tissue path length is relevant to (a) the selection of X-ray input beam spectral characteristics (determination of tube potential and filters, see FIGS. 10 to 12), and (b) for a given X-ray treatment beam, the tissue path length as the beam is actually administered to a patient determines the dose rate at target in Gy/min (see pre-target absorption indicated in the eye model of FIG. 20). Similarly, the eye axial length and other eye geometry are relevant to tracking motion of the retina during administration of treatment, as is described further herein and in U.S. Application No. 61/093,092 filed Aug. 29, 2008 and No. 61/076,128 filed Jun. 26, 2008; each of which is incorporated herein by reference.

Thus it may be seen that measuring and/predicting the tissue path length for the patient permits accurate calculation of the rate at which radiation is absorbed by target tissue. In certain radiotherapy embodiments, for a known dose rate based on tissue path length, the duration of beam emission is conveniently controlled (e.g., a timer to shut off power to tube) so as to administer a planned dose to the target (e.g., one third of total planned dose for a 3-beam stereotactic procedure). For this purpose, a series of experiments were performed to determine appropriate eye measurements to establish the depth of target on the retina. A correlation model was established to show the relation of the path-length to axial length of the eye.

Using a 3D laser scanner, a device which can precisely map the coordinates on a surface, a series of points in three dimensional space was derived from the surface of several cadaver eyes. FIG. 31A shows a typical example of the mapping results from this protocol, which permits mapping the shape and contours of the cadaver eye to a high degree of accuracy. With this model derived from the surface of cadaver eyes, the axial length and path length can be measured directly. The axial length (AL) and path length (L3) are indicated, the beam path corresponding approximately to the beam path shown in FIGS. 18 and 20, directed through the sclera entry spot 311 to the target center 318 (e.g., macula or fovea), the beam entering the eye beyond the limbus of cornea 35 of eye 30.

As shown in FIG. 31B, the tissue path length and axial length can then be correlated or related to one another. In the initial dataset, this correlation has been determined to be fairly linear, which depicts a series of seven cadaver eyes. The relationship can be conveniently and usefully approximated by a variety of linear or non-linear equations or curve fits. A simple example expressing the data is a linear curve of the form $Y=aX+b$, where Y=tissue path length (PL), and X=axial length (AL). For example where $a=1$ and $b=-3$, the equation is $PL=AL-3$, express in millimeters. Alternative expressions may be used, and additional data (or more specialized data sets) may also be analyzed by the methods shown. Alternative equations can be used to characterize the same data (e.g., $PL=0.49*AL+9.7$) without departing from the spirit of the inventions.

An A-scan is an ultrasonic measurement conventionally used in ophthalmology where eye geometry is relevant, such as in refractive vision correction. It has be found by inventors herein that A-scan measured axial length can usefully be performed on the example cadaver eyes and compared with Axial lengths determined from the laser scanner data.

As shown in FIG. 31B, which depicts the measurements on a series of seven cadaver eyes, the tissue path length (PL) and axial length (AL) can then be correlated or related to one another. In living patients and study populations, axial length may be obtained by an A-scan. An A-scan is an ultrasonic measurement conventionally used in ophthalmology where eye geometry is relevant, such as in refractive vision correction. It has be found by inventors herein that A-scan measured axial length can usefully be performed on the example cadaver eyes and compared with Axial lengths determined from the laser scanner data. In general, this relationship can be conveniently and usefully approximated by a variety of linear or non-linear equations or curve fits where tissue path length is a function of axial length, or PL=f(AL). In this example dataset, this correlation can be represented effectively as a linear function. This may be an equation of the form Y=aX+b, where Y=tissue path length (PL), and X=axial length (AL). An example where a=1 and b=−3, the equation is PL=AL−3, expressed in millimeters (curve 200*a* in FIG. 31B).

It should be understood that different equations may be used as effective mathematical representations of this data or similar data (e.g., PL=AL/2+9.5) without departing from the spirit of the inventions. Likewise, this or similar data may be expressed as a non-linear function, such as a quadratic equation or the like (curve 200*b* in FIG. 31B). Alternative expressions may be used, and additional data (or more specialized data sets) may also be analyzed by the methods shown. For example, such ocular data may be represented by alternative non-linear functions, or may be embodied or carried out by look-up table interpolations rather than function evaluations, and the like. Additionally, anatomic data sets correlating additional patient attributes (age, gender, or the like), may be assembled, and predictive relationships obtained relevant to these patient populations. Mathematical relationships representing this data may be including in the software of radiotherapy system 10, and used to predict treatment tissue path length, based on physician measurements and inputs for a particular patient.

In certain alternative embodiments, the functional relationship for tissue path length may be based on more than one anatomic measurement, other measureable patient characteristics (e.g., refractive data), or other patient history data (age, gender, and the like). Advantageously and more generally, the method illustrated in the above example may be extended to other radiotherapy procedures in addition to its use in ocular treatments for to the macula. One embodiment of the method may be summarized as comprising the steps:

(a) selecting one or more input parameters (anatomical measurements, other human measurements and/or other patient-specific characteristics such as age, gender, and the like), such as $P_1, P_2 \ldots P_i$;

(b) characterizing variation in a relevant patient population with respect to the selected parameters (e.g., studies of anatomical or other measurement variation in patient populations, optionally as a function of other patient-specific characteristics);

(c) correlating the population variation with the treatment tissue path length PL for a radiotherapy treatment plan;

(d) determining a mathematical function and/or calculation algorithm effectively expressing a relationship between the selected parameters and the tissue path length, which may have the form PL=f $(P_1, P_2 \ldots P_i)$;

(e) determining data for the selected parameters for a specific patient to be treated;

(f) using the mathematical function and/or calculation algorithm to determine PL for specific patient to be treated ($PL_0$);

(g) modifying or adjusting one or more parameters of the radiotherapy treatment plan based on the value of $PL_0$. (e.g., beam duration or dose, spectral energy, filtration, collimation geometry, beam orientation, or the like); and (h) treating the patient according to the modified or adjusted treatment plan Method embodiments such as the above example may be integrated into radiotherapy treatment devices having aspects of the invention, such as by including effectuating software code in computer processor-controllers of a radiotherapy system, so as to enable the treatment device to carry out one or more of the steps of the method.

In FIG. 31C, for each of seven example cadaver eyes, the A-scan derived axial length is shown, together with the laser-scanner value of tissue path length, and a calculated tissue path length according to the example linear formula (PL=AL−3). For clarity of presentation, the seven example eyes are ordered by increasing A-scan axial length. It can be see that with minimal scatter, the results of the A-scan are a good predictor of path length. The maximum error introduced by the A-scan in these data is approximately 0.3 mm. It has been shown by inventors herein that an error of 1 mm in path length would introduce approximately 3% error into the dose calculation for absorption at a retinal target. Therefore, an error of 0.30 mm introduces approximately 1% error in dose, which quite small and clinically acceptable. Based on this discovery, a method embodiment having aspects of the invention comprises determination a patient's eye axial length by means of a pre-operative A-scan, and then predicting the tissue path length of a treatment beam, and adjusting at least one treatment parameter based on the tissue path length (e.g., beam duration time).

FIG. 31D is a plot depicting the relation between measured patient anatomy and tissue path length for an exemplary radiotherapy treatment plan including X-ray beam paths such as are described in FIGS. 13-20 and 29. In the particular example shown, these include narrowly collimated beams entering the eye at the pars plana (see beams b1-b3 in FIG. 17 and beams 1400*a-c* in FIG. 30A), and propagating to a macular target approximately centered on the fovea (see FIG. 19A).

The graph in FIG. 31D below depicts the correlation between the axial length (AL) as compared to the path length (PL) through which the X-ray travels. Data such as shown in FIG. 31 may be included in treatment planning methods and devices, such as in software as a computational formula (e.g., the formula PL (mm)=AL (mm)−3), look-up table, or the like. A patient-specific anatomic measurement 280, such as an ultrasound A-scan axial length (e.g., 23.5 mm) may then be used (e.g., input to a patient-specific system configuration file accessed by a computer processor) to determine a treatment path length 281 (e.g., 20.5 mm). The tissue path length effects the propagation of X-ray energy to the treatment target as photons are absorbed in the tissue (see FIGS. 12 and 20).

The tissue path length determined as depicted in FIG. 31 may be used in treatment planning methods and devices to regulate the applied X-ray intensity and/or duration so as to achieve a planned target dosage. Conveniently, the duration of X-ray beam emission may be timed and controlled to account for variation in patient specific tissue path lengths. FIG. 32 is a plot depicting the relation between the beam tissue path length and the duration of beam emission required to deliver a planned target dose for an exemplary embodiment of a X-ray treatment system having aspects of the invention. In this example, the target dose is about 8 Gy delivered to the macula. A patient-specific tissue path length 290 (e.g., 20.5 mm) may then be used to determine a beam duration 291 (e.g., 119 sec), such as be software implementation in a system processor/controller.

Radiotherapy System Embodiments—Overview

FIG. 33 is a perspective view of an exemplary embodiment of an X-ray treatment system 10 having aspects of the invention, for treating ocular diseases. The system is shown with a phantom of a patient's head engaged with head-chin restraint device 160, the head aligned in treatment position. System 10 includes a radiotherapy beam generation module, for example comprising one or more X-ray tubes 112, each having a collimator 118 for producing a tightly collimated X-ray treatment beam. The system 10 includes a radiotherapy control module or subsystem (not shown) which preferably includes an interface display, processing module, a power supply. The system includes an imaging module 400, which can include one or more cameras and associated light sources, such as LEDs or low-powered lasers.

FIG. 33A is a perspective view of an exemplary embodiment having aspects of the invention of an X-ray treatment system 10 for treating ocular diseases. FIG. 33B is a plan view of the treatment system embodiment of FIG. 33A, further showing associated system processors 501 and operator input/output devices 502-503, depicted as installed in an exemplary operating console 500. FIGS. 34-40 illustrate alternative or additional aspects of system 10.

With reference to FIG. 33A, the system is shown with a phantom of a patient's head engaged with head-chin restraint device 160 and head fastening 161, the head aligned in treatment position. System 10 includes a radiotherapy generation module or X-ray source assembly 420, for example comprising one or more X-ray tubes 112, each having a collimator for producing a tightly collimated X-ray treatment beam. The system 10 includes a radiotherapy control module which preferably includes an interface display 502, processing module 501, operator input devices 503 and a power supply (not shown). The system includes an imaging module 400, which can include one or more cameras and associated light sources, such as LEDs or low-powered lasers.

In the embodiment shown, system 10 includes an automated positioning system (APS) 115 for moving and aiming the X-ray source assembly 420 (including X-ray tube 112 and collimator 118) to direct a treatment beam to a target from one or more selected directions. The system 10 further includes eye-guide, eye alignment and stabilizing module 625. Further description of system 10 follows below.

FIG. 33B illustrates one particular embodiment of an operating consol 500 having aspects of the invention, suited to house the components of system 10 and to provide for its effective and safe operation in patient treatment. It should be understood that the intercommunicating components of system 10 can be mounted in a variety of different architectural configurations, and the components may be distributed remotely and/or integrated with other devices without departing from spirit of the invention. For example, components shown in FIG. 1B in a "desktop" type mounting (e.g., X-ray source positioning system 115) may alternatively be supported in a ceiling or wall-mount configuration, or may be mounted on wheeled carts, or the like. Similarly, alternative embodiments of system 10 having aspects of the invention may be optimized to reduce size, weight and volume to permit integration of components into one (or a few) physical modules, for integration into other medical systems, and/or to provide portability.

The exemplary operating consol 500 provides seating 506, 507 for patient and one or more operators, and may also include supplemental radiation shielding 508*a,b* between the operator and X-ray source assembly 420. Cameras of imaging system 410 (e.g., one or more CCD or other electronic image capture devices) communicate with computer processors 501 of system 10. Processors 501 communicate with operator displays 502 and operator input devices, such as keyboard 503. The console also houses one or more computer processors 501, operator input/output/display devices 502*a*-503*a*, and interconnections 505 to various system components, such as imaging system 420, positioning system 115 and X-ray source assembly 420.

In should be understood that computer processor elements, and associated input, output, display, memory and/or control components can be distributed, embedded and/or linked in a number of alternative arrangements by means known in the electronic arts, and the arrangement shown in FIG. 33B is exemplary. Likewise, intercommunication of electronic elements of system 10 may be wireless, and alternatively certain processor, memory and/or I/O functions may be performed remotely or over a network.

For example, supplemental displays and control devices communicating with processor 501 can be positioned to assist or interact with an operator or physician while working close to the patient (e.g., prior to X-ray beam emission). An auxiliary display/input device 402*b*-403*b* is shown to adjacent to eye-guide positioner 600, e.g., to assist an operator in engaging and aligning an eye-guide (110 in FIG. 40) on a patient's eye, and/or in adjusting the positioner 115 and X-ray source 420 to an initial treatment position.

In addition, a number of sensor elements may be embedded in the components of system 10 in communication with processor 501 of provide feedback, monitoring and safety functions. For example, chin-head restraint assembly 160 may include a right-left pair of hand grips 163 for the patient to hold, helping to maintain the patient's torso and shoulders in perpendicular alignment to eye-guide 110. The hand grips may include force or contact sensor to monitor that the patient is in position. Similar sensors may be included in head-fastening 161, e.g., to monitor head position and/or motion. Such safety/monitoring sensors may produce trigger signals to alert an operator and/or may be employed to gate or interrupt X-ray emission during treatment. In another example, light intensity and/or spectral sensors (not shown) may be positioned on system 10, and configured to automatically control the lighting elements of imaging system 400 (e.g., lights 405,406) so as to maximize image recognition performance as well as other operating parameters.

The console 500 comprises a power/accessories assembly 509 which may include power supply, power regulators, high voltage source and/or other accessories needed for operation of X-ray tube 112. It should be noted that a number of alternative commercially-available types of X-ray tubes or sources (as well as dedicated tube designs) may be included in X-ray source assembly 420 without departing from the spirit of the invention. An X-ray power supply/high voltage source may be a relatively large unit which is most conveniently housed separately from movable X-ray source assembly 420. In the example shown, conduits 425 lead from X-ray power/accessories assembly 509 in console 500 via guide spool 426 to connect to X-ray tube 112. The guide spool 426 is configured to support conduits 425 as X-ray source assembly 420 moves during system operation, as is described further herein.

Additionally, many commercially-available X-ray tubes are designed to use liquid cooling to increase output capacity. Power supply/accessories assembly 509 and conduits 425 may optionally include connections to coolant and/or an integrated coolant supply/chiller, so as to supply coolant to X-ray tube 112. Optionally, assembly 509 may include batteries or an uninterruptible power supply (UPS), e.g. of sufficient capacity to permit system 10 to complete a radiotherapy treatment notwithstanding a loss of line power during the treatment.

The exemplary operating consol 500 provides seating 506, 507 for patient and one or more operators. System 10 may be configured to minimize stray X-ray radiation. However, as a radiation safety practice, console 500 may include supplemental radiation shielding **508*a* between the operator seating position 507 and the X-ray source assembly 420. The shielding may optionally include a radio-opaque window 508*b*** (e.g., comprising a transparent silicate glass including heavy nuclei such as lead) to permit direct observation of (and reassurance to) the patient during X-ray emission. Such an operator station configuration allows close monitoring of the patient during irradiation treatment, and promotes easy access for direct assistance to the patient when radiation is not being emitted. Alternatively or additionally, observation cameras (not shown) may be mounted so as to allow an operator and/or physician to monitor the patient during treatment via electronic displays.

X-Ray Source and Positioning System

FIGS. 34-36 depict the X-ray source and collimator (112 and 118 in FIG. 33) having aspects of the invention, shown in FIG. 3 as aligned in position for treatment of the retina of an eye. FIG. 34 shows a patient's head including cross-section of an eye in the vertical plane of symmetry of the eye, shown in association with imaging system 410, and an X-ray source assembly comprising X-ray tube 112 and collimator 118. FIG. 35 is a perspective detail view of the system components shown in FIG. 34 together with portions of the positioning system 115 (see FIG. 37), illustrated in association with a phantom patient eye 30 coupled to eye-guide 110. FIG. 36 is a longitudinal cross-sectional view of collimator 118 and a portion of X-ray tube 112. FIG. 37 is a perspective illustration of an embodiment of a positioning system 115 having aspects of the invention, in this example a 5-degree of freedom automated positioning assembly, shown supporting X-ray tube 112 and collimator 118 in association with a phantom eye 30. FIG. 38 depicts embodiments of a motion control system in which the collimator 118.

As shown in FIGS. 34 and 35, the X-ray source assembly 420 is aligned in position for treatment of the retina target 318 of an eye 30. For clarity and simplicity of illustration, the example of FIGS. 34-35 shows the assembly 420 aligned in the vertical plane including treatment axis 2820 with an upwardly directed X-ray beam axis 1400. This corresponds to example beam 2 (b2) as shown in FIGS. 15 and 17, such that the value of azimuth angle θ is 180 degrees. The polar angle (angle between treatment axis 2820 and beam axis 1400) is shown as approximately 30 degrees. It should be understood that orientation of beam 1400 may be selected and adjusted to suit a particular treatment plan method having aspects of the invention, and need not be restricted to any of the orientations shown in these examples.

FIG. 34 shows components of imaging/data acquisition system 410 including data acquisition devices functioning to track and/or identify the position of the eye 30, its anatomical structures (e.g., the limbus of the eye), and/or an eye-guide 110. In the example shown, the data acquisition devices comprise one or more cameras (e.g., camera 401 located aligned with the eye geometric axis 2810, camera 402 aligned off axis, or both). The cameras may be sensitive to visible and/or non-visible wave lengths (e.g., IR) and may include filters configured to tune sensitivity to certain ranges of wavelength. Alternatively or additionally, the data acquisition devices may comprise non-light emitters and detectors, such as ultrasound transducers/generators, radio-frequency devices and the like. A number of types of fiducials, transponders and/or mirrors may be included as system components to enhance the function of the data acquisition system. Likewise, radiation emitters may be included, such as lights, lasers, LEDs and the like.

In certain exemplary embodiments described herein in detail, the imaging system 410 comprises an off-axis camera configured to measure the eye-guide 110 and eye position relative to the Z axis, optionally assisted by one or more lights 406 (e.g., visible or IR LEDs). An on-axis camera 401 is included, configured to determine the alignment or offset of the eye 30 and/or eyeguide 110 with axis 2810. Similarly, one or more lights 405 (e.g., LEDs) may be included to assist camera 401.

In certain embodiments described in detail herein, eye-guide 110 includes an axially perpendicular mirror (not shown in FIG. 34), and imaging system 410 includes a axial collimated light pointer 403 (e.g., including a diode laser, beam splitter, and camera filter) aligned to reflect off the mirror to be received by camera 401, permitting determination of the axial alignment (or alignment difference) of eye-guide 110 with respect to axis 2810.

In alternative embodiments described in detail herein, eye-guide 110 includes a geometric pattern of highly-reflective fiducials, and camera 401 is configured to image the pattern, the camera in communication with a system processor unit programmed to determine the alignment (or alignment difference of eye-guide 110 with respect to axis 2810.

The collimator 118 is positioned close to the eye of the patient, so as to allow for an acceptable penumbra as well as a tightly collimated radiation beam as described in the above noted U.S. application Ser. No. 12/103,534 filed Apr. 15, 2008; Ser. No. 12/027,069 filed Feb. 1, 2008; and Ser. No. 12/100,398 filed Apr. 9, 2008; each of which is incorporated by reference. In certain embodiments, the collimator exit aperture diameter is between about 1 mm and about 4 mm so that the spot size on the back of the retina is approximately about 2 mm to about 7 mm.

FIG. 36 depicts a cross-section schematic view of a portion of an X-ray source assembly 420 of system 10. Laser pointer 1410 travels through a beam splitter 1220 and exits the collimator with its center aligned with the radiation beam. In the example shown, the x-ray anode 1420 has a greatest dimension between about 0.1 mm and about 5 mm and can be placed at a distance L from the retina of about 50 mm to about 250 mm, and preferably from about 100-200 mm, and more preferably about 150 mm. Maintaining the anode 1420 at such a distance from the retina in one embodiment allows maintaining a low penumbra. The radiation beam 1400 is delivered through the collimator 118, and its diverging path enters the eye approximately in the pars plana region, missing the important structures of the anterior chamber such as the lens and the cornea. In the example shown, eye-guide 110 lens contacts the sclera and/or the cornea of the eye.

As shown in FIGS. 34 and 36, the collimator 1405 is preferably collinear with the light source 1450, which can act as a pointer to indicate the point on the eye through which the radiation enters the eye 1300. In some embodiments, the light pointer position is used to track the radiotherapy source vis-à-vis an image recognition system which identifies the position of the pointer relative to an ocular structure (e.g., the limbus) and the radiotherapy device is then moved based on the image (e.g., to a region further away from or closer to the limbus of the eye). In some embodiments, the physician visualizes the position of the laser pointer relative to the limbus and manually adjusts the x-ray source into position.

Light pointer 1410 (e.g., a laser beam emitted from a source 1450) is coupled to a collimator 1405, or behind the collimator 1405, so that the light pointer 1410 is coincident with an x-ray beam 1400; the light pointer 1410 can indicate the position 311 on a surface of an eye through which the radiation source enters by tracking angles of incidence of the collimator and x-ray beam. Cameras of imaging module 400 (see FIG. 33A) can track point 311 and image processors can be used to confirm this position to a user, or to trigger automated controls, if position 311 should be out of a threshold of accuracy, per a treatment plan.

As illustrated in FIG. 34, for convenience certain dimensions relevant to beam collimation and treatment anatomy may be identified as L0, L1, L2 and L3, where:

L0 is the total distance from the X-ray source anode 1420 to a treatment target 318 (e.g., macula or fovea);

L1 is the distance from the X-ray source anode 1420 to the collimator exit aperture plane 1405;

L2 is the distance from the collimator exit aperture plane 1405 to the tissue surface beam spot 311 (e.g., sclera surface at or near pars plana); and L3 is the length of the propagation path of the X-ray beam within tissue to reach the treatment target, the distance from beam tissue entry spot 311 to the treatment target 318.

In an exemplary ocular treatment plan having aspects of the invention, the collimator exit plane 1405 is typically within a distance L2 of about 1 cm to about 12 cm from the beam entry point 311 on the sclera. However, in alternative embodiments, the collimator may be configured to be in contact with the surface of the eye or adjacent face, and may include a suitable resilient or cushioning biocompatible contact surface. The distance D may be selected as a trade-off between the goal of minimizing penumbra of beam 1400 at the retina, and in avoiding interference and discomfort of the patent, e.g., due to space limitations when working close to the face. In certain embodiments, a high degree-of-freedom (DOF), high range-of-motion robotic positioner may be employed to position X-ray tube 112 and collimator 118, which can be programmed and/or controlled to maneuver so as to avoid interference with objects and parts of the patients body. See for example, high degree-of-freedom robotic surgical control systems such as employed in the CyberKnife® robotic radiosurgery system (Accuray, Inc. Sunnyvale, Calif.) and the da Vinci® minimally-invasive surgical system (Intuitive Surgical, Inc., Sunnyvale, Calif.). However, the da Vinci is not autonomous and requires an expert surgeon to move its arms. The Cyberknife is in fact autonomous. However, the linear accelerator which moves around the patient is over 1 ton in weight and cannot move close enough to the patient to deliver beams of X-ray to the eye. Furthermore, the system does not include an eye stabilization system to allow for alignment relative to the eye.

However, alternatively and advantageously, a limited range-of-motion positioner (see 115 in FIG. 33) may provide greater precision and accuracy of radiotherapy, particularly where a single DOF is moved to stereotactically re-position the X-ray source 112 for sequential beam treatment applications, e.g., by minimizing positioning error, vibration and dynamic effects. In addition, a real or at least conceptual hazard of high degree-of-freedom robotic systems employing energy beam treatment, is the large possible range of beam paths (e.g., upon a control system failure), and associated risk issues, regulatory complexity, and high end-user installation and site modification costs.

In one example, L2 is selected to be about 55 mm and L0 is selected to be about 150 mm, suitable for use with APS 115 shown in FIG. 33 and described further in FIGS. 37-38. See, for example, embodiments described in the above noted U.S. application Ser. No. 12/100,398 filed Apr. 9, 2008; which is incorporated by reference.

In many embodiments, only a small amount of movement is required of the x-ray source 112 to treat a disease of the retina, such as macular degeneration and/or diabetic macular edema. In these embodiments, six degrees of freedom can be applied to the x-ray source 110, but the range of each degree of freedom is may be limited. Because each treatment dose is relatively short and applied over a small distance, the robot can sacrifice speed and travel distance for smaller size.

Alternatively, multiple X-ray sources 420 may be employed, e.g., having a fixed relationship to each other, to supply multiple stereotactic beams for treatment. However, embodiments employing an APS such as shown in FIGS. 33-38 can be more compact, lighter, and less expensive, and avoid the space limitations of excessive equipment working close to the face.

FIGS. 37 and 38 depict embodiments of a constrained X-ray positioning system to treat the eye (e.g., as included in APS 115). Positioning system 115 is depicted. Translation in the X-Y-Z motion is shown and in angular orientations Φ and θ. This positioning system is customized for close treatment and to treat the eye. The range of motion along each degree of freedom is limited and the positioning system 155 delivers x-rays to the eye. X-ray source 112 is positionable with respect to the eye, which can be tracked, in some embodiments, with a contact member 110 and module 625.

Note that imaging support 412 (see also FIG. 35) is shown in this example projecting from XYZ stage 416, so that imaging system (410 in FIG. 35) may be supported independently of the Φ and θ actuators 413 and 414 respectively, but may be positioned by XYZ stage 416 so as to be in alignment with the eye geometric axis 2810 or treatment axis 2820, for example. However, it should be noted that all or portions of imaging system 410 may be supported either together with or independently of any of the degrees of freedom of positioning system 115, without departing from the spirit of the invention. For example, one component of imaging system 410 (e.g., a camera) may be mounted directly to tube 112, while other components are mounted to XYZ stage 116, and yet other components are mounted and positioned independently of all of the 5 DOF of the exemplary positioning system 115, e.g., by an independently actuated and controlled robotic support, or the like.

FIG. 38 depicts embodiments of a motion control system in which the collimator 118 is moved by the positioning system around the tip of a cone with the x-rays converging on a focal spot within the eye, such as the macula. The distance along the center of the cone to the collimator is constant for a given angle Φ which refers to the angle the collimator 118 makes with treatment axis 2820. The distance from the edge of the collimator to the focal spot is constant for any Φ or θ. Because the motion system is rigidly constrained around an axis, the error is very small in terms of positioning and movement. In some embodiments, the distance from the X-ray source anode 1420 to the retinal target can be from about 200 mm to about 100 mm, and in an embodiment described in detail herein, this distance L0 may be about 150 mm. Angle Φ can change depending on the distance prescribed or desired. In some embodiments, the angle Φ is variable and can be changed depending on the desired entry position of the beam into the eye. Nonetheless, to achieve the desired motion around the point of focus, the collimator moves around the rim of a cylinder such that the collimator can emit radiation from points at a constant angle with respect to the target. Such movement enables the positioning system to accurately position the collimator and x-rays tube along an arc. This single degree of freedom after positioning makes the therapy efficient and precise.

In the exemplary embodiment of positioning system 115 shown in FIG. 37, the system comprises a base (421 in FIG. 33A). Note that the base 421 is shown as a table-mount type base, but may be alternatively supported by other mounting structures known for medical devices, such as overhead mountings, cantilevered wall mountings, wheeled cart mounting, retractable or folding mountings, or the like.

In this example, base 421 supports a proximal XYZ stage 116 having three sequentially-supporting mutually-perpendicular linear actuators, which in turn supports a more distal rotational θ actuator 414 which has an axis of rotation parallel to the Z axis, which in turn supports a still more distal rotational Φ actuator which adjusts the polar angle relative to the Z axis. The most distal X-ray source assembly 420 is supported by the Φ actuator. This exemplary positioning arrangement shown may be operated in a number of alternative modes. However, it is particularly well suited to a stereotactic mode of operation wherein the X, Y, Z and Φ degrees of freedom are adjusted and fixed relative to treatment axis 2820 and target 318, and subsequently X-ray source assembly 420 is re-positioned by motion of the θ actuator 414 to successive beam treatment positions, as shown in FIG. 38. Alternative embodiments of positioning system 115 for the X-ray source assembly 420 having aspects of the invention have differing proximal-to-distal ordering of the degrees of freedom shown, and may have greater or fewer than 5 degrees of freedom.

Eye Alignment, Stabilization and/or Tracking

FIG. 39 illustrates a top view of one embodiment of a system 625 for controllably positioning and/or stabilizing the eye of a subject for therapeutic treatment. The upper portion of FIG. 39 shows a block diagram of a system 100 for carrying out a method having aspects of the invention. The lower portion of FIG. 39 shows an eye-guide module to permit alignment, stabilization and/or tracking of an eye prior to and during treatment.

In the illustrated embodiment, system 100 includes one or more cameras 102 positioned to image eye 10 along the geometric axis 810 (or 2810). Camera 102 provides video image data of eye 10 to a processor 106 and preferably to a display 104. Coupled to display 104 is an image generator/processor 106, such as a personal computer programmed with commercially-available computer aided design software, capable of generating and overlaying geometric images onto the image of eye 10 appearing on display 104, and preferably configured to perform image recognition algorithms using eye images. Processor 106 may also include patent specific data and images obtained prior to operation of system 100, e.g., to include in displayed images, and/or to be used to provide patient specific geometry for treatment.

Eye-contact device 110 may be equipped with a plurality of position indicators that are capable, in combination with detectors located in the external coordinate system, to locate the position of the contact device in the external coordinate system. This type of tool-tracking system, has been described for use in image guided surgery, where it is necessary to place a movable surgical tool, and typically also pre-op patient images, in a common surgical frame of reference containing the patient. In the present application, the position indicators may be three or more beam-directing elements designed to reflect external positioning beams, e.g., microwave beams from known-position beam sources to known-position beam detectors, with the position of the contact device being determined by a processor operatively linked to the beam detectors. Alternatively, the beam-directing elements in the eye-contact device can be equipped with a plurality of LEDs mounted on the device for directing, for example, a plurality of beams at known-position detectors to determine the position coordinates of the contact device in the external coordinate system. Such tool registration systems have been described, for example, in U.S. Pat. Nos. 7,139,601, 7,302,288, and 7,314,430, all of which are incorporated herein by reference in their entirety.

In a third general embodiment the position-determining means takes the form of a collimated light-beam assembly, including a laser light source and one or more optical components, such as a half-silvered mirror, for aligning the laser beam with the collimated irradiation beam produced by beam source 108; such that the two beams are essentially coincident, along the same axis 810. In this embodiment, the beam-positioning assembly is moved with respect to the patient's eye until the laser beam is aimed directly onto the selected target region of the patient's eye, e.g., the macula region at the central rear portion of the retina. As can be appreciated, this will place the selected target region of the eye in registry with the therapeutic irradiation-beam; that is, the laser beam acts as a reference beam that functions to place the eye in the same frame of reference (coordinate system) as the irradiation beam.

More generally, the spatial registration and guidance of the contact device 110 may be through optical or electromagnetic sensor detection. In general, cameras or other detectors are mounted either on the system, or optionally in the treatment room, and are used to track and register the position of the eye or contact device 110. Cameras or detectors are then able to determine and record the three dimensional position of the contact device 110 in real time, and therefore the position of the eye as it is positioned. A calibration process can be used to determine the relative spatial position of the contact device to a known reference frame, as well as in combination with optional images. The calibration information can be stored in a reference file on the computer and used by a software program.

System 100 also may includes a processor or control unit which has a graphical user interface for receiving instructions from, and presenting information such as alignment and system functionality data to, a system operator. Further, the control unit may be in electronic communication with one or more of the other components of system 100 described above, e.g., the motors controlling the beam-positioning assembly, the motors controlling the eye-positioning assembly, and sensors, detectors and beam sources for determining the position of the eye-contact device in the external coordinate system, as described above.

FIGS. 40A-B illustrate perspective views of an exemplary embodiment 625 having aspects of the invention of a contact device or eye-guide and eye alignment and stabilizing module configured for use with system 10 (it additionally may be usefully employed independent of system 10). This may be used together with head-chin restraint device 160, which includes a head support or support 170 for stabilizing the head of subject, and includes a chin rest 172.

FIGS. 40A-B and 41A-B depict one example embodiment of an method of aligning and/or stabilizing a patients eye 30 and engaged eye-guide 110 with the coordinates of radiotherapy system 10, using a laser beacon 150 a mechanism by which the contact device 110 can be used to align the eye with laser alignment system 800, including laser device 150 (alternative image-based alignment subsystems are described herein). Optionally, the alignment mechanism also directly aligns a treatment system, such as a radiotherapy system (not shown in FIG. 40) in which the radiotherapy system directs its energy toward the eye in relation to the alignment system. Laser pointer beam 810 (which is collinear with the therapeutic beam in some embodiments) is emitted from laser system 800 through a collimator opening 820 and reflects off the surface of beam-directing mirror 230 of the contact device 110. In the non-alignment case depicted in FIG. 40A, the laser pointer beam 810 will not reflect off the surface of mirror 230 collinearly with the collimator opening 820, but will be off-axis, as shown by reflection beam 830. The orientation of the laser system 800 and/or the contact device 600 can be manually or automatically adjusted by direct visualization of the location of the reflection beam 830 or by sensors that detect the location of the reflection beam 830 and adjust the laser system 800 to bring the laser reflection beam 830 into alignment. FIG. 40B shows a case where the laser pointer is in fact aligned, the laser pointer beam 810 is reflected, and the laser reflection beam 830 is substantially collinear with the laser pointer beam 830.

See description regarding FIGS. 54A-B regarding geometry of mirror 230 and angular alignment of eye-guide 110. FIG. 34 depicts a laser beacon 403 mounted to project coaxially with a system image detection camera 401. The image processing and recognition methodology description herein concerned other embodiments for image based eye alignment with respect to FIGS. 34-35 and FIGS. 21A-E are applicable to detecting the deflection of laser beacon 150 (403 in FIG. 3A) from mirror 230, and measuring any alignment error thereby. For further description of laser-beacon alignment, reference is made to application Ser. No. 12/027,083 filed Feb. 1, 2008; Ser. No. 12/027,094 filed Feb. 1, 2008; Ser. No. 12/027,069 filed Feb. 1, 2008, each of which is incorporated by reference.

Alternatively or additionally, alignment of eyeguide 110 with a system coordinate axis may be determined by image capture and recognition methods. See device and method embodiments described herein with respect to FIGS. 48, 50, 55 and 57, for example, and the sections captioned "Imaging subsystem" and "Example of image-based eye and eye-guide measurements.".

The eye-positioning assembly 600 used to position the eye-contact or eye-guide device at a selected orientation. Contact device 110 may be attached to a control arm 180 in the positioning assembly 625, which is being fed into slot 610 of drive mechanism 600. In some embodiments, the contact device 110 of the system can be attached to a coupling component to hold the eye in place.

Eye-guide device 110 is preferably disposable such that a separate (e.g. disposable) contact device 110 is employed for each subject and/or use. Alternatively, contact device 110 may be non-disposable and be treated, e.g., with anti-infective agents, prior to being utilized in multiple subjects' eyes. Drive mechanism 600 is fixed to base 620 through connector 640, which may robotically controlled or manually controlled, and has a known coordinate system. In one embodiment, drive mechanism 600 is fixed in a known, or predetermined, location with respect to the head positioning system (not shown) and/or the eye of the subject (not shown) and/or the positioning system of the radiotherapy device. Push button 630 allows free manual positioning of contact device 110 into and/or out of slot 610. The control arm 180 is fully engaged with the drive mechanism 600 and is fixed in a known, or predetermined location, which allows the eye of the subject to be fixed in a known, or predetermined location, when contact device 110 engages the eye. Although not shown, the eye-positioning device may include internal position sensors operable to detect the position of the end of arm 110 in the external coordinate system, in accordance with movement of the arm in any selected direction.

Note that the eye-guide support arm 180 is illustrated in the examples shown as extending primarily in the "X" direction of the system ordinates. It should be understood that alternative embodiments of module 625 may have the eye-guide 110 supporting from below or above in the Y direction, or from the Z direction, or combinations of these. Eye-guide 110 and eye alignment and stabilizing module 625 is described further with respect to FIG. 41 et seq.

Imaging Subsystem

FIGS. 34 and 35 illustrate a particular example of an imaging system 410 having aspects of the invention. In operation, the imaging system 410 may be configured for several functions, most of which may be performed automatically using image processing and pattern recognition, including:

1. Alignment of eye 30 to eye-guide 110.

Monitor and assist in initial placement of the eye-guide lens 120 by physician (display and guidance).

Confirm alignment of eye-guide 110 (may be automatic).

Monitor and measure the relation of eye-guide lens 120 to the patient's limbus 26, may be performed automatically using image processing and pattern recognition (may be automatic).

Measurement and verification to identify the center of the lens and the limbus in x-y (may be automatic).

Locate and measure the I-Guide in depth z (may be automatic).

Measure orientation of eye-Guide in angular space (may be automatic).

2. Verification of entry position 311 of X-ray beam 1400.

Identify and calculate the position of the laser spot 1410 indicating scleral entry of the X-ray beam and relation to limbus 26 (may be automatically performed, and may also be operator-verified prior to X-ray emission).

The algorithm used may be based on imaging analysis of the border of the limbus 26 as compared to the center of the limbus. In one treatment plan example, the center of the X-ray beam is placed about 4 mm from the limbus border, the beam diameter being about 3.5 mm, so that the beam edge is about 2.25 mm beyond the limbus (the beam 1400 traverses the pars plana region to reach the target 318 at or near the fovea, and so minimizes dosage to the lens.

3. Treatment monitoring (gating)

Continuous x-y-z-θ spatial monitoring of the eye-guide 110.

Continuous measurement of x-y limbus position (may be automatic).

In the example shown in FIGS. 34 and 35, imaging system 410 comprises two cameras. The cameras may interface to computer processors (not shown) of system 10, e.g. via USB connectors. Illumination (e.g., LED lights) may be controlled by signals from computer processors. The cameras may include:

1 Main system X-Y camera 401 (on-axis)

Located along the center axis of the Automated Positioning System (APS).

Will display live images to the physician at video rate (30 Hz).

2 Range Z camera (off-axis)

Mounted above the system axis.

Angled downward to obtain a perspective view of the fiducials 1-3 of eye-guide 110.

The lights 405, 406 and 407 may be configured provide safe, regulated light levels coordinated with imaging procedures, such that imaging applications are insensitive to room light conditions. Regulation of light level and/or wavelength spectrum (e.g., color specific or IR LEDs) may be automatic, such as 1 sensor feedback, and/or image processor feedback, e.g., to account for ambient light, to maximize feature contrast, process optimization and the like. Lighting functions may include:

Lighting the field of view for the main system X-Y camera to see the patient's eye.

Directing light along each camera path onto the retro-reflecting fiducial targets for I-Guide monitoring Lighting the lower limbus boundary 26 for enhancing the contract for limbus detection.

Marking the X-ray entrance point with a laser spot that has been aligned with the x-ray source.

Please see description below with respect to FIGS. 43A-E and the example captioned "Example of image-based eye and eye-guide measurements" for further description of the methods of use of imaging system 410.

Eye Guide Systems

FIGS. 41A-B illustrate top views of an embodiment of a system for engaging the eye of a subject, the contact device 110 being reversibly and controllably coupled to the cornea 200 and/or limbus and/or sclera 239 of the eye 130 is schematically illustrated. The eye 130 includes a cornea 200 and a lens 132 posterior to the cornea 200. The eye 130 also includes a retina 134, which lines the interior of the rear surface of the eye 130. The retina 200 includes a highly sensitive region, known as the macula, where signals are received and transmitted to the visual centers of the brain via the optic nerve 136. The retina 200 also includes a point with particularly high sensitivity known as the fovea. The eye 130 also includes a ring of pigmented tissue known as the iris 138. The iris 138 includes smooth muscle for controlling and regulating the size of an opening in the iris 138, which is known as the pupil. The eye 130 resides in an eye socket 140 in the skull and is able to rotate therein about a center of rotation.

The eye-contact device 110 functions to stabilize the eye in a first position to provide interactive support (e.g. stabilization and/or controllable movement) for the eye while the eye is being treated. The contact device 110 includes a cup or eye-contact member 120 which contacts eye 130. The contact member 120 can be positioned on the eye in a variety of positions, and is therefore useful in a wide variety of ocular treatment procedures. In one embodiment, the eye-contact member is in at least partial contact with the cornea 200. In the embodiment illustrated in FIG. 12B, the eye-contact member covers a substantial portion of the cornea (but does not necessarily touches the cornea). The member 120 may also cover portions of the sclera. The contact member 120 includes preferably a curved structure or "lens" that is substantially centered on the axis 235 and overlying the cornea 200.

The curved contact member 120 is preferably shaped with a concave eye-contact surface that will substantially conform to the anterior surface of the cornea 200 of the eye 130. The contact surface of the contact member 120 preferably has a radius of curvature that is greater than about 5 mm. In one embodiment of the invention, the radius of curvature of the inner surface of the eye-contact member 120 is 7.38 mm. Likewise, in a preferred embodiment, the radius of curvature of the outer surface of the eye-contact member 120 is preferably 7.38 mm. It will be appreciated that a 1:1 ratio of inner and outer curvatures minimizes or eliminates refraction of energy through the eye-contact member 120 in certain embodiments of the invention; in this embodiment, the contact member 120 is a simple cup for the eye 130. Alternatively, the inner and outer curvatures may differ to permit desired focusing or diffraction of energy as it is transmitted through the eye-contact member 120. In some embodiments, the contact member 120 is produced in a variety of shapes, one or more of which can be chosen for a given patient depending on his or her specific anatomy.

In one example embodiment, the eye-guide assembly 110 may comprise a sterile, disposable cup or lens 120. Preferably, the eye-contact member 120 can be fashioned from suitable material with attention to biocompatibility, such as a number of materials well known in the art, such as poly (methylmethacrylate), or PMMA. Thermoset and/or thermoplast PMMA are contemplated by the present invention and are supplied by a number of sources, such as Perspex CQ (ICI Derby, England) or Vistracryl®, PMMA (FDA MAF 1189). Teflon and tantalum are also noted. It is also possible to coat eye-contact member 120 with biocompatible materials if elements of the eye-contact member 120 are not biocompatible. In some embodiments, the eye-contact member 120 contains pigments or dyes. In particular embodiments, the eye-contact member 120 is coated or impregnated with bioactive substances including anti-inflammatory agents/immunomodulating agents and/or anti-infective agents. Particular eye-contact members will contain radio-opaque, radioactive, fluorescent, NMR contrast or other reporter materials.

In an exemplary embodiment of the invention, the contact member 120 is made from poly(methylmethacrylate), or PMMA. The internal contour 122 may replicates the curvature of a typical photocoagulation lens used in ophthalmology practice (e.g. Haag-Streit). In operation, a lubricant (e.g., Genteal) may applied to the lens to keep the eye moist during the procedure. A light vacuum (e.g., from about 10 to about 50 mm Hg, and preferably less than about 25 mm Hg) may applied to the device through the vacuum tube (e.g., by a spring loaded syringe device, which may be clipped to patient clothing), and the eye-guide positioner 600 may apply a bias force against the eye (e.g., spring loading of arm 180). The combination of light vacuum and light bias force has been demonstrated by inventors herein to provide adequate eye stabilization, while promoting patient comfort. The I Guide may have a breakaway feature (e.g., a axial post-and-ferrule connection of lens 120 to post 222) that allows the patient to exit from the positioning arm quickly and seamlessly as needed (e.g. during a sneeze). In this case, the vacuum and cup 120 may remain on the patient in the event of movement away from the positioning arm, allowing easy re-attachment. A certain degree of rigidity, or hardness, of eye-contact member 120 is of use in physically coupling with the eye and with the pivot which attaches to the control arm as described in further detail below. However, the eye-contact member 120 includes, in certain embodiments, a certain degree of flexibility, or softness, such that the eye-contact member 120 has a degree of flexibility, but still retains an arcuate shape in its resting position. In some embodiments, eye-contact member can break away from the contact device at a predetermined position along connector 222, as described in greater detail below.

With continued reference to FIGS. 41A-B, the contact member forms, with a back plate 121 of the contact device, an internal reservoir 122 by which a negative pressure (partial vacuum) applied to the device, through a vacuum port 210, is distributed across the contact surface of the device, as can be appreciated. The vacuum port is connected to a suitable vacuum source though a tube 275. In this embodiment, the vacuum port 210 is positioned through the eye-contact member 120 such that an air or fluid communication space is formed through eye-contact member 120 to allow air trapped between eye-contact member 120 and the anterior surface of the cornea 200 of eye 130 to be reversibly removed, thereby reversibly engaging the eye-contact member 120 with the anterior surface of the cornea 200. In an alternative embodiment not shown, vacuum port 210 is attached to connector 270 which can contain a hollow lumen along axis 235 through eye-contact member 120 such that air between eye-contact member 120 and the anterior surface of the cornea 200 is capable of being reversibly removed as described above. Vacuum or suction assistance is useful for locating and adhering the scleral lens base on the eye 130 of the subject and securing the contact device 110 to the subject's eye 130. Once in a desired treatment position, the contact device 110 can couple with the system 100 during the treatment procedure, as described below. Following treatment, the contact device 110 can be decoupled from the system 110 and removed from the subject.

In one preferred embodiment, negative pressure applied to the eye, for example, a negative pressure of 20-50 mm Hg, is effective to stabilize the position of the eye on the device, that is, substantially prevent movement of the eye with respect to the device, but by itself is not sufficient to hold the eye-contact device on the eye. Rather, the contact device is secured to the eye by a biasing force acting to bias the device against the patient's eye, acting in combination with the negative pressure applied to the eye by the device. In the embodiment illustrated, the contact device is secured to the eye by the biasing force acting through arm 180, where the negative pressure applied to the contact device functions to prevent the eye form moving with respect to the device. As noted above, the contact device is typically biased against the eye with a force of between about 1-25, typically 5-25 grams, by a biasing spring, electromagnetic force, or the like. The advantage of this system is that the negative pressure applied to the eye can be substantially less than that which would be required if the vacuum alone were acting to hold the device to the eye, and this substantially lower negative pressure increases comfort and reduces irritation and deformation of the front portion of the eye. The biasing force is illustrated in the figures, e.g., FIG. 40A-B, by an arrow 119, which indicates the direction of action of the force in the figures.

When the eye-contact member 120 contacts eye 130, negative pressure is applied to remove air from between the eye and contact member, to stabilize the position the eye 130 with respect to the contact member. A primary vacuum fitting is in fluid communication with the air passage. A vacuum line 275 is connected to the vacuum port 210. Additionally, a vacuum pump is in air or fluid communication with the vacuum line 275 for evacuating the air trapped between eye-contact member 120 and the corneal surface 200. Collectively, the vacuum port 210, line 275, and pump (not shown) constitute a primary vacuum subsystem. The degree of strength of the vacuum required to seal can be varied, and preferably controllably and continuously monitored, by the system of the invention. In one embodiment of the invention, between about 0.5 mm Hg and about 50 mm Hg are utilized to provide the negative pressure effective to stabilize the position of the eye with respect to the contact member 120. Preferably, the vacuum is between about 20 mm Hg and about 50 mm Hg. More preferably, the vacuum force applied is about 25 mm Hg and is monitored by pressure sensors and/or by directly monitoring the vacuum source. In some embodiments, the pressure is held passively, for example, by a bladder. The bladder can be produced such that it can apply a given maximum pressure.

It should be noted that the vacuum pressures described herein are dramatically lower than are used in many prior art forms of ocular surgery, such as laser radial keratotomy. This system having aspects of the invention also avoids the need for temporary paralysis of the eye, and avoids patient discomfort. Contact member 122 may be mechanically biased by a light force (such as a spring applied to support arm 180) to bear against the eye, assisting in maintaining engagement with the cornea, without heavy suction.

By engaging the contact member 120 with the eye 130, the eye 130 becomes fixed in a first position, the patient unable to move the contact member with intra-ocular movements. The contact member can, however, be moved using control arm 180; the movement by the control arm rotates the eye through the eye-contact member. Thus, one embodiment of the invention includes substantially stabilizing the eye 130 in a selected position with the eye-contact member 120.

FIGS. 42A-D depicts perspective views of the contact device with the control arm attached having aspects of the invention. As shown in the figures, a preferred embodiments of contact device 110 includes a pivot joint or connector 220 which accommodates pivot movement between the contact member and positioning arm 180, as the arm moves the contact device to a desired orientation in the external coordinate system. In one embodiment, pivotable connector 220 is a spherical or ball pivot joint which allows rotation in three dimensions. In the example shown, positioning arm 180 may be releasably coupled to the contact device through a stem-and-socket arrangement which fastens the end of arm 180 to a socket formed in ball joint 220.

FIG. 42 C-D show an alternative embodiment in which the contact member or lens 320 is supported from one or more off-center points (e.g., by side-post 302) so that a central portion may be transparent, permitting retinal imaging while the eye is engaged by device 312 (e.g., by a fundus camera, which may be employed as a module in system 10, or may be separate). With a contact member or lens 320 which is transparent in its center, direct imaging of the retina can be performed so that rather than fiducials, the retinal coordinates and movement can be imaged directly. Pivot point 220 is off center and post 302 is off center as well. The apex 320*a* of the lens 320 is free to transmit incident and reflected light, allowing the retina and other ocular structures to be seen through the lens 320.

Method of Use of Eye-Guide in Carrying Out Treatment

Figure 43A:
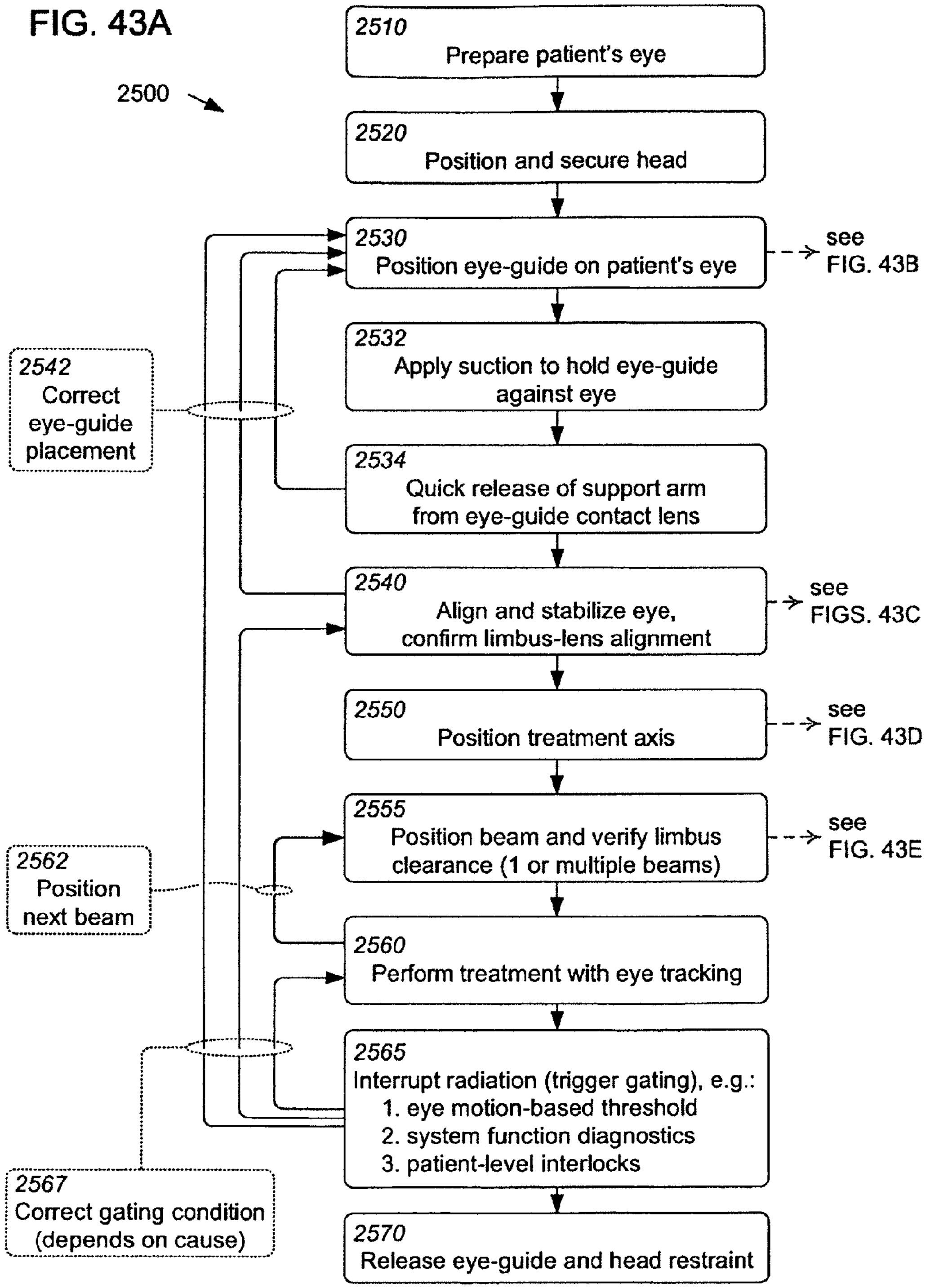

FIG. 43A is a flow chart illustrating one method of utilizing the system for stabilizing and positioning an eye for treatment. It should be noted that the devices described having aspects of the invention may be used in a wide variety of ocular treatment methods. FIGS. 43B-E are diagrams of an eye associated with the radiotherapy system, illustrating examples of steps included in the flowchart of FIG. 43A. As illustrated in FIG. 43A, a preferred method 2500 of employing the system described above includes:

Step 2510

Prepare Eye—

Preparing a subject's or patient's eye for treatment which can include delivering an anesthetic, taping the upper or lower lid, fitting an opposite-eye patch, measuring biometric parameters such as axial length, corneal diameter, etc. Optionally the eye may be dilated, particularly when employing alternative device/method embodiments having aspects of the invention which include integrated retinal imaging optics (not shown) with radiotherapy treatment system 10 (e.g., OCT or fundus camera).

Step 2520

Position and Secure Head—

Following preparation, the subject's head is secured in a suitable position to the system, such as in head and chin rest 160 and head fastening 161. This assembly may include a gating interlock detector (see Step 2565) to assure it remains engaged during radiation emission. Other patient position detectors may optionally be included, such as contact-sensitive hand grips 163.

Step 2530

Position Eye Holder on Subject's Eye—

The eye contact member or eye-guide 110 is then positioned on the subject's eye. The eye-guide contact lens 120 and/or eye surface may be coated with an ophthalmic lubricating solution or gel (e.g., GenTeal® formulations, produced by Novartis Ophthalmics).

As further shown in FIGS. 20 and 43B, the limbus 26 comprises the generally circular boundary of sclera 17 and cornea 35, the limbus lying substantially within the projected plane 26*a*. A corneal tangent plane 35*a* projected parallel to limbus plane 26*a* intersects the cornea center 35*b* closely adjacent the limbus center 26*b*. The geometric axis 2810 of the eye 30 may be defined as an axis through the center 26*b* of the limbus 26, perpendicular to the center 35*b* of the external surface of cornea 35, and intersecting the surface of retina 1435 at retina pole 1436).

The alignment in step 2530 includes engaging the eye-guide 110 with eye 30 so that the eye-guide has a known or measurable orientation and position relative to the center 26*a* of limbus 26. In the example shown, the eye-guide contact portion or lens 120 may advantageously be formed to be substantially circular and concentrically aligned with an eye-guide center axis 110*a*. Similarly, the central axis 110*a* of the eye-guide 110 in the example shown is substantially collinear with the eye-guide support post 222. This symmetry conveniently assists a physician to positioning of the holder or eye-guide 110 on the eye 30 by visually aligning the lens 120 symmetrically with limbus 26. In this position, the post 222 of the eye-guide 110 is aligned with the center of the limbus 26 so as to indicate the geometric axis of the eye. The lens 120 may be transparent, advantageously permitting visual confirmation of concentric alignment of the lens edge 120*a* on the limbus 26 in embodiments in which lens 120 is larger than limbus 26 (i.e., covering a portion of adjacent sclera 17).

However, the lens 120 need not be circular, and the eye-guide support post 222 need not be collinear with the eye-guide axis 110*a* (see examples FIGS. 42C-D). As described herein in detail, camera image-based feature recognition methods having aspects of the invention provide for computer processor determination of the position of the center 26*b* of limbus 26, and fiducials located on eye guide 110 may similarly be tracked to determine the relative position and orientation of eye-guide 110 with the center of limbus 26. These determinations provide a non-visual method to guide and confirm the alignment of the eye-guide 110 with the geometric axis 2810 (see step 2540).

The eye-guide placement and alignment can be performed by a physician while observing the both the holder and the eye of the patient directly, or on a computer monitor, or both of these interactively. Alternatively, an imaging camera-processor of imaging system 410 can determine the center of the limbus automatically and aid in the positioning of the holder with its center aligned with the center of the limbus (see axial camera view of FIG. 43C(2)). In some embodiments, the holder is positioned in place automatically rather than manually by the device operator. Note that at this step the X-ray source positioning system (see 115 in FIG. 33A) need not be aligned with the geometric axis 2810, and is shown in FIG. 43B at an arbitrary relative orientation P1.

Step 2532

Apply Suction to Hold Eye Holder Against Eye—

Once the position of the holder or eye-guide lens 120 relative to the limbus is determined, suction may be applied through the holder to appose it to the eye. With the holder firmly attached to the eye, the holder (and eye) can be moved into position relative to the treatment device in known coordinates within the system. Note that the degree of vacuum suction is selectable, and greater or lesser levels may be employed. In the embodiments described in detail, a relatively light suction (e.g., about 25-50 mm Hg), has been shown to adequately couple the eye-guide lens 120 to the patient's cornea 12. Such modest levels of suction may promote patient comfort and acceptance of treatment.

Step 2534

Quick Release of Control/Support Arm from Eye-Guide Contact Lens—

As described above, a quick release is built into the contact device in some embodiments of the invention. In case of an emergency or fatigue, the patient can release from the holder by a applying a modicum of force which results in the eye-contact member or lens 120 releasing or breaking away from the remainder of the eye-guide device 110. In such a case, the method step returns to the step prior to positioning and securing the head 2520, or to the step of positioning the eye-guide contact device on the subject's eye 2530, as indicated in FIG. 43A.

Step 2540

Align and Stabilize Eye—

As shown in FIG. 43C(1), the treatment device and positioning system axis is adjusted as needed to be positioned relative to the eye so as to bring as to bring the X-ray source positioner reference axis (system Z axis) into alignment with the geometric axis of the eye. In the figures, the system axis when aligned relative to the eye geometric axis 2810 is depicted as P2. The movement, indicated in the figure as M(x, y, Φ, θ), may include movement or rotation of either or both of the patient's head and/or eye, and alternatively or in combination, may include movement or rotation of the treatment system components. For example with reference to FIGS. 33A, 40A and 40B, either one or both of the patient's head, eye and/or treatment system 10 may be moved so as to accomplish alignment.

In certain embodiments, the adjustments may include principally X and Y direction adjustments of eye-guide positioner 600, which may include a manual or powered multi-axis micro manipulator. An auxiliary display (see 503*b* in FIG. 1B) may be positioned to give an physician imaging system feedback while operating the eye-guide positioner 600. With the head stable, movement of the eye guide 110 in the X and Y direction by eye-guide positioner 600 may be used to rotate the eye geometric axis 2810 (e.g., by rotating the eye globe in the orbit) to lie parallel to the reference axis of positioning system 115 (system axis). Movement of the positioning system 115 in the X and Y direction can then be employed to bring the two axes into collinearity. Alternatively or additionally, the system axis may also be rotated to align parallel with an initial orientation of eye geometric axis 2810. Additional adjustments may be provided to adjust the patient's head in rotational degrees of freedom, such as rotation in the X-Y plane. However it has been demonstrated that providing a comfortable but firm head and chin restraint assembly 160 typically is effective to stabilize the patient's head in a generally level and horizontal orientation. See examples shown in FIGS. 1-2 including chin rest 172, forehead support 171 and head fastener 173, preferably used together with adjustable patient seating height.

FIG. 43C(2), depicts an example of a view as captured using an Z-axis camera (e.g., camera 401 in FIGS. 34-35) showing an example contact device or eye-guide 110 positioned on patient's eye 30 (see FIGS. 46 and 48). The eyeguide post fiducial 1 is shown centered on the Z axis and the left and right hand support bar fiducials 2 and 3 are shown horizontally aligned and equally-distant from the post fiducial 1, indicating that the eye guide is aligned parallel and coaxially with the camera axis. This alignment is confirmed and calculated automatically by image recognition software from captured camera images by the system processor 501, and such data may be displayed as a image superimposed on a camera image to the operator (display 502). Note that in alternative embodiments employing a Z-axis laser pointer or beacon (403 in FIG. 34, see FIGS. 53A-B), the eye-guide 110 may be positioned by coaxially aligning the reflected laser spot.

Note in FIG. 43C(2) that eye-guide contact lens member 120 is shown positioned slightly off-center with respect to the limbus 26 (boundary of iris 24 and sclera 17 on patients eye 30). The image processor 501 may also track the limbus position as described herein, and compute a divergence of the center of the limbus from the Z alignment axis (indicated as δx and δy). This divergence may be automatically compared to a preselected tolerance threshold, and also may be displayed to the operator within the camera image frame.

Step 2542.

In the event that the limbus divergence is determined to be unacceptable (either at Step 2540 or at any other step), Steps 2530 through 2540 may be repeated as shown by the return arrows on flow chart FIG. 43A.

Note that the processor 501 may be programmed to monitor eye camera image data (e.g., cameras 401, 402) to re-determine limbus-to-lens alignment on an ongoing basis during treatment, and to determine an error condition (one example of patient-interlock diagnostic in Step 2565) linked to radiation or X-ray source 420 so as to trigger gating when a selected alignment threshold is exceeded.

Note that in certain embodiments having aspects of the invention, a treatment system reference coordinate system may have an arbitrary, but known, orientation/position to an eye anatomical reference, as shown in FIG. 43B. From this known eye reference orientation/position, suitable mathematical transformations may be performed, e.g., by a control processor of a robotic positioner, to move an X-ray source to a selected treatment orientation with respect to an treatment target. However, it is advantageous in ocular radiotherapy devices having aspects of the invention, to have a principal mechanical movement axis of the X-ray source positioning system aligned parallel to, and preferably collinearly with, the geometric axis of the eye. For example, the geometric axis of the eye 2810 may be aligned, as shown the Z axis of positioning system 115, which may also be the θ rotational axis. In embodiments described in detail herein and illustrated in FIGS. 43C-E, such an alignment method is conducive to precision calibration and control of X-ray source movement. With this initial system alignment relative to eye anatomy accomplished (FIG. 43C), only a limited set of subsequent movement ranges and directions are required for carrying out a stereotactic treatment plan. For example, these may include a small X/Y shift to treatment axis 2820 (step 2550, FIG. 43D), small Φ and/or Z adjustment to target convergence angle and limbus clearance, and a modest θ adjustment for each subsequent beam path (step 2555, FIG. 43E). Such limited and constrained motion serves to minimize mechanical backlash, uncertainties and vibration, and to maximize accuracy, repeatability, patient confidence and intuitive operation.

Step 2550

Position Treatment Axis—

A radiotherapy treatment plan for an ocular condition may be developed specifying a target location relative to an anatomical reference point such as the macula or fovea as described herein (see also the examples and description in U.S. patent Ser. No. 12/100,398 filed Apr. 9, 2008, which is incorporated by reference).

In certain embodiments, the X-ray source may be positioned for treatment while maintaining the system Z coordinate axis aligned with the geometric eye axis 2810, either for central axis targets, or by suitable robotic controls transformations for off-axis targets.

Figure 43D:
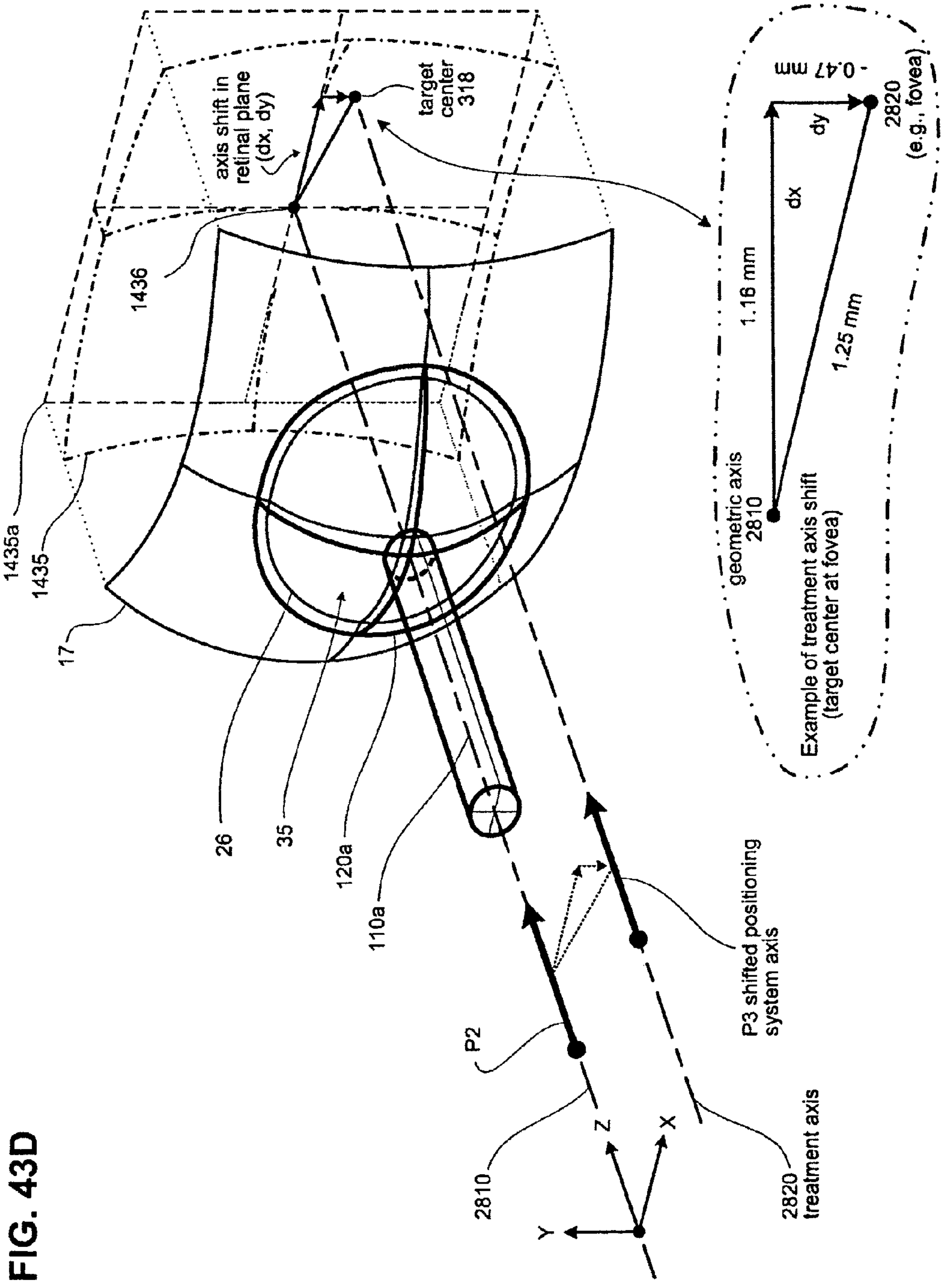
Figure 43E:
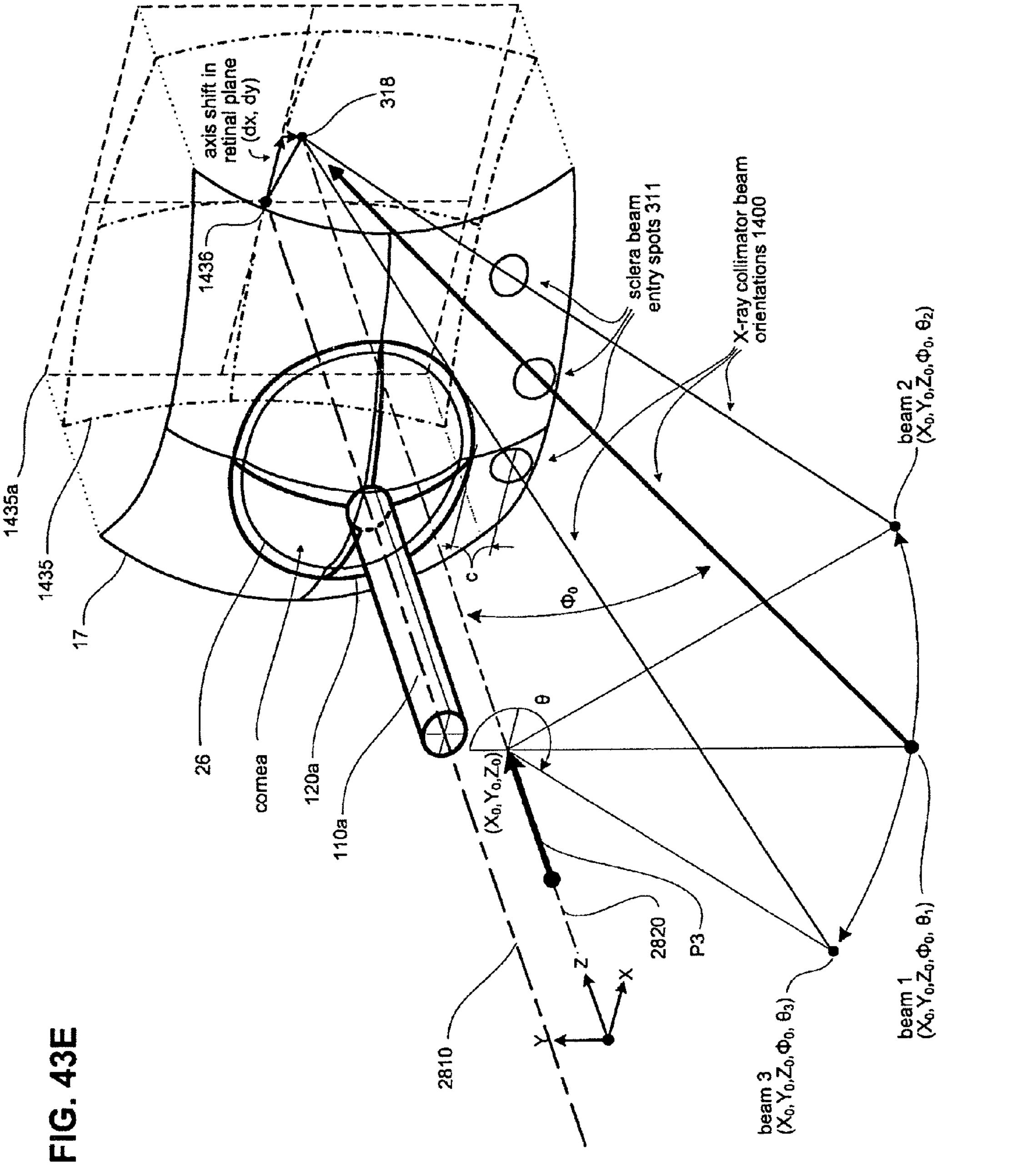

However, in the embodiments described in detail herein, and as shown in FIG. 43D, the system Z-axis (e.g., the Z axis of X-ray source positioning system 115) may be shifted to realign with treatment axis 2820 which intersects the center of treatment target 318. The system axis thus realigned is indicated as P3 in the figure. In this example, a lesion of the macula is treated by radiation to a target 318 approximately centered on the fovea. An exemplary treatment plan may define offsets relative to the pole of the retina (intersection of geometric axis 2810 with the retinal anterior surface), the offsets being defined as X and Y movements in the plane tangent to the retinal pole (dx, dy). The detail diagram indicates offset dimensions taken from fundus images of a representative sample of persons, defining mean values of offsets of the fovea from the retinal pole of about 1.16 mm and −0.47 mm respectively, although these values are purely exemplary. In this example, the X-ray source positioning system 115 is moved the specified dx and dy offsets by action of the X and Y axis actuators (see FIG. 37), so as to shift the system Z axis (translate without rotation) so as to intersect the defined target 318.

Step 2555

Position Beam and Verify Limbus Clearance—

FIG. 43E illustrates the motion of the X-ray source to carry out an exemplary stereotactic treatment following the shift of the system Z axis to intersect the target 318, as depicted in FIG. 43D.

The Z and Φ axis actuators may be moved to orient the collimator assembly 118 so that the beam axis 1400 intersects the Z axis at the target 318, forming a triangular arrangement (see FIGS. 34-38). With the Z and Φ axis positions thus fixed (values $Z_0$ and $\Phi_0$), the collimator assembly 118 may be subsequently re-oriented solely using the θ actuator to selected treatment beam positions (e.g., beams 1, 2 and 3 at values $\theta_1$, $\theta_2$ and $\theta_3$ respectively) to align the beam axis 1400 to propagate to target 318 and intersecting the body surface at respective selected beam entry points (e.g., sclera beam-spots 311). Note that while it is advantageous to re-orient the collimator assembly 118 for multiple beam paths by single degree-of-freedom motion, it need not be so, and alternative embodiments may provide for more complex movement.

The clearance c of the (each) X-ray beam 1400 at scleral entry spot 311 may be confirmed both visually by the operator and/or by image recognition by the processor 501. As shown in greater detail in the camera-frame image of FIG. 43C(2), a laser beacon 1410 (see FIG. 36) may be aligned along the beam axis 1400 (the intended beam path as aimed prior to X-ray emission) to create a small visible spot on the sclera of known position relative to the beam 1400 (e.g., concentric), the spot lying within the camera frame. The laser spot may be recognized by processor 501, its position calculated, and compared with the tracked position of limbus 26, so as to calculate the beam-center-to-limbus-edge clearance c. The clearance c may then be compared with a minimum tolerance (optionally also a maximum tolerance). For example, based on a predicted collimated beam radius of about 1.5 mm at the sclera, a selected limbus minimum margin of 2.0 mm may be determined by a value of c≈1.5+2.0=3.5 mm. The beam margin from the limbus may be specified in a treatment plan, e.g., from about 1 to about 5 mm. The X-ray beam radius at the sclera (e.g., from about 0.5 to about 5 mm) may also be predicted, such as by calculation of collimator geometry and/or radiographic measurement as described in detail herein. The clearance c may be adjusted if needed, e.g., by small movements of the X-ray source 420 in Z and/or Φ directions.

Step 2560

Perform Treatment with Eye Tracking—

X-ray treatment may be administered according to the treatment plan, such as at a pre-selected beam configuration, intensity and spectrum, the beam being emitted for a time interval selected to deposit a desired absorbed dosage to the target. Multiple beams may be emitted stereotactically to delivery a desired total target dosage, while exposing non-target regions (such as sclera beam entry spots 311) to less dosage than that of an equivalent single-beam treatment.

During treatment, the eye position relative to the system 10 may be continually tracked as described in detail herein and the eye position data so obtained by be automatically monitored by processor 501 on a real time basis as treatment progresses, including calculation of the motion of target and other eye anatomy (an resultant dose variation) based on eye tracking motion data. See description regarding FIGS. 49-54, and detail description in co-invented Application No. 61/093,092 filed Aug. 29, 2008 and well as the other applications which are incorporated by reference. As described below with respect to Step 2565, such eye tracking data and calculations may serve as a basis for radiation interruption or gating.

In the embodiments described in detail herein, the X-ray collimator assembly 118 may remain fixed during the emission of an X-ray treatment beam. However, in alternative embodiments, positioning system 115 may be configured to provide real-time repositioning of the X-ray source during X-ray emission, for example, to compensate for residual motion of the retinal target during treatment. Alternatively In certain embodiments, all or certain ones of the actuators described with respect to FIG. 37 for positioning of the X-ray source (X, Y, Z, Φ and θ of positioner 115) may be used to re-position the X-ray source so as to compensate for motion of the retina. Alternatively, additional actuators and/or degrees of freedom may be provided so as to provide fast-response, small-range (Vernier) adjustment of the X-ray beam orientation (e.g., re-aiming the retinal beamspot) and/or shaping (e.g., responsively blocking a portion of the beam spot, such as proximal to the optic disk), so as to permit rapid adaptation of the beam to compensate for a moving retinal target. Such embodiments are describe further in co-invented Application No. 61/093,092 filed Aug. 29, 2008, which is incorporated by reference.

Step 2562.

For multiple beam path or stereotactic treatment, method Steps 2555-2560 can be repeated as indicated by Step 2562 until a desired treatment is completed, for example for a pattern of three stereotactic beams as described in detail herein.

Step 2565

Interrupt Radiation (Trigger Gating)—

During the course of Step 2560 as radiation is being emitted along beam path 1400, radiation may be interrupted (gating of X-ray source 420) in response to selected criteria, such as threshold values of measured criteria, discrete system-level diagnostic error or failure states, or patient-level interlock or diagnostic triggers. Upon triggering of gating, various devices may be used to interrupt X-ray or other radiation emission, as described herein.

Step 2567.

Following gating, corrective action may be taken as indicated in depending on the particular triggering cause (may require repeating one or more preceding steps), and treatment irradiation then resumed until a desired beam fractional dose is delivered.

(i) In motion-threshold gating, such as Subsection 1 below, all or portions of alignment and positioning steps 2540-2455 generally are repeated to bring the beam center into alignment with target center, prior to completing the treatment fraction.

(ii) In some cases, such as transitory system conditions in Subsection 2 below, the corrective action may involve brief system corrections not requiring repetition of pre-radiation steps 2555 or before, and treatment may be resumed at step 2560. In other cases, the positioning actions included in steps 2450-2550 may not need to be entirely repeated, but verification of alignment and position (visually or by image processing) may be desirable before resuming treatment.

(iii) if the gating is triggered by decoupling of limbus 26 and eye-guide lens 120, as in the example of Subsection 3 below, corrective action may include repeating the eye-guide positioning steps 2530 and 2354 as well as steps 2450-2550.

Examples of gating criteria may include one or more of:

1. Exceeding Retinal Motion Threshold.

As described herein and in the incorporated applications, the eye tracking data may be employed to determine one or more discrepancy or error values based on a target movement or motion-related dose distribution, such as a maximum target displacement, a cumulative retina displacement vector, a dose distribution indicator, or the like. The error value may in turn be compared on a real-time basis with a gating threshold value to trigger a gating event. Optionally, eye tracking algorithms may be used to track motion or dose relative to non-target structures, such as the limbus, lens of the eye, optic nerve and the like, with respective gating thresholds.

(a) In a one motion-threshold example embodiment for a retinal target region, the error value may be the current scalar magnitude of a summation vector representing cumulative retina target motion derived on a time increment basis (e.g., camera frame-by-frame rate or a selected sub-sampling rate) from eye tracking data. For example the vector inputs may include components in the X and Y directions of the retinal target plane, indicating the X and Y deviations at each measured time of the beam center from the target center. The vector summation accumulates these components as directional vector quantities, the scalar magnitude representing the radial distance from the target center of the summation vector (square root of the sum of the squares of the components). Such a summation vector magnitude represents the time-weighted cumulative displacement error in the position of the beam-spot center from the planned retina target center point. The vector may be linear, or alternatively have quadratic or other non-linear distance weighting so as to de-emphasize small fluctuations in position (e.g., jitter or vibration) relative to larger, continuous displacements. Upon reaching a pre-selected scalar magnitude threshold, gating (interruption) of the X-ray source can then be triggered.

(b) A calibrated "motion-free" dose distribution may be determined experimentally and/or computationally (e.g., Monte Carlo simulation and/or radiographic beam-spot measurements) representing the dose distribution either at the target region (e.g., macula surface) or at any other tissue location within or adjacent to the radiation beam path. From the calibrated dose distribution, an equivalent time-increment dose distribution may be determined for a desired time increment (e.g. video frame rate). Retina or other tissue motion can then be derived from eye tracking data as described herein, and such motion data can be used to modulated with time-increment dose distribution so as to yield a contribution for each time increment to a cumulative dose distribution accounting for measure eye motion. Such motion-modulated dose distribution may be used to validate or determine a motion-threshold value as in 1(a) above by determining the dose distribution at the gating trigger point. Alternatively the motion-modulated dose distribution may be used to evaluate the adequacy of treatment dose level within the planned target region 318.

(c) Alternatively, the motion-modulated dose distribution of 1(b) may be determined on a real-time basis at any desired anatomical location within the distribution, and such dose may compared to a dose-threshold be used to trigger gating. For example, a maximum cumulative dose at the edge of the optic disk may be used to trigger gating.

(d) Alternatively or additionally, the real-time determined cumulative dose distribution of 1(c) may be evaluated within the planned target region, and may be used to trigger termination of treatment at a desired target treatment profile, including motion-related eye-dose distribution effects. Examples include triggering gating-termination upon (i) reaching a selected maximum treatment dose level at highest-dose point in a defined target region; (ii) reaching a selected minimum treatment dose level at the lowest dose point within a defined target region; (iii) reaching a selected average dose within a defined target region; (iv) a combination of these (e.g., reaching at least a selected average dose after achieving a selected low-point minimum); or the like.

2. System-Level Functional Diagnostics.

Gating may be triggered by error or failure conditions such as loss of eye tracking by the system, loss of limbus tracking, or other system-based failure deemed justification for interruption of radiation treatment, e.g., due to electronic conditions, camera conditions, lighting conditions, inadvertent blocking or interference with imaging, and the like. Alternatively or additionally, processor 501 may determine and monitor a selected number of different diagnostic conditions which can be used to trigger gating, such as X-ray tube parameters, lighting parameters, laser pointer 1410 position tracked relative to the limbus (limbus clearance), and the like.

3. Patient-Level Interlocks.

Alternatively or additionally, processor 501 may determine and an monitor a selected number of patient-based interlock or diagnostic conditions which can be used to trigger gating.

(a) These may include specific patient interlock sensor signals, such as indicating disconnect of head restraint fasteners, disconnect of eye-guide lens mounting (see step 2534); patient hand grip 163 contact sensors (See FIG. 33A), and the like.

(b) The patient-based condition may also be determined by image processing/recognition from one or more cameras or other remote sensors. For example, the relative positions of eye-guide 110 and limbus 26 may be monitored continuously during treatment via camera-based eye tracking and compared against a selected threshold indicating disconnect or decoupling of the eye-guide lens 120 from the patients eye (such as by sliding of the lens over the cornea). An error condition may be determined so as to trigger gating of radiation. (c) In a further example, transitory "blinking" compensation gating embodiments are described in co-invented Application No. 61/093,092 filed Aug. 29, 2008, which is incorporated by reference. The transitory gating embodiments compensate for sudden, brief, large magnitude, generally vertical displacements which result from involuntary blinking or spasmodic movements of the eye, typically followed by a quick return to a generally well-aligned eye position. These eye movements may be rapidly detected by image-based eye tracking so as to trigger a rapid-response radiation gating. Treatment radiation may be automatically resumed, either after a fixed time delay or an automatic realignment confirmation. This "blinking" type gating may be used independently or in combination with retinal motion threshold gating described in Subsection 1 above.

Step 2540

Release Eye Holder—

Following treatment, the patient may be released from the eye-guide 110 (e.g., release of vacuum suction) and head restraint 160.

Pixel-Level Image Alignment Methods.

In certain embodiments having aspects of the invention, the image recognition and processing may be conveniently and advantageously performed on a digital pixel-level of camera resolution based on camera image signals (e.g., cameras 401, 402), such as a selected video frame representing an image at a defined image capture time. The eye alignment method of Step 2540 may be applied similarly to the alignment of other anatomic features as a step in carrying out treatment with a radiation device.

Conventional video frame image data may be stored for processing in a manner known in the electronic arts, such as by defining a two-dimensional array of pixel data in a computer memory, wherein each array element is mapped to a particular pixel position of the camera image and wherein each array element is associated with one or a plurality of values indicating pixel color and/or intensity. For example, a 24-bit RBG color-encoded pixel values of an array for a 1000×1000 pixels image dimensions may be stored. Where the image capture is focused and delimited by a specific area of interest, (e.g., a portion of the patient's face including an eye, eye lids and adjacent skin surface), the pixel position may be mapped to a particular point on the area of interest. For example, where the area of interest is an approximately 10 cm×10 cm area of the patients face, each pixel of a 1 Mega-pixel image represents about region of about 0.1 mm×0.1 mm, or about 100 micron resolution. A 4 Mega-pixel image represents about region of about 0.05 mm×0.05 mm, or about 50 micron resolution.

The imaging camera may conveniently be aligned with the radiotherapy coordinate system axes (or alternatively, at a known orientation and position relative to the coordinate system). For example, and axial camera may be aligned so that the camera optical axis is parallel to the system Z axis, and so that the center pixel of the camera sensor chip corresponds accurately to the system Z axis. For this orientation, the camera "sees" its field of view in direct relation to the system X-Y plane origin, as shown in FIG. 43C(2). Deviations and directions of imaged features may then be measured in pixel scale in this reference frame.

The storage of image data may continue for subsequent video frames. If desired, image processing and feature recognition may be carried out on a real-time basis on all, or a selected sub-sample, of the captured video frames. Camera sensor resolution and image size (e.g., conventional CCD image sensor chip), frame capture rate, and other imaging parameters may be selected in consideration of associated optical and mechanical components, to optimize system performance, cost, speed and the like, as is known in the electronic arts.

Referring to the axial camera view shown in FIG. 43C(2), in an example sub-method embodiment, the processor 501 may be programmed with suitable software code, acting on image data in computer memory, to carry out all or a portion of the sub-steps of an image alignment algorithm, including:

(a) Identifying a pixel of the image representing the eye-guide central axis. For example, the processor may:

(i) determine the portion of the image including center-post fiducial 1 (e.g., by contrasting edge detection);

(ii) determine the geometric center of the fiducial image area; and (iii) select the pixel lying closest to the fiducial center.

(b) Determining that the eye-guide 110 is aligned with the camera (system Z axis). For example, the processor may:

(i) repeat step (a) with respect to each of fiducials 2 and 3 so as to select a pixel representing the center of each fiducial;

(ii) calculate the horizontal (X) center-to-center the distance between each of fiducials 2 and 3 and fiducial 1 (e.g., count number of intervening pixels);

(iii) determine whether fiducials 2 and 3 are equidistant from fiducial 1 (no horizontal tilt) [*optionally display any error magnitude to operator];

(iv) calculate the vertical displacement (Y) of the fiducials 2 and 3 from fiducial 1;

(v) determine if fiducials 2 and 3 lie on a horizontal line including fiducial 1 (no vertical tilt) [*optionally display any Y and θ error magnitudes to operator];

(vi) determine if the pixel representing the eye-guide center is located at (0,0) of image system Z axis (center pixel of camera image) [optionally display any X and Y error magnitudes to operator];

(vii) determine, if (iii), (v) and (vi) are true, that eye-guide 110 is aligned with the system Z axis [*optionally compare with selected tolerance thresholds and display compliance or non-compliance to operator];

(c) Determining the location of the center of limbus 26 in the system coordinates. For example, the processor may:

(i) determine the portion of the image including all or the exposed portion of the limbus boundary (e.g., by contrasting edge detection) and identify the pixel locations corresponding to the limbus boundary image;

(ii) mathematically determine a "best fit" shape corresponding to limbus boundary data, for example using boundary pixel locations as inputs to determine an equation for a circle or ellipse with lowest error function;

(iii) calculate the center of "best fit" shape, and identify the image pixel closest to center.

(d) Determining any deviation of the location of the center of limbus 26 from either or both of the system Z axis. For example, the processor may calculate the horizontal (X) and vertical displacement (Y) of the limbus center from pixel representing the system Z axis (e.g., by counting intervening vertical and horizontal pixels) [*optionally displaying the X and Y values to operator].

(e) Registering the positions and/or orientations determined in steps (a-d) of one or both of eye-guide 110 and limbus 26 in a virtual eye model, e.g. eye anatomic geometry stored in computer memory. For example, the eye model may additionally include measured patient-specific data and/or imagery such as eye axial length, and a scaled OCT or fundus image.

(f) Calculating the position of the retina (or other structures) in the system coordinates based on the registered eye model.

As described above with respect to FIG. 43A, the placement of eye-guide 110 relative to the limbus 26 on the eye surface may be adjusted until the limbus-to-lens alignment (measured step (d) above) is reduced to as close to zero as is desired. Likewise, alignment of eye-guide 110 relative the system Z axis may be adjusted (e.g., by positioner 600 in FIG. 33A) until the eye-guide alignment error (measured in step (b) above) is reduced to as close to zero as is desired.

A related method having aspects of the invention, including an algorithm for aligning a body part with a radiation device, may be summarized: (a) defining a normal axis to said body part; (b) aligning said normal axis to a pixel on a camera image visualizing said body part; and (c) linking said pixel on said camera image to a coordinate frame of a robotic positioning system thereby linking said normal axis of the body part to an axis of the robotic positioning system.

The algorithm may further comprise determining the distance between said body part and said robotic positioning system wherein said distance is measure along said normal axis. The algorithm may further comprise defining a normal step comprises locating fiducials on said body part. The algorithm may include that the detection of said fiducials directs said aligning of said normal axis, such as where the fiducials are attached to a device which contacts the sclera of an eye, and which may have a contact member fitted to the limbus of the eye. The algorithm may include that an axial length of an eye is used to define a position on a retina of the eye and said position is utilized to define movement to a macula from said position.

Radiometric Confirmation of Eye Alignment and X-Ray Dose Targeting

FIGS. 44A-B depicts a method of confirming an embodiment of a radiotherapy treatment plan having aspects of the invention. FIG. 44A illustrates a cadaver eye 30 which has been fixed in a mounting 500, configured to be aligned with radiotherapy system 10 using a suitable mechanical support (not shown) in generally the manner and orientation shown in FIG. 35. The mounting 500 positions the cadaver eye as, in effect, a phantom eye for purposes of confirming both eye alignment method and the dosimetry of the treatment system. FIG. 44A shows that the cadaver eye 30 has been partially dissected to expose the tissue adjacent the posterior retina, so as to permit a backing of radiographic film 502 to be positioned behind the eye parallel to the retina.

The procedure includes the following: The eye in mounting 500 with film is mounted in the eye alignment and stabilization system 625 (see FIGS. 39 and 40 for example) by a suitable mechanical support (not shown), and the eye is aligned using the methodology described with respect to FIGS. 43A-E, is the same general manner as the alignment of the eye of a human patient. The eye-guide (represented by eye-guide lens 2860 in FIG. 44A) is applied to the cornea so as to be centered on the limbus, vacuum suction is applied, and X-ray source 420 is moved into treatment position as shown in FIG. 35. As with the treatment plans described herein, the X-ray beam is aligned to a treatment axis 2820, which is positioned relative to eye geometric axis 2810 by a pre-determined offset 2850.

A series of three treatment beams are applied to eye 30 (see FIGS. 30A-B), so as to expose the radiographic film 502 adjacent the retina so as to produce an exposed spot 504 indicative of the target absorbed dose distribution. The radiographic film is formulated to produce a visible spot, permitting a marking pin 506 to be inserted through the film into eye 30, in this example at the center of spot 504, so as to register and maintain the orientation of the film 502 as exposed with the eye tissue.

Eye 30 is then dissected along a retinal section as shown in FIG. 44A to expose a the posterior retina, registered to the exposed film 502. The flattened retinal superimposed on exposed film is depicted in FIG. 44B. The retinal geometry is shown in the detail on the left at the left, the retinal dissection shown schematically on the right view of the figure. As may be seen, the exposed film spot 504 is substantially centered on the macular target, covering the 4 mm target region. The spot 504 is also substantially separated from the optic disk 350. The geometry of dosage may be compared with the phantom mannequin dose map of FIG. 30C.

The procedure thus confirms the effectiveness of the eye alignment method and ocular targeting methods having aspects of the invention, by demonstrating that the applied radiation dose is targeted to the macular tissue (and avoiding the optic disk), as provided by the treatment plans described herein.

Eye-Guide Placement and Eyelid Retraction

FIGS. 45A and 46A are drawings of a patient's eye showing an eye-guide 110 having aspects of the invention as engaged with the eye in an operative position, in this case with the eye substantially as it appears when aligned with the eye-alignment axis 2810 of radiotherapy system 10. The eye-guide lens 120 is shown approximately centered on limbus 26, the lens being supported by arm 180.

In the example of FIG. 45A, the eye-guide 110 includes a plurality of reflective fiducials (as further described herein), having two or more fiducials 240 positioned spaced-apart on the lens 120, and one or more fiducials 250 positioned on the crown of center post 222. In this example, the center post may also include a mirrored surface 230, which may be used to track alignment with a axial pointer beacon or laser beam, as further described herein (see also FIGS. 40 and 53). The eye-guide embodiment shown is of the type employed during acquisition of the example eye-tracking data shown in FIG. 49A-E. using an eye alignment/tracking system having an alignment-axis-centered low powered laser pointer 403 (see FIG. 34).

In this example, the lower eyelid is retracted downward by a retractor or lid speculum 320*a* to expose an area of the sclera for treatment beam entry. The upper lid may ride over the eye guide lens 120 upper portion, but the system cameras can effectively track both the lens fiducials 240, and detect and compute the image of the limbus (as further described), permitting the positions of each to be determined automatically (including extrapolations to covered portions shown as dashed lines).

The retractor 320*a* is shown in detail if FIG. 45B and includes a smooth and non-abrasive hook-like portion 323 comprising a wire-loop configured to overlap and engage the eyelid, the hook mounted on a handle portion 324. The handle portion may be supported a number of alternative ways (e.g., hand-held, taped to a support, mounting to a base, or the like), but a advantageous alternative is to connect the handle via an elastic tether portion 325 to an attachment 326, such as a spring clip or the like. The tether may comprise a stretchable elastic member, which may comprise an elastic strap, an elastomeric tube or the like. A terminal attachment is included to mount the tether to a convenient base, such as a spring clip, snap fitting, or the like. Either or both of the tether length or attachment position may be adjusted to provide a selected tether tension acting upon the eyelid. A length-adjustment fitting (not shown) may be included in the tether 325, such as a friction loop, Velcro fitting, or the like.

In certain embodiments, the tether is configured to be attached to the patient so that the relation of attachment to eye is relatively constant, notwithstanding patient movement. For example, the attachment 326 may include a spring clip which can be clamped to patient clothing adjacent the face, such as a shirt collar, button hole, pocket, or the like. Optionally, the tether 325 may include a force-limiting coupling, such as a magnetic or adhesive coupling, the coupling configured to release if excessive tension is applied to the tether. For example, see co-invented Application No. 61/093,092 filed Aug. 29, 2008 which is incorporated herein by reference, in particular coupling 327 shown in FIG. 23C of that application.

FIG. 46A shows the alternative eye-guide embodiment 110 as engaged with the eye in an operative position. The eye-guide shown is of the type depicted in detail herein and shown in FIGS. 47A-F. The lower eyelid is retracted downward by retractor embodiment 320*d*. FIG. 46B illustrates an alternative retractor embodiment 20*b* which includes a non-abrasive smoothly curved or saddle-shaped spoon-like hook member (e.g., a Desmarres-type member) mounted on a handle portion 324. The handle portion may be supported as described above with respect to FIG. 45. In the example shown, the handle 324 is mounted to a tether, in this case by means of a handle with a cylindrical cross section which may be conveniently inserted into a rubber or elastomeric plastic tube, so as to bind to the tube by stretching and friction.

In a further exemplary refractor embodiment shown in FIG. 46A, the saddle-shaped surface is elongated and configured to provide a curved border adjacent scleral X-ray beam spots 311. All or a portion of the body of retractor 320*c* may comprise a radio-opaque material so as to provide effective shielding of the eyelid and adjacent tissue from stray or scattered radiation during X-ray treatment beam emission.

Detection of Eye-Guide Fiducial Patterns

FIGS. 47 through 52 illustrate various method and device embodiments having aspects of the invention using fiducials to determine eye alignment and track eye motion in association with a medical device. FIGS. 47-48 illustrate embodiments of eye-guide devices (110, and 512) for use in a eye stabilizing system having aspects of the invention, and having patterned fiducials, and a method of determining orientation by image recognition.

Turning initially to FIG. 47A, the figure shows a perspective view of an embodiment of contact or eye-guide device 512 including the contact member 120, spherical pivot 220, mirror 230 and vacuum port 210. In this embodiment of the invention, the contact device 110 includes one or more fiducial markers 240, 242, 244, 246, 248 which define the geometry of the contact device 110 or geometric relationships between the contact device 110 and additional components of the system and/or eye as described throughout the specification. The fiducial markers, in one embodiment of the invention, contribute to the positional knowledge of the eye when the contact device 110 is engaged with the eye 130, and a coordinate system is known. Spatial registration can be used record and monitor the three dimensional spatial position of the contact device 110 relative to a known reference point.

In the embodiment illustrated, one or more of the fiducial markers 240, 242, 244, 246, 248 includes an imageable fiducial locator. The fiducial locator is locatable using one or more imaging system modalities. In this embodiment, the fiducial is capable of being mounted in or on the eye-contact member 120, such as being either flush to, or recessed from, an outer surface of eye-contact member 120. However, in alternative embodiments, the fiducial need not be configured for mounting flush to or recessed from contact member 120, and can be mounted to extend from eye-contact member 120. In another embodiment, one or more fiducials are positioned on, within, or on the perimeter of mirror 230. This allows the mirror 230, along with contact device 110, to be centered or aligned with respect to the limbus or other ocular structure.

The fiducial may include a liquid or gel housed in a sealed interior cavity. Preferably, the fiducial is a solid. The solid, gel, or fluid may be visible by one or more imaging modalities (e.g., MR, CT, etc.). In one embodiment, the fiducial is integrated into the eye-contact member itself. The imaging fiducial is visible and provides good contrast on images produced by at least one imaging modality. In one embodiment, the imaging fiducial is multimodal (i.e., locatable by more than one imaging modality), such as by using a mixture of different imaging fluids, gels or solids that are locatable on different imaging modalities.

In one embodiment, the one or more of the fiducial markers 240, 242, 244 includes a substance that is viewable on a first imaging modality, while one or more of the fiducial markers 246, 248 includes a substance that is viewable on a different second imaging modality. In one such illustrative embodiment, the one or more of the fiducial markers 240, 242, 244 includes, or is doped with, a substance having a high atomic number (Z), such as barium, titanium, iodine, gold, silver, platinum, stainless steel, titanium dioxide, etc. that provides good contrast on a CT or other radiographic imaging system. In this embodiment, one or more of the fiducial markers 246, 248 include gadopentatate dimeglumine, gadoteridol, ferric chloride, copper sulfate, or any other suitable MRI contrast agent, such as described in chapter 14 of Magnetic Resonance Imaging, 2nd ed., edited by Stark and Bradley, 1992, which is incorporated herein by reference.

In an alternative multimodal embodiment, the fiducial marker is constructed of a substantially solid plastic or other material that is hygroscopic, i.e., capable of receiving and retaining a fluid, such as an imaging fluid that is viewable on an imaging system (e.g., an MRI imaging system or the like). In a further embodiment, the plastic forming the fiducial marker is doped or otherwise includes a substance that is viewable on a different imaging system, such as, for example, a CT or other radiographic imaging system. Illustrative examples of solid plastics that can be made hygroscopic include, among other things, nylon and polyurethane. Using a hygroscopic material avoids the complexity and cost associated with manufacturing a sealed cavity for retaining an imaging fluid. Moreover, by adapting the solid hygroscopic plastic for imaging using a first modality, and by using the imaging fluid for imaging using a second modality, each of the solid and the fluid can be separately tailored toward providing better contrast for its particular imaging modality.

In a further embodiment of the fiducial markers illustrated in FIG. 47A, the outer surface of one or more of the fiducial markers is reflective of light or other electromagnetic energy. Consequently, it is locatable by a camera in an optical positioning system that is coupled to an image-guided workstation (e.g., during subject registration). One additional function of such fiducials is measurement calibration where the distance between fiducials is used to calibrate distance on or within the eye. In one such example, the outer surface of the imaging spherical fiducial marker includes light-reflective microspheres (e.g., embedded in an adhesive covering the fiducial or eye-contact member 120). In another such example, the outer surface of the fiducial is covered with an adhesive-backed light-reflective tape, such as SCOTCHLITE 9810 Reflective Material Multipurpose Tape sold by Minnesota Mining and Manufacturing Co. ("3M"), of Saint Paul, Minn.

In one embodiment of the invention, the spherical pivot 220, mirror 230 and/or the control arm 180 includes one or more fiducial markers. In an alternative embodiment of the invention, the one or more fiducial markers are configured to be locatable by a remote positioning system as well as imageable using one or more imaging modalities. In one such embodiment, the outer surface of the eye-contact member is configured to be light reflective, such as discussed above. The fiducial markers are still advantageously locatable using one or more imaging modalities (e.g., MR, CT, or other imaging system providing 3D or other internal images within a subject) as well as also being locatable external to the subject, such as by using a remote camera or like component of an optical or other positioning system, e.g., that is coupled to an image-guided workstation. In one embodiment, this permits automatic registration of the actual location of the subject's eye (e.g., using cameras to locate the light reflective fiducial markers) to pretreatment images of the system on which additional imageable fiducial markers are positioned. This eliminates the need to register the eye of the subject by inserting an optically-locatable positioning control arm onto the contact device, and eliminates the need for other absolute position reference, because the fiducial markers themselves are optically locatable and registerable to known locations on pretreatment images of the system.

Control arm 180 may be coupled to an image-guided workstation or platform (not shown). In this embodiment, control arm 180 includes an end that is sized and shaped to permit being coupled to spherical pivot 220. The control arm 180 includes, in this embodiment, a plurality of fiducial markers 520, 522, 524, 526, 528, 530 that are locatable by a camera or other like device of the optical positioning system. The fiducial markers 520, 522, 524, 526, 528, 530 on the control arm 180 are positioned in a known spatial relationship to each other and to the tip of the control arm 180. By recognizing the locations of the fiducial markers, the optical positioning system is capable of computing the location of the control arm tip, which is in a known spatial relationship with the configuration of the fiducial markers. This permits the control arm 180 to be used in conjunction with the optical positioning system to register the eye of the subject and to further plan and/or perform the treatment procedure using an image-guided workstation. An image guided treatment computer workstation, which is capable of displaying previously acquired and loaded pretreatment images of a the system. The optical positioning system connected to the workstation includes an infrared light (or other energy source) that provides light that is reflected from the reflective fiducial markers. This permits the reflective fiducial markers on the control arm 180 to be located and recognized by the cameras.

Pattern Detection

FIGS. 47B1 to 47I schematically illustrate a eye-guide device for use in a eye stabilizing system having aspects of the invention, and having patterned fiducials, and a method of determining orientation by image recognition. In the exemplary embodiment shown, a pattern of highly reflective fiducials is mounted to the device. In the example shown this is a triangular three-fiducial pattern (4), comprising fiducial 1 (on center bar 190) and fiducials 2 and 3 (on lens 120), although other patterns may be used. For example, the fiducials may have a surface including an adhesive-backed light-reflective tape, such as SCOTCHLITE 9810 Reflective Material Multipurpose Tape sold by Minnesota Mining and Manufacturing Co. ("3M"), of Saint Paul, Minn. Likewise, other methods of applying or forming a reflective surface may be used, such as reflective ink compositions, and the like.

Placement of the fiducials may conveniently be chosen such that they form right triangle (90-45-45) when eye-guide is in alignment—perpendicular and coaxial to system center (see FIG. 2B). For two lens fiducials, angle of 45 degrees is preferred as a best compromise for horizontal and vertical sensitivity during measurement (i.e., if for example selected angle is 60 degrees it would provide greater horizontal sensitivity, but less vertical). Also, lens fiducials are surrounded by the dark area in order to provide for easier detection.

By virtue of the center pivot 220 the center fiducial 250 can move in horizontal and vertical direction in relationship to lens fiducials. That movement causes triangle relationship of the angles to change, which provides feedback of the alignment position, and hence the patient's eye.

Reference is made to the description above with respect to the imaging system pattern recognition functions, illustrated also in FIGS. 34-35. In summary, the fiducials as illuminated by lights 405 provide a high-contrast image to axial camera 401 Computer processor 501 may be programmed by suitable software to process the electronic image signals to delineate the image regions corresponding to the fiducials (using known image processing algorithms, such as contrast enhancement, filtering, intensity thresholds, edge recognition, and the like). The processor can then define a center of mass for each fiducial image, and locate the corresponding points in a coordinate frame of reference, so as to create a mathematical representation of the fiducial pattern from the camera perspective. The mathematical representation then permits calculation of relevant angles and dimensions, and so derive eye-guide position and orientation information. Note that scaling information can be used to derive Z axis distance information, alternatively or additionally to the off-axis camera 402 described with respect to FIGS. 3A,B. The process can be repeated from sequential camera images at any selected position update rate (e.g., about 1 to 50 Hz) to provide continuing position and motion data.

Once fiducials are recognized, and triangle angles and leg lengths calculated, the processor 501 may provide feedback (e.g., via display images) to the user indicating which direction to move the eye-guide in order to have it aligned. All three angles and their spatial relationship may be considered in order to provide feedback to the user, for people it is easier to understand, and react to, one variable per direction (i.e. up/down for vertical, and left/right for horizontal), lens fiducial angles are represented as a ratio to the user—A2/A1. This gives only one number for direction of movement. For example, in aligned condition ratio would be one because 45/45=1; if mirror is tilted at some angle to the right ratio might be 48/52=0.9231, etc.

In FIG. 47C the angles are identified as a, b and c, where a is the angle of the center fiducial 250 with respect to the lens fiducials. Angles b and c are the left hand and right hand angles. Angles a, b, and c determined by fiducial image recognition. Leg lengths l1, l2 and l3 may be scaled to confirm Z position. A pattern height h (or width) may also be defined from detected data representing the distance between fiducial 1 and a line joining fiducials 2 and 3. Similarly, pattern widths may be defined (w1, w2). It should be understood that the same detected image data may be expressed and organized as a number of alternative sets of geometric parameters as steps in calculations, without departing from the spirit of the invention.

FIGS. 47B1 and 47B2 illustrate the effect of tilt of eye-guide 110, the rotation of the center-post 222 about pivot 220, causing fiducial 1 to move in the opposite direction to lens 120. Tilt may be horizontal, vertical or combinations of these. Note that the effect of tilt is to cause a ±change in the distance between fiducial 1 and the lens fiducials 2 and 3, depending on direction of tilt (compare h1 un-tilted with h2 tilted).

Six cases are illustrated in FIGS. 47D-I:

FIG. 47D shows the eye-guide aligned with geometric axis, where a=90 deg.; b=45 deg.; and c=45 deg. This corresponds to the left-hand image of FIG. 20H.

FIG. 47E shows the eye-guide positioned upward (post tilted up relative to lens), but aligned horizontally, where a<90 deg.; and b=c>45 deg. This corresponds to a tilt in which height h is increased.

FIG. 47F shows eye-guide positioned downward (post tilted down), but aligned horizontally, where a>90 deg.; and b=c<45 deg. This corresponds to a tilt in which height h is decreased, as shown in the right-hand image of FIG. 20H.

FIG. 47G shows eye-guide positioned to the right (post tilted right), aligned vertically, where a<90 deg.; b>45 deg.; and c<45 deg. This corresponds to a tilt in which width w1 is decreased and width w2 is increased.

FIG. 47H shows eye-guide positioned to the left (post tilted left), aligned vertically, where a<90 deg.; b<45 deg.; and c>45 deg. This corresponds to a tilt in which width w2 is decreased and width w1 is increased.

FIG. 47I shows general case: eye-guide positioned off-center vertically and horizontally, where a≠90 deg.; and b≠c, specific angles values determine orientation This corresponds to a case in which each of h, w1 and w2 differ from the nominal values as shown in the aligned case of FIG. 20B.

Note that the methodology described with respect to FIG. 47A-I may be applied to fiducial patterns distributed in different structural elements of eye-guide 110. FIGS. 48A-F illustrate an eye-guide device 110 having a pattern of fiducials, the guide for use in a eye stabilizing system having aspects of the invention, shown in contact with an eye and depicting the method of determining alignment. In this example, the fiducials 2, 3 are on an extended cross bar 190 and fiducial 1 is on an elevated center-post 222, so as to create a linear pattern when aligned. As shown, the eye-guide does not necessarily have a mirror surface, but includes a plurality of fiducials, e.g., 3 fiducials having a highly reflective material (e.g., "Scotchbright"), one at the top of the center post (1), and two on the support arm on either side of the center post (2, 3). The fiducial arrangement shown permits a transparent lens 120 to be free of fiducials, which promotes digital image-recognition of the limbus. In addition the eye-guide may be tracked by camera image processing without a collimated and aligned light source (e.g., a laser), and may be tracked under simple lighting, such as LEDs positioned adjacent the eye.

In the case of alignment with the system coordinate axis (see FIG. 48D, compare with FIG. 47D), the angles b and c=0°, the angle a=180° and the lengths l2=l3. Note the effect of the horizontal tilt of center-post 222 (FIGS. 44E-F) is to render the lengths l2 and l3 unequal, even when the eye-guide center pivot 220 intersects the system axis 2810. In the similar case of vertical tilt (not shown), the angles a,b are not zero.

FIGS. 48 B-D show three perspective views, each with a different orientation to the viewpoint, which can be a camera. View B is angled substantially, so that the fiducials 1-3 form a triangular pattern 4, which may be measured by image recognition methods. View C is angled less and presents a correspondingly smaller triangular pattern. View D is aligned with the view point, and show a straight line arrangement, with equal right (2-1) and left (3-1) legs between fiducials. Note that the aligned pattern of View D is very easy for a operator to recognize visually, either directly or as displayed on a user interface.

FIGS. 48 E-F illustrate that rotation of the center post 222 about pivot 220 will result in a shift of the center fiducial 1 (in X or Y or both), even when the eye-guide support arm 190 is perpendicular to the viewing axis.

Example of Alignment Method

As shown if FIGS. 33-37, the imaging system 410 has a known position and orientation relative to X-ray source positioning system 115 of radiotherapy system 10 in a global coordinate system. In preferred embodiments, the imaging system is supported to be movable by positioner 115. For example, as shown in FIGS. 3B and 5, imaging system 410 may be mounted to imaging support 412, which in turn may be mounted to move in concert with XYZ stage 416 while remaining independent of Φ actuator 413 and θ actuator 414.

In an example method using particular device and sub-method embodiments described in detail herein (e.g., as shown FIGS. 39-40 and 48 using methods shown in FIGS. 43A-E), the method may include all or some of the following:

(a) Initially, the patient is positioned in head restraint 160 of system 10, with eye guide 110 engaged and lens 120 centered on limbus 26.

(b) The imaging system 410 is moved into a position (e.g., by positioner 115 X, Y and/or Z motion) where the retro-reflecting fiducials 1-3 of the I-Guide 110 can be viewed by the imaging system 410 (e.g., by cameras 401-402 in FIGS. 34-35 communicating with a system processor 501 and an operator display 403).

(c) As image data from the fiducials is processed into spatial information (see flowchart FIGS. 50-51, described further herein), the positioner 115 may be configured so as to auto-align (or manually) to the center of the I-Guide crown in X and Y (center fiducial 2 in FIGS. 48A-F).

(d) The operator then adjusts the I-Guide angle until it is oriented along the system axis as shown in FIG. 43C, for example by rotation about eye-guide pivot 220 by adjustment of eye-guide positioner 600 along X', Y' and/or Z' axes. Further auto-alignment of the X and Y axes of positioner 115 brings the eyeguide axis into co-linearity with the system Z axis. In this configuration the eye geometric axis 2810 is collinear with the Z axis of positioner 115.

(e) The positioner 115 may then be offset in X and Y to shift the system Z axis from alignment with geometric axis 2810 to align with an off-set treatment axis 2820 ($X_0$, $Y_0$ in FIG. 43E). In one treatment plan example, this is a shift of 1.16 mm temporally (may be ±X depending on if the left or right eye is being treated) and −0.47 mm caudally (−Y), as shown in FIG. 43D. Note that this shift may alternatively be done before or after the $Z_0$ and $\Phi_0$ adjustments.

(f) With the eye-guide 110 and positioner 115 aligned as described, the positioner 115 is moved axially along the Z axis until it reaches the selected treatment position ($Z_0$ in FIG. 43E), and the x-ray source 112 is rotated about the Φ axis to the selected beam angle ($\Phi_0$ in FIG. 43E). In this configuration, the spot of laser beacon 1410 is directed to appear on beam entry spot 311 (see FIGS. 34 and 36). The operator may confirm beam position and clearance of the beam from the limbus 26 by visual display via cameras 401-402, and the system 10 may confirm alignment by image processing and recognition of both laser beacon and limbus.

(g) (i) In a preferred treatment practice, the system is maintained in this configuration in four degrees of freedom ($X_0$, $Y_0$, $Z_0$, $\Phi_0$), and further stereotactic re-positioning of the X-ray source assembly 420 is confined to rotation about the θ axis of positioner 115.

(ii) Note that where the treatment axis 2820 at ($X_0$, $Y_0$) intersects a retina-surface target center 318 (e.g., center of the macula) and the combination of ($Z_0$, $\Phi_0$) aims the beam path 1400 to intersect the treatment axis 2820 at the target center, subsequent rotation about the θ axis causes the stereotactic beam paths to describe a cone with the apex at the target center 318. The combination of ($Z_0$, $\Phi_0$) may also be selected to provide clearance from limbus 26 and eye lens 36, so as to have sclera entry points $311_i$ distributed spaced-apart in a roughly circular arc outside but adjacent to limbus 26 (see FIG. 30A).

(iii) For example, the first treatment beam may be at an angle of θ=180°. For convenience, a θ angle of 180 degrees (referenced from 0° north) may be referred to as the 6 o'clock position (beam 1 at $\theta_1$ in FIG. 43E). Other treatment positions may be selected by adjusting the θ angle e.g., beam 2 at $\theta_2$ and beam 3 at $\theta_3$, at roughly the "5 o'clock" and "6 o'clock positions" (θ≈150° and 210°, respectively).

(iv) Alternatively or in combination, adjustment of other DOF may be performed, targeting beam 1400 to suit an alternative treatment plan.

Example of Image-Based Eye and Eye-Guide Measurements.

The exemplary embodiment of the imaging system 410 may be configured to acquire data at a selected rate for each camera, and typically the processor processes and calculates data at a selected update rate, e.g. about 10-50 HZ. In one example, a set of direct measurements are made at an update rate of 30 Hz, and used to calculate an additional set of inferred measurements as data is updated.

As shown in the eye-guide example shown in FIGS. 48A-F, the direct measurements are performed automatically using image processing and pattern recognition software on a frame-by-frame basis from camera video input signals, and include:

1 Eye Limbus Center X-Y Position.

Viewed from the on-axis main system camera 401.

Locates anatomical transition between the dark of the iris and light of the sclera (limbus margin 26 in FIG. 30A).

Defined by center of mass of the best fit circle using limbus detection software 2 Eye-Guide 110 Yoke X-Y Position (Yoke or Tie Rode 190 in FIG. 48).

Viewed from the main system camera 401.

Locates 2 fiducials on the tie rod (fiducials 2 and 3 in FIG. 48)

Defined by the center of mass between 2 fiducials (Yoke)

Note that the relative positions of yoke 190 and crown

3 Eye-Guide 110 Crown X-Y Position.

Viewed from the main system camera 401.

Uses infrared light from the IR LED bank of lights 406, close to axis of camera 401.

Locates the fiducial on the tip of the Eye-guide 110 (fiducial 1 in FIG. 48).

Defined by the center of mass of the fiducial (crown)

4 Eye-Guide 110 Yoke 190 Z Position.

Viewed from the off axis range Z camera 402.

Defined by the center of mass between the 2 fiducials on the tie rod (fiducials 2 and 3 in FIG. 48)

The calculated measurements are performed automatically using system computer processors on a real-time basis as direct measurements are updated, and include:

5 Base Lens 120 X-Y Position.

(a) This is a projected estimation of the center of the base lens 120 approximately at the same plane of the limbus measurement. The inputs include measurements 2 and 3 (X-Y of yoke 190 and crown fiducial 1, respectively), which define an eye-guide longitudinal axis, which can be extrapolated from the known structural geometry of eye-guide 110 to determine the lens X-Y.

(b) Note that the relative detected X-Y positions of yoke 190 and crown fiducial 1 also define an eye-guide axis angle relative to system 10 coordinates (analogous to eye-guide 110 "pitch and yaw", designated here as eye-guide (I)).

(c) Note also that the relative detected vertical positions of fiducials 2 and 3 on yoke 190 define an eye-guide angle in the system X-Y plane (analogous to eye-guide 110 "roll", described here as eye-guide θ). In certain embodiments, this may be largely be controlled by the support of head-chin restraints 160 and eye-guide positioner 600, and the eye-guide θ value may be small or negligible.

6 Limbus-to-Lens Coupling.

This is a functional measure based on the amount of relative movement between the base lens 120 X-Y position and the limbus 26 X-Y position.

Relative motion that exceeds a threshold value (e.g., 500 microns) may be interpreted as an indication that the base lens 120 has shifted from its original location at eye alignment or has become decoupled.

7 Retinal Target 318 X-Y-Z Position.

This computation involves all detected motion parameters so as to estimate the related motion at the back of the eye, inferred as motion of the retinal target 318. (See retinal motion tracking embodiments as described further in co-invented Application No. 61/093,092 filed Aug. 29, 2008, which is incorporated by reference).

Gating algorithms and criteria are based on these calculations (See X-ray source gating embodiments as describe further in Application No. 61/093,092).

Note the eye alignment method flowchart and geometric diagrams of FIGS. 43A-E in regard to examples of the use of the measurement as described above by the system 10 computer processors 501 (via suitable software) and displays 503*a,b*: For example:

Measurements 1, 5 and 6 (relative position of eye-guide lens 120 and limbus 26) may be displayed to assist a physician in placement of eye-guide 110 as shown in FIG. 43B as centered on the limbus, and used to automatically confirm eye-guide placement accuracy.

Measurements 2, 3 and 5a,b (eye-guide angle and eye-guide X-Y) may be used to guide and/or automatically drive the motion M(x, y, Φ, θ) of FIG. 43C(1) to align the eye geometric axis 2810 coaxially with system Z axis (relative values eye-guide X, Y, Φ, θ versus system 10 coordinates and Z axis become zero).

Measurements 2, 3 and 5 may be used to confirm accuracy of the X-Y shift of positioning system 115 from geometric axis 2810 to treatment axis 2820, as shown in FIG. 43D.

Measurement 4 may be used to confirm accuracy of positioning system 115 movement to the treatment Z position ($Z_0$) as shown in FIG. 43E.

All the above measurements may be used to track eye position and retinal position on a real-time basis during treatment.

Example of Eye-Guide Data Extraction and Eye Motion

FIGS. 49 through 54 pertain to measurements of eye motion of patients who are engaged by an eye alignment, stabilization and tracking system having aspects of the invention, such as are depicted in FIGS. 39-48. These aspects also include mechanisms and methods for assuring that any residual motion of the stabilized eye does not prevent radiotherapy to be effectuated with dosage distribution adjacent a target region remains within planned parameters. In should be understood that the imaging and measurement methodology described in this section are exemplary, and other methods and devices having aspects of the invention are described herein and in the applications incorporated by reference.

FIGS. 49A-E are plots showing eye movements experimentally measured with an embodiment of a system for controllably positioning and/or stabilizing the eye of a subject. In the this particular embodiment, the data was acquired using three video cameras mounted on an embodiment eye stabilization and tracking system having aspects of the invention. Note that the particular camera/imaging configuration used in the example illustrates one of a range of alternative embodiments comprising cameras and/or other sensor configured for acquiring motion data of the nature shown. For example, FIGS. 3A-B illustrate and imaging system employing two cameras, capable of acquiring comparable eye motion data. In the example of FIGS. 49A-E, for each patient, video from each camera was processed, frame by frame, in order to extract desired data. The cameras were configured as follows:

"PSD camera", also referred to as "fine angle data". Coaxial laser beam is reflected from the eye guide's mirror and detected by the camera. Although enabling high resolution data to be extracted, this setup can only collect data within very limited range of +/−1.25 deg.

"Central camera"—the eye-guide fiducial data; camera is mounted perpendicular to patient's eye and can view eye guide's lens and mirror, as well as anatomic data such as limbus position.

"Z-range" camera—distance data; camera is able to see eye-guide mirror but is mounted to the side of central axis. eye guide's, and hence patient's fore and aft movement (Z axis) is accurately easily detected.

Fine Angle Data

PSD camera is set up such that reflected laser beam is visible as a white (bright) area contrasted on the dark background in the camera view. Every frame from the video is individually extracted, and using custom algorithm and software, location and centroid of the laser area is determined. Centroid data is expressed in (x,y) pixel coordinates and using predetermined conversion factor translated to angle in X direction and angle in Y direction. Conversion factor is (pre)determined based on set-up and calibration data. Since knowing patient's head movement during the treatment was desired (i.e. relative movement) each angle in X and Y direction was subtracted from the very first recorded data point.

Fiducial Data

Using custom algorithm and software each frame from the central camera's video is extracted, and fiducials on Eye guide's lens (2) and mirror (1) are detected. Center of each fiducial is expressed in (x,y) pixel coordinates. By design fiducials form a triangle, therefore it is possible to calculate angles within a 'fiducial' triangle. Angle formed at center of the eye-guide mirror is used for vertical determination (Y angle), and ratio of angles formed by fiducials on the lens is used for horizontal determination (X angle). Relative motion data was desired so each acquired data set was subtracted from the first data point. During the study, the fiducial location differed slightly on each lens, without effecting the method. Fine X and Y angles were paired to X and Y fiducials and correlation factor was determined per each patient's data set. Correlation factor was determined by using line equation $y=ax+b$, where y is fiducial data, a is slope, x is fine angle data, and b is offset. Variables a and b were determined using few points from data set (in future whole set should be interrogated).

Distance Data

Laser spot reflection on the eye-guide's mirror, as seen by set "Z-range" camera was used to determine distance data. For each video frame, center of laser spot was detected using custom algorithm and software (see further description of measurements under caption "Example of image-based eye and eye-guide measurements.". Note that in addition to the image-based methods described, range data may be obtained by ultrasound or other reflected-signal techniques. Using predetermined calibration and correlation factors, each detected location was converted from pixels to millimeters. Other image data may be used in lieu of laser spot, such as light impinging on eye-guide 110 from an LED lights source (e.g., visible or IR).

The measurements shown in FIGS. 49A-E are from a typical patient who was tolerating the procedure well for the administered period of about 300 seconds (5 min.), and are as follows:

A. Horizontal X motion of the eye-guide and the limbus, plotted together to show relative motion of these.

B. Vertical Y motion of the eye-guide and the limbus, plotted together to show relative motion of these.

C. Horizontal X motion of the eye-guide mirror due to angular deflection about the pivot.

D. Vertical Y motion of the eye-guide mirror due to angular deflection about the pivot.

E. Z motion of the eye-guide due to motion of the eye posteriorly.

It may be seen that each parameter includes movements of on the order of 1 mm or less, and most less than 0.5 mm, over a substantial period of 5 minutes without any realignment procedures.

FIGS. 50 and 51A-B are flowcharts illustrating data acquisition and processing used in this example, and are self-explanatory to one of ordinary skill in the art. It should be understood that the algorithms and methods depicted are merely an example to demonstrate the functionality of one embodiment of the system, and alternative or additional particulars and sub-methods may be included without departing from the spirit of the invention.

The flowchart of FIG. 50 (on two sheets) is a summary of the fiducial detection algorithm employed in obtaining the data of FIG. 49. The input to the method is a video signal captured by system cameras. The data flow is a loop which processes each frame of video data, preferably on a real-time basis as each frame is captured. Alternative methods can select particular frames for data computation (e.g., in a timed sequence to support a desired data update rate), for example where a greater frame rate is desired for a user visual display than is desired for data computation. As may be seen, the output from the method are particular computed values, which in this example are depicted as being written as correlated with the particular video frame to memory media, indicated as "save file". It is to be understood that these output values may additionally or alternatively be directly accessed by system electronic processors for further display, computation or control functions.

The flowcharts of FIGS. 51A and 51B depict further processing and conversion steps based on raw date obtained from the video frames, such as in the process of FIG. 50.

Extrapolation of Eye Movement to Retinal Movement, and Dosage Mapping

Tracking of eye motion as described above may be correlated with a virtual eye model having aspects of the invention, such as are described herein to assess movement of particular eye anatomy during radiotherapy treatment, for example, the movement of a retinal target region relative to the path of an X-ray beam during treatment. Such anatomical movement may in turn be used to assess actual absorbed radiation dosage and its distribution in relation to a planned radiotherapy treatment.

It has been demonstrated the low levels of suction (e.g., 25-50 mm Hg) are sufficient to provide reliable coupling of the eye-guide 110 to the eye, so as to maintain the eye guide at a selected position (e.g., with lens 120 centered on limbus 26 in contact with cornea 12 and sclera 17).

However, eye motion may still occur on the scale of a fraction of a millimeter to a few millimeters even where the eye-guide 110 and eye-guide support assembly are substantially rigid and coupled to the eye, and where chin-head restraint assembly 160 provides firm head support (e.g., generally firm chin and forehead members 171, 172 and a snug head fastener 161). Sources of residual voluntary or involuntary eye movement include: (a) the eye is movably mounted in the skull, and may be moved within the orbit and adjacent soft tissue, such as by the eye muscles or head motion; and (b) the skin and soft tissue covering the skull, face and chin is generally loose and free to move within limits over the underlying boney support, and such motion may permit in small head movement, which then applies rotational and/or translational forces to the eye, as the eye tends to follow the head motion.

It should be understood that the certain eye stabilization methods and devices having aspects of the invention may omit more aggressive measures to eliminate eye motion, such as temporary eye paralysis, high-suction contact eye-holders and/or rigid and forceful mechanical clamping of the skull, or the like. Less aggressive stabilization measures can lower treatment costs, improve patient acceptance, and reduce treatment time. Trade-offs in patient comfort, convenience, and cost can be made which favor tolerating and/or compensating for a selected modest level of eye position/orientation change during treatment versus absolute eye motion prevention.

Alternative retina target tracking, dosage mapping and compensation method and device embodiments having aspects of the invention provide safe dosage control where a residual level of eye motion is present during treatment. In addition, the methods and device embodiments provide a "fail-safe" functionality for treatment procedures which have low levels of eye motion.

Figure 52:
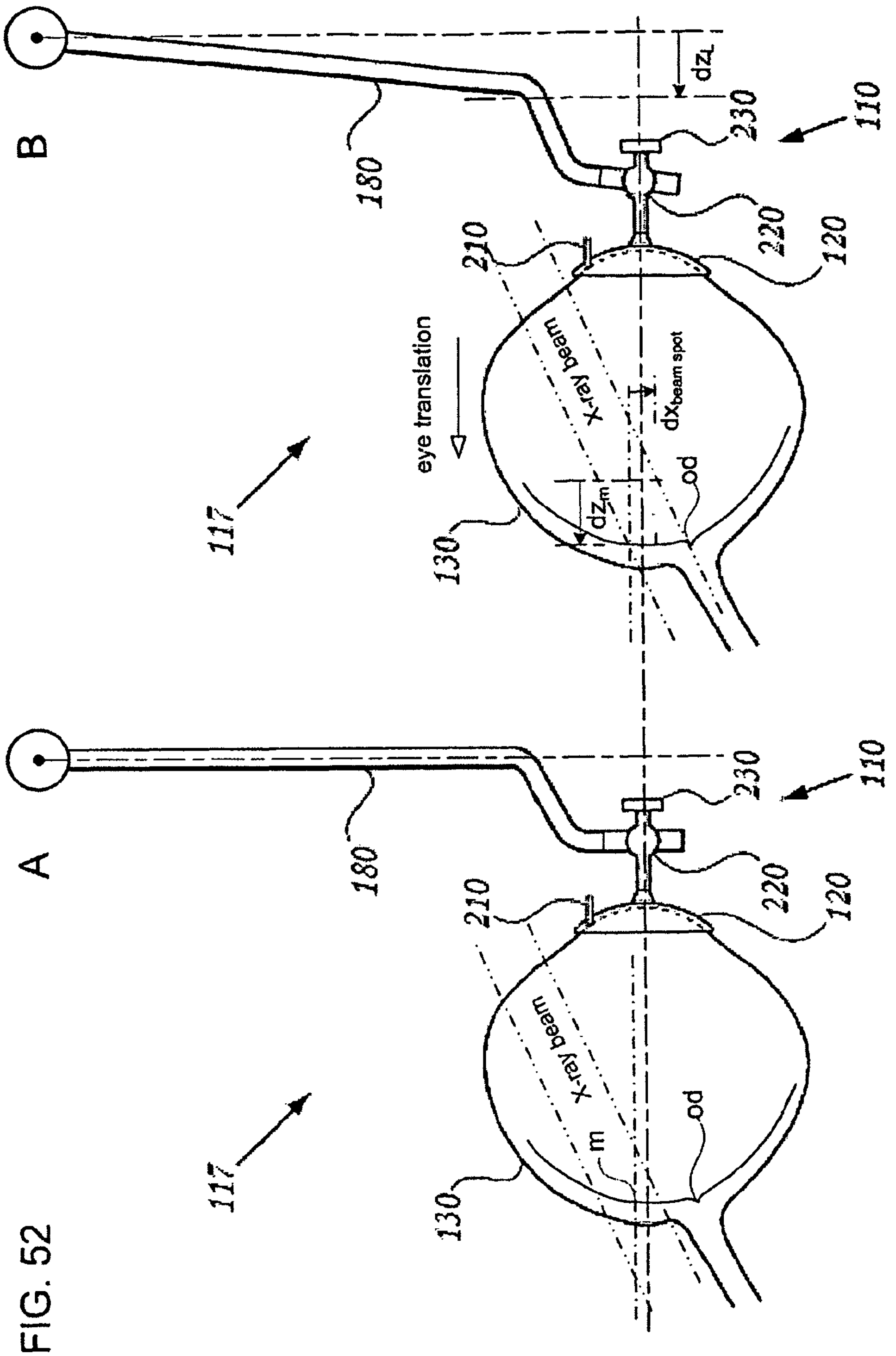
Figure 53:
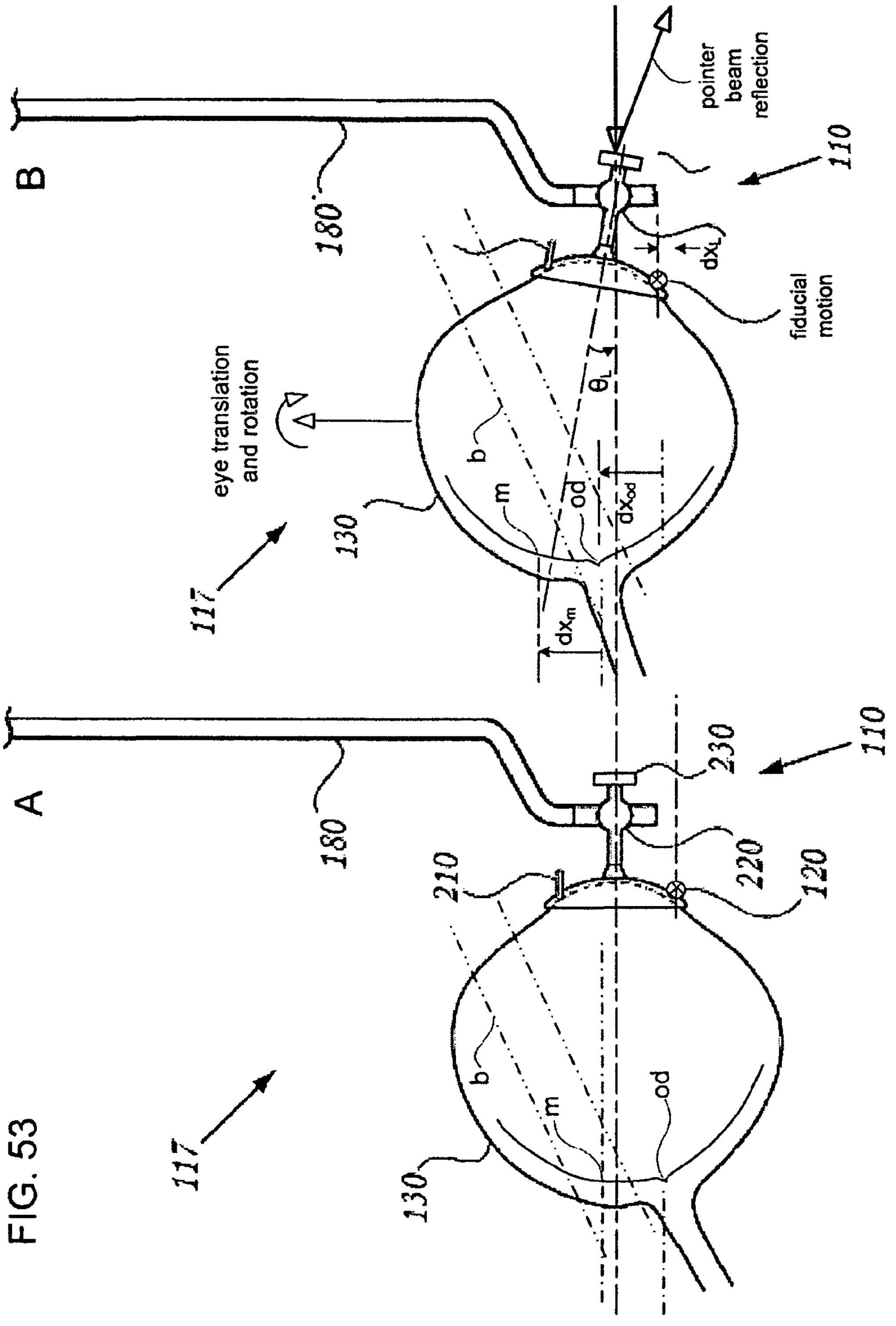
Figure 54:
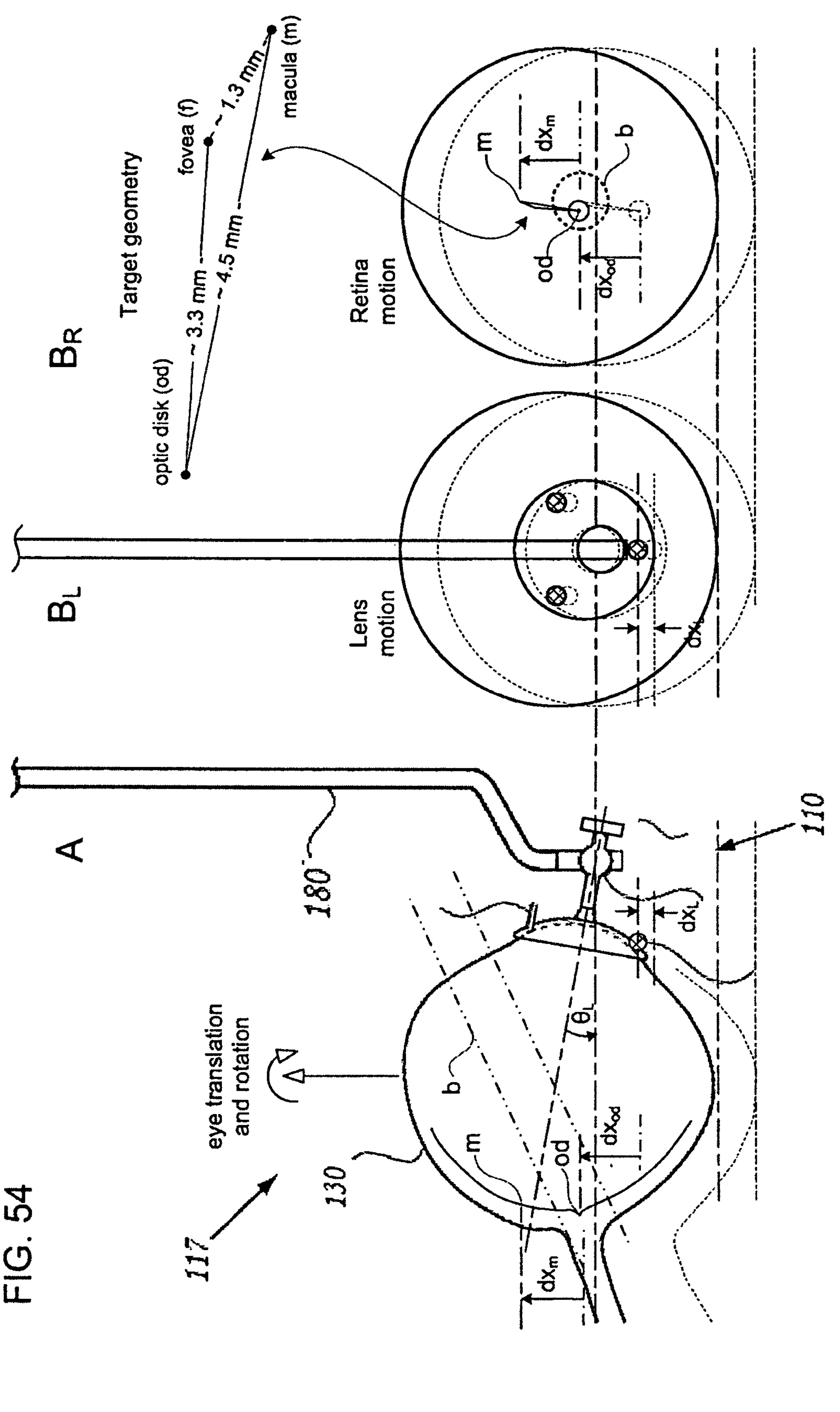

FIGS. 52-54 graphically illustrate the effect of particular eye motions of an eye engaged by an eye-stabilization system having aspects of the invention on motion of the retinal, including a treatment target (e.g., the macula) and a sensitive structure (e.g., the optic disk). In each case a radiotherapy beam is targeted on a region encompassing at least a portion of the macula, and the views show the beam initially aligned on the target, and show the effect of a particular movement away from alignment. The structure of the assembly 117 is essentially similar to that shown in FIGS. 41-42.

FIGS. 52A-B are two views from above of an eye-guide included in a eye stabilizing system having aspects of the invention, shown in contact with an eye during X-ray treatment, illustrating the effect on retinal position of motion of the eye in the system Z direction. In this case, a posterior Z movement (see FIG. 49E) can be seen that the eye motion translates the retina along the Z axis without components of motion of the retina in the X or Y axis. However, the eye motion does result in a relative motion of the beam spot on the retina due to the angled alignment of the beam with the retina. In this illustration, the beamspot moves relatively in the X direction as shown, for a beam angled from the opposite direction.

It will be apparent that the direction of relative motion of the beamspot is dependent on the X-ray beam orientation relative to the Z axis (see angles Φ and θ in FIG. 37), and in the general case of an arbitrary angle, a motion of the eye in the Z direction will result in both X and Y components of the relative motion of the beam-spot in relation to the planned target. It will also be apparent that the scale of such relative motion is dependent on the angle Φ of the beam with the treatment axis, a small angle Φ resulting in a relatively small movement of the beam-spot in relation to eye motion on the Z axis. In a preferred embodiment, angle Φ is kept constant during stereotactic re-positioning, with angle Θ changed for each beam application.

FIGS. 53A-B are two views from above of an eye-guide in contact with an eye during X-ray treatment, illustrating the effect on retinal position of motion of the eye angularly about the pivot of the eye guide. In this case, the eye and lens are pivoted through a small angular change dα (see FIGS. 49 C-D). Note that although the pivot is assumed here to be fixed, the eye motion is both in translation and in angular orientation. This can be seen to result in a motion both of the eye-guide lens fiducials (shown in the X direction, but generally in both X and Y), and in a larger motion of the retinal target in the same direction, due to the longer moment arm pivot-to-retina relative to the shorter moment arm pivot-to-lens.

FIGS. 54A-B are a comparison between the lateral illustration of FIG. 52B (reproduced as FIG. 54A) and two frontal schematic views of a phantom eye, wherein FIG. 54$B_L$ shows frontal projection of lens movement, and FIG. 54$B_R$ shows frontal projection of corresponding retinal movement. Note that FIG. 54$B_L$ shows a relatively small movement lens fiducials relative to the movement of the eye body.

FIG. 54$B_R$ has a projection of retinal target geometry, as show more clearly in attached detail view, and shows retina beamspot b. Note that the motion of the retina in this example moves the optic disk (od) into the path of beamspot b, and move the macula out of the treatment beamspot, both undesired effects with respect to the exemplary treatment plan.

FIG. 54C is a flow chart illustrating an exemplary planning method including determining a safe or allowable eye movement threshold to be permitted during treatment. The method may comprise the steps of:

(a) Aligning an ocular axis (e.g., eye geometric axis 2810) with treatment system reference axis (e.g., Z axis of positioner 115) in system External Coordinate System (ECS).

(b) Determining macula and optic nerve coordinates in ECS, inputs may include (1) Direct measurement or visualization of patient ocular anatomy, such as OCT, CT and fundus imagery, or the like; and (2) Application of a predetermined eye model (e.g., see FIGS. 19-20).

(c) Establishing treatment beam axes in ECS (e.g., see FIG. 43E).

(d) Determining maximum safe eye movement and duration for each axis (FIG. 54D).

(e) Output is a Treatment plan with beam-source settings, irradiation time, and allowed eye movement for each treatment axis.

FIG. 54D, Views (1)-(3) illustrate the relation of retinal motion to radiation dose distribution. Views (1) and (2) are schematic representations of anatomy of retinal surface 1435 including optic disk center 32, optic disk edge 32*a*, macula center 318 (approximately the fovea) and the retinal pole or intersection of geometric axis 2810. Also shown are one or more treatment beams 1400, impinging (e.g., stereotactically) to form a beamspot on or adjacent the macula center 318. In View (1) the distance in the retinal X-Y plane between macula center 318 and optic disk center 32 is indicated as $L_M$. Views (1) and (2) represent the relative geometry at different time instances during the course of treatment.

In View (1), indicated as time t=0 (although this need not be the beginning of treatment), the one or more beams are aligned according to an exemplary treatment plan to center (in combination for plural beams) on macula 318, to that the distance R between beamspot center 1441 and optic disk 32 is the same as $L_M$. ($Rt=_0$=LM)

In View (2), indicated as time t=1 (where 1 represents an arbitrary time interval), eye motion has occurred having the effect of moving the retina by increments dx and dy in the retinal X-Y plane. Note from FIGS. 52 through 54B that motion of the eye in the Z direction and angular eye motion can produce consequent X and Y motion of the retina in the External Coordinate System. The beamspot 1441 has moved relative to the optic nerve 32, so that distance R at (t=1) is no longer equal to $L_M$. In the example shown, R (to that the distance R between beamspot center 1441 and optic disk 32 is the same (e.g., $Rt=_1$<LM).

View (3), indicated is a plot showing the effect of retinal motion of the cumulative distribution of radiation dose at the retina, where the vertical axis is increasing dose (either at a given time point or a total for the treatment), and the horizontal axis is increasing distance from macula center 318 toward optic disk center 32. The bold curves, solid and dashed, show the maximum allowable threshold dose and planned dose, for each point, for the entire treatment. the light curves show the cumulative dose to time t=1 for the planned treatment (dashed) and the treatment accounting for retinal motion (solid). As may be seen in this example, a low threshold is permissible at the optic disk, and in the case shown, at t=1 this threshold has been exceeded, triggering a system response, such as gating of radiation emission.

The total dose of radiation to tissue may be assessed either at end of treatment or at any point during treatment, or both. The total dose between two time points at any point within ocular anatomy may be represented by a summation or integral of the dose received during the included time increments. For example, where $R_t$ represents the distance from the beamspot center to the selected tissue location any time t, the Total Dose$\int_{0\ to\ t} D_R(Rt)dt$, where $D_R$ is the time increment fractional dose at the tissue location (which is a function of beamspot location Rt). Alternative mathematical representations may be employed without departing from the spirit of the invention.

Real-Time Retinal Motion Dose Mapping, and X-Ray Source Gating/Realignment.

The co-invention U.S. Application No. 61/093,092 filed Aug. 29, 2008 and No. 61/076,128 filed Jun. 26, 2008 (each of which is incorporated by reference) provide, among other things, detailed description of methods and devices having aspects of the invention for:

(a) extrapolating measured eye motion to provide a real-time signal of the motion of a retinal target (or other ocular structure);

(b) methods for real-time summation of radiation dose distribution to a treatment target and to tissues adjacent the radiation beam path based on measured eye motion;

(c) methods and trigger algorithms for gating (interrupting) treatment radiation upon threshold departures of dose distribution from planned treatment; and (d) methods and devices for re-orienting a radiation source (e.g., X-ray beam collimator) to compensate for measured eye motion so as to maintain the beam substantially on target.

Method and device embodiments include combinations of these aspects with the methods and devices for radiotherapy treatment and planning described in detail herein.

Combination and Radiodynamic Therapies

Radiotherapy device 10 can be used in combination with other therapeutics for the eye. Radiotherapy can be used to limit the side effects of other treatments or can work synergistically with other therapies. For example, radiotherapy can be applied to laser burns on the retina or to implants or surgery on the anterior region of the eye. Radiotherapy can be combined with one or more pharmaceutical, medical treatments, and/or photodynamic treatments or agents. As used herein, "photodynamic agents" are intended to have their plain and ordinary meaning, which includes, without limitation, agents that react to light and agents that sensitize a tissue to the effects of light. For example, radiotherapy can be used in conjunction with anti-VEGF treatment, VEGF receptors, steroids, anti-inflammatory compounds, DNA binding molecules, oxygen radical forming therapies, oxygen carrying molecules, porphyryn molecules/therapies, gadolinium, particulate based formulations, oncologic chemotherapies, heat therapies, ultrasound therapies, and laser therapies. See for example, Small, W. Jr, ed.; "*Combining Targeted Biological Agents with Radiotherapy*" Demos Med. Pub., New York 2008, which is incorporated by reference.

In some embodiments, radiosensitizers and/or radioprotectors can be combined with treatment to decrease or increase the effects of radiotherapy, as discussed in Thomas, et al., Radiation Modifiers Treatment Overview and Future Investigations, Hematol. Oncol. Clin. N. Am. 20 (2006) 119-139; Senan, et al., Design of Clinical Trials of Radiation Combined with Antiangiogenic Therapy, Oncologist 12 (2007) 465-477; the entirety of both these articles are hereby incorporated herein by reference. Some embodiments include radiotherapy with the following radiosensitizers and/or treatments: 5-fluorouracil, fluorinated pyrimidine antimetabolite, anti-S phase cytotoxin, 5-fluorouridine triphosphate, 2-deoxyfluorouridine monophosphate (Fd-UMP), and 2-deoxyfluorouridine triphosphate capecitabine, platinum analogues such as cisplatin and carboplatin, fluoropyrimidine, gemcitabine, antimetabolites, taxanes, docetaxel, topoisomerase I inhibitors, Irinotecan, cyclo-oxygenase-2 inhibitors, hypoxic cell radiosensitizers, antiangiogenic therapy, bevacizumab, recombinant monoclonal antibody, ras mediation and epidermal growth factor receptor, tumor necrosis factor vector, adenoviral vector Egr-TNF (Ad5.Egr-TNF), and hyperthermia. In some embodiments, embodiments include radiotherapy with the following radioprotectors and/or treatments: amifostine, sucralfate, cytoprotective thiol, vitamins and antioxidants, vitamin C, tocopherol-monoglucoside, pentoxifylline, alpha-tocopherol, beta-carotene, and pilocarpine.

Other agents include complementary DNA, RNA, microRNA inhibitors (e.g., U.S. Pat. No. 7,176,304, incorporated herein by reference), and SiRNA (e.g., see U.S. Pat. No. 7,148,342, incorporated herein by reference), all of which can be combined with radiation treatment. In some embodiments, these agents are provided with radiation treatment to improve tumor control; treat inflammatory conditions; and prevent, reduce, limit, or stabilize angiogenesis.

Antiangiogenic Agents (AAs) aim to inhibit growth of new blood vessels. Bevacizumab is a humanized monoclonal antibody that acts by binding and neutralizing VEGF, which is a ligand with a central role in signaling pathways controlling blood vessel development. Findings suggest that anti-VEGF therapy has a direct antivascular effect in human tissues. See for example U.S. Pat. No. 7,060,269 and US Published Application No. 2005/0112126, each entitled "Anti-VEGF Antibodies"; each of which is incorporated by reference. In contrast, small molecule tyrosine kinase inhibitors (TKIs) prevent activation of VEGFRs, thus inhibiting downstream signaling pathways rather than binding to VEGF directly. Vascular damaging agents (VDAs) cause a rapid shutdown of established vasculature, leading to secondary tissue death. The microtubule-destabilizing agents, including combretastatins and ZD6126, and drugs related to 5,6-dimethylxanthenone-4-acetic acid (DMXAA) are two main groups of VDAs. Mixed inhibitors, including agents such as EGFR inhibitors or neutralizing agents and cytotoxic anticancer agents can also be used.

In one combination therapy method embodiment for AMD having aspects of the invention, advantageously at least one intravitreal injection treatment with an anti-VEGF antibody or antibody-derived agent such as e.g., ranibizumab or Lucentis® by Genentech may be administered to the treated eye shortly before or close to the time of radiotherapy treatment with system 10 as described herein, such as by a treatment of about 5 Gy to about 35 Gy (preferably from about 10-25 Gy) absorbed in a retinal treatment region including the macular lesion (e.g., about 4 to 6 mm diameter region centered approximately on the fovea). Preferably at least a second anti-VEGF treatment is administered about 2-6 weeks following the radiotherapy treatment. In an alternative combination therapy method embodiment, intravitreal injection treatments with bevacizumab (Avastin®) may be used.

Radiodynamic therapy refers to the combination of collimated x-rays with a concomitantly administered systemic therapy. As used herein, the term "radiodynamic agents" is intended to have its ordinary and plain meaning, which includes, without limitation, agents that respond to radiation, such as x-rays, and agents that sensitize a tissue to the effects of radiation. Similar to photodynamic therapy, a compound is administered either systemically or into the vitreous; the region in the eye to be treated is then directly targeted with radiotherapy using the eye model described above. The targeted region can be precisely localized using the eye model and then radiation can be precisely applied to that region using the PORT system and virtual imaging system based on ocular data. Beam sizes of about 1 mm or less can be used in radiodynamic therapy to treat ocular disorders if the target is drusen for example. In other examples, the beam size is less than about 6 mm.

Other compounds that can increase the local efficacy of radiation therapy are metallic nanoparticles, such as gold, silver, copper, or combinations thereof. These particles can further be tagged with targeting binding agents so that the nanoparticles can bind to targets on blood vessels or macrophages to target higher doses of radiation to specific areas of the patient. For example, Carter et. al. (Journal Physical Chemistry Letters, 111, 11622-11625, which is incorporated by reference) report improved and enhanced targeting using nanoparticles of gold. They further report even further targeting with targeting agents cross-linked to the gold particles. These nanoparticles can be combined with highly localized radiotherapy during treatment.

Alternative Corneal Beam Entry Radiotherapy Methods and Devices

FIGS. 55A-D depict alternative method and device embodiments having aspects of the invention, for retinal external-beam therapy, such as treatment employing orthovoltage X-rays, laser light of various wavelengths, or the like. In an example shown, the irradiation step is carried out by directing X-rays to penetrate the cornea at beam entry, then propagating to retinal target such as the macula (or other posterior eye target). See for example, see co-invented application Ser. No. 11/879,901 filed Jul. 18, 2007, especially FIGS. 7B, 7C and 7E, which application is incorporated by reference. Multiple stereotactic beams may be emitted so as to spread the surface dose over a relatively large portion of the cornea, so as to reduce local radiation intensity to the cornea and the lens, while concentrating dose on a retinal target such as the macula (or other posterior eye target). In certain embodiments a small opening may be repositioned sequentially to provide a sparse or low average intensity pattern on the cornea while concentrating dosage on a retinal target.

Alternatively or in combination, the X-ray dose may be micro-fractionated, such as where the radiotherapy system comprises a collimator configured to emit a beam cross section with a plurality of regions of maximal intensity that are disposed in a spaced-apart checkered, speckled, or dotted arrangement, so as to provide micro-fractionated radiation application to both the cornea and lens, during beam propagation to the target area. See co-invented application Ser. No. 12/100,398 filed Apr. 9, 2008, especially the description of FIGS. 2 and 11G, which application is incorporated by reference (FIG. 55F herein is a reproduction of FIG. 11G of '398).

X-Ray Beam Parameter Selection.

Note that the methods described above with respect to FIGS. 8 to 14 may be repeated for a treatment plan having an alternative beam path to a retinal target tissue, such as a path intersecting the cornea 12 rather than the pars plana of the sclera 17. In this manner, in certain embodiments a maximum X-ray photon energy and a filtration thickness (filter 1423 in FIGS. 21 and 56A) may be selected to achieve a desired surface-to-target dose ratio (inverse of fractional dose to target) suited to a specific treatment plan. Likewise, the effect of a different tissue path length (e.g., close to eye axial length), the dosage received by a pre-target structure such as the lens 36 (see FIG. 20, 1412), or the dosage received by a post-target organ such as the brain (see FIG. 20, 1413), may each be modeled as exemplified in FIG. 12 and considered in this selection. For example, a treatment plan for cornea/lens beam passage may select a somewhat higher maximum keV photon energy and/or a somewhat thicker filter material than a otherwise comparable treatment plan for pars plana entry such as shown in FIG. 20, so as to achieve a relatively larger dose fraction absorbed at the retina (and conversely a smaller dose fraction absorbed at the cornea and lens).

Micro-Fractionated Beam.

FIG. 55C is a schematic diagram of a collimator 118 associated with an X-ray tube 112, the anode spot 1420 positioned a distance L1 from collimator exit aperture plane 1405, with is in turn offset a distance L2 from the surface of cornea 12 of eye 30 (shown as planar eye model similar to FIG. 21). Aperture plane 1405 includes a plurality of small openings 1405*a*, which may be arranged in a random or in a geometrically regular pattern. Preferably, the plurality of openings sparsely cover a beam exit area sized to produce a overall beam spot 1441 having pattern of comparatively minute sub-spots 3090, upon propagation of beam 1400 to retinal surface 1435 (e.g. the macula). Beam spot 1441 may be circular in general shape, or may have another shape, such as oval, crescent shaped, elongate, polygonal or irregular.

Preferably, a combination of anode size 1420, collimator length L1, opening diameter 1405*a*, and exit offset L2 (which may be zero) is selected so that the penumbra of each sub-spot 3090 is small in relation to the distance between sub-spots in the pattern of beam spot 1441 ("matrix" portions 1441*a* of the dotted pattern of beam spot 1441). This permits substantial areas of the corneal beam entry spot 311 to have low X-ray dose intensity relative to the sub-spots 3090, and consequent reduced physiologic radiation effects. Similarly, intra-ocular structures such as the lens 36 have substantial volumes within the diameter beam 1440 of reduced dose intensity.

In certain micro-fractionated embodiments, the anode size, the collimator offset L2, and/or the anode-to-target distance (L0=L1+L2+L3) may optionally be different (e.g., smaller) than typically employed in the uniform beam embodiments described in detail herein, or a different type of X-ray tube 112 may be selected. Filtering (such as filter 1423 in FIG. 21) and/or maximum photon energy may be selected to accommodate differing tissue path length L3 and/or to produce a selected surface-to-depth dose ratio suited to micro-fractionated corneal entry targeting. The treatment planning methods having aspects of the invention and described herein in detail may be used to selected these parameters (see FIGS. 8-13 for example). Numerical simulation such as Monte Carlo simulation and radiographic phantom modeling as described herein may be used to optimize and validate parameter selections.

The collimator-X-ray assembly 118-112 may be mounted and operated in the manner of X-ray source assembly 420 of radiotherapy system 10, as shown in FIGS. 33-37 and described in detail herein, the beam positioning geometry in this exemplary embodiment being adapted to suit the treatment plan and targeting method illustrated in FIGS. 55 A-D. In this example, the tissue path length is approximately the eye axial length (distance from cornea anterior center to retinal surface), with small variations due to beam orientation.

FIG. 55D is a cross-section of an eye 30 showing, the a plurality of different beam paths b1-b2 having different corneal entry points 311*a*-311*d*, the beam paths being generally distinct when traversing cornea 12 and lens 36, and converging to overlap at retina 1435, in this example covering a macular target region 318.

Method embodiments may include the administration, e.g. in eye-drops prior to patient treatment, of a known ophthalmic mydriatic agent (e.g., Paremyd, Mydriacyl, Cyclogyl, or the like.) to induce dilation of pupil 25 to facilitate visualization and targeting of the retina, as shown in FIGS. 55A and D. A pharmacologically-dilated pupil in a typical population may range from about 7.0 mm to about 8.5 mm in diameter, although individuals vary considerably and older adults tend to have somewhat less dilation. See for example, Yang Y. et al; "*Pupil Location under Mesopic, Photopic, and Pharmacologically Dilated Conditions*"; (2002) Investigative Ophthalmology and Visual Science 43:2508-2512, which is incorporated by reference. Alternatively or in combination, all or a portion of the beam 1440 may penetrate the iris 24.

FIG. 55A illustrates one embodiment of a micro-fractionated treatment method. In this example, a plurality of beams (six beams b1-b6 are shown) are oriented so as to intersect the cornea near the edge of the iris at entry spots 311*a*-311*f*). For example, the collimator 118 may be oriented by positioning system 115 in FIG. 33-37). In this example, the entry spots 311 are space to avoid overlap with one another, and to leave a substantial area of the central cornea un-radiated (the arrangement need not be hexagonal, as shown). However alternative embodiments may have overlapping and centrally targeted entry spots 311. The plurality of beams converge on retina 1435 at target region 318. In addition to the concentration due to stereotactic orientation, the individual beam spot patterns 1441 may be rotated or slightly offset to one another, so as to approximate uniform radiation dose to target region 318 (e.g., disposed so that sub-spots 3090 only minimally overlap).

Although treatment axis 2820 is illustrated in FIG. 55D as being substantially parallel to geometric axis 2810, in certain embodiments it may be non-parallel. For example, for treatment of a macular target 318 may have a treatment axis 2820 offset from the geometric axis by offset 2850 defined by dx and dy in the retinal plane 1435. as shown in FIGS. 55A and D In such a method, treatment beam axis 2820 may be defined at a slight angle to axis 2810, so that a conical stereotactic beam pattern (b1-b6) which has a cone base defined by entry spots (311*a*-*f*) which are centered symmetrically near the iris edge 25, while providing that the cone apex (beam intersection) is located at the center of off-set target 318. As with other embodiments described herein, this arrangement permits a single DOF rotational motion (e.g., by motion in θ by actuator 414 in FIG. 37) to move the collimator 118 to each successive beam path b1-b6.

Stereotactic Corneal Pattern of Narrow Beams.

FIGS. 56A-E depict alternative method and device embodiments having aspects of the invention, for retinal external-beam radiotherapy employing a plurality of narrow X-ray beams 1440$_i$ having a stereotactic pattern 312 at point of entry into corneal tissue surface, focusing to define a concentrated dose distribution at a target region 318 deep to the surface of the eye, such as a macular lesion. The surface pattern 312 and the target pattern 318 collectively define a plurality of linear stereotactic beam paths 1441$_i$ to which an X-ray source may be sequentially aligned.

FIG. 56A depicts an example of a collimator assembly modeled in association with a planar eye representation in the manner of FIG. 21, comprising X-ray tube 112 having a source anode 1420 positioned adjacent collimator 118, in this example having a filter 1423 and a collimator exit aperture 1405. In operation, the X-ray source and collimator 118 may be positioned (such as by a robotic positioner 115) so as to emit an incremental beam along a beam path 1400, to intersect an incremental corneal entry spot 311$_i$, then propagating through eye tissue to an incremental retinal beam-spot 1441$_i$.

Attention is drawn to the description herein regarding the selection among alternative X-ray sources and tubes, such as shown in FIG. 33A-B. An embodiment such as shown in FIG. 56A may employ a comparatively small anode spot size 1420 (e.g., a commercially available tube 112 having a fixed anode and a variable-focus permitting selection from a range of anode spot sizes). Along with anode size, the dimension of collimator 118 (aperture 1405, and longitudinal distances L0, L1, and offset L2) may be selected to provide the desired dimensions of retinal beam spot 1441 and penumbra 1442.

For example, in certain embodiments, the effective anode size 1420 and the collimator aperture diameter 1405 may be of the same order of magnitude, such as an anode diameter 1420 between about 0.4 mm and about 1.0 mm and aperture 1405 diameter ≤about 2.0 mm. Likewise, the aperture-to-eye offset L2 for an embodiment such as shown in FIGS. 56A-E (e.g., incremental retinal beam-spot diameter 1441*i* substantially smaller than the treated retinal lesion 318) may be comparatively smaller than for a wider beam radiotherapy treatment plan such as shown in FIGS. 30A-B (e.g., retinal beam-spot diameter similar to the size of the treated retinal lesion).

FIG. 56B depicts an example of a schematic frontal view of the center portion of an eye including limbus 26, iris 24 and a dilated pupil 25 providing an enlarged open area (not superimposed on iris) of cornea surface 12. A relatively sparse pattern 312 of cornea entry beam-spots 311 (surface spot pattern) comprising n individual beam spots 311$_i$ (where i=1, 2, . . . , n−1, n). In the embodiment shown the pattern comprises narrow beam spots (having a diameter of a small fraction of the cornea width) which are spaced apart to permit an area of lower dose or less effected tissue between beam spots, although alternative embodiments may be employed. In the example shown, the pattern 312 does not place beam-spots in the central region of cornea 12, although alternative embodiments may include central beam-spots. In one example, the surface spot pattern is arranged in one or more concentric circles about the corneal center, as illustrated in FIG. 56B, which also indicates the intersection of the eye alignment axis (geometric axis 2810) as well as an off-set treatment axis 2820, as described herein.

FIG. 56C depicts a schematic frontal view of the eye as in FIG. 56B, further depicting the underlying surface of retina 1435 as if viewed through the cornea and lens (the corneal beam-spot pattern 312 is shown superimposed in light, dashed lines). A retinal beam-spot pattern 318*a* is shown on the surface of retina 1435, offset and centered on treatment axis 2820. As may be seen, in this example, retinal pattern 318*a* includes n individual beam spots 317$_i$, the same number as corneal pattern 312, the retinal beam-spots being shown slightly larger to exemplify beam divergence along the eye tissue path. Note that the retinal pattern 318*a* is tight and overlapped, indicating focus of the target depth dosage in a relatively small target area. In contrast, the cornea pattern 312 is loose, having space-apart beam-spots, indicating the dispersion of the surface dosage over a larger area of tissue, reducing average local dose intensity. Note in the general case, retinal pattern 318*a* may have an included area substantially larger any single beam-spot 317. However, in an alternative embodiment, the beamspots 317 may be superimposed (in the manner of FIG. 30B.

FIG. 56D is a view combining the features of FIGS. 56B and 56C, further depicting n individual X-ray beam paths 1440$_i$, each linearly connecting and intersecting a respective patterned corneal beam-spot 311$_i$ and target retinal beam-spot 317$_i$. Implied, but not shown in FIG. 56D, are the X-ray anode 1420 and collimator aperture 1405 located (at the sequenced time of beam emission) axially along each of paths 1440$_i$.

In on example method of planning a radiotherapy treatment as illustrated in FIGS. 56A-D, the method includes the steps of:

(a) determining X-ray beam parameters of an X-ray source/collimator 112-118 as indicated in FIG. 56A, including one or more of energy, filtration, anode size, collimator dimensions L0, L1, and L2, beam duration, and the like, optionally taking into consideration patient-specific parameters such as disease state, lesion dimensions and location, eye size or axial length (≈L3), and the like;

(b) providing an eye model relating X-ray source/collimator geometry to eye geometry;

(c) determining, and including in the eye model, a cornea surface pattern 312 containing n beam-spots 311$_i$;

(d) determining, and including the eye model, a retinal surface target pattern 318*a* containing n beam-spots 317$_i$;

(e) determining from patterns 312 and 318*a*, and including the eye model, n treatment beam paths 1440*i*;

(f) programming (optionally this may be manually controlled) a robotic X-ray source positioner controller (e.g., processor 501 and positioner 115 in FIG. 33A-B) to move through a sequence of n X-ray collimator locations/orientations corresponding to the beam paths n treatment beam paths 1440*i* determined in step (e);

(g) emitting n sequential treatment beams along paths 1440*i* according to the parameters determined in step (a), noting that the parameter may be, but do not need to be, identical for each beam.

(h) optional steps may include, in any operative order, eye alignment, stabilization, tracking, dose mapping and eye motion compensation or gating as described herein with respect to alternative treatment methods and embodiments.

FIG. 56E depict alternative retinal beam pattern 318*b* and 318*c* on the surface of retina 1435, depicting an example where a target lesion is irregular or discontinuous. Thus, the pattern of beam spots 317*i* need not form a circular pattern, or even a single region. Note also the associated examples of non-circular beam-spots 317' and 317", corresponding to a corresponding non-circular collimator aperture 1405 (or other beam shaping members, such as adjustable or exchangeable shutters or the like). Alternative retinal pattern configurations such as shown in FIG. 56E may permit more efficient or limited distribution of dose to the retina, reducing the magnitude of dose applied to other areas, such as the cornea, lens, or adjacent structures such as the optic nerve.

Continuous Track/Continuous Motion Stereotactic Treatment.

FIGS. 57A-E depict alternative method and device embodiments having aspects of the invention, for retinal external-beam radiotherapy employing one (or more) narrow X-ray beams 1440 such as shown in FIG. 56A, whereby the beam may be emitted while X-ray source/collimator 112/118 is in motion, the beam being emitted so as to intersect a defined body surface and defined target region track. In the example depicted in the figures, the body surface includes the cornea 12 and the target region includes retinal surface 1435.

FIG. 57A depicts an example of a schematic frontal view of the center portion of an eye, which as in FIG. 56B includes limbus 26, iris 24 and a dilated pupil 25 providing an enlarged open area of cornea surface 12. A surface track 313 is defined on cornea 12, in this example formed as a spiral-like shape, proceeding from a initiation point 31*a* near the limbus 26 to a terminal point 313*b*. Many other track configurations are possible, including discontinuous tracks; a plurality of isolated rings, radial paths or the like. FIG. 57A illustrates three examples of beam configuration:

(a) In the case of a beam-spot 311*a* corresponding to a continuously moving beam intersection point formed by, for example, a circular cross-section collimated X-ray beam (e.g., beam 1440 of FIG. 56A), the beam spot may be represented by an elongated shape or "swath" having a width representing the collimated beam diameter, and a length representing the distance of motion of the intersection point along surface track 313 during the duration of emission of radiation.

(b) Where collimator motion is continuous and radiation emission is intermittent or pulsed, the beam-spot may be represented by a sequence of short "dashed line" spot shapes 311*b*.

(c) Where collimator motion is discontinuous and radiation emission is coordinated on a "start-stop" sequence (fixed position emission), the beam-spots may be a series of circular shapes 311*c*, generally resembling the pattern of FIG. 56B.

FIG. 57B depicts an example of a schematic frontal view of the eye as in FIG. 57A, further depicting the underlying surface of retina 1435 as if viewed through the cornea and lens. A retinal surface track 318*a* is shown on the surface of retina 1435, generally lying adjacent of a treatment region 318, offset and centered on treatment axis 2820. An exemplary retinal beam spot $\mathbf{1441}_i$ is shown, but it should be noted that a corresponding retinal beam spot or swath is implied for each of the example cornea entry spots or swaths 311*a*, 311*b* and 311*c* shown in FIG. 57A. It may be noted that where the surface area of corneal pattern 313 is substantially larger than the area of the target region 318 (as in preferred embodiments), the beam entry spots or swaths 311*a, b* or *c* are in general spaced apart from one another laterally, and in the example shown avoid the central cornea. In contrast, the retinal beam spots or beam swaths 1441 along retinal track 318*a* are shown overlapped laterally to provide continuous dose distribution in the target region 318.

In an embodiment of a method having aspects of the invention as shown in FIGS. 57C and 57D, a point-to-point or segment-to-segment mapping 400 is defined between each point or segment of cornea track 313 and a corresponding point or segment of retinal track 318*a*. Based on mapping 400, any desired number of beam paths 1440*i* may be defined by lines intersecting a selected point on retinal path 318*a* and its corresponding point on corneal track 313. The segment so defined represents the tissue path length L3 for beam 1440*i*, and may be nearly equal to the eye axial length.

Note that as described above with respect to FIGS. 57A-B, a beam path $\mathbf{1440}_i$ may be defined independently of whether radiation is emitted along the path. Thus a given path $\mathbf{1440}_i$ may lie within a beam entry point or swath 311*a,b*, or *c*, (and thus being a radiation path) or alternatively may lie within a gap in radiation emission along track 313 (a "null" path). For example, a beam path may be defined at the beginning and at the termination of radiation emission in a swath such as 311*a*, a beam path may be defined to be the initiation point for a radiation pulse of fixed duration 311*b*, or may define a halt point for a "stop-start" fixed position beam emission 311*c*.

The beam path 1440*i* may be extrapolated towards the X-ray anode (or other radiation source, such as a laser output or other optical element; a RF emitter, wave-guide, or the like), in the example shown defining a collimator exit aperture location at distance L2 (collectively aperture track 1405*a*), and defining an anode location at a further distance L1 (collectively anode track 1420*a*). Note that for non-refracted or non-reflected photons such as X-rays, the radiation source geometry may be modeled shown in FIG. 21. For other treatment modalities, such as laser treatment, RF treatment and the like, models may be most conveniently take into account particular components for those sources, such as lenses, mirrors, slits, waveguides, and the like.

For orthovoltage X-ray treatment systems described in detail herein, the lengths L1, L2, and L3 (and their sum L0) need not be constant for each beam path 1440*i*, although in certain embodiments, these dimensions may be approximately constant.

(1) For a fixed collimator geometry, L1 will be constant. However, as shown in FIGS. 28 and 58, collimator embodiments having aspects of the invention may have variable geometry, such a telescoping exit aperture position, aperture or collimator rotation (e.g., for asymmetrical or offset apertures), and aperture lateral motion in one or two dimensions. Alternatively, the collimator aperture 1405 may have a variable diameter. In yet other embodiments, the radiation system may include additional beam shaping elements, such as separately positionable shields, lenses (e.g., in laser treatments), and the like.

(2) L2, the distance from collimator exit to eye or other body surface, the distance may be selected to be constant. Alternatively, the distance may be varied, such as to modify penumbra size, or to adjust the overall anode-to-target distance L0 for different tissue path lengths L3.

(3) Depending on cornea contour, eye shape and size, the shape and location of the target lesion, and the configuration of the cornea track 313, the tissue path length L3 may vary modestly, but may be approximately constant.

Thus in the example method, each identified or selected point or segment p3 of retinal track 318*a* corresponds to three other defined points: p2 (cornea), p1 (aperture), and p0 (anode). These locations may be automatically computed based on computer eye/system model (or may be determined manually), and the data stored, for example by suitable software and memory devices of system processor 501 as shown in FIG. 33B. The anode-aperture points p0, p1 define a line segment indicating a position and orientation of X-ray source assembly 420 corresponding to the particular beam path 1440*i*.

As may be seen, collectively the defined points p0, p1 of successive beam paths 1440*i* define a track followed by the anode 1420*a* and a track followed by the aperture 1405*a* corresponding to the corneal track 313 and the retinal track 318*a*. Likewise, the velocity of progression of the treatment system along its respective tracks, such as by translation and/or rotation of X-ray tube/collimator 112/118, in turn define a velocity of progression of the emitted X-ray beam (or "null" beam for tube "off") at the corneal surface track 313 and the retinal track 318*a*. These velocities may be constant, or may be selected to vary according to a chosen velocity profile. Similarly, X-ray emission may be selected to be triggered or stopped at selected locations based on system position, or at selected times during system movement, e.g., based on system velocity. A robotic X-ray source positioner (e.g., positioner 115 controlled by processor 501) may be programmed with the modeled data as described above to carry out a particular planned radiation treatment.

A number of strategies may be used to provide a selected total dose profile within the target region (e.g., a generally uniform "table top" dose over region 318 with a sharp fall off at its edgy, see FIG. 28). In the example depicted in FIGS. 57A-D, the shape and spacing of the corneal track 313 and the retinal track 318*a* may be configured to provide an approximately uniform dose profile across target region 318 when the system progresses along track 318*a* at constant velocity with constant X-ray emission at a constant energy spectrum and collimation parameters (continuous beam swath 311*a*).

Alternatively or in combination, the system may be programmed to progress along retinal track 318*a* at a variable velocity, so as to adjust dose application (integral of intensity and time) to be uniform with respect to area of region 318, taking into account the areas of overlap of adjacent loops of the spiral shape of track 318*a*. In yet further alternatives, the collimator or source parameters may be varied during beam progression (L2, L1 and/or L0, photon maximum energy, variable filtration, adjustable aperture diameter, and the like) so as to adjust dosage distribution within target region 318.

In the example shown in FIGS. 57A-D, the retinal track 318*a* is configured as a spiral form generally filling a circular target region 318. In alternative embodiments, target region 318 may be noncircular, irregular or discontinuous. FIG. 57E depicts two examples of alternatively configured retinal tracks: track 318*b* of spiral-like form, configured to fill a elliptical target region 318; and track 318*c* configured to be non-spiral in character and delimited to fill the shape of the irregular target 318.

In an exemplary alternative embodiment shown in FIG. 57F, both corneal track pattern 313' and retinal track pattern 318*d* may be arranged as a series of n short track segments 311$_i$ and 1441$_i$ respectively are may be spaced apart to converge along radial lines emanating from the center 2820 of target region 318, which may be centered on a treatment axis 2820. In the example 313' shown, n=24 and the tracks are arranged at 15 deg. angles on radii about target center 2820. The geometry of the tracks 313' and 318*d* are selected so that the beam swaths 1441*i* on target region 318 overlap and provide continuous dose application.

The starting and stopping points of segments 311$_i$ and 1441$_i$ may correspond to the beginning and ending of the motion of an external radiation beam source. Alternatively, the initiation or termination points of treatment radiation even while a physical source continues to be moved or re-oriented in the direction of the track. Examples include on-off switching of a laser source being moveably oriented by mirror deflection; open/close state of a radio-opaque shutter isolating an isotope; and the startup/shutdown of the power supply or bias grid of an X-ray tube being translated and/or rotated by an automated positioner (tube 112 by positioner 115 in FIG. 33). In yet other alternatives, the radiation beam may reverse direction and move back over all or a portion of the track extent (within the track and/or at track endpoints).

In alternative embodiments, the individual track segments 311$_i$ and 1441$_i$ need not be straight line segments and need not progress radially inward. Likewise the segments do not need to be similarly shaped or delimited by constant radii with respect to the corneal center. Also shown in FIG. 57F is an examples of corneal track 313" in which the segments are arranged as nested curves progressing outward, and corneal track 313'" in which the track is generally circumferential. Similarly, although example corneal track 313'-313'" avoid the center region of cornea 12, although alternative embodiments may include central beam-spots.

FIGS. 57G,H are a frontal view and corresponding cross-section of an eye 30, showing in greater detail the example of the corneal track pattern 313' and retinal track pattern 318*d* of FIG. 57F. The corneal track segments 311$_i$ may be delimited by defining starting and stopping points, such as on intersection of the track with two concentric circles, in this example centered on the geometric axis 2810 of the eye. The retinal track segments are delimited 1441$_i$ similarly by a starting point adjacent the edge of circular target region 318 and stopping point adjacent the treatment axis 2820. Note in this example the incremental track segments 311$_i$ and 1441$_i$, do not have identical length even though they are delimited by concentric circles about eye geometric axis 2810, because the segments are oriented radially about a treatment axis 2820, which in the general case may be offset from geometric axis 2810. In this example, the X, Y and Z axes are for convenience defined with respect to the off-set treatment axis 2820.

In FIGS. 57G-H, two example corneal incremental track segments are depicted, indicated as 311*i*, 311*j*, along with their corresponding retinal track segments 1441*i* and 1441*j* (as dashed lined areas). The cross section of FIG. 57H shows the respective beam paths 1440*i* and 1440*j*, intersecting the respective corneal track (indicated as suspended arrows) at the cornea surface 12; then propagating at an angle to the treatment axis ($\Phi_{0,i}$, and $\Phi_{0,j}$, respectively) so as to intersect the retina surface 1435 within target region 318. The corneal and retinal tracks in this example are so arranged that none of the beam paths 1440$_i$ passes through or near optic nerve 32. In addition, the corneal and retinal tracks may be arranged to take into account any secondary effects that the particular radiation spectrum and dose employed (e.g., visible light, IR, UV, RF, isotope decay species, X-ray, or the like) may have on corneal or lens tissue, such as alteration of refractive shape or transparency, so as to minimize any adverse effects.

In this example, the corneal and retinal tracks are defined as lying within parallel corneal and retinal tangent planes 12*a*, 1435*a* (heavy, solid arrows) positioned closely adjacent the respective corneal and retinal surfaces 12, 1435 respectively, with very little cumulative error. Alternatively, the tracks may be defined as parallel to the respective tissue surfaces, such as lying on, near or within the actual tissue surface (light, dashed arrows).

Note also from FIGS. 57F-H that due to the radial arrangement of both tracks 313' and 318*d*, in the particular case where both retina 1435 and cornea 12 may be approximated with sufficient accuracy as parallel planes, the X-ray tube/collimator assembly 112/118 may progress to move the beam along each segment 1441$_i$ solely by translation in a plane perpendicular to the treatment axis 2820 (X-Y plane), and without rotation ($\Phi$ or $\theta$) or motion in the axial direction (Z) during radiation emission.

In the example shown, the respective corneal track and retinal track segments (311*i*/1441*i*) are linear, parallel and equal length (this need not be so). In this case, the collimator angle $\Phi$ for each may be held constant within the track segment ($\Phi_{0,i}$), and the collimator may be moved only in linear translation in the XY plane (indicated as dx,dx) to accomplish progression of beam 1440*i* over the length of the segments.

Such constrained and limited degree of freedom motion, as in other embodiments described herein, promotes accuracy and precision of actuator performance and consequently more predictable radiation dose application to tissue.

However, note that in the example shown due to the offset position of target 318, the angle although $\Phi_0$ varies from segment to segment, the examples 311$i$, 311$j$ shown being relatively extreme examples arranged on opposite sides of off-set target 318, so that the angle is much larger for the left-hand beam $\Phi_{0,i}$ than the right hand beam $\Phi_{0,j}$. Movement between successive track segments 1441' may be by adjustment of θ (15 deg. increments are shown), and with small adjustments of X, Y and/or Φ to align the beam 1441$_i$ prior to the next increment of radiation emission (see embodiment of FIGS. 58A-C in this regard).

Furthermore, by adjustment of the velocity of beam progression (e.g., an acceleration profile of collimator 118 as the track progresses radially inward), the integrated dose distribution may be provided to be greater near the beginning of each segment than near the end of the segment (gradient-dose segment). The overlapped segments 1441 (i from 1 to n) may be configured in dose gradient to provide, in cumulative effect, a substantially uniform dose over target region 318.

Beam Configuration Control and Actuation Via Movable Collimator Elements.

FIGS. 58A-C and also FIG. 28 depict embodiments of collimator assemblies 118 which comprise additional actuators and movable elements configured for rapid and precise motion (e.g., small-range "Vernier actuators") in addition to primary radiation source positioning actuators (e.g., as shown in FIG. 37 for one or more of the X, Y, Z, and/or Φ system axes). These are described further in co-invented U.S. Application No. 61/093,092 filed Aug. 29, 2008, which is incorporated herein by reference. In this application, the embodiments shown in FIGS. 58A-C are described with respect to methods of tracking eye motion, calculating the motion of selected eye structures (e.g., a retinal target and/or a vulnerable tissue) base on eye motion signals, and repositioning and/or reorienting an X-ray or other radiation beam source on a real-time basis to compensate for such eye motion.

Independently or in combination with eye motion compensation and other embodiments herein, the embodiments of FIGS. 58A-C and FIG. 28 having aspects of the invention are also useful for rapid and precise motion control (or beam parameter control, such as penumbra size) as a radiation beam is emitted for treatment in any of the corneal-entry method and device embodiments shown in FIGS. 55-57 herein.

The examples of FIGS. 58A-C and FIG. 28 comprise an orthovoltage X-ray source 112, and describes an example including scleral beam entry spots (see FIG. 43E for example), but the devices and methods are useful for other types of collimated radiation beams and for other targeting methods described herein as well. In particular, these embodiment provide a means of moving a radiation beam between incremental beam paths 311 as shown in FIGS. 55 and 56, and for moving a radiation beam along a continuous beam track or segment, or re-positioning between adjacent beam segments, as shown in FIGS. 57A-H.

In the example shown in FIGS. 58 A-C, one or more additional degrees of freedom are provided for structure to move the retinal beam-spot relative to the initial beam axis 1400. Advantageously, the X-ray source mass (weight and inertia) which must be moved for fine scale re-orientation of the beam may be reduced by having an actuator configured to reorient only a portion of the collimator assembly structure 118 to delimit the beam to a slightly adjusted beam path. In the example shown, only a very small fraction of the mass of the X-ray source assembly need be moved to make small compensatory movements of the retinal beam-spot, where one or more actuators 119$a$ are configured to engage and move a collimator exit aperture plate 1405$b$ of modest mass, the actuator assembly 118$b$ being arranged adjacent the distal end of collimator assembly 118. Typically, a small mass may be repositioned more responsively and accurately than a relatively large mass, such as the total mass of X-ray source tube 112.

As shown in FIGS. 58A-C, aperture plate 1405 is supported by aperture mounting 119$b$ (e.g., may be held in position by holders 119$c$) and engaged by actuators 119$a$. In the example shown, the plate is supported to move in two dimensions (directions I and J for relative motion di and dj respectively) in a plane perpendicular to the beam axis 1400, but this need not be so. Similarly, the example depicts pairs of linear actuators in a parallel "push-pull" arrangement for each direction, but this is purely exemplary. For example, the actuator assembly 118$b$ may alternatively provide a rotational degree of freedom (not shown) in addition to a lateral translation of plate 1405$b$, so as to provide motion via polar coordinates lateral to axis 1400.

FIG. 58A provides a cross-sectional "ray-tracing" beam model similar to that of FIG. 21, with elements generally identified by the same numerals, and having collimator dimensions similarly identified as L0, L1, L2 and L3. X-ray tube 112 emits a beam 1400 via collimator 118 to propagate to sclera surface 1430, penetrating to retinal surface 1435 to form retinal beam spot 1441. Lateral motion of aperture plate 1405$b$ moves the exit aperture 1405 through a distance indicated as aperture travel 1406. Both the aperture plate 1405$b$ and the beam 1400 is shown both in an initial position/orientation (dashed or light lines) and a shifted position/orientation (solid or dark lines) as beam 1400'.

FIGS. 58B and C are frontal elevations of collimator 118, showing the arrangement of linear actuators 119$c$ to plate 1405$b$, wherein figure B represents an initial position, and C represents a shifted position, where the plate 1405$b$ has moved in two directions (di, dj respectively).

Because plate 1405$b$ is mounted at a distance between anode 1420 and retina 1435, the aperture travel 1406 results in a respective retinal beam spot travel 1407 which is magnified to a degree. For example, if aperture 1405 is exactly at the midpoint (L0=2*L1), the beam-spot travel 1407 will be twice the aperture travel 1406. Thus a movement of 1 mm by plate 1405$b$ would in this case result in a shift of approximately 2 mm in beam-spot 1441. Note that retinal motion of a restrained patient may be on the order of 1-2 mm or less over reasonable treatment periods. For embodiments in which the aperture is close to sclera surface 1430, the magnification of motion may be modest.

In one alternative, the actuators 119$b$ comprise one or more electromechanical actuators known in the art. In another alternative, the actuators 119$b$ comprise one or more piezoelectric actuators, such as a 2-D a piezoelectric actuator stage. Such actuators may be configured to controllably translate rapidly (e.g., millisecond order response) over a distance a few mm with accuracy on the order of a few microns.

Note from FIG. 58A that the entry point 311 of beam 1400 at sclera 1430 is shifted by a distance comparable to beam-spot travel 1407. In the treatment systems described herein and in incorporated U.S. Application No. 61/093,092, the relationship of sclera beam-spot 311 may be actively tracked by imaging system and processors, and accurately predicted based on eye motion detection. The collimator assembly 118 may include a steerable mirror 1220' (see laser beacon 1410 and mirror 1220 in FIG. 36) to permit a beam-aligned laser beacon to be steered to remain aligned with beam 1400', so as to assist in automated or operator monitoring of beam shift. System processors may be configured (e.g., by suitable software) to predict motion sclera beam-spot 311 so as to avoid motion of plate 1405*b* which would bring the sclera beam-spot 311 within a selected threshold distance of a vulnerable structure, such as the cornea or the lens of the eye (e.g., source-gating could be used to control retinal dose distribution in this case). In many cases, the motion of spot 311 will be away from or at least not towards a vulnerable structure.

Alternative Eye-Guide Embodiments Configured for Intra-Ocular Imaging.

FIGS. 59A-D illustrate an eye-guide device 110 for use in a eye stabilizing system having aspects of the invention, the guide having a widow or transparent portion 300 permitting retinal imaging during treatment (note alternative example in FIGS. 42C-D). In the example shown, the lens 120 is supported by one or more posts or extensions 222, which engage a Y-shaped yoke 190 comprising arms 191, 192. Yoke 190 is mounted to support arm 180 by a swivel 223. Arms 191-192 mount to extensions 222 by means of pivots 224. Pivots 224 and swivel 223 provide freedom of motion for lens 120 two perpendicular directions. Window 300 is formed in the center of lens 120 (which may be entirely transparent), so as to permit an image to be obtained from the interior of eye 130 while eye-guide 110 is engage to the eye. Vacuum connection 275 communicates off-center on lens 120 and does not obstruct window 300.

FIGS. 60A-D illustrate an alternative eye-guide device 110 for use in a eye stabilizing system having aspects of the invention, similar in many respects to the embodiment shown in FIGS. 59A-D. As in the eye-guide of FIG. 59, the guide has a widow or transparent portion permitting retinal imaging during treatment, and has a vacuum line to provide suction at the lens contact surface. In this example, the lens 120 is supported by a frame comprising a first jointed post 225*b* linked to the end of support arm 180, and by a second jointed post 225*a* via tie rod 226 and attachment 227 to a medial portion of support arm 180. The arrangement of these components forms a generally quadrilateral frame, which may be made adjustable by an adjustment mechanism, in this case the tie bar being jointed to a slide-and-set screw assembly 227, which may be selectively repositioned along the axis of the support arm 180. The arrangement shown permits the eye-guide 110 to have asymmetric pivoting characteristics, whereby pivot resistance may be selected to be different is the X and Y directions.

Figure 60A:
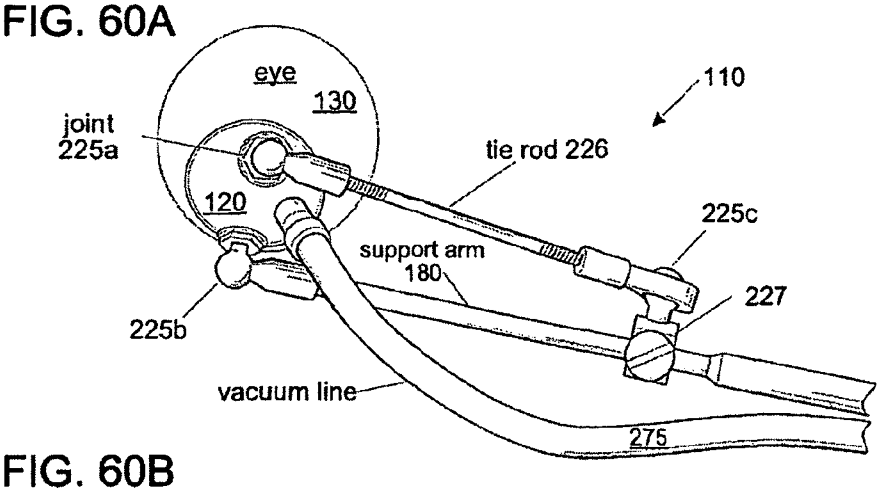
Figure 60B:
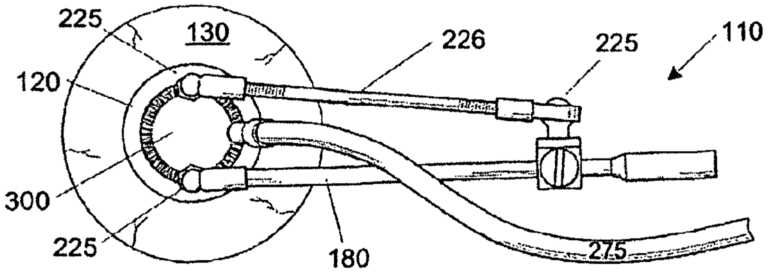
Figure 60C:
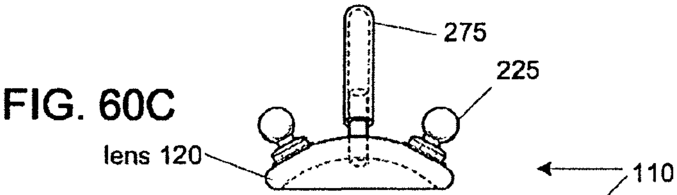
Figure 60D:
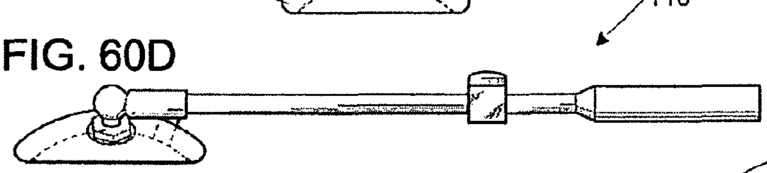
Figure 60E:
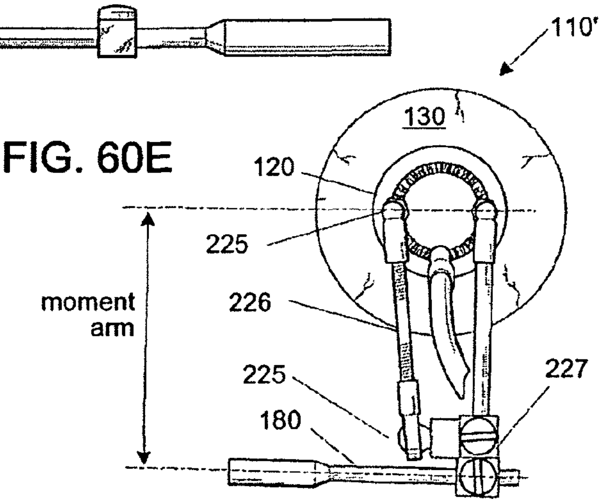

FIG. 60E illustrates an alternative embodiment similar to that of FIGS. 60A-D, in which the support frame for lens 120 is rotated approximately 90 deg. with respect to the support arm 180, so that the lens 120 is at the end of a moment arm about the axis of the support arm 180. The moment arm permits a bias or reaction force of the lens 120 upon eye 30 to be transmitted as a torque about the support arm 180. This may be exploited or regulated by means of a torque spring or other actuator within eye guide support (600 in FIG. 40).

From the foregoing, it can be seen how various objects and features of the invention are met. While certain aspects and embodiments of the disclosure have been described, these have been presented by way of example only, and are not intended to limit the scope of the disclosure. The methods and systems described herein may be embodied in a variety of other forms without departing from the spirit thereof. All publications and patents cited herein are expressly incorporated herein by reference for the purpose of describing and disclosing systems and methodologies which might be used in connection with the invention.

It is claimed:

1. A treatment planning method for treating macular degeneration in a patient, comprising:

scaling, to a measured ocular dimension of an eye, a model of the eye that includes coordinates of retinal features, including a macula and a virtual ocular medium;

establishing at least two treatment axes along which a collimated beam of X-radiation is directable from an external radiation source at the macula in the eye model;

determining, from the known distance of travel of the beam within the model along each treatment axis and from the virtual ocular medium through which the beam travels, the dose of radiation from the source that needs to be delivered along each treatment axis to produce a predetermined total radiation dose at the macula of the eye; and directing collimated X-radiation beams at the macula in the eye.

2. The method of claim 1, wherein scaling the model includes measuring along an ocular axis, the ocular length of the patient's eye between the cornea and retina of the eye, and scaling the ocular length of the model to the patient's measured ocular length.

3. The method of claim 1, wherein establishing the at least two treatment axes includes establishing at least three treatment axes directed through the sclera and converging at the macula in the eye model, and having a total beam-to-beam angular divergence of between 20-60 degrees.

4. The method of claim 1, wherein the eye model includes coordinates of the optic nerve at the retina, the dose of radiation is determined as specified beam intensity over a given irradiation period, and the determining the dose further includes determining a permitted extent of eye movement over the irradiation period that maintains the radiation dose received at the patient optic nerve below a predetermined level.

5. The method of claim 1, wherein directing collimated X-radiation beams comprises producing the predetermined total radiation dose at the macula of the eye.

6. Non-transitory machine-readable medium which operates with a computer to execute machine-readable instructions for treating macular degeneration in a patient, comprising the steps of:

scaling, to a patient-eye ocular dimension supplied as input, a model of an eye that represents retinal features, including the macula and a virtual ocular medium;

establishing at least two treatment axes along which a collimated beam of X-radiation will be directed from an external radiation source at the macula in the eye model;

determining from a known distance of travel of the beam within the model along each treatment axis and from the virtual ocular medium through which the beam travels, the dose of radiation from the source that needs to be delivered along each treatment axis to produce a predetermined total radiation dose at the macula of the eye; and directing collimated X-radiation beams at the macula in the eye.

7. The non-transitory machine-readable medium of claim 6, wherein directing collimated X-radiation beams comprises producing the predetermined total radiation dose at the macula of the eye.

* * * * *